US008367322B2

(12) United States Patent
Barany et al.

(10) Patent No.: US 8,367,322 B2
(45) Date of Patent: Feb. 5, 2013

(54) ACCELERATING IDENTIFICATION OF SINGLE NUCLEOTIDE POLYMORPHISMS AND ALIGNMENT OF CLONES IN GENOMIC SEQUENCING

(75) Inventors: Francis Barany, New York, NY (US); Jianzhao Kiu, Boston, MA (US); Brian W. Kirk, New York, NY (US); Monib Zirvi, Willingboro, NJ (US); Norman P. Gerry, Boston, MA (US); Philip B. Paty, New York, NY (US)

(73) Assignees: Cornell Research Foundation, Inc., Ithaca, NY (US); Sloan-Kettering Institute for Cancer Research, New York, NY (US)

( * ) Notice: Subject to any disclaimer, the term of this patent is extended or adjusted under 35 U.S.C. 154(b) by 710 days.

(21) Appl. No.: 10/198,235

(22) Filed: Jul. 17, 2002

(65) Prior Publication Data

US 2003/0190634 A1 Oct. 9, 2003

Related U.S. Application Data

(63) Continuation-in-part of application No. 09/478,189, filed on Jan. 5, 2000, now Pat. No. 6,534,293.

(60) Provisional application No. 60/114,881, filed on Jan. 6, 1999.

(51) Int. Cl.
*C12Q 1/68* (2006.01)
*C12P 19/34* (2006.01)
*C07H 21/02* (2006.01)
*C07H 21/04* (2006.01)
*C07H 21/00* (2006.01)

(52) U.S. Cl. ...... 435/6.1; 435/6.11; 435/6.12; 435/91.1; 435/91.2

(58) Field of Classification Search .............. 435/6, 91.1, 435/91.2, 183, 6.1, 6.11, 6.12; 436/94; 536/23.1, 536/24.3, 24.33, 25.3
See application file for complete search history.

(56) References Cited

U.S. PATENT DOCUMENTS 5,710,000 A 1/1998 Sapolsky et al.
5,916,763 A * 6/1999 Williams et al. ............. 435/69.1

FOREIGN PATENT DOCUMENTS

| EP | 0 593 095 A1 | 4/1994 |
|---|---|---|
| GB | 2 295 228 A | 5/1996 |
| WO | WO 94/01582 | 1/1994 |
| WO | WO 94/29486 | 12/1994 |
| WO | WO 97/15690 | 5/1997 |
| WO | WO 97/31256 | 8/1997 |
| WO | WO 97/43449 | 11/1997 |
| WO | WO 98/10095 | 3/1998 |
| WO | WO 98/15652 | 4/1998 |
| WO | WO 98/20165 | 5/1998 |
| WO | WO 98/40518 | 9/1998 |
| WO | WO 98/46621 | 10/1998 |
| WO | WO 99/23256 | 5/1999 |

OTHER PUBLICATIONS

Onda et al., Genomic organization of glycophorin A gene family revealed by yeast artificial chromosomes containing human genomic DNA. The Journal of Biological Chemistry, 269, 13013-13020, 1994.*
Botstein et al., "Construction of a Genetic Linkage Map in Man Using Restriction Fragment Length Polymorphisms," *Amer. J. Hum. Genet.* 32:314-331 (1980).
Schwab et al., "Amplified DNA with Limited Homology to *myc* Cellular Oncogene is Shared by Human Neuroblastoma Cell Lines and a Neuroblastoma Tumour," *Nature* 305(5931):245-248 (1983).
White et al., "Structure of Human Steroid 21-Hydroxylase Genes," *Proc. Natl. Acad. Sci. USA* 83:5111-5115 (1986).
Solomon et al., "Chromosome 5 Allele Loss in Human Colorectal Carcinomas," *Nature* 328(6131):616-619 (1987).
Law et al., "Concerted Nonsyntenic Allelic Loss in Human Colorectal Carcinoma," *Science* 241(4868):961-965 (1988).
Frye et al., "Detection of Amplified Oncogenes by Differential Polymerase Chain Reaction," *Oncogene* 4(9):1153-1157.
Weber et al., "Abundant Class of Human DNA Polymorphisms Which Can be Typed Using the Polymerase Chain Reaction," *Amer. J. Hum. Genet.* 44:388-396 (1989).
Bishop, "Molecular Themes in Oncogenesis," *Cell* 64(2):235-248 (1991).
Barany et al., "Cloning, Overexpression, and Nucleotide Sequence of a Thermostable DNA Ligase Gene," *Gene* 109:1-11, (1991).
Barany, "Genetic Disease Detection and DNA Amplification Using Cloned Thermostable Ligase," *Proc. Natl. Acad. Sci. USA*, 88:189-193 (1991).
Barany, "The Ligase Chain Reaction in a PCR World," *PCR Methods and Applications* 1:5-16 (1991).
Zhang et al., "Single-Base Mutational Analysis of Cancer and Genetic Diseases Using Membrane Bound Modified Oligonucleotides," *Nucleic Acids Research* 19(14):3929-3933 (1991).
Neubauer et al., "Analysis of Gene Amplification in Archival Tissue by Differential Polymerase Chain Reaction," *Oncogene* 7(5):1019-1025 (1992).

(Continued)

Primary Examiner — Frank W Lu
(74) *Attorney, Agent, or Firm* — LeClairRyan, a Professional Corporation

(57) ABSTRACT

The present invention is directed to a method of assembling genomic maps of an organism's DNA or portions thereof. A library of an organism's DNA is provided where the individual genomic segments or sequences are found on more than one clone in the library. Representations of the genome are created, and nucleic acid sequence information is generated from the representations. The sequence information is analyzed to determine clone overlap from a representation. The clone overlap and sequence information from different representations is combined to assemble a genomic map of the organism. Once the genomic map is obtained, genomic sequence information from multiple individuals can be applied to the map and compared with one another to identify single nucleotide polymorphisms. These single nucleotide polymorphisms can be detected, and alleles quantified, by conducting (1) a global PCR amplification which creates a genome representation, and (2) a ligation detection reaction process whose ligation products are captured by hybridization to a support.

20 Claims, 104 Drawing Sheets

OTHER PUBLICATIONS

Kallioniemi et al., "ERBB2 Amplification in Breast Cancer Analyzed by Fluorescence in Situ Hybridization," *Proc. Natl. Acad. Sci. USA* 89(12):5321-5325 (1992).

Nickerson et al., "Identification of Clusters of Biallelic Polymorphic Sequence-Tagged Sites (pSTSs) that Generate Highly Informative and Automatable Markers for Genetic Linkage Mapping," *Genomics* 12(2):377-387 (1992).

Kallioniemi et al., "Comparative Genomic Hybridization: A Rapid New Method for Detecting and Mapping DNA Amplification in Tumors," *Seminars in Cancer Biol.* 4(1):41-46 (1993).

Feero et al., "Hyperkalemic Periodic Paralysis: Rapid Molecular Diagnosis and Relationship of Genotype to Phenotype in 12 Families," *Neurology* 43:668-673 (1993).

Lisitsyn et al., "Cloning the Differences Between Two Complex Genomes," *Science* 259:946-951 (1993) (Abstract only).

Winn-Deen et al., "High Density Multiplex Mutation Analysis Using the Oligonucleotide Ligation Assay (OLA) and Sequence-Coded Separation," *Amer. J. Human Genetics* 53:1512 (1993).

Grossman et al., "High-Density Multiplex Detection of Nucleic Acid Sequences: Oligonucleotide Ligation Assay and Sequence-Coded Separation," *Nucleic Acids Res.* 22(21):4527-4534 (1994).

Kallioniemi et al., "Detection and Mapping of Amplified DNA Sequences in Breast Cancer by Comparative Genomic Hybridization," *Proc. Natl. Acad. Sci. USA* 91(6):2156-2160 (1994).

Lisitsyn et al., "Direct Isolation of Polymorphic Markers Linked to a Trait by Genetically Directed Representational Difference Analysis," *Nat. Genet.* 6(0:57-63 (1994).

Pease et al., "Light-Generated Oligonucleotide Arrays for Rapid DNA Sequence Analysis," *Proc. Natl.. Acad. Sci. USA* 91(11):5022-5026(1994).

Eggers et al., "A Microchip for Quantitative Detection of Molecules Utilizing Luminescent and Radioisotope Reporter Groups," *BioTechniques* 17(3):516-520, 522, 524-525 (1994) (Missing pages are advertisements).

Guo et al., "Direct Fluorescence Analysis of Genetic Polymorphisms by Hybridization with Oligonucleotide Arrays on Glass Supports," *Nucleic Acids Res.* 22(24):5456-5465 (1994).

Cawkwell et al., "Frequency of Allele Loss of *DCC*, p53, *RBI*, *WT1*, *NF1*, *NM23* and *APC/MCC* in Colorectal Cancer Assayed by Fluorescent Multiplex Polymerase Chain Reaction," *Br. J. Cancer* 70(5):813-818 (1994).

Beattie et al., "Advances in Genosensor Research," *Clinical Chemistry* 41(5):700-706 (1995).

Kallioniemi et al., "Identification of Gains and Losses of DNA Sequences in Primary Bladder Cancer by Comparative Genomic Hybridization," *Genes, Chromosomes & Cancer* 12:213-219 (1995).

Lipshutz et al., "Using Oligonucleotide Probe Arrays to Access Genetic Diversity," *BioTechniques* 19(3):442-447 (1995).

Lisitsyn et al., "Comparative Genomic Analysis of Tumors: Detection of DNA Losses and Amplification," *Proc. Natl. Acad. Sci. USA*, 92(1):151-155 (1995).

Schutte et al., "Identification by Representational Difference Analysis of a Homozygous Deletion in Pancreatic Carcinoma That Lies Within the *BRCA2* Region," *Proc. Nat'l. Acad. Sci. USA* 92(13):5950-5954 (1995).

Hampton et al., "Simultaneous Assessment of Loss of Heterozygosity at Multiple Microsatellite Loci Using Semi-Automated Fluorescence-Based Detection: Subregional Mapping of Chromosome 4 in Cervical Carcinoma," *Proc. Natl'l. Acad. Sci. USA* 93(13):6704-6709 (1996).

Nikiforov et al., "Genetic Bit Analysis: A Solid Phase Method for Typing Single Nucleotide Polymorphisms," *Nucleic Acids Research* 22(20):4167-4175 (1994).

Reed et al., "Chromosome-Specific Microsatellite Sets for Fluorescence-Based, Semi-Automated Genome Mapping," *Nature Genetics* 7(3):390-395 (1994).

Boland et al., "Microallelotyping Defines the Sequence and Tempo of Allelic Losses at Tumour Suppressor Gene Loci During Colorectal Cancer Progression" *Nature Medicine* 1(9):902-909 (1995).

Hensel et al., "Simultaneous Identification of Bacterial Vinlence Genes by Negative Selection," *Science* 269(5222):400-403 (1995).

Thomas et al., "Identification of Amplified Restriction Fragment Polymorphism (AFLP) Markers Tightly Linked to the Tomato Cf-9 Gene for Resistance to *Cladosporium fulvum*," *Plant J.* 8(5):785-794 (1995).

Vos et al., "AFLP: A New Technique for DNA Fingerprinting," *Nucleic Acids Res.* 23(21):4407-4414 (1995).

Day et al., "Detection of Steroid 21-Hydroxylase Alleles Using Gene-Specific PCR and a Multiplexed Ligation Detection Reaction," *Genomics* 29:152-162 (1995).

Eggerding et al., "Fluorescence-Based Oligonucleotide Ligation Assay for Analysis of Cystic Fibrosis Transmembrane Conductance Regulator Gene Mutations," *Human Mutation* 5:153-165 (1995).

Collins, "Positional Cloning Moves From Perditional to Traditional," *Nat. Genet.* 9(4):347-350 (1995).

Belgrader et al., "A Multiplex PCR-Ligasc Detection Reaction Assay for Human Identity Testing," *Genome Science and Technology* 1(2):77-87(1996).

Meksem et al., "A High-Resolution Map of the Vicinity of the *R1* Locus on Chromosome V of Potato Based on RFLP and AFLP Markers," *Mol. Gen. Genet.* 249(1):74-81 (1995).

Bachem et al., "Visualization of Differential Gene Expression Using a Novel Method of RNA Fingerprinting Based on AFLP: Analysis of Gene Expression During Potato Tuber Development," *Plant J.* 9(5):745-753 (1996).

Chiang et al., "Use of a Fluorescent-PCR Reaction to Detect Genomic Sequence Copy Number and Transcriptional Abundance," *Genome Research* 6(10):1013-1026 (1996).

Heid et al., "Real Time Quantitative PCR," *Genome Research* 6(10):986-994 (1996).

Day et al., "Identification of Non-Amplifying CYP21 Genes When Using PCR-Based Diagnosis of 21-Hydroxylase Deficiency in Congenital Adrenal Hyperplasia (CAH) Affected Pedigrees," *Hum. Mol. Genet.* 5(12):2039-2048 (1996).

Shumaker et al., "Mutation Detection by Solid Phase Primer Extension," *Human Mutation* 7(4):346-354 (1996).

Southern, "DNA Chips: Analyzing Sequence by Hybridization to Oligonucleotides on a Large Scale," *Trends in Genetics* 12(3):110-115 (1996).

Thiagalingam et al., "Evaluation of the *FHIT* Gene in Colorectal Cancers," *Cancer Res.* 56(13):2936-2939 (1996).

Tanner et al., "Independent Amplification and Frequent Co-Amplification of Three Nonsyntenic Regions on the Long Arm of Chromosome 20 in Human Breast Cancer," *Cancer Research* 56(15):3441-3445 (1996).

Janssen et al., "Evaluation of the DNA Fingerprinting Method AFLP as an New Tool in Bacterial Taxonomy," *Microbiology* 142(Pt 7):1881-1893 (1996).

Schena et al., "Parallel Human Genome Analysis: Microarray-Based Expression Monitoring of 1000 Genes," *Proc. Natl. Acad. Sci. USA* 93(20):10614-10619 (1996).

Shalon et al., "A DNA Microarray System for Analyzing Complex DNA Samples Using Two-Color Fluorescent Probe Hybridization," *Genome Research* 6(7):639-645 (1996).

Ried et al., "Comparative Genomic Hybridization Reveals a Specific Pattern of Chromosomal Gains and Losses During the Genesis of Colorectal Tumors," *Genes, Chromosomes & Cancer* 15(4):234-245 (1996).

Risch et al., "The Future of Genetic Studies of Complex Human Diseases," *Science* 273(5281):1516-1517 (1996).

Lin et al., "Multiplex Genotype Determination at a Large Number Of Gene Loci," *Proc. Natl. Acad. Sci. USA* 93(6):2582-2587 (1996).

Shoemaker et al., "Quantitive Phenotypic Analysis of Yeast Deletion Mutants Using a Highly Parallel Molecular Bar-Coding Strategy," *Nature Genet.* 14(4):450-456 (1996).

Lander, "The New Genomics: Global Views of Biology," *Science* 274(5287):536-539 (1996).

Hacia et al., "Detection of Heterozygous Mutations in *BRCA1* Using High Density Oligonucleotide Arrays and Two-Colour Fluorescence Analysis," *Nature Genetics* 14(4):441-447 (1996).

Chee et al., "Accessing Genetic Information With High-Density DNA Arrays," *Science* 274(5287):610-614 (1996).

Delahunty et al., "Testing the Feasibility of DNA Typing for Human Identification by PCR and an Oligonucleotide Ligation Assay," *Am. J. Hum. Genet.* 58:1239-1246 (1996).

Cronin et al., "Cystic Fibrosis Mutation Detection by Hybridization to Light-Generated DNA Probe Arrays," *Hum Mutat.* 7(3):244-255 (1996).

Kozal et al., "Extensive Polymorphisms Observed in HIV-1 Clade B Protease Gene Using High-Density Oligonucleotide Arrays," *Nature Medicine* 2(7):753-759 (1996).

Yershov et al., "DNA Analysis and Diagnostics on Oligonucleotide Microchips," *Proc. Natl. Acad. Sci. USA* 93(10):4913-4918 (1996).

DeRisi et al., "Use of a eDNA Microarray to Analyse Gene Expression Patterns in Human Cancer," *Nature Genetics* 14(4):457-460 (1996).

Fanning et al., "Polymerase Chain Reaction Haplotyping Using 3' Mismatches in the Forward and Reverse Primers: Application to the Biallelic Polymorphisms of Tumor Necrosis Factor and Lymphotoxin α," *Tissue Antigens* 50(1):23-31 (1997).

Drobyshev et al., "Sequence Analysis by Hybridization with Oligonucleotide Microchip: Identification Of β-Thalassemia Mutations," *Gene* 188(1):45-52 (1997).

Zhang et al., "Gene Expression Profiles in Normal and Cancer Cells," *Science* 276:1268-1272 (1997).

Guo et al., "Enhanced Discrimination of Single Nucleotide Polymorphisms by Artificial Mismatch Hybridization," *Nature Biotech.* 15:331-335 (1997).

Lee et al, "Rapid Detection of Trisomy 21 by Homologous Gene Quantitative PCR (HGQ-PCR)," *Human Genetics* 99(3):364-367(1997).

Li et al., "*PTEN*, a Putative Protein Tyrosine Phosphatase Gene Mutated in Human Brain, Breast, and Prostate Cancer," *Science* 275(5308):1943-1947 (1997).

Heller et al., "Discovery and Analysis of Inflammatory Disease-Related Genes Using cDNA Microarrays " *Proc. Nat'l.. Acad. Sci. USA* 94(6):2150-2155 (1997).

Lockley et al., "Colorimetric Detection of Immobilised PCR Products Generated on a Solid Support," *Nucleic Acids Research* 25(6)1313-1314 (1997).

Pastinen et al., "Minisequencing: A Specific Tool for DNA Analysis and Diagnostics on Oligonucleotide Arrays," *Genome Reearch* 7(6):606-614 (1997).

Kruglyak, "The Use of a Genetic Map of Biallelic Markers in Linkage Studies," *Nature Genetics* 17:21-24 (1997).

Cheung et al., "Genomic Mismatch Scanning Identifies Human Genomic DNA Shared Identical by Descent," *Genomics* 47(1):1-6 (1998).

Kyger et. al. "Detection of the Hereditary Hemochromatosis Gene Mutation by Real-time Fluorescence Polymerase Chain Reaction and Peptide Nucleic Acid Clamping," *Analytical Biochemistry* 260:142-148 (1998).

Cochet et. al. "Selective PCR Amplification of Functional Immunoglobulin Light Chain from Hybridoma Containing the Aberrant MOPC 21-Derived V κ by PNA-Mediated PCR Clamping," *BioTechniques* 26(5):818-822 (1999) (Missing pages are advertisements).

Cheung et al., "Linkage-Disequilibrium Mapping Without Genotyping," *Nature Genetics* 18(3):225-230 (1998).

McAllister et al., "Enrichment for Loci Identical-by-Descent Between Pairs of Mouse or Human Genomes by Genomic Mismatch Scanning," *Genomics* 47(1):7-11 (1998).

Pinkel et al., "High Resolution Analysis of DNA Copy Number Variation Using Comparative Genomic Hybridization to Microarrays," *Nature Genetics* 20(2):207-211 (1998).

Wang et al., "Large-Scale Identification, Mapping, and Genotyping of Single-Nucleotide Polymorphisms in the Human Genome," *Science* 280:1077-1082 (1998).

Khanna et al.. "Multiplex PCR/LDR for Detection of K-*ras* Mutations in Primary Colon Tumors," *Oncogene* 18(1):27-38 (1999).

Gerry et al.. "Universal DNA Microarray Method for Multiplex Detection of Low Abundance Point Mutations," *J. Mol. Biol.* 292:251-262 (1999).

Fan et al., "Genetic Mapping: Finding and Analyzing Single-Nucleotide Polymorphisms with High-Density DNA Arrays," American Journal of Human Genetics 61(4) Supp. 1:1601 (1997) (Abstract only).

\* cited by examiner

Scheme 1 for sequencing restriction endonuclease generated representations

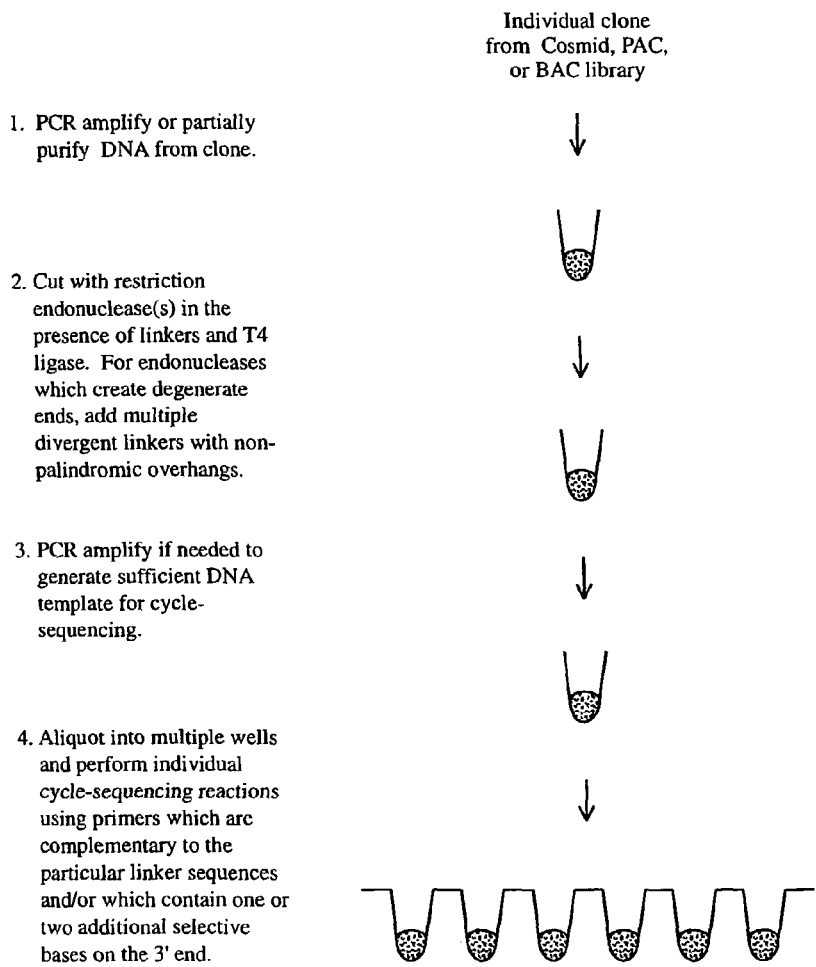

1. PCR amplify or partially purify DNA from clone.

2. Cut with restriction endonuclease(s) in the presence of linkers and T4 ligase. For endonucleases which create degenerate ends, add multiple divergent linkers with non-palindromic overhangs.

3. PCR amplify if needed to generate sufficient DNA template for cycle-sequencing.

4. Aliquot into multiple wells and perform individual cycle-sequencing reactions using primers which are complementary to the particular linker sequences and/or which contain one or two additional selective bases on the 3' end.

*FIG. 2*

Scheme 2 for sequencing restriction endonuclease generated representations

DNA sequencing directly from PCR amplified DNA without primer interference

1. PCR amplify using oligonucleotides containing ribose U replacing dT, add dNTPs and *Taq* polymerase.

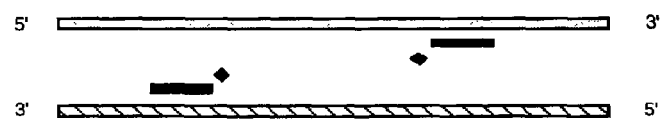

2. Add 0.1 N NaOH and heat to 95°C for 5 min to destroy unused primers.

3. Neutralize, dilute into two new wells. Anneal forward and reverse primers in separate reactions to run fluorescent dideoxy-sequencing reactions.

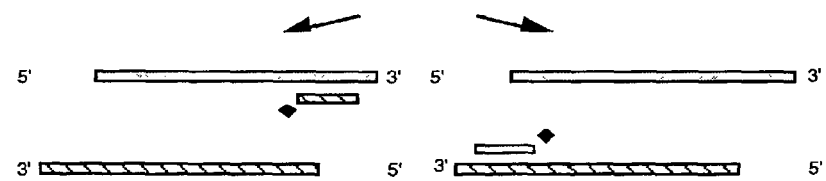

*FIG. 4*

Sequencing DrdI islands in random BAC clones

1. Cut BAC DNA with MspI and DrdI in the presence of linkers and T4 ligase. Linker for DrdI site is phosphorylated and contains a 3' AA overhang. Linker for MspI site is not phosphorylated, and contains a bubble. Biochemical selection assures that most sites contain linkers.

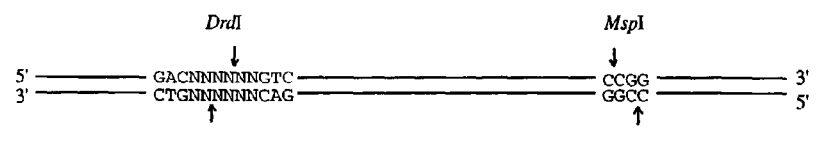

2. Inactivate T4 ligase and restriction endonucleases at 95°C for 5 min. PCR amplify using primers containing ribose U replacing dT, dNTPs, and Taq polymerase. Primer specific to the DrdI site linker will extend through bubble of MspI site linker. This allows the primer specific to the MspI site linker to amplify the DrdI-MspI fragment. MspI-MspI fragments will not amplify since they contain bubbles on both ends.

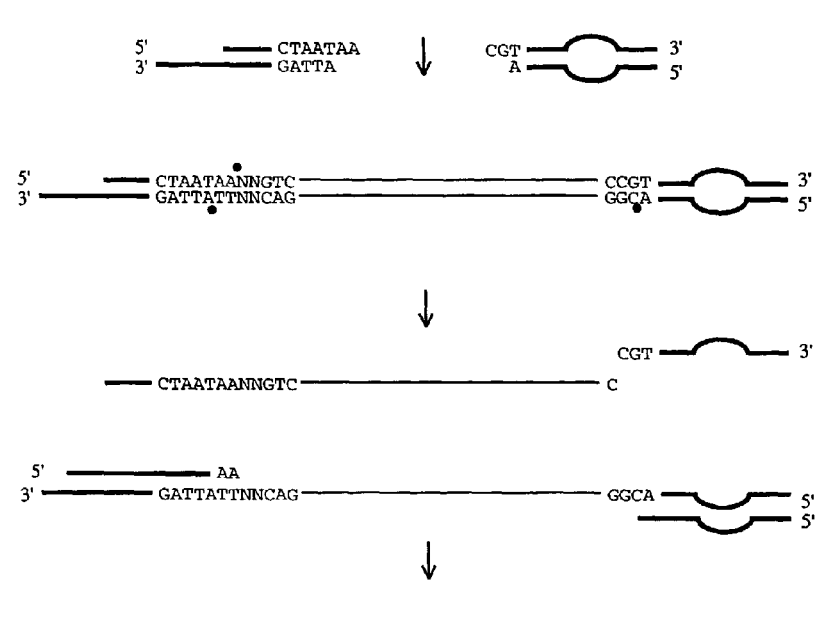

3. Add 0.1N NaOH and heat to 95 °C for 5 min to destroy unused primers.

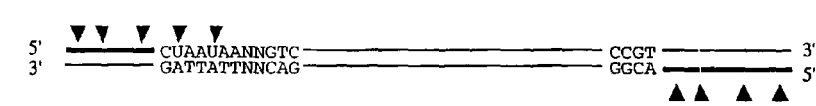

4. Neutralize and dilute. Anneal sequencing primer to the DrdI site linker and perform a cycle-sequencing reaction. (A separate reaction may be performed using a primer annealing to the MspI site linker).

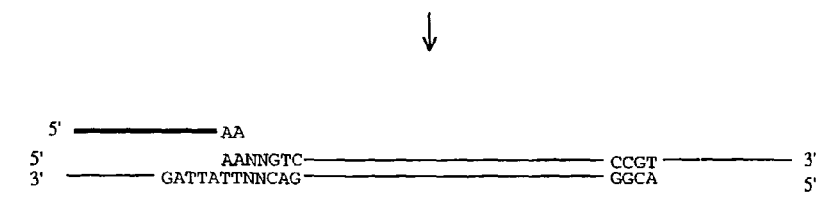

*FIG. 5*

Sequencing *DrdI* islands in random BAC clones

1. Cut BAC DNA with *DrdI*, *MspI* and *TaqI* in the presence of linkers and T4 ligase. Linker for *DrdI* site is phosphorylated and contains a 3' AA overhang. Linker for *MspI/TaqI* site is phosphorylated, 3' blocked and contains a bubble. Biochemical selection assures that most sites contain linkers.

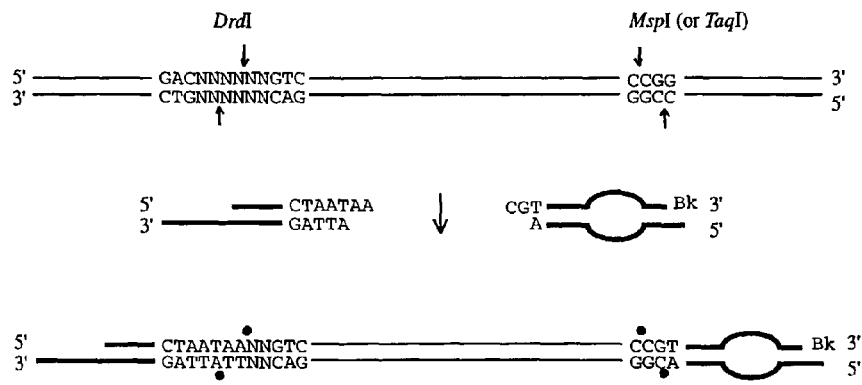

2. Inactivate T4 ligase and restriction endonucleases at 95°C for 5 min. PCR amplify using primers containing ribose U replacing dT, dNTPs, and *Taq* polymerase. Primer specific to the *DrdI* site linker will extend through bubble of *MspI* site linker. This allows the primer specific to the *MspI* site linker to amplify the *DrdI*-*MspI* fragment. Other fragments will not amplify since they contain bubbles on both ends.

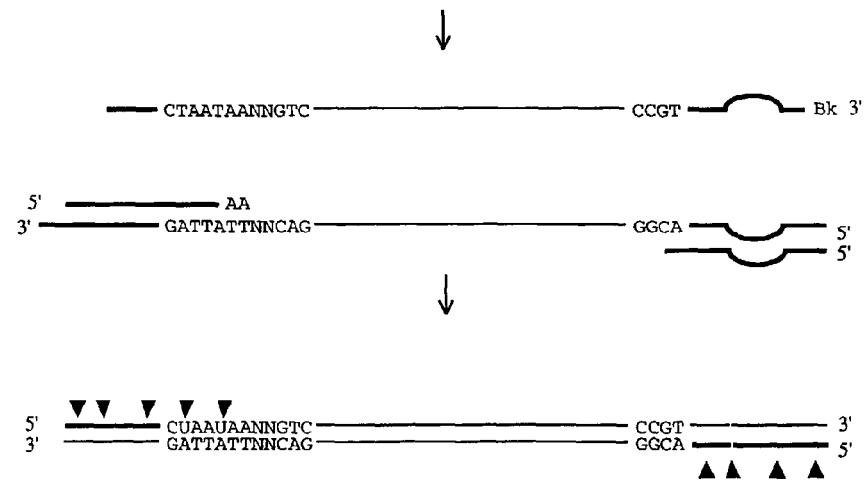

3. Add 0.1N NaOH and heat to 95 °C for 5 min to destroy unused primers.

4. Neutralize and dilute. Anneal sequencing primer to the *DrdI* site linker and perform a cycle-sequencing reaction. (A separate reaction may be performed using a primer annealing to the *MspI/TaqI* site linker).

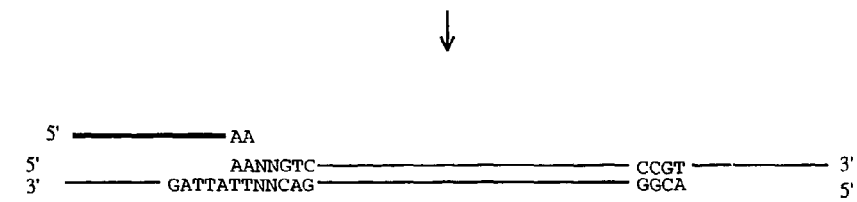

FIG. 6

Three degrees of specificity in amplifying a *Drd*I representation.

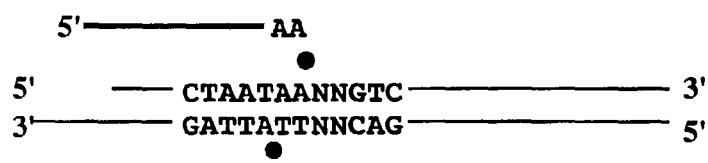

1. Ligation of the top strand requires perfect complementarity at the 3' side of the junction (50-fold specificity).
2. Ligation of the bottom strand requires perfect complementarity at the 3' side of the junction (50-fold specificity).
3. Extension of polymerase off the sequencing primer is most efficient if the 3' base is perfectly matched (10 to 100-fold specificity).

*FIG. 7*

RG253B13, 7q31 Met Oncogene
25 *Sap*I Sites in 171,905 bp

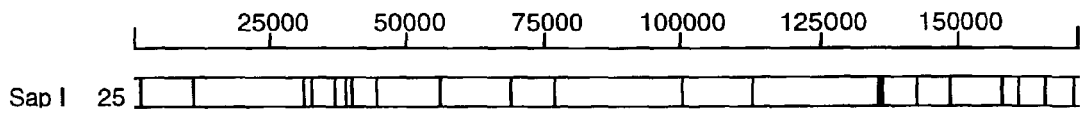

| *Sap*I# | Location | *Sap*I Overhang | Ligated Complement |
|---|---|---|---|
| 1. | 1,198 | CTA | TAG[#] |
| 2. | 1,456 | AGG | CCT[#] |
| 3. | 10,943 | GCT | AGC[x] |
| 4. | 10,955 | GCT | ACG[@] |
| 5. | 11,041 | CAA | TTG[@] |
| 6. | 31,031 | AAT | ATT[@] |
| 7. | 32,599 | GAT | ATC[#] |
| 8. | 37,053 | AGA | TCT[#] |
| 9. | 38,931 | GGG | CCC[x] |
| 10. | 39,877 | ATC | GAT[#] |
| 11. | 44,325 | CTT | AAG[#] |
| 12. | 56,040 | ACA | TGT[x] |
| 13. | 68,850 | ACC | GGT[x] |
| 14. | 76,930 | GTG | CAC[#] |
| 15. | 100,250 | GGG | CCC[x] |
| 16. | 112,850 | GAT | ATC[#] |
| 17. | 135,473 | ACA | TGT[x] |
| 18. | 135,608 | GGA | TCC[x] |
| 19. | 136,239 | TTG | CAA[@] |
| 20. | 142,243 | GCC | GGC[x] |
| 21. | 148,475 | GCG | CGC[x] |
| 22. | 157,978 | TCT | AGA[@] |
| 23. | 160,833 | ACC | GGT[x] |
| 24. | 166,153 | ATT | AAT[#] |
| 25. | 171,460 | GTT | AAC[#] |

|  | *Sap*I |
|---|---|
| [@]Same last 2 bases of 3' overhang within BAC used exactly once(singlet). | 5 |
| [#]Same last 2 bases of 3' overhang within BAC used exactly twice (doublet). | 10 |
| [x]Same last 2 bases of 3' overhang within BAC used more than twice. | 3 |

FIG. 9

RG363E19, 7q3.1 HMG gene
11 *Drd*I and 12 *Bgl*ISites in 165,608 bp

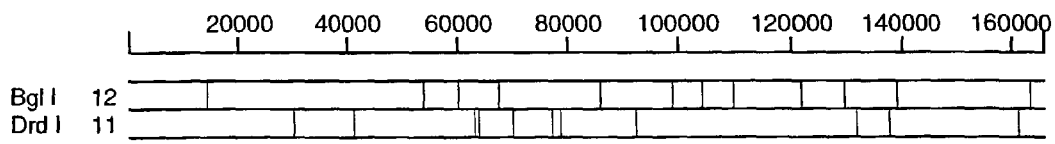

| *Drd*I# | Location | Overhang | Complement |
|---|---|---|---|
| 1. | 30,500 | CT*# | AG*# |
| 2. | 41,442 | GG# | CC# |
| 3. | 63,326 | AG*# | CT*# |
| 4. | 64,189 | TT@ | AA@ |
| 5. | 70,300 | GT@ | AC@ |
| 6. | 77,512 | CA*x | TG*x |
| 7. | 78,858 | TG*x | CA*x |
| 8. | 92,723 | TG*x | CA*x |
| 9. | 132,104 | GA@ | TC@ |
| 10. | 137,827 | CC# | GG# |
| 11. | 161,478 | AT^ | AT^ |

| *Bgl*I# | Location | Overhang | Complement |
|---|---|---|---|
| 1. | 14,666 | GAG# | CTC# |
| 2. | 54,284 | AGA*x | TCT*x |
| 3. | 60,389 | AGA*x | TCT*x |
| 4. | 67,808 | CCT*x | AGG*x |
| 5. | 86,331 | TGG*x | CCA# |
| 6. | 99,283 | CTC# | GAG# |
| 7. | 104,281 | GTT# | AAC@ |
| 8. | 109,938 | CGG*x | CCG@ |
| 9. | 122,096 | GGG*x | CCC@ |
| 10. | 129,631 | TGT@ | ACA# |
| 11. | 139,404 | AAA@ | TTT# |
| 12. | 163,611 | TCT x | AGA x |

|  | *Drd*I | *Bgl*I |
|---|---|---|
| Unique sites, per 40 kb (singlet). | (1.2) | (3.9) |
| *Same last 2 bases of 3' overhang, per 40 kb (doublet). | (1.2) | (2.0) |
| ^Palindromic overhang, not used. | 1 | |

FIG. 10

RG363E19, 7q3.1 HMG gene
12 *Sap*I Sites in 165,608 bp

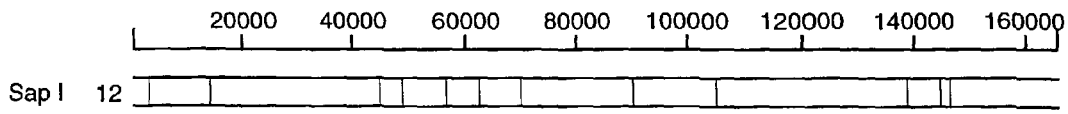

| *Sap*I# | Location | *Sap*I Overhang | Ligated Complement |
|---|---|---|---|
| 1. | 3,048 | ACA | TGT@ |
| 2. | 14,192 | CGG | CCG@ |
| 3. | 45,137 | CTA | TAG$^x$ |
| 4. | 49,039 | TAC | GTA# |
| 5. | 56,731 | CCT | AGG@ |
| 6. | 62,838 | TAA | TTA# |
| 7. | 70,117 | TGG | CCA@ |
| 8. | 90,393 | AAA | TTT$^x$ |
| 9. | 104,917 | CTT | AAG$^x$ |
| 10. | 138,863 | CTG | CAG$^x$ |
| 11. | 144,649 | AAA | TTT$^x$ |
| 12. | 146,805 | AAA | TTT$^x$ |

|  | *Sap*I |
|---|---|
| @Same last 2 bases of 3' overhang within BAC used exactly once (singlet). | 4 |
| #Same last 2 bases of 3' overhang within BAC used exactly twice (doublet). | 1 |
| $^x$Same last 2 bases of 3' overhang within BAC used more than twice. | 2 |

FIG. 11

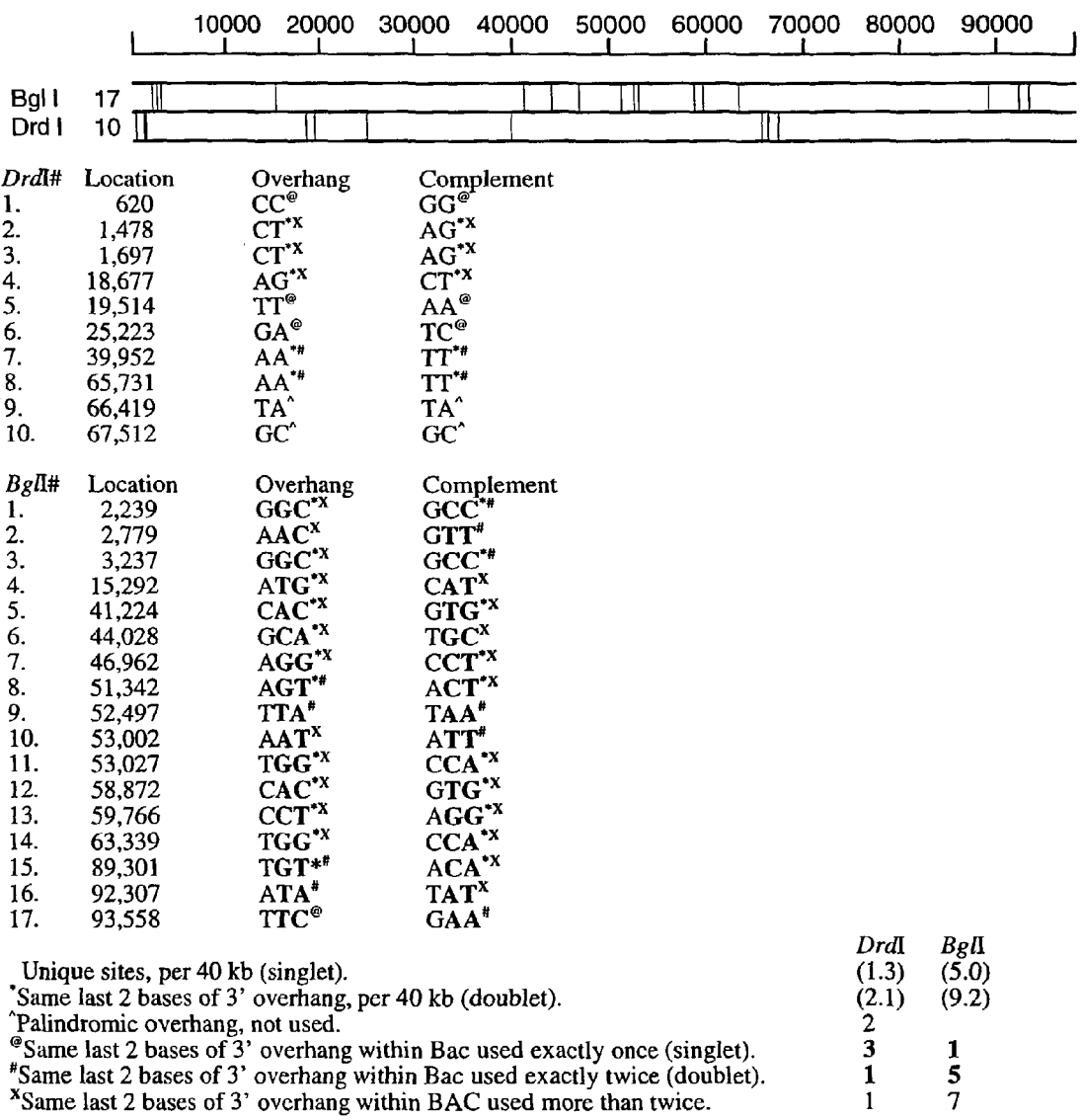

RG364P16, 7q31 Pendrin gene
10 *DrdI* and 17 *BglI*Sites in 97,943 bp

| *DrdI*# | Location | Overhang | Complement |
|---|---|---|---|
| 1. | 620 | CC@ | GG@ |
| 2. | 1,478 | CT*x | AG*x |
| 3. | 1,697 | CT*x | AG*x |
| 4. | 18,677 | AG*x | CT*x |
| 5. | 19,514 | TT@ | AA@ |
| 6. | 25,223 | GA@ | TC@ |
| 7. | 39,952 | AA*# | TT*# |
| 8. | 65,731 | AA*# | TT*# |
| 9. | 66,419 | TA^ | TA^ |
| 10. | 67,512 | GC^ | GC^ |

| *BglI*# | Location | Overhang | Complement |
|---|---|---|---|
| 1. | 2,239 | GGC*x | GCC*# |
| 2. | 2,779 | AACx | GTT# |
| 3. | 3,237 | GGC*x | GCC*# |
| 4. | 15,292 | ATG*x | CATx |
| 5. | 41,224 | CAC*x | GTG*x |
| 6. | 44,028 | GCA*x | TGCx |
| 7. | 46,962 | AGG*x | CCT*x |
| 8. | 51,342 | AGT*# | ACT*x |
| 9. | 52,497 | TTA# | TAA# |
| 10. | 53,002 | AATx | ATT# |
| 11. | 53,027 | TGG*x | CCA*x |
| 12. | 58,872 | CAC*x | GTG*x |
| 13. | 59,766 | CCT*x | AGG*x |
| 14. | 63,339 | TGG*x | CCA*x |
| 15. | 89,301 | TGT*# | ACA*x |
| 16. | 92,307 | ATA# | TATx |
| 17. | 93,558 | TTC@ | GAA# |

|  | *DrdI* | *BglI* |
|---|---|---|
| Unique sites, per 40 kb (singlet). | (1.3) | (5.0) |
| *Same last 2 bases of 3' overhang, per 40 kb (doublet). | (2.1) | (9.2) |
| ^Palindromic overhang, not used. | 2 | |
| @Same last 2 bases of 3' overhang within Bac used exactly once (singlet). | 3 | 1 |
| #Same last 2 bases of 3' overhang within Bac used exactly twice (doublet). | 1 | 5 |
| xSame last 2 bases of 3' overhang within BAC used more than twice. | 1 | 7 |

FIG. 12

RG364P16, 7q31 Pendrin gene
14 *Sap*I Sites in 97,943 bp

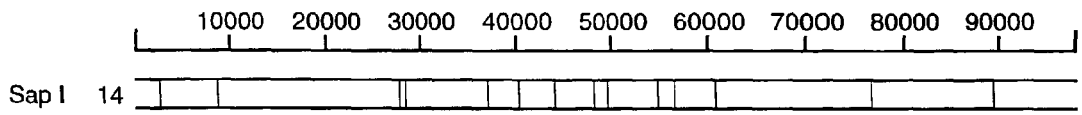

| *Sap*I# | Location | *Sap*I Overhang | Ligated Complement |
|---|---|---|---|
| 1. | 2,731 | CTA | TAG[#] |
| 2. | 8,819 | ATA | TAT[@] |
| 3. | 27,714 | CAG | CTG[x] |
| 4. | 28,452 | TCT | AGA[@] |
| 5. | 37,174 | GAA | TTC[@] |
| 6. | 40,339 | GTT | AAC[@] |
| 7. | 44,149 | CAC | GTG[x] |
| 8. | 48,133 | AAC | GTT[@] |
| 9. | 49,746 | CTT | AAG[#] |
| 10. | 55,020 | TTT | AAA[#] |
| 11. | 56,593 | CAG | CTG[x] |
| 12. | 60,911 | AGA | TCT[@] |
| 13. | 76,747 | TTA | TAA[#] |
| 14. | 89,658 | TGA | TCA[@] |

|   | *Sap*I |
|---|---|
| [@]Same last 2 bases of 3' overhang within BAC used exactly once (singlet). | 7 |
| [#]Same last 2 bases of 3' overhang within BAC used exactly twice (doublet). | 2 |
| [x]Same last 2 bases of 3' overhang within BAC used more than twice. | 1 |

FIG. 13

GS056H18, 7q31 alpha2(I) collagen
11 *DrdI* and 15 *BglI* Sites in 116,466 bp

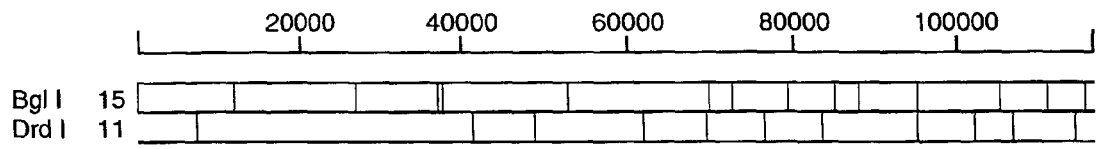

| *DrdI*# | Location | Overhang | Complement |
|---|---|---|---|
| 1. | 7,281 | AA*# | TT*# |
| 2. | 41,553 | AA*# | TT*# |
| 3. | 49,116 | TG# | CA# |
| 4. | 61,875 | GT*# | AC*# |
| 5. | 69,731 | AC*# | GT*# |
| 6. | 76,744 | AG@ | CT@ |
| 7. | 83,697 | GG@ | CC@ |
| 8. | 95,410 | TA^ | TA^ |
| 9. | 102,312 | TC*# | GA*# |
| 10. | 107,014 | TC*# | GA*# |
| 11. | 114,581 | CA# | TG# |

| *BglI*# | Location | Overhang | Complement |
|---|---|---|---|
| 1. | 26 | CAG*x | CTG*x |
| 2. | 12,014 | TTA# | TAA*# |
| 3. | 27,316 | CTG*x | CAG*x |
| 4. | 37,513 | AAA*@ | TTT@ |
| 5. | 37,810 | GTA*# | TAC# |
| 6. | 52,919 | CTG*x | CAG*x |
| 7. | 70,083 | ACA*x | TGT*x |
| 8. | 72,753 | ACA*x | TGT*x |
| 9. | 79,674 | CGA# | TCG*# |
| 10. | 85,304 | GCG*# | CGC@ |
| 11. | 88,200 | GTC*# | GAC# |
| 12. | 95,350 | GAA# | TTC*# |
| 13. | 105,353 | ACA*x | TGT*x |
| 14. | 111,096 | CCC*# | GGG@ |
| 15. | 115,757 | TCC*# | GGA# |

|  | *DrdI* | *BglI* |
|---|---|---|
| Unique sites, per 40 kb (singlet). | (1.4) | (3.1) |
| *Same last 2 bases of 3' overhang, per 40 kb (doublet). | (2.1) | (7.2) |
| ^Palindromic overhang, not used. | 1 | |
| @Same last 2 bases of 3' overhang within Bac used exactly once (singlet). | 2 | 4 |
| #Same last 2 bases of 3' overhang within Bac used exactly twice (doublet). | 4 | 7 |
| xSame last 2 bases of 3' overhang within BAC used more than twice. | 0 | 3 |

FIG. 14

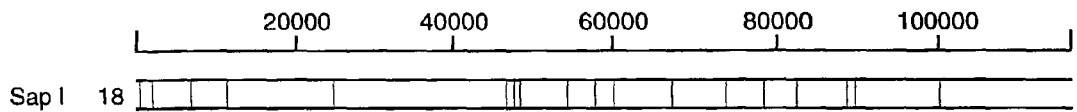

| SapI# | Location | SapI Overhang | Ligated Complement |
|---|---|---|---|
| 1. | 676 | AAA | TTT[x] |
| 2. | 2,235 | CTC | GAG[x] |
| 3. | 6,921 | CTG | CAG[x] |
| 4. | 11,596 | ACC | GGT[#] |
| 5. | 24,903 | GCT | AGC[#] |
| 6. | 46,819 | AAA | TTT[x] |
| 7. | 47,742 | TCC | GGA[#] |
| 8. | 48,563 | ATT | AAT[@] |
| 9. | 54,507 | TCT | AGA[#] |
| 10. | 57,797 | ACT | AGT[#] |
| 11. | 60,140 | TAC | GTA[@] |
| 12. | 67,461 | AAG | CTT[x] |
| 13. | 73,821 | AAT | ATT[x] |
| 14. | 78,670 | CTG | CAG[x] |
| 15. | 82,755 | CCT | AGG[@] |
| 16. | 88,654 | AGT | ACT[@] |
| 17. | 89,773 | GCA | TGC[#] |
| 18. | 100,380 | CTC | GAG[x] |

|  | SapI |
|---|---|
| [@]Same last 2 bases of 3' overhang within BAC used exactly once(singlet). | 4 |
| [#]Same last 2 bases of 3' overhang within BAC used exactly twice (doublet). | 3 |
| [x]Same last 2 bases of 3' overhang within BAC used more than twice. | 2 |

FIG. 15

Sequencing BgII islands in random BAC clones

1. Cut BAC DNA with MspI and BgII in the presence of linkers and T4 ligase. Linker for BgII site is phosphorylated and ends in 3' ACN overhang. Linker for MspI site is not phosphorylated, and contains a bubble. Biochemical selection assures that most sites contain linkers.

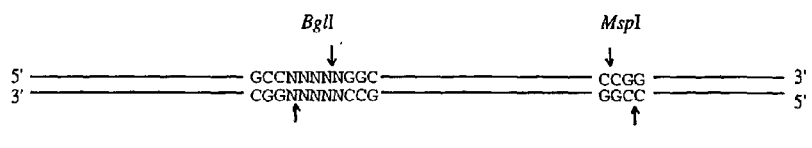

2. Inactivate T4 ligase and restriction endonucleases at 95°C for 5 min. PCR amplify using primers containing ribose U replacing dT, dNTPs, and Taq polymerase. Primer specific to the BgII site linker will extend through bubble of MspI site linker. This allows the primer specific to the MspI site linker to amplify the DrdI-MspI fragment. MspI-MspI fragments will not amplify since they contain bubbles on both ends.

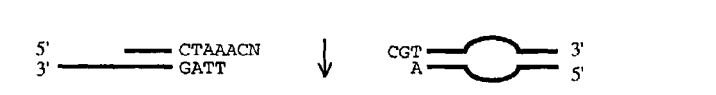

3. Add 0.1N NaOH and heat to 95 °C for 5 min to destroy unused primers.

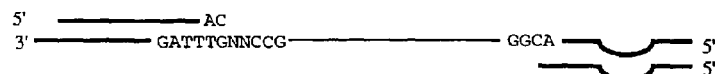

4. Neutralize and dilute. Anneal sequencing primer to the BgII site linker and perform a cycle-sequencing reaction. (A separate reaction may be performed using a primer annealing to the MspI site linker).

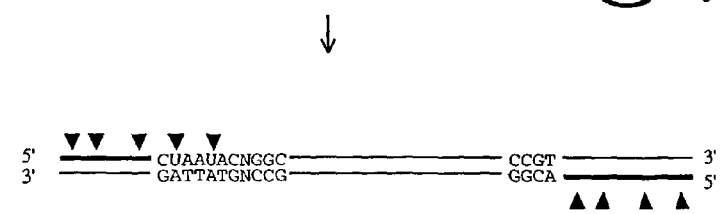

*FIG. 16A*

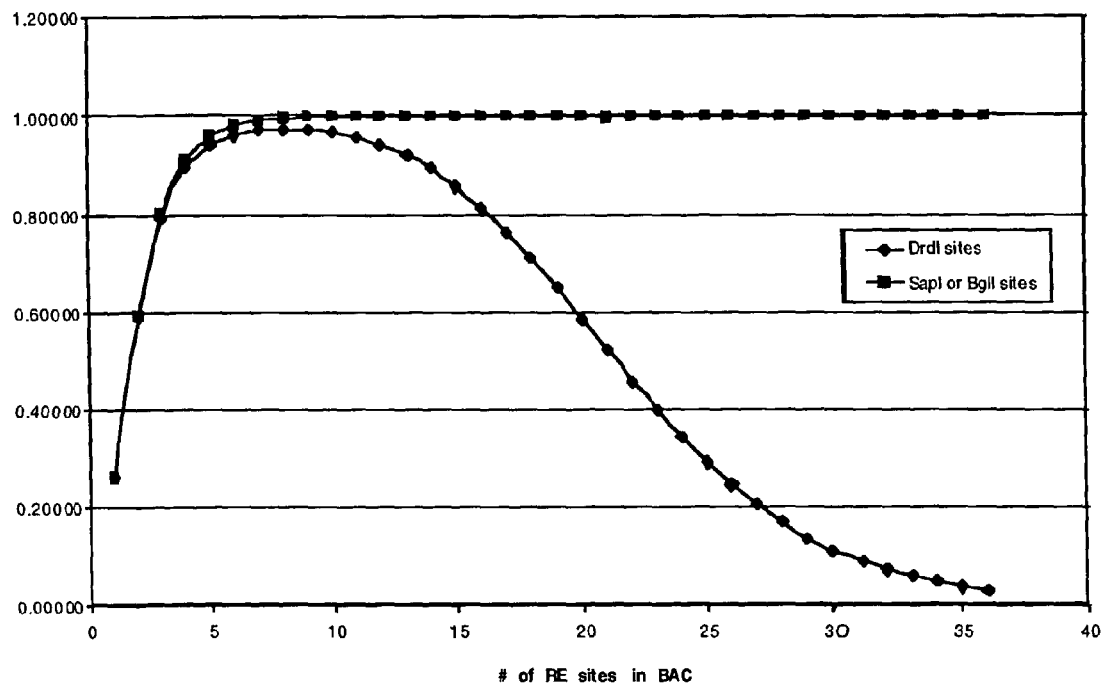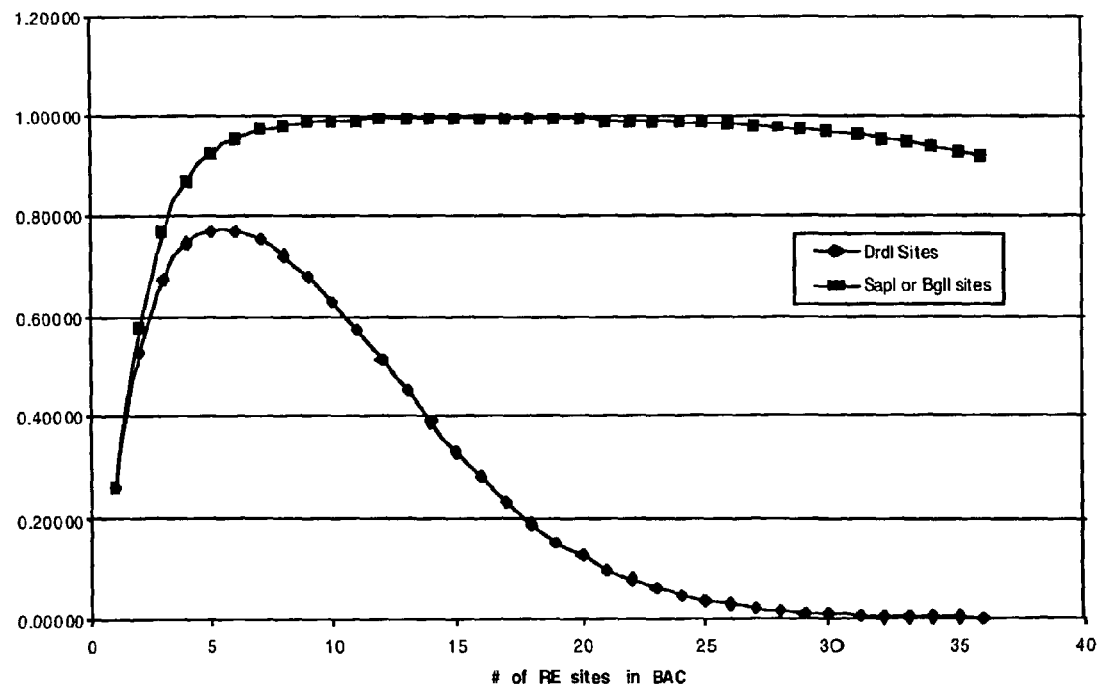
FIG. 17A

**Alignment of BAC sequences generated from *DrdI* sites:**
1. TCGTCCTCAGGAACTGAAGCTATATAATCAGTTAAGTCCCTGCTTCTGATCTCTTCTGATTTTCTTCTAAGAAGAGAATA
2. GTGTCAAGTAAAGAAGTACAGCAGATAAGTAAAACGGAAAAAAATAATGAAAGAATTACAAAGGAAGACTAAGGAAAGAG
3. AAGTCTACAATCAAGAGGCCAACTGATTCCATGTCTGGTGAGGGTCTATTTCCTGGTGCATAGATGGCTCCTTCTCACTG
4. TAGTCCTCAATTTCACCATGGATTAAATAACAGAACACAGAGTTACTGTGAGACTTGTGGTAGAAAATCTTTAATTCATT
5. GTGTCATCTAGCTATAAATCTAAAGATAATAATAAAATTGGAAAGATTTTCATCAGATAGACTTTTAACACCAAGCTTGA Concordant sequences: Doublet to singlet.

1. TCGTCCTCAGGAACTGAAGCTATATAATCAGTTAAGTCCCTGCTTCTGATCTCTTCTGATTTTCTTCTAAGAAGAGAATA
2. GTGTCAAGTAAAGAAGTACAGCAGATAAGTAAAACGGAAAAAAATAATGAAAGAATTACAAAGGAAGACTAAGGAAAGAG
1. TCGTCCTCAGGAACTGAAGCTATATAATCAGTTAAGTCCCTGCTTCTGATCTCTTCTGATTTTCTTCTAAGAAGAGAATA

Concordant sequences: Doublet to Doublet.

1. TCGTCCTCAGGAACTGAAGCTATATAATCAGTTAAGTCCCTGCTTCTGATCTCTTCTGATTTTCTTCTAAGAAGAGAATA
2. GTGTCAAGTAAAGAAGTACAGCAGATAAGTAAAACGGAAAAAAATAATGAAAGAATTACAAAGGAAGACTAAGGAAAGAG
3. AAGTCTACAATCAAGAGGCCAACTGATTCCATGTCTGGTGAGGGTCTATTTCCTGGTGCATAGATGGCTCCTTCTCACTG
2. GTGTCAAGTAAAGAAGTACAGCAGATAAGTAAAACGGAAAAAAATAATGAAAGAATTACAAAGGAAGACTAAGGAAAGAG

Concordant sequences: Doublet to Triplet.

1. TCGTCCTCAGGAACTGAAGCTATATAATCAGTTAAGTCCCTGCTTCTGATCTCTTCTGATTTTCTTCTAAGAAGAGAATA
2. GTGTCAAGTAAAGAAGTACAGCAGATAAGTAAAACGGAAAAAAATAATGAAAGAATTACAAAGGAAGACTAAGGAAAGAG
3. AAGTCTACAATCAAGAGGCCAACTGATTCCATGTCTGGTGAGGGTCTATTTCCTGGTGCATAGATGGCTCCTTCTCACTG
2. GTGTCAAGTAAAGAAGTACAGCAGATAAGTAAAACGGAAAAAAATAATGAAAGAATTACAAAGGAAGACTAAGGAAAGAG
4. TAGTCCTCAATTTCACCATGGATTAAATAACAGAACACAGAGTTACTGTGAGACTTGTGGTAGAAAATCTTTAATTCATT

Discordant sequences: Doublet to singlet.

1. TCGTCCTCAGGAACTGAAGCTATATAATCAGTTAAGTCCCTGCTTCTGATCTCTTCTGATTTTCTTCTAAGAAGAGAATA
2. GTGTCAAGTAAAGAAGTACAGCAGATAAGTAAAACGGAAAAAAATAATGAAAGAATTACAAAGGAAGACTAAGGAAAGAG
3. AAGTCTACAATCAAGAGGCCAACTGATTCCATGTCTGGTGAGGGTCTATTTCCTGGTGCATAGATGGCTCCTTCTCACTG

Discordant sequences: Doublet to Doublet.

1. TCGTCCTCAGGAACTGAAGCTATATAATCAGTTAAGTCCCTGCTTCTGATCTCTTCTGATTTTCTTCTAAGAAGAGAATA
2. GTGTCAAGTAAAGAAGTACAGCAGATAAGTAAAACGGAAAAAAATAATGAAAGAATTACAAAGGAAGACTAAGGAAAGAG
3. AAGTCTACAATCAAGAGGCCAACTGATTCCATGTCTGGTGAGGGTCTATTTCCTGGTGCATAGATGGCTCCTTCTCACTG
4. TAGTCCTCAATTTCACCATGGATTAAATAACAGAACACAGAGTTACTGTGAGACTTGTGGTAGAAAATCTTTAATTCATT

Discordant sequences: Doublet to Triplet.

1. TCGTCCTCAGGAACTGAAGCTATATAATCAGTTAAGTCCCTGCTTCTGATCTCTTCTGATTTTCTTCTAAGAAGAGAATA
2. GTGTCAAGTAAAGAAGTACAGCAGATAAGTAAAACGGAAAAAAATAATGAAAGAATTACAAAGGAAGACTAAGGAAAGAG
3. AAGTCTACAATCAAGAGGCCAACTGATTCCATGTCTGGTGAGGGTCTATTTCCTGGTGCATAGATGGCTCCTTCTCACTG
4. TAGTCCTCAATTTCACCATGGATTAAATAACAGAACACAGAGTTACTGTGAGACTTGTGGTAGAAAATCTTTAATTCATT
5. GTGTCATCTAGCTATAAATCTAAAGATAATAATAAAATTGGAAAGATTTTCATCAGATAGACTTTTAACACCAAGCTTGA

FIG. 18

DrdI/MseI Fragments in approximately 2 MB of human DNA

(BACs analyzed: RG253B13, RG013N12, RG300C03, RG022J17, RG067E13, RG011J21, RG022C01, RG043K06, RG343P13, RG205G13, O68P20, H_133K23, RG363E19, RG364P16, GS056H18, RG083J23, RG103H13, and RG118D07)

For AA overhangs (30 Fragments)

| DrdI# | Location | Overhang | Complement | Nearest MseI | Fragment Length |
|---|---|---|---|---|---|
| 9. | 101,440 | | AA*(T) | 100753 | 687 |
| 8. | 125,589 | | AA* | 124941 | 648 |
| 8. | 65,737 | AA*(C) | | 66359 | 622 |
| 2. | 41,548 | AA*(C) | | 41918 | 370 |
| 3. | 21,755 | AA* | | 22080 | 325 |
| 11. | 148,484 | AA* | | 148770 | 286 |
| 15. | 180,054 | | AA* | 179781 | 273 |
| 1. | 7,287 | AA*(A) | | 7551 | 264 |
| 4. | 64,195 | | AA* | 63964 | 231 |
| 2. | 16192 | | AA* | 16002 | 190 |
| 5. | 19,520 | | AA* | 19354 | 166 |
| 7. | 112,864 | | AA* | 112716 | 148 |
| 9. | 67,981 | AA*(A) | | 68102 | 121 |
| 10. | 76,325 | AA*(C) | | 76443 | 118 |
| 6. | 73,322 | AA* | | 73424 | 102 |
| 10. | 158,579 | | AA* | 158499 | 80 |
| 1. | 9,941 | | AA*(C) | 9867 | 74 |
| 8. | 65,625 | | AA* | 65554 | 71 |
| 6. | 45,326 | | AA* | 45263 | 63 |
| 14. | 168,400 | | AA* | 168352 | 48 |
| 7. | 39,958 | AA*(C) | | 40005 | 47 |
| 2. | 27,073 | | AA*(A) | 27027 | 46 |
| 8. | 144,712 | AA*(A) | | 144750 | 38 |
| 3. | 30,987 | AA* | | 31013 | 26 |
| 10. | 114962 | AA* | | 114986 | 24 |
| 4. | 89309 | | AA* | 89290 | 19 |
| 1. | 4518 | AA* | | 4532 | 14 |
| 11. | 137,177 | | AA*(A) | 137176 | 1 |
| 12. | 165,140 | | AA* | 165139 | 1 |
| 9. | 86,690 | | AA* | 86689 | 1 |

For AC overhangs (14 Fragments)

| DrdI# | Location | Overhang | Complement | Nearest MseI | Fragment Length |
|---|---|---|---|---|---|
| 4. | 61,881 | | AC* | 61424 | 457 |
| 5. | 70,306 | | AC* | 69996 | 400 |

FIG. 19A

| | | | | | |
|---|---|---|---|---|---|
| 5. | 51333 | AC* | | 51712 | 379 |
| 2. | 17,346 | | AC* | 17135 | 211 |
| 2. | 26,871 | | AC* | 26668 | 203 |
| 2. | 16,508 | AC* | | 16703 | 195 |
| 4. | 45929 | AC* | | 46051 | 132 |
| 6. | 104,064 | | AC* | 103955 | 109 |
| 8. | 80,512 | | AC* | 80423 | 89 |
| 9. | 113,009 | | AC* | 112938 | 71 |
| 6. | 100,564 | | AC* | 100500 | 64 |
| 5. | 69,737 | AC* | | 69789 | 52 |
| 10. | 113,048 | AC* | | 113095 | 47 |
| 5. | 89,050 | AC* | | 89180 | 30 |

For AG overhangs ( 18 Fragments)

| DrdI# | Location | Overhang | Complement | Nearest MseI | Fragment Length |
|---|---|---|---|---|---|
| 7. | 124,720 | | AG* | 123644 | 1076 |
| 8. | 99,628 | | AG* | 99513 | 546 |
| 7. | 55,076 | | AG* | 54728 | 348 |
| 11. | 146,074 | AG* | | 146412 | 338 |
| 3. | 63,332 | AG* | | 63546 | 214 |
| 2. | 1,484 | | AG* | 1273 | 211 |
| 1. | 30,506 | | AG* | 30700 | 194 |
| 4. | 51345 | AG* | | 51500 | 155 |
| 12. | 159,685 | AG* | | 159827 | 142 |
| 3. | 1,703 | | AG* | 1593 | 110 |
| 5. | 26,574 | | AG* | 26478 | 96 |
| 9. | 125,495 | AG* | | 125587 | 92 |
| 9. | 84,646 | | AG* | 84587 | 59 |
| 6. | 76,750 | AG* | | 76794 | 44 |
| 11. | 137111 | | AG* | 137072 | 39 |
| 5. | 71871 | AG* | | 71907 | 36 |
| 4. | 18,683 | AG* | | 18707 | 24 |
| 2. | 27,400 | AG* | | 27409 | 9 |

For CA overhangs ( 28 Fragments)

| DrdI# | Location | Overhang | Complement | Nearest MseI | Fragment Length |
|---|---|---|---|---|---|
| 1. | 11,050 | | CA*(T) | 10453 | 597 |
| 5. | 40,727 | CA*(G) | | 41277 | 550 |
| 8. | 92,729 | | CA*(G) | 92225 | 504 |
| 4. | 28263 | | CA* | 27859 | 404 |
| 7. | 96,506 | CA*(A) | | 96800 | 294 |
| 7. | 68476 | CA* | | 68753 | 277 |

*FIG. 19B*

| Drd1# | Location | Overhang | Complement | Nearest MseI | Fragment Length |
|---|---|---|---|---|---|
| 3. | 40,167 | | CA*(T) | 39891 | 276 |
| 7. | 104,893 | CA*(G) | | 105141 | 248 |
| 12. | 174,759 | | CA*(G) | 174553 | 206 |
| 3. | 24,762 | CA* | | 24967 | 205 |
| 7. | 78,864 | | CA*(T) | 78672 | 192 |
| 3. | 27,738 | CA*(A) | | 27922 | 184 |
| 11. | 114,587 | CA*(G) | | 114739 | 152 |
| 4. | 25,393 | CA*(G) | | 25529 | 136 |
| 1. | 1797 | | CA*(T) | 1663 | 134 |
| 7. | 56,328 | | CA*(A) | 56194 | 134 |
| 5. | 47,359 | | CA*(T) | 47234 | 125 |
| 3. | 49,122 | | CA*(G) | 48998 | 124 |
| 11. | 92,418 | CA*(T) | | 92512 | 94 |
| 7. | 142,867 | | CA*(G) | 142773 | 94 |
| 12. | 98,198 | CA*(A) | | 98284 | 86 |
| 6. | 60,501 | | CA*(T) | 60424 | 77 |
| 8. | 83,536 | CA*(A) | | 83598 | 62 |
| 6. | 77,518 | CA* | | 77578 | 60 |
| 7. | 41,602 | CA*(T) | | 41644 | 42 |
| 9. | 149,703 | CA*(A) | | 149735 | 32 |
| 10. | 128,190 | | CA*(G) | 128168 | 22 |
| 5. | 40,370 | | CA*(G) | 40357 | 13 |

For GA overhangs (15 Fragments)

| Drd1# | Location | Overhang | Complement | Nearest MseI | Fragment Length |
|---|---|---|---|---|---|
| 10. | 138,792 | | GA* | 138206 | 586 |
| 10. | 107,020 | | GA* | 106698 | 322 |
| 8. | 105,928 | | GA* | 105714 | 214 |
| 9. | 132,110 | GA* | | 132317 | 207 |
| 6. | 25,229 | GA* | | 25384 | 155 |

Figure 19 (cont.)

| | | | | | |
|---|---|---|---|---|---|
| 1. | 4,328 | | GA* | 4225 | 103 |
| 4. | 29,833 | GA* | | 29929 | 96 |
| 13. | 166,309 | GA* | | 166386 | 77 |
| 4. | 66,836 | | GA* | 66763 | 73 |
| 8. | 139,856 | | GA* | 139797 | 59 |
| 9. | 102,318 | | GA* | 102277 | 41 |
| 5. | 97330 | | GA* | 97292 | 38 |
| 6. | 91,681 | | GA* | 91645 | 36 |
| 11. | 153,548 | GA* | | 153569 | 21 |
| 14. | 169,979 | GA* | | 169996 | 17 |

FIG. 19C

For GG overhangs (14 Fragments)

| DrdI# | Location | Overhang | Complement | Nearest MseI | Fragment Length |
|---|---|---|---|---|---|
| 3. | 33,306 | GG* | | 34241 | 935 |
| 3. | 43,961 | GG* | | 44471 | 510 |
| 2. | 41,448 | GG* | | 41745 | 297 |
| 7. | 83,703 | GG* | | 83957 | 254 |
| 13. | 180,666 | | GG* | 180498 | 168 |
| 2. | 19,383 | | GG* | 19227 | 156 |
| 10. | 137,833 | | GG* | 137722 | 111 |
| 5. | 89,627 | | GG* | 89570 | 57 |
| 9. | 129,058 | | GG* | 129003 | 55 |
| 9. | 74,360 | GG* | | 74409 | 49 |
| 12. | 154,063 | | GG* | 154021 | 42 |
| 1. | 5,385 | GG* | | 5417 | 32 |
| 1. | 626 | | GG | 596 | 30 |
| 6. | 49,989 | GG* | | 50001 | 12 |

FIG. 19D

DrdI/MspI/TaqI Fragments in approximately 2 MB of human DNA

(RG253B13, RG013N12, RG300C03, RG022J17, RG067E13, RG011J21, RG022C01, RG043K06, RG343P13, RG205G13, O68P20, H_133K23, RG363E19, RG364P16, GS056H18, RG083J23, RG103H13, and RG118D07)

For AA overhangs (28 Fragments)

| DrdI# | Location | Overhang | Complement | Nearest MspI | Nearest TaqI | Fragment Length |
|---|---|---|---|---|---|---|
| 14. | 168,400 | | AA* | DrdI(157,688) | 162,381 | 6,019 |
| 10. | 158,579 | | AA* | 151,605 | 153,001 | 5,578 |
| 2. | 41,548 | AA*(C) | | | 46,609 | 5,061 |
| 1. | 9,941 | | AA*(C) | 296 | 6,494 | 3,447 |
| 7. | 39,958 | AA*(C) | | 43,295 | 45,578 | 3,337 |
| 7. | 112,864 | | AA* | 110,256 | DrdI(104,064) | 2,608 |
| 10. | 114962 | AA* | | 117286 | 120674 | 2324 |
| 9. | 86,690 | | AA* | 82,301 | 84,647 | 2,043 |
| 3. | 21,755 | AA* | | 27,904 | 23,795 | 2,040 |
| 9. | 67,981 | AA*(A) | | 71,232 | 69,660 | 1,679 |
| 10. | 76,325 | AA*(C) | | 79,607 | 77,651 | 1,326 |
| 8. | 65,625 | | AA* | 63,673 | 64,515 | 1,110 |
| 1. | 4518 | AA* | | 5549 | 5792 | 1031 |
| 4. | 89309 | AA* | | 88376 | 86730 | 933 |
| 11. | 137,177 | | AA*(A) | 135,890 | 136,580 | 597 |
| 3. | 30,987 | AA* | | 31,504 | DrdI(32,405) | 517 |
| 15. | 180,054 | AA* | | 179562 | 176427 | 492 |
| 8. | 125,589 | | AA* | DrdI(124,720) | 125,163 | 426 |
| 5. | 73,322 | AA* | | 75,251 | 73,738 | 416 |
| 8. | 65,737 | AA*(C) | | 66,175 | 66,077 | 340 |
| 1. | 7,287 | AA*(A) | | 8,799 | 7,614 | 327 |
| 2. | 16192 | | AA* | 15865 | 15964 | 228 |
| 2. | 27,073 | | AA*(A) | 25,402 | 26,872 | 201 |
| 9. | 101,440 | | AA*(T) | | 101,248 | 192 |
| 6. | 45,326 | | AA* | 45,207 | 43,098 | 119 |
| 8. | 144,712 | AA*(A) | | 145,939 | 144,809 | 97 |
| 12. | 165,140 | | AA* | 165069 | 158079 | 71 |
| 11. | 148,484 | AA* | | 148,536 | | 52 |

For AC overhangs (14 Fragments)

| DrdI# | Location | Overhang | Complement | Nearest MspI | Nearest TaqI | Fragment Length |
|---|---|---|---|---|---|---|
| 9. | 113,009 | | AC* | 109,696 | 111,008 | 2,001 |
| 6. | 100,564 | | AC* | 99,222 | 99,117 | 1,342 |
| 5. | 70,306 | | AC* | 69,207 | 67,458 | 1,099 |
| 2. | 16,508 | AC* | | 17,607 | 20,496 | 1,099 |

*FIG. 20A*

| | | | | | | |
|---|---|---|---|---|---|---|
| 4. | 45929 | AC* | | 46933 | 49057 | 1004 |
| 5. | 69,737 | AC* | | 72,665 | 70,593 | 856 |
| 5. | 89,050 | AC* | | 93,107 | 89,749 | 699 |
| 6. | 104,064 | | AC* | 103501 | 103223 | 563 |
| 2. | 17,346 | | AC* | 16,821 | 14,081 | 525 |
| 2. | 26,871 | | AC* | 26,363 | 21,540 | 508 |
| 8. | 80,512 | | AC* | 78,243 | 80,116 | 396 |
| 10. | 113,042 | AC* | | 122,429 | 113,429 | 381 |
| 5. | 51333 | AC* | | 54102 | 51541 | 208 |
| 4. | 61,881 | | AC* | 61,786 | 60,430 | 95 |

For AG overhangs (12 Fragments)

| DrdI# | Location | Overhang | Complement | Nearest MspI | Nearest TaqI | Fragment Length |
|---|---|---|---|---|---|---|
| 4. | 51345 | AG* | | 57329 | 59409 | 5984 |
| 7. | 55,076 | | AG* | 51,621 | 53,820 | 1,256 |
| 11. | 146,074 | AG* | | 147289 | 149991 | 1215 |
| 11. | 137111 | | AG* | 135970 | 133640 | 1141 |
| 5. | 26,574 | | AG* | 25,682 | | 892 |
| 9. | 84,646 | | AG* | DrdI(83,536) | 83,821 | 825 |
| 5. | 71871 | AG* | | 73210 | 72675 | 804 |
| 6. | 76,750 | AG* | | 77,964 | 77,104 | 354 |
| 12. | 159,685 | AG* | | 160,038 | 161,212 | 353 |
| 1. | 30,506 | | AG* | 30,330 | 30,080 | 176 |
| 7. | 124,720 | | AG* | 124,563 | 123,299 | 157 |
| 8. | 99,628 | | AG* | 99513 | 99,370 | 115 |

For CA overhangs (25 Fragments)

| DrdI# | Location | Overhang | Complement | Nearest MspI | Nearest TaqI | Fragment Length |
|---|---|---|---|---|---|---|
| 11. | 92,418 | CA*(T) | | 97,628 | 97,710 | 5,210 |
| 10. | 128,190 | | CA*(G) | 111,800 | 125,432 | 2,758 |
| 8. | 92,729 | | CA*(G) | 90,558 | 90,541 | 2,171 |
| 5. | 40,727 | CA*(G) | | 42,854 | 43,404 | 2,127 |
| 7. | 41,602 | CA*(T) | | 50,849 | 43,487 | 1,885 |
| 11. | 114,587 | CA*(G) | | 116,105 | 116,257 | 1,518 |
| 5. | 47,359 | | CA*(T) | 41,626 | 45,860 | 1,499 |
| 7. | 56,328 | | CA*(A) | 52,005 | 55,150 | 1,178 |
| 12. | 174,759 | | CA*(G) | 171,992 | 173,598 | 1,161 |
| 3. | 49,122 | | CA*(G) | | 48,199 | 923 |
| 1. | 11,050 | | CA*(T) | 10,189 | 8,861 | 861 |

*FIG. 20B*

| | | | | | | |
|---|---|---|---|---|---|---|
| 7. | 78,864 | | CA*(T) | | 78,112 | 752 |
| 7. | 96,506 | CA*(A) | | 98,602 | 97,059 | 559 |
| 7. | 142,867 | | CA*(G) | 135,955 | 142,371 | 496 |
| 4. | 28,263 | | CA* | 27,904 | 23,795 | 359 |
| 12. | 98,198 | CA*(A) | | 98,497 | 98,862 | 299 |
| 4. | 25,393 | CA*(G) | | 25,682 | | 289 |
| 8. | 83,536 | CA*(A) | | DrdI(84,646) | 83,821 | 285 |
| 7. | 104,893 | CA*(G) | | 105,128 | 105,920 | 235 |
| 5. | 40,370 | | CA*(G) | DrdI(32,405) | 40,215 | 155 |
| 6. | 60,501 | | CA*(T) | 57,989 | 60,462 | 39 |
| 7. | 68476 | CA* | | 70850 | 68488 | 8 |
| 3. | 27,738 | CA*(A) | | 30,751 | 27,742 | 4 |
| 6. | 77,518 | CA* | | | 77522 | 4 |
| 9. | 149,703 | CA*(A) | | 151,530 | 149,707 | 4 |

For GA overhangs (15 Fragments)

| DrdI# | Location | Overhang | Complement | Nearest MspI | Nearest TaqI | Fragment Length |
|---|---|---|---|---|---|---|
| 6. | 25,229 | GA* | | 31,564 | 30,045 | 4,816 |
| 14. | 169,979 | GA* | | 179562 | 174481 | 4502 |
| 6. | 91,681 | | GA* | 88,256 | 81,884 | 3,419 |
| 5. | 97330 | | GA* | 94353 | 89615 | 2977 |
| 4. | 29,833 | GA* | | 41,626 | 31,251 | 1,418 |
| 4. | 66,836 | | GA* | 65,504 | 62,654 | 1,332 |
| 13. | 166,309 | GA* | | 167668 | 166451 | 1311 |

Figure 20 (cont.)

| | | | | | | |
|---|---|---|---|---|---|---|
| 9. | 132,110 | GA* | | 133,806 | 132,976 | 866 |
| 8. | 139,856 | | GA* | 139,346 | 139,218 | 510 |
| 11. | 153,548 | GA* | | 153,789 | 160,722 | 241 |
| 4. | 42,388 | GA* | | 42,584 | DrdI (42,586) | (196) |
| 9. | 102,318 | | GA* | 98,975 | 102,155 | 163 |
| 10. | 107,020 | | GA* | 106,882 | 105,288 | 138 |
| 10. | 138,792 | | GA* | 137757 | 138715 | 77 |
| 8. | 105,928 | | GA* | 105,592 | 105,920 | 8 |

For GG overhangs (12 Fragments)

| DrdI# | Location | Overhang | Complement | Nearest MspI | Nearest TaqI | Fragment Length |
|---|---|---|---|---|---|---|
| 3. | 33,306 | GG* | | 38,218 | 40,389 | 4,918 |
| 7. | 83,703 | GG* | | 87,372 | 90,806 | 3,669 |
| 12. | 154,063 | | GG* | 142,944 | 150,402 | 3,661 |
| 2. | 19,383 | | GG* | 13,868 | 17,667 | 1,710 |
| 6. | 49,989 | GG* | | 51,421 | 51,451 | 1,432 |
| 9. | 74,360 | GG* | | 75,697 | 75,962 | 1,337 |

FIG. 20C

| | | | | | | |
|---|---|---|---|---|---|---|
| 1. | 5,385 | GG* | | 6,381 | 6,249 | 864 |
| 13. | 180,666 | | GG* | 179,917 | 177,380 | 749 |
| 3. | 43,961 | GG* | | 48,573 | 44,652 | 691 |
| 2. | 41,448 | GG* | | 42,084 | 42,010 | 562 |
| 10. | 137,833 | | GG* | 137,329 | 136,062 | 504 |
| 5. | 89,627 | | GG* | 80,801 | 89,331 | 294 |

*FIG. 20D*

Determining four unique singlet *Dra*I sequences from two overlapping doublet BAC sequences.

Concordant sequences: Doublet to Doublet.

1. TCGTCCTCAGGAACTGAAGCTATATAATCAGTTAAGTCCCTGCTTCTGATCTCTTCTGATTTTCTTCTAAGAAGAGAATA
2. GTGTCAAGTAAAGAAGTACAGCAGATAAGTAAAACGGAAAAAAATAATGAAAGAATTACAAAGGAAGACTAAGGAAAGAG
   ddSSSdsiisdsisdsdssididdddisiidsidsssssdddsiddSiiddiddiiddSississsdidsddddsdssdSdis
3. AAGTCTACAATCAAGAGGCCAACTGATTCCATGTCTGGTGAGGGTCTATTTCCTGGTGCATAGATGGCTCCTTCTCACTG
2. GTGTCAAGTAAAGAAGTACAGCAGATAAGTAAAACGGAAAAAAATAATGAAAGAATTACAAAGGAAGACTAAGGAAAGAG From above 2 BACs, sequence #2 is:

```
         CA    A      C  A   A TC  T         G  CT  T  CT   G  T    T                T
2? GTGTCAAGTAAAGAAGTACAGCAGATAAGTAAAACGGAAAAAAATAATGAAAGAATTACAAAGGAAGACTAAGGAAAGAG
```

Concordant sequences: Doublet to Doublet.

3. AAGTCTACAATCAAGAGGCCAACTGATTCCATGTCTGGTGAGGGTCTATTTCCTGGTGCATAGATGGCTCCTTCTCACTG
2. GTGTCAAGTAAAGAAGTACAGCAGATAAGTAAAACGGAAAAAAATAATGAAAGAATTACAAAGGAAGACTAAGGAAAGAG
   dsSSSdsssSsddsiddisdsisdsisisddsisisdsdsisSsddsssdsdiddddisdsssSSsiisdiidsddsdsdss
3. AAGTCTACAATCAAGAGGCCAACTGATTCCATGTCTGGTGAGGGTCTATTTCCTGGTGCATAGATGGCTCCTTCTCACTG
4. TAGTCCTCAATTTCACCATGGATTAAATAACAGAACACAGAGTTACTGTGAGACTTGTGGTAGAAAATCTTTAATTCATT From above 2 BACs, sequence #3 is:

```
3? AAGTCTACAATCAAGAGGCCAACTGATTCCATGTCTGGTGAGGGTCTATTTCCTGGTGCATAGATGGCTCCTTCTCACTG
              A  G  AA    A A    A           A    T          AA  CT
         CA    A      C  A   A TC  T         G  CT  T  CT   G  T    T                T
2? GTGTCAAGTAAAGAAGTACAGCAGATAAGTAAAACGGAAAAAAATAATGAAAGAATTACAAAGGAAGACTAAGGAAAGAG
```

By comparing the consensus sequence between 2 and 3, one can determine the overlap.
In this case, only two positions are indeterminate (A or T). Hence 2 and 3 are:

```
                        T                                      T
2= GTGTCAAGTAAAGAAGTACAGCAGATAAGTAAAACGGAAAAAAATAATGAAAGAATTACAAAGGAAGACTAAGGAAAGAG

A                                      A
3= AAGTCTACAATCAAGAGGCCAACTGATTCCATGTCTGGTGAGGGTCTATTTCCTGGTGCATAGATGGCTCCTTCTCACTG
``` and by subtraction, one can determine 1 and 4:

```
                        A                                      A
1= TCGTCCTCAGGAACTGAAGCTATATAATCAGTTAAGTCCCTGCTTCTGATCTCTTCTGATTTTCTTCTAAGAAGAGAATA
                        T                                      T
4= TAGTCCTCAATTTCACCATGGATTAAATAACAGAACACAGAGTTACTGTGAGACTTGTGGTAGAAAATCTTTAATTCATT
```

*FIG. 21*

**Determining three unique singlet *Drd*I sequences from overlapping doublet and triplet BAC sequences.**

Concordant sequences: Doublet to Doublet.

1. TCGTCCTCAGGAACTGAAGCTATATAATCAGTTAAGTCCCTGCTTCTGATCTCTTCTGATTTTCTTCTAAGAAGAGAATA
2. GTGTCAAGTAAAGAAGTACAGCAGATAAGTAAAACGGAAAAAAATAATGAAAGAATTACAAAGGAAGACTAAGGAAAGAG
    ddSSSdsiisdsisdsdssididdddisiidsidssssdddsiddSiiddiddiiddSississdidsddddsdssdSdis 3. AAGTCTACAATCAAGAGGCCAACTGATTCCATGTCTGGTGAGGGTCTATTTCCTGGTGCATAGATGGCTCCTTCTCACTG
2. GTGTCAAGTAAAGAAGTACAGCAGATAAGTAAAACGGAAAAAAATAATGAAAGAATTACAAAGGAAGACTAAGGAAAGAG From above 2 BACs, sequence #2 is:

```
          CA      A      CA    ATC  T          G   CT  T  CT   G  T  T                T
2? GTGTCAAGTAAAGAAGTACAGCAGATAAGTAAAACGGAAAAAAATAATGAAAGAATTACAAAGGAAGACTAAGGAAAGAG
```

Concordant sequences: Doublet to Triplet.

3. AAGTCTACAATCAAGAGGCCAACTGATTCCATGTCTGGTGAGGGTCTATTTCCTGGTGCATAGATGGCTCCTTCTCACTG
2. GTGTCAAGTAAAGAAGTACAGCAGATAAGTAAAACGGAAAAAAATAATGAAAGAATTACAAAGGAAGACTAAGGAAAGAG
    iiSSSdssiSdddsiddisdisidisiidisidsdsdissiiisisisdiiddiisdssisssiisiiiddddddsdds 3. AAGTCTACAATCAAGAGGCCAACTGATTCCATGTCTGGTGAGGGTCTATTTCCTGGTGCATAGATGGCTCCTTCTCACTG
4. TAGTCCTCAATTTCACCATGGATTAAATAACAGAACACAGAGTTACTGTGAGACTTGTGGTAGAAAATCTTTAATTCATT
5. GTGTCATCTAGCTATAAATCTAAAGATAATAATAAAATTGGAAAGATTTTCATCAGATAGACTTTTAACACCAAGCTTGA From above 2 BACs, sequence #3 is:

```
3? AAGTCTACAATCAAGAGGCCAACTGATTCCATGTCTGGTGAGGGTCTATTTCCTGGTGCATAGATGGCTCCTTCTCACTG
   GT     T    A A  GA AA T A A    A   AAA A T AA AT    A   AA ACT
          CA     A    CA   ATC T         G    CT T CT   G  T  T            T
2? GTGTCAAGTAAAGAAGTACAGCAGATAAGTAAAACGGAAAAAAATAATGAAAGAATTACAAAGGAAGACTAAGGAAAGAG
```

By comparing the consensus sequence between 2 and 3, one can determine the overlap. In this case, only two positions are indeterminate (A or T). Hence 2 and 3 are:

```
        A                          T  T         G  C               T  T
2= GTGTCAAGTAAAGAAGTACAGCAGATAAGTAAAACGGAAAAAAATAATGAAAGAATTACAAAGGAAGACTAAGGAAAGAG

T                          A  A         A  A               A  A
3= AAGTCTACAATCAAGAGGCCAACTGATTCCATGTCTGGTGAGGGTCTATTTCCTGGTGCATAGATGGCTCCTTCTCACTG
``` and by subtraction, one can determine 1 is:

```
           T             A  A             A  A                A  A
1= TCGTCCTCAGGAACTGAAGCTATATAATCAGTTAAGTCCCTGCTTCTGATCTCTTCTGATTTTCTTCTAAGAAGAGAATA
```

From the above data, one cannot determine sequence 4 & 5, although one can reduce it to a doublet sequence by subtracting sequence 3. The alignment of this triplet BAC with another singlet or doublet from the neighboring BAC on the other side (i.e. 5 alone or 5 & 6 doublet) will allow one to decipher sequences 4, 5, and 6

*FIG. 22*

BglI, DrdI, and SapI sites in the pBeloBAC11 cloning vector.

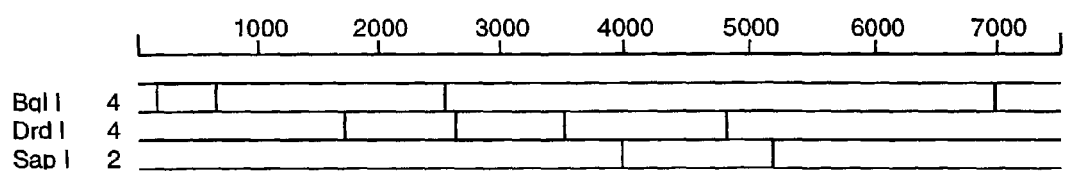

| BgI# | Location | Nearby Site | Overhang (BgI) | Overlapping Site | Complement (BgI) | Nearby Site |
|---|---|---|---|---|---|---|
| 1. | 155 | FspI | TTC | | GAA | NarI |
| 2. | 634 | | CCC | XmaI | GGG | |
| 3. | 2,533 | | TGT | StuI | ACA | |
| 4. | 6,982 | | TGC | NgoMIV | GCA | |

| DrdI# | Location | Nearby Site | Overhang (DrdI) | Overlapping Site | Complement (DrdI) | Nearby Site |
|---|---|---|---|---|---|---|
| 1. | 1,704 | AlwNI | AA | | TT | |
| 2. | 2,616 | | TC | | GA | |
| 3. | 3,511 | | GA | | TC | EcoRI |
| 4. | 4,807 | | TG | BspHI | CA | |

| SapI# | Location | Nearby Site | Overhang (SapI) | Overlapping Site | Complement (SapI) | Nearby Site |
|---|---|---|---|---|---|---|
| 1. | 3,964 | DraI | TAT | | ATA | |
| 2. | 5,174 | | ACT | | AGT | BclI |

*FIG. 23*

*Bgl*I, *Drd*I, and *Sap*I sites in the pUC19 cloning vector.

| *Bgl*I# | Location | Nearby Site | Overhang (*Bgl*I) | Overlapping Site | Complement (*Bgl*I) | Nearby Site |
|---|---|---|---|---|---|---|
| 1. | 429 | *Nar*I | GAA | | TTC | *Fsp*I |
| 2. | 1,547 | | TTC | *Msp*I | GAA | |

| *Drd*I# | Location | Nearby Site | Overhang (*Drd*I) | Overlapping Site | Complement (*Drd*I) | Nearby Site |
|---|---|---|---|---|---|---|
| 1. | 582 | | GC | | GC | |
| 2. | 2,450 | | GA | *Taq*I | TC | |

*Sap*I sites: None

EcoRI, HindIII, and Bam HI site frequencies in a sequenced BAC from 7q31.

RG253B13, 7q31 Met Oncogene
19 BamHI Sites in 171,905 bp

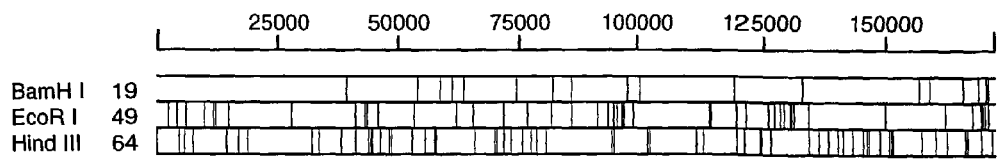

```
Enzyme          Freq        Position(s)

BamH I           19      :    39474      53874      53955      58547
  ↓                     :    61411      63629      74716      82491
  G GATC C              :    86169      97907     100558     120206
  C CTAG G              :   132953     156707     159016     165913
    ↑                   :   169171     170414     170908

Number of fragments 4 kb or less:  9
```

| BamHI Location#1 | Location#2 | + 2 bases | Complement + 2 bases |
|---|---|---|---|
| 1. 53,874 | 53,955 | AT[x] | TG[x] |
| 2. 58,547 | 61,411 | TA[@] | AA[@] |
| 3. 61,411 | 63,629 | TG[x] | AT[x] |
| 4. 82,491 | 86,169 | TG[x] | CT[#] |
| 5. 97,907 | 100,558 | AC[@] | TT[@] |
| 6. 156,707 | 159,016 | CA[@] | AG[@] |
| 7. 165,913 | 169,171 | TG[x] | AT[x] |
| 8. 169,171 | 170,414 | TC[#] | TC[#] |
| 9. 170,414 | 170,908 | CT[#] | TG[x] |

Clusters: (2, 3); (7, 8, 9)

|  | BamHI |
|---|---|
| [@]Same + 2 bases next to site within BAC used exactly once (singlet). | 6 |
| [#]Same + 2 bases next to site within BAC used exactly twice (doublet). | 2 |
| [x]Same + 2 bases next to site within BAC used more than twice. | 2 |

FIG. 26A

```
EcoR I         49   :      2446      4350      6140      6158
   ↓                :      6225     10073     12053     12399
   G AATT C         :     15083     28087     41401     43549
   C TTAA G         :     43806     46037     53312     62042
       ↑            :     65700     72180     77101     81978
                    :     86301     91655     93891     94983
                    :     95739     96841     97167     99214
                    :    114696    114949    115133    115232
                    :    120578    122208    126085    127496
                    :    128732    129314    130523    130710
                    :    131286    134360    150100    162281
                    :    167783    169521    169653    170292
                    :    170998

Number of fragments 4 kb or less:  34

Hind III       64   :         1       321      4834      5918
   ↓                :      7959     14843     16895     18994
   A AGCT T         :     32159     33703     38308     41512
   T TCGA A         :     44158     44521     44717     46402
       ↑            :     48209     48692     52752     55612
                    :     57379     57727     65779     70218
                    :     70601     71947     73380     75933
                    :     77773     78860     80726     94474
                    :     94886    102267    102578    112246
                    :    113833    120486    121556    121647
                    :    124186    124409    124818    126795
                    :    134126    136011    137970    140077
                    :    141184    143075    145328    146005
                    :    146673    148906    150711    150993
                    :    151617    157093    160311    162518
                    :    166369    166672    169514    171900

Number of fragments 4 kb or less:  52
```

*AvrII, NheI,* and *SpeI* site frequencies in a sequenced BAC from 7q31.

RG253B13, 7q31 Met Oncogene
25 *AvrII*, 22 *NheI*, and 21 *SpeI* Sites in 171,905 bp

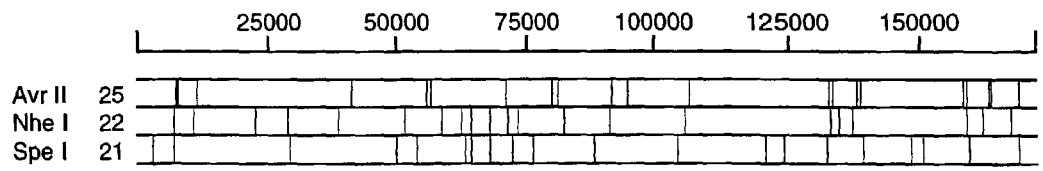

| Enzyme | Freq | Position(s) | | | |
|---|---|---|---|---|---|
| Avr II | 25 | : | 7350 | 7990 | 11781 | 41276 |
| ↓ | | : | 56073 | 56739 | 71378 | 80285 |
| C CTAG G | | : | 80378 | 80418 | 81455 | 92044 |
| G GATC C | | : | 95088 | 106812 | 132860 | 133491 |
| ↑ | | : | 138089 | 138866 | 138891 | 138919 |
| | | : | 158473 | 159109 | 163153 | 163762 |
| | | : | 168991 | | | |

Number of fragments 4 kb or less:  14  (Clustering)

| | *AvrII* Location#1 | Location#2 | + 2 bases | Complement + 2 bases |
|---|---|---|---|---|
| 1. | 7,350 | 7,990 | CT$^x$ | AA$^x$ |
| 2. | 7,990 | 11,781 | CC$^@$ | CT$^x$ |
| 3. | 56,073 | 56,739 | CA$^\#$ | TG$^@$ |
| 4. | 80,285 | 80,378 | TT$^x$ | AC$^\#$ |
| 5. | 80,378 | 80,418 | CA | CA  (40 bp fragment) |
| 6. | 80,418 | 81,455 | AC$^\#$ | AA$^x$ |
| 7. | 92,044 | 95,088 | GG$^@$ | TC$^@$ |
| 8. | 132,860 | 133,491 | TT$^x$ | AA$^x$ |
| 9. | 138,089 | 138,866 | CT$^x$ | TT$^x$ |
| 10. | 138,866 | 138,891 | TG | TG  (25 bp fragment) |
| 11. | 138,891 | 138,919 | CT | AG  (28 bp fragment) |
| 12. | 158,473 | 159,109 | AA$^x$ | TT$^x$ |
| 13. | 159,109 | 163,153 | CA$^\#$ | TA$^@$ |
| 14. | 163,153 | 163,762 | AA$^x$ | TT$^x$ |

Clusters: (4, 5, 6); (9, 10, 11); (13, 14)

|  | *AvrII* |
|---|---|
| $^@$Same + 2 bases next to site within BAC used exactly once (singlet). | 5 |
| $^\#$Same + 2 bases next to site within BAC used exactly twice (doublet). | 2 |
| $^x$Same + 2 bases next to site within BAC used more than twice. | 3 |

*FIG. 27A*

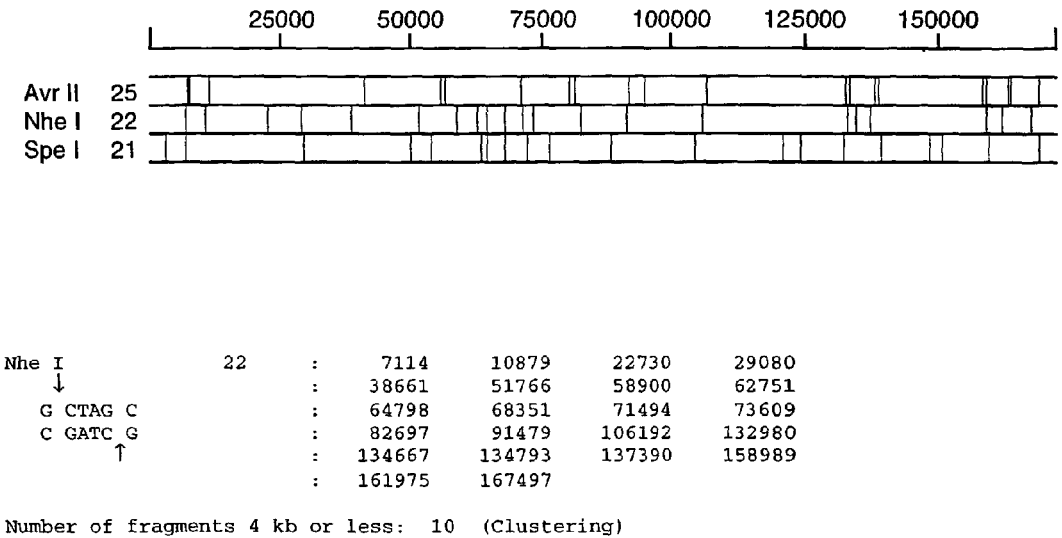

```
Nhe I        22      :    7114    10879    22730    29080
 ↓                   :   38661    51766    58900    62751
 G CTAG C            :   64798    68351    71494    73609
 C GATC G            :   82697    91479   106192   132980
      ↑              :  134667   134793   137390   158989
                     :  161975   167497
```

Number of fragments 4 kb or less:  10   (Clustering)

| *Nhe*I | Location#1 | Location#2 | + 2 bases | Complement + 2 bases |
|---|---|---|---|---|
| 1.  | 7,114   | 10,879  | TT#  | TCx  |
| 2.  | 58,900  | 62,751  | TG#  | CAx  |
| 3.  | 62,751  | 64,798  | ACx  | ACx  |
| 4.  | 64,798  | 68,351  | TCx  | TCx  |
| 5.  | 68,351  | 71,494  | ACx  | TG#  |
| 6.  | 71,494  | 73,609  | TA@  | CAx  |
| 7.  | 132,980 | 134,667 | CAx  | AA@  |
| 8.  | 134,667 | 134,793 | GG@  | AG#  |
| 9.  | 134,793 | 137,390 | TT#  | ACx  |
| 10. | 158,989 | 161,975 | CAx  | AG#  |

Clusters: (3, 4, 5, 6); (7, 8, 9)

|  | *Nhe*I |
|---|---|
| @Same + 2 bases next to site within BAC used exactly once (singlet). | 3 |
| #Same + 2 bases next to site within BAC used exactly twice (doublet). | 3 |
| xSame + 2 bases next to site within BAC used more than twice. | 3 |

*FIG. 27B*

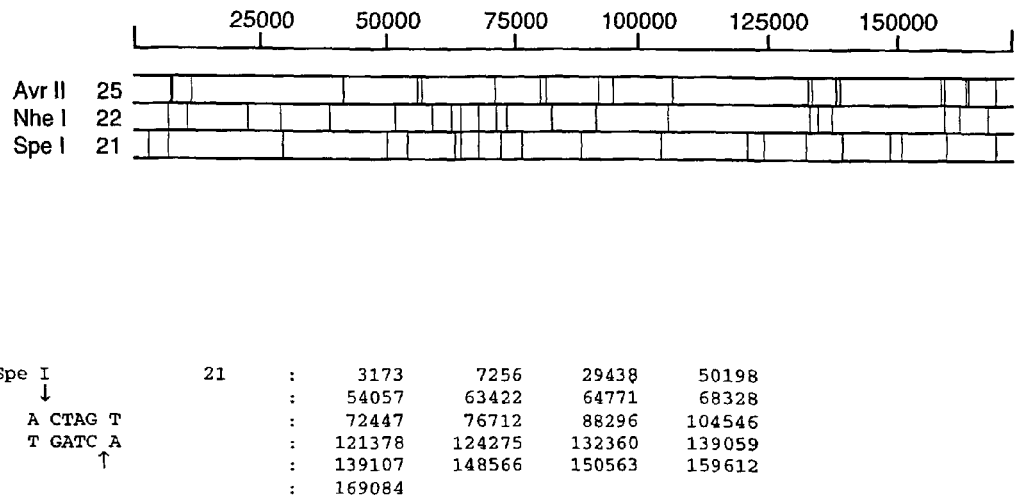

```
Spe I              21       :    3173      7256     29438     50198
     ↓                      :   54057     63422     64771     68328
   A CTAG T                 :   72447     76712     88296    104546
   T GATC A                 :  121378    124275    132360    139059
       ↑                    :  139107    148566    150563    159612
                            :  169084
```

Number of fragments 4 kb or less:  9    (Clustering)

| SpeI | Location#1 | Location#2 | + 2 bases | Complement + 2 bases |
|---|---|---|---|---|
| 1. | 3,173 | 7,256 | TC# | GA$^x$ |
| 2. | 50,198 | 54,057 | TG# | GG$^x$ |
| 3. | 63,422 | 64,777 | GA$^x$ | GG$^x$ |
| 4. | 64,777 | 68,328 | CA@ | GG$^x$ |
| 5. | 68,328 | 72,447 | TT$^x$ | TT$^x$ |
| 6. | 72,447 | 76,712 | GT@ | GC@ |
| 7. | 121,378 | 124,275 | GA$^x$ | TC# |
| 8. | 139,059 | 139,107 | AT | AC (48 bp fragment) |
| 9. | 148,566 | 150,563 | TG# | TT$^x$ |

Clusters: (3, 4, 5, 6)

|  | SpeI |
|---|---|
| @Same + 2 bases next to site within BAC used exactly once (singlet). | 3 |
| #Same + 2 bases next to site within BAC used exactly twice (doublet). | 3 |
| $^x$Same + 2 bases next to site within BAC used more than twice. | 3 |

*FIG. 27C*

AccI and BsiHKAI site frequencies in a sequenced BAC from 7q31.

RG253B13, 7q31 Met Oncogene
71 AccI and 127 BsiHKAI Sites in 171,905 bp

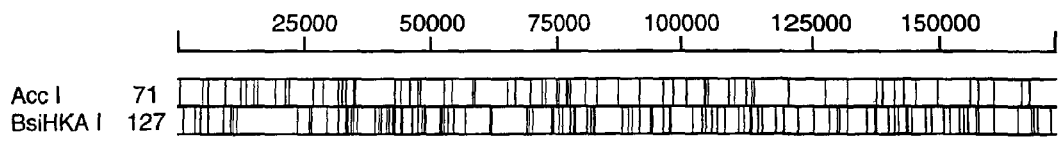

| Enzyme | Freq | Position(s) | | | |
|---|---|---|---|---|---|
| Acc I | 71 | : | 523 | 5182 | 6465 | 9711 |
| ↓ | | : | 12950 | 13976 | 15332 | 16332 |
| GT MK AC | | : | 19814 | 21540 | 22269 | 22322 |
| CA KM TG | | : | 26959 | 28705 | 32048 | 32661 |
| ↑ | | : | 33298 | 33310 | 34799 | 35425 |
| | | : | 42895 | 44110 | 46004 | 47636 |
| | | : | 47861 | 52446 | 54000 | 58216 |
| | | : | 58826 | 65238 | 66475 | 69750 |
| | | : | 71833 | 72783 | 74938 | 75538 |
| | | : | 77087 | 77368 | 77642 | 80744 |
| | | : | 82917 | 87470 | 91592 | 96498 |
| | | : | 98545 | 100882 | 100965 | 104551 |
| | | : | 104725 | 105186 | 109580 | 110415 |
| | | : | 112720 | 114135 | 114242 | 120913 |
| | | : | 127597 | 131831 | 137724 | 139036 |
| | | : | 141043 | 142923 | 142963 | 145284 |
| | | : | 149681 | 155647 | 157032 | 160140 |
| | | : | 165449 | 167062 | 167292 | |

| AccI# | Location#1 | Location#2 | AG#1+ 2 | AG#2 + 2 |
|---|---|---|---|---|
| 1. | 13,976 | 15,332 | TT[#] | AT[#] |
| 2. | 33,298 | 33,310 | (10 bp fragment) | |
| 3. | 35,425 | 42,895 | (Too long) | |
| 4. | 69,750 | 71,833 | TT[#] | AA[@] |
| 5. | 96,498 | 98,545 | CC[@] | AT[@] |
| 6. | 109,580 | 110,415 | AT[#] | TG[@] |

|  | AccI |
|---|---|
| [@]Same + 2 bases next to site within BAC used exactly once (singlet). | 4 |
| [#]Same + 2 bases next to site within BAC used exactly twice (doublet). | 2 |
| [x]Same + 2 bases next to site within BAC used more than twice. | 0 |

*FIG. 29A*

```
Enzyme        Freq      Position(s)

BsiHKA I      127    :    1200     1274     3588     4610
   ↓                 :    6151     9251     9358    10891
 G WGCW C            :   11182    12046    23820    26072
 C WCGW G            :   26538    29548    31865    33417
    ↑                :   33620    33828    34406    34818
                     :   35750    39076    39888    40291
                     :   41356    41605    41622    41723
                     :   42439    43101    43155    43959
                     :   44003    44572    46346    47692
                     :   48495    48608    49119    51943
                     :   52138    52540    53172    53348
                     :   54384    56608    61639    61987
                     :   68891    69195    70155    73864
                     :   74122    75448    76167    77810
                     :   78326    78825    81275    81950
                     :   82251    82594    87958    89375
                     :   90017    91434    91584    93846
                     :   94001    96276    97766    97942
                     :  102220   104114   105012   106105
                     :  107321   108501   111466   112396
                     :  113542   114132   115157   116106
                     :  118786   120094   122269   122357
                     :  122376   122400   125590   128460
                     :  130102   130144   130366   131806
                     :  135930   137267   137611   139881
                     :  141326   141747   143572   143995
                     :  144453   144701   147329   148398
                     :  150702   150741   151888   153643
                     :  154630   155122   156946   157058
                     :  160171   160400   164987   167605
                     :  167618   167660   167683   168011
                     :  168643   168776   171471
```

| BsiHKAI | Location#1 | Location#2 | AGCA#1+2 | AGCA#2+2 |
|---|---|---|---|---|
| 1. | 3,588 | 4,610 | AC# | TT# |
| 2. | 23,820 | 26,072 | AA@ | TG# |
| 3. | 43,959 | 44,003 | TT | AA (44 bp fragment) |
| 4. | 48,608 | 49,119 | AG@ | GA@ |
| 5. | 52,138 | 52,540 | CT@ | GG@ |
| 6. | 76,167 | 77,810 | AC# | TT# |
| 7. | 102,220 | 104,114 | CC | CC (24 bp fragment) |
| 8. | 155,122 | 156,946 | AT@ | TG# |

|  | BsiHKAI |
|---|---|
| @Same + 2 bases next to site within BAC used exactly once (singlet). | 6 |
| #Same + 2 bases next to site within BAC used exactly twice (doublet). | 3 |
| xSame + 2 bases next to site within BAC used more than twice. | 0 |

*Sa*nDI and *Sex*AI site frequencies in a sequenced BAC from 7q31.

RG253B13, 7q31 Met Oncogene
13 *San*DI and 15 *Sex*AI Sites in 171,905 bp

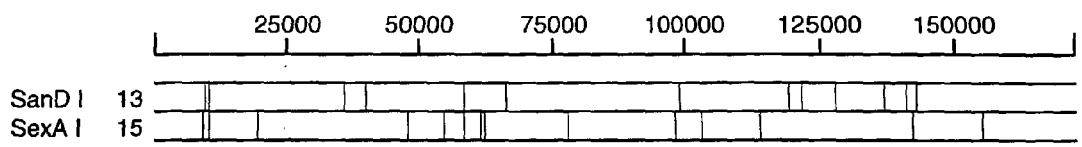

| Enzyme | Freq | Position(s) | | | |
|---|---|---|---|---|---|
| SanD I | 13 | : | 9761 | 10644 | 36269 | 40440 |
| ↓ | | : | 58583 | 66380 | 99267 | 119927 |
| GG GWC CC | | : | 122060 | 128057 | 137082 | 140964 |
| CC CWG GG | | : | 143225 | | | |
| ↑ | | : | | | | |

| *San*DI#Location | | GAC + 2 bases |
|---|---|---|
| 1. | 9,761 | CT# |
| 2. | 10,644 | TC# |
| 3. | 36,269 | AC# |
| 4. | 40,440 | TC# |
| 5. | 58,583 | TG# |
| 6. | 66,380 | CA@ |
| 7. | 99,267 | TG# |
| 8. | 119,927 | AT@ |
| 9. | 122,060 | CG@ |
| 10. | 128,057 | TA# |
| 11. | 137,082 | AC# |
| 12. | 140,964 | CT# |
| 13. | 143,225 | TA# |

| | *San*DI |
|---|---|
| @Same + 2 bases next to site within BAC used exactly once (singlet). | 3 |
| #Same + 2 bases next to site within BAC used exactly twice (doublet). | 5 |
| xSame + 2 bases next to site within BAC used more than twice. | 0 |

*FIG. 31A*

```
Enzyme        Freq      Position(s)

SexA I         15    :    9499     10411    19691    47816
  ↓                 :   54773    58714    61533    62534
  A CCWGG T         :   78279    98356   103356   114268
  T GGWCC A         :  114440   142141   155393
      ↑             :
```

| SexAI#Location | | CCAGG + 2 bases |
|---|---|---|
| 1. | 9,499 | TG@ |
| 2. | 10,411 | CTX |
| 3. | 19,691 | TT# |
| 4. | 47,816 | CC@ |
| 5. | 54,773 | CTX |
| 6. | 58,714 | GG@ |
| 7. | 61,533 | GC@ |
| 8. | 62,534 | TC@ |
| 9. | 78,279 | CTX |
| 10. | 98,356 | TT# |
| 11. | 103,356 | AT@ |
| 12. | 114,268 | AA@ |
| 13. | 114,440 | GA# |
| 14. | 142,141 | CA@ |
| 15. | 155,393 | GA# |

|  | SexAI |
|---|---|
| @Same + 2 bases next to site within BAC used exactly once (singlet). | 8 |
| #Same + 2 bases next to site within BAC used exactly twice (doublet). | 2 |
| XSame + 2 bases next to site within BAC used more than twice. | 1 |

AccI and BsiHKAI sites in the pBeloBAC11 cloning vector.

```
Enzyme    Freq     Position(s)
Acc I      6    :     367     647    1832    1891    6262    7031
  ↓            :
GT MK AC        :
CA KM TG        :
   ↑            :
```

AccI#   Location#1   Location#2   AG#1+ 2   AG#2 + 2

None with head to head AG overhangs.

```
BsiHKA I    8    :      91     343    2352    3966    5458    7040
    ↓            :    7048    7458
G WGCW C         :
C WCGW G         :
   ↑             :
```

BsiHKAI Location#1   Location#2   AGCA#1+ 2   AGCA#2 + 2

None with head to head AGCA overhangs.

*Avr*II, *Bam* HI, *Nhe*I, and *Spe*I, sites in the pBeloBAC11 cloning vector.

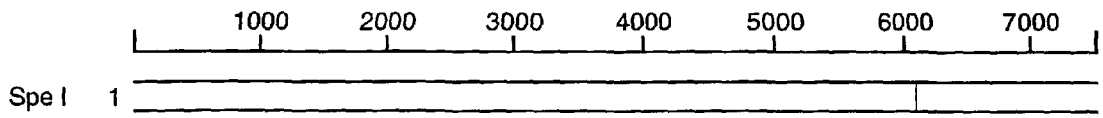

Spe I   1

*Avr*II   Location#1   Location#2   + 2 bases   Complement + 2 bases

Non-cutting enzymes :
  Avr II      Nhe I

*Nhe*I   Location#1   Location#2   + 2 bases   Complement + 2 bases

Non-cutting enzymes :
  Avr II      Nhe I

```
Enzyme          Freq        Position(s)
Spe I            1       :    6090
  ↓                      :
  A CTAG T               :
  T GATC A               :
       ↑                 :
```

*Spe*I   Location#1   Location#2   + 2 bases   Complement + 2 bases

No PCR vector fragment under 4 kb.

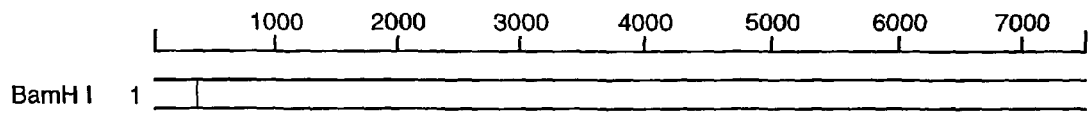

BamH I   1

```
Enzyme          Freq        Position(s)
BamH I           1       :    354
  ↓                      :
  G GATC C               :
  C CTAG G               :
       ↑                 :
```

*Bam*HI Location#1   Location#2   + 2 bases   Complement + 2 bases

No PCR vector fragment under 4 kb.

*FIG. 33*

SanDI and SexAI sites in the pBeloBAC11 cloning vector.

SanDI#Location     A + 2 bases

```
Non-cutting enzymes :
 SanD I
```

```
Enzyme              Freq       Position(s)
SexA I              1      :   6968
  ↓                        :
  A CCWGG T                :
  T GGWCC A                :
        ↑                  :
```

SexAI#Location    CCAGG + 2 bases
1.    6,968      AT

```
161237  Msp I
161467  Bgl I
162462  Taq I

165127  Taq I
165703  Bgl I
165714  Msp I
166152  Sap I
166163  Msp I

168336  Taq I

171459  Sap I
```

*FIG. 35B*

*DrdI* site: For AA, AC, AG, CA, GA, and GG overhangs

| DrdI# | Location | Overhang | Complement | Nearest MspI or TaqI | Fragment Length |
|---|---|---|---|---|---|
| 1. | 5,379 | GG* | CC | 6,249 | 864 |
| 2. | 26,865 | GT | AC* | 26,363 | 502 |
| 3. | 33,300 | GG* | CC | 38,218 | 4,918# |
| 4. | 45,528 | AT | AT | | |
| 5. | 70,522 | AT | AT | | |
| 6. | 91,675 | TC | GA* | 88,256 | 3,419 |
| 7. | 96,500 | CA* | TG | 97,059 | 559 |
| 8. | 99,622 | CT | AG* | 99,513 | 115 |
| 9. | 101,434 | TT | AA* | 101,248 | 192 |
| 10. | 113,042 | AC* | GT | 113,429 | 381 |
| 11. | 137,171 | TT | AA* | 136,580 | 597 |
| 12. | 159,679 | AG* | CT | 160,038 | 353 |

\* To obtain sequence information on AA, AC, AG, CA, GA, or GG overhangs in the sense direction, the *DrdI* island is amplified using a downstream *MspI* or *TaqI* site. For such two base sequences on the complementary strand, the *DrdI* island is amplified using an upstream *MspI* or *TaqI* site.

Same last 2 bases of 3' overhang within BAC used exactly once (singlet).  3
Same last 2 bases of 3' overhang within BAC used exactly twice (doublet).  3
Same last 2 bases of 3' overhang within BAC used more than twice.  0

*DrdI* site: For TT, GT, CT, TG, TC, and CC overhangs

| DrdI# | Location | Overhang | Complement | Nearest MspI or TaqI | Fragment Length |
|---|---|---|---|---|---|
| 1. | 5,379 | GG | CC* | 1,744 | 3,635 |
| 2. | 26,865 | GT* | AC | 31,368 | 4,503# |
| 3. | 33,300 | GG | CC* | 31,440 | 1,860 |
| 4. | 45,528 | AT | AT | | |
| 5. | 70,522 | AT | AT | | |
| 6. | 91,675 | TC* | GA | 92,596 | 921 |
| 7. | 96,500 | CA | TG* | 95,752 | 748 |
| 8. | 99,622 | CT* | AG | 101,248 | 1,626 |
| 9. | 101,434 | TT* | AA | 103,234 | 1,800 |
| 10. | 113,042 | AC | GT* | 112,992 | 50# |
| 11. | 137,171 | TT* | AA | 137,473 | 302 |
| 12. | 159,679 | AG | CT* | 158,054 | 1,625 |

\* To obtain sequence information on TT, GT, CT, TG, TC, or CC overhangs in the sense direction, the *DrdI* island is amplified using a downstream *MspI* or *TaqI* site. For such two base sequences on the complementary strand, the *DrdI* island is amplified using an upstream *MspI* or *TaqI* site.

Same last 2 bases of 3' overhang within BAC used exactly once (singlet).  2
Same last 2 bases of 3' overhang within BAC used exactly twice (doublet).  3
Same last 2 bases of 3' overhang within BAC used more than twice.  0
Fragment too small to give interpretable sequence (>80), or too large to amplify properly.

*FIG. 35C*

*Bgl*I site: For AAN, CAN, GAN, TAN, AGN, CGN, GGN, and TGN overhangs

| *Bgl*I# | Location | Overhang | Complement | Nearest *Msp*I or *Taq*I | Fragment Length |
|---|---|---|---|---|---|
| 1. | 13,833 | TGT* | ACA | 14,933 | 1,100 |
| 2. | 25,115 | ACA | TGT* | 22,165 | 2,950 |
| 3. | 33,890 | GAA* | TTC | 37,052 | 3,162 |
| 4. | 51,623 | TGT* | ACA | 51,633 | 10# |
| 5. | 58,308 | CTA | TAG* | 57,978 | 330 |
| 6. | 88,316 | TTA | TAA* | 88,256 | 60# |
| 7. | 94,134 | GGG* | CCC | 95,752 | 1,618 |
| 8. | 99,463 | ACA | TGT* | 99,370 | 93 |
| 9. | 100,045 | ACC | GGT* | 99,628 | 417 |
| 10. | 106,613 | CCA | TGG* | 105,244 | 1,369 |
| 11. | 129,192 | TGT* | ACA | 129,286 | 94 |
| 12. | 137,747 | TCT | AGA* | 137,728 | 19# |
| 13. | 149,246 | TGT* | ACA | 150,256 | 110 |
| 14. | 156,577 | TTT | AAA* | 156,469 | 108 |
| 15. | 161,461 | CGA* | TCG | 162,462 | 101 |
| 16. | 165,697 | CTG | CAG* | 165,127 | 570 |

* To obtain sequence information on AAN, CAN, GAN, TAN, AGN, CGN, GGN, or TGN overhangs in the sense direction, the *Bgl*I island is amplified using a downstream *Msp*I or *Taq*I site. For such three base sequences on the complementary strand, the *Bgl*I island is amplified using an upstream *Msp*I or *Taq*I site.

| | |
|---|---|
| Same last 2 bases of 3' overhang within BAC used exactly once (singlet). | 5 |
| Same last 2 bases of 3' overhang within BAC used exactly twice (doublet). | 2 |
| Same last 2 bases of 3' overhang within BAC used more than twice. | 1 |

*Bgl*I site: For ACN, CCN, GCN, TCN, ATN, CTN, GTN, and TTN overhangs

| *Bgl*I# | Location | Overhang | Complement | Nearest *Msp*I or *Taq*I | Fragment Length |
|---|---|---|---|---|---|
| 1. | 13,833 | TGT | ACA* | 12,529 | 1,304 |
| 2. | 25,115 | ACA* | TGT | 25,228 | 113 |
| 3. | 33,890 | GAA | TTC* | 33,306 | 584 |
| 4. | 51,623 | TGT | ACA* | 51,614 | 9# |
| 5. | 58,308 | CTA* | TAG | 58,886 | 578 |
| 6. | 88,316 | TTA* | TAA | 91,681 | 3,365 |
| 7. | 94,134 | GGG | CCC* | 92,596 | 1,538 |
| 8. | 99,463 | ACA* | TGT | 99,513 | 50# |
| 9. | 100,045 | ACC* | GGT | 100,257 | 212 |
| 10. | 106,613 | CCA* | TGG | 109,494 | 2,881 |
| 11. | 129,192 | TGT | ACA* | 127,710 | 1,482 |
| 12. | 137,747 | TCT* | AGA | 137,987 | 240 |
| 13. | 149,246 | TGT | ACA* | 148,482 | 764 |
| 14. | 156,577 | TTT* | AAA | 157,032 | 455 |
| 15. | 161,461 | CGA | TCG* | 161,237 | 224 |
| 16. | 165,697 | CTG* | CAG | 165,714 | 17# |

*FIG. 35D*

\* To obtain sequence information on ACN, CCN, GCN, TCN, ATN, CTN, GTN, or TTN overhangs in the sense direction, the *Bgl*I island is amplified using a downstream *Msp*I or *Taq*I site. For such three base sequences on the complementary strand, the *Bgl*I island is amplified using an upstream *Msp*I or *Taq*I site.

Same last 2 bases of 3' overhang within BAC used exactly once (singlet).   0
Same last 2 bases of 3' overhang within BAC used exactly twice (doublet).  3
Same last 2 bases of 3' overhang within BAC used more than twice.          2
\# Fragment too small to give interpretable sequence (>80), or too large to amplify properly.

Or, alternatively, mix and match the above to include trinucleotides where the middle base of the upper strand is either A or C, corresponding to the 3' end of the PCR primer.

BgII site: For AAN, CAN, GAN, TAN, ACN, CCN, GCN, and TCN overhangs

| BgII# | Location | Overhang | Complement | Nearest MspI or TaqI | Fragment Length |
|---|---|---|---|---|---|
| 1.  | 13,833  | TGT  | ACA* | 12,529  | 1,304 |
| 2.  | 25,115  | ACA* | TGT  | 25,228  | 113   |
| 3.  | 33,890  | GAA* | TTC  | 37,052  | 3,162 |
| 4.  | 51,623  | TGT  | ACA* | 51,614  | 9#    |
| 5.  | 58,308  | CTA  | TAG* | 57,978  | 330   |
| 6.  | 88,316  | TTA  | TAA* | 88,256  | 60#   |
| 7.  | 94,134  | GGG  | CCC* | 92,596  | 1,538 |
| 8.  | 99,463  | ACA* | TGT  | 99,513  | 50#   |
| 9.  | 100,045 | ACC* | GGT  | 100,257 | 212   |
| 10. | 106,613 | CCA* | TGG  | 109,494 | 2,881 |
| 11. | 129,192 | TGT  | ACA* | 127,710 | 1,482 |
| 12. | 137,747 | TCT* | AGA  | 137,987 | 240   |
| 13. | 149,246 | TGT  | ACA* | 148,482 | 764   |
| 14. | 156,577 | TTT  | AAA* | 156,469 | 108   |
| 15. | 161,461 | CGA  | TCG* | 161,237 | 224   |
| 16. | 165,697 | CTG  | CAG* | 165,127 | 570   |

\* To obtain sequence information on AAN, CAN, GAN, TAN, ACN, CCN, GCN, or TCN overhangs in the sense direction, the *Bgl*I island is amplified using a downstream *Msp*I or *Taq*I site. For such three base sequences on the complementary strand, the *Bgl*I island is amplified using an upstream *Msp*I or *Taq*I site.

Same last 2 bases of 3' overhang within BAC used exactly once (singlet).   3
Same last 2 bases of 3' overhang within BAC used exactly twice (doublet).  3
Same last 2 bases of 3' overhang within BAC used more than twice.          1
\# Fragment too small to give interpretable sequence (>80), or too large to amplify properly.

*FIG. 35E*

For AA, AC, AG, AT, GA, GC, GG and GT overhangs

| SapI# | Location | SapI Overhang | Ligated Complement | | Nearest MspI or TaqI | Fragment Length |
|---|---|---|---|---|---|---|
| 1. | 1,198 | CTA | TAG* | down | No | |
| 2. | 1,456 | AGG | CCT | up | No | |
| 3. | 10,943 | GCT | AGC* | up | 10,904 | 39# |
| 4. | 10,955 | GCT | ACG | down | No | |
| 5. | 11,041 | CAA | TTG | up | No | |
| 6. | 31,031 | AAT | ATT | down | 31,368 | |
| 7. | 32,599 | GAT | ATC | down | No | |
| 8. | 37,053 | AGA | TCT | up | No | |
| 9. | 38,931 | GGG | CCC | down | 39,316 | |
| 10. | 39,877 | ATC | GAT* | up | 39,316 | 571 |
| 11. | 44,325 | CTT | AAG* | down | 44,477 | 152 |
| 12. | 56,040 | ACA | TGT* | down | 57,978 | 1,938 |
| 13. | 68,850 | ACC | GGT* | up | 64,973 | 3,877 |
| 14. | 76,930 | GTG | CAC* | up | 76,855 | 75# |
| 15. | 100,250 | GGG | CCC | down | 101,248 | |
| 16. | 112,850 | GAT | ATC | up | 112,720 | |
| 17. | 135,473 | ACA | TGT* | down | No | |
| 18. | 135,608 | GGA | TCC | down | 135,890 | |
| 19. | 136,239 | TTG | CAA* | up | 135,890 | 349 |
| 20. | 142,243 | GCC | GGC* | up | 140,465 | 1,778 |
| 21. | 148,475 | GCG | CGC* | down | 150,256 | 1,781 |
| 22. | 157,978 | TCT | AGA* | up | 157,032 | 946 |
| 23. | 160,833 | ACC | GGT* | up | 160,434 | 399 |
| 24. | 166,153 | ATT | AAT* | up | 165,714 | 439 |
| 25. | 171,460 | GTT | AAC* | up | 168,336 | 3,124 |

\* To obtain sequence information on AA, AC, AG, AT, GA, GC, GG or GT overhangs in the sense direction, the *Sap*I island is amplified using a downstream *Msp*I or *Taq*I site. For such two base sequences on the complementary strand, the *Bgl*I island is amplified using an upstream *Msp*I or *Taq*I site.

Same last 2 bases of 3' overhang within BAC used exactly once(singlet).  3
Same last 2 bases of 3' overhang within BAC used exactly twice (doublet).  3
Same last 2 bases of 3' overhang within BAC used more than twice.  1
\# Fragment too small to give interpretable sequence (>80), or too large to amplify properly.

*FIG. 35F*

For CA, CC, CG, CT, TA, TC, TG, and TT overhangs

| SapI# | Location | SapI Overhang | Ligated Complement | | Nearest MspI or TaqI | Fragment Length |
|---|---|---|---|---|---|---|
| 1. | 1,198 | CTA | TAG | down | No | |
| 2. | 1,456 | AGG | CCT* | up | No | |
| 3. | 10,943 | GCT | AGC | up | 10,904 | |
| 4. | 10,955 | GCT | ACG* | down | No | |
| 5. | 11,041 | CAA | TTG* | up | No | |
| 6. | 31,031 | AAT | ATT* | down | 31,368 | 337 |
| 7. | 32,599 | GAT | ATC* | down | No | |
| 8. | 37,053 | AGA | TCT* | up | No | |
| 9. | 38,931 | GGG | CCC* | down | 39,316 | 385 |
| 10. | 39,877 | ATC | GAT | up | 39,316 | |
| 11. | 44,325 | CTT | AAG | down | 44,477 | |
| 12. | 56,040 | ACA | TGT | down | 57,978 | |
| 13. | 68,850 | ACC | GGT | up | 64,973 | |
| 14. | 76,930 | GTG | CAC | up | 76,855 | |
| 15. | 100,250 | GGG | CCC* | down | 101,248 | 998 |
| 16. | 112,850 | GAT | ATC* | up | 112,720 | 134 |
| 17. | 135,473 | ACA | TGT | down | No | |
| 18. | 135,608 | GGA | TCC* | down | 135,890 | 282 |
| 19. | 136,239 | TTG | CAA | up | 135,890 | |
| 20. | 142,243 | GCC | GGC | up | 140,465 | |
| 21. | 148,475 | GCG | CGC | down | 150,256 | |
| 22. | 157,978 | TCT | AGA | up | 157,032 | |
| 23. | 160,833 | ACC | GGT | up | 160,434 | |
| 24. | 166,153 | ATT | AAT | up | 165,714 | |
| 25. | 171,460 | GTT | AAC | up | 168,336 | |

* To obtain sequence information on CA, CC, CG, CT, TA, TC, TG or TT overhangs in the sense direction, the SapI island is amplified using a downstream MspI or TaqI site. For such two base sequences on the complementary strand, the BglII island is amplified using an upstream MspI or TaqI site.

Same last 2 bases of 3' overhang within BAC used exactly once(singlet).   1
Same last 2 bases of 3' overhang within BAC used exactly twice (doublet).   1
Same last 2 bases of 3' overhang within BAC used more than twice.   1
Fragment too small to give interpretable sequence (>80), or too large to amplify properly.

*FIG. 35G*

Three degrees of specificity in amplifying a *Bgl*I representation.

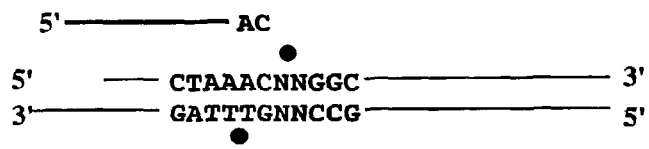

1. Ligation of the top strand requires perfect complementarity at the penultimate base to the 3' side of the junction (20-fold specificity).
2. Ligation of the bottom strand requires perfect complementarity at the 3' side of the junction (50-fold specificity).
3. Extension of polymerase off the sequencing primer is most efficient if the 3' base is perfectly matched (10 to 100-fold specificity).

*FIG. 36*

**Overlapping *Dra*I islands in four hypothetical BAC clones: 1 AA overhangs**
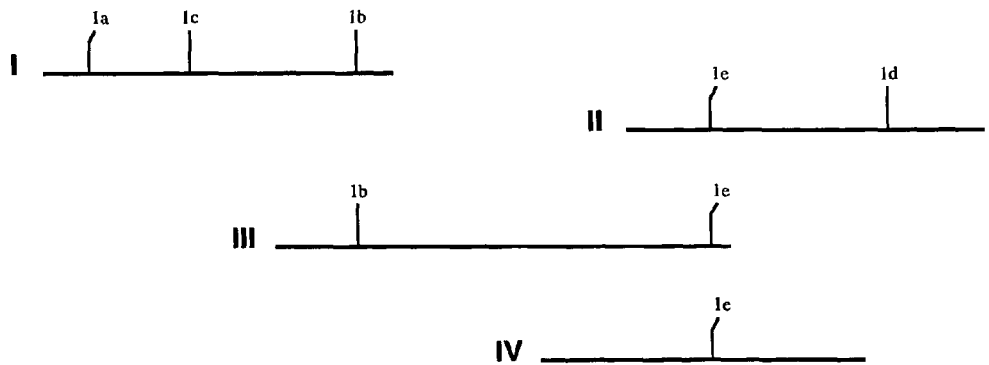
| BAC Clone # | 1 = AA | Concordance | 1 = AA | Discordance | 1 = AA |
|---|---|---|---|---|---|
| I | Triplet 1a, 1b, 1c | I & III | Triplet & Doublet (1b) | I & II | 1a, b, c ≠ 1d, e |
| II | Doublet 1d, 1e | II & III | Doublet & Doublet (1e) | I & IV | 1a, b, c ≠ 1e |
| III | Doublet 1b, 1e | III & IV | Doublet & Singlet (1e) | | |
| IV | Singlet 1e | II & IV | Doublet & Singlet (1e) | | |
Order of *Dra*I islands in four BAC clones.
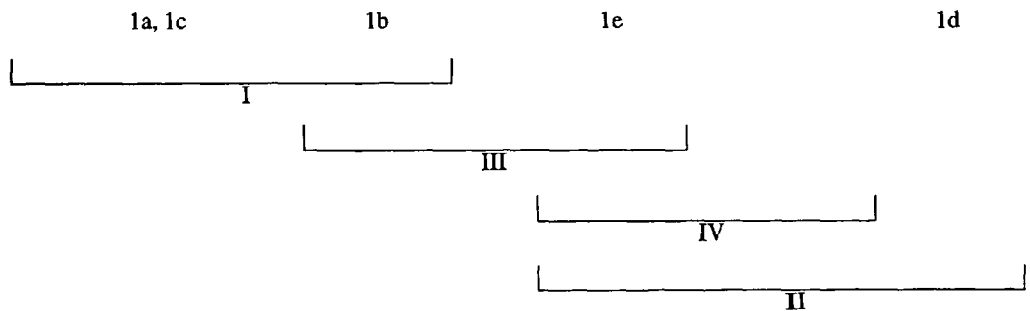
*FIG. 38*

**Overlapping *DrdI* islands in four hypothetical BAC clones: 2 AC overhangs**
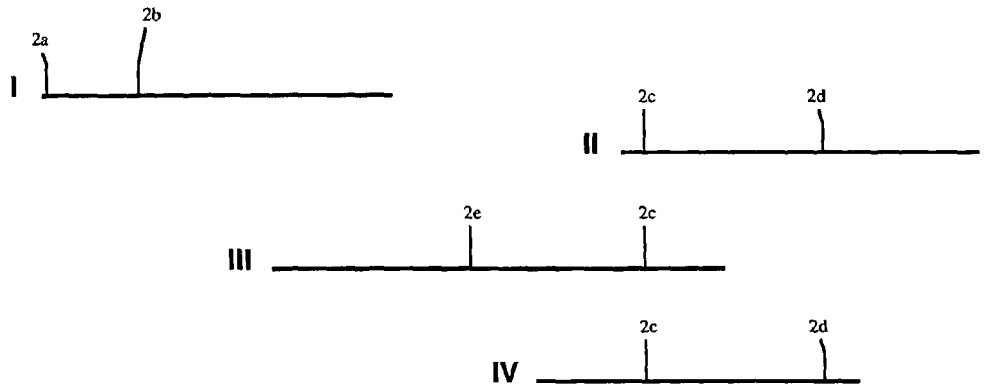
| BAC Clone # | 2 = AC | Concordance | 2 = AC | Discordance | 2 = AC |
|---|---|---|---|---|---|
| I | Doublet 2a, 2b | I & III | No overlap | I & II | 2a, b ≠ 2c, d |
| II | Doublet 2c, 2d | II & III | Doublet & Doublet (2c) | I & IV | 2a, b ≠ 2c, d |
| III | Doublet 2c, 2e | III & IV | Doublet & Doublet (2c) | | |
| IV | Doublet 2c, 2d | II & IV | Doublet & Doublet (2c, d) | | |
Order of *DrdI* islands in four BAC clones.
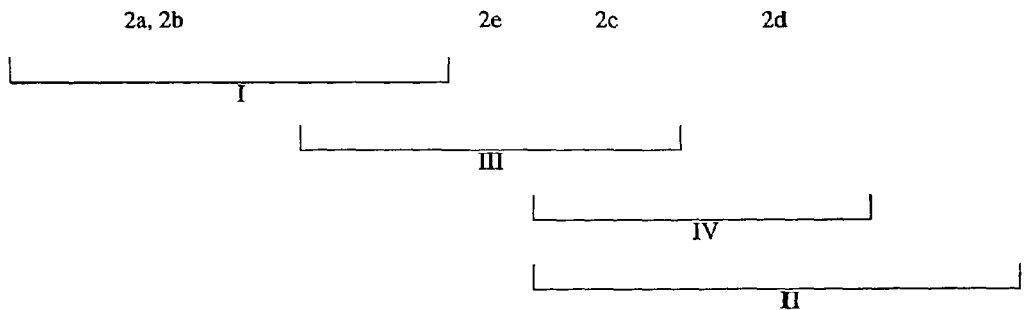
*FIG. 39*

**Overlapping *DrdI* islands in four hypothetical BAC clones: 3 AG overhangs**
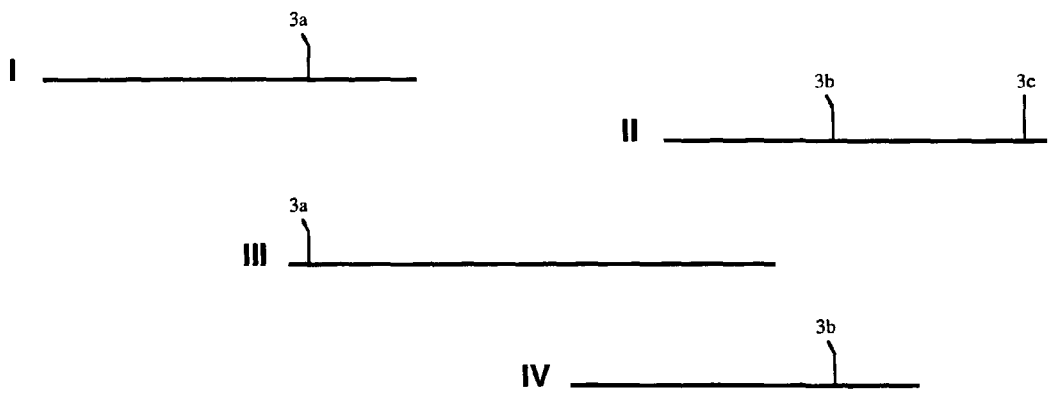
| BAC Clone # | 3 = AG | Concordance | 3 = AG | Discordance | 3 = AG |
|---|---|---|---|---|---|
| I | Singlet 3a | I & III | Singlet & Singlet (3a) | I & II | 3a ≠ 3b, c |
| II | Doublet 3b, 3c | II & III | No overlap | I & IV | 3a ≠ 3b |
| III | Singlet 3a | III & IV | No overlap | | |
| IV | Singlet 3b | II & IV | Doublet & Singlet (3b) | | |
Order of *DrdI* islands in four BAC clones.
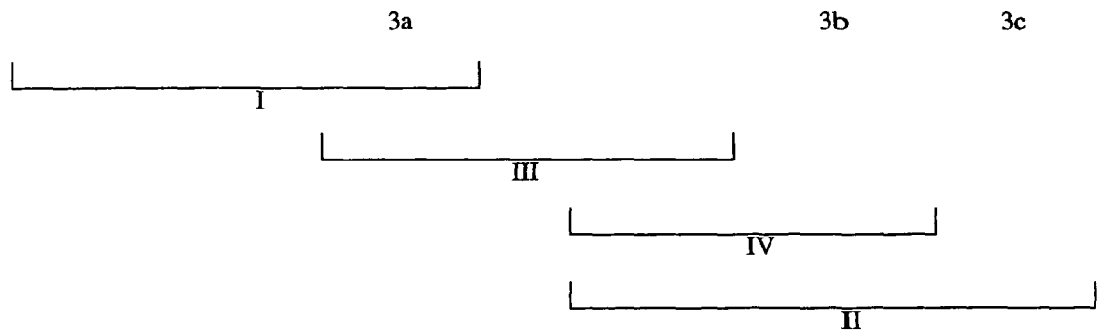
*FIG. 40*

**Overlapping *Drd*I islands in four hypothetical BAC clones: 4 CA overhangs**
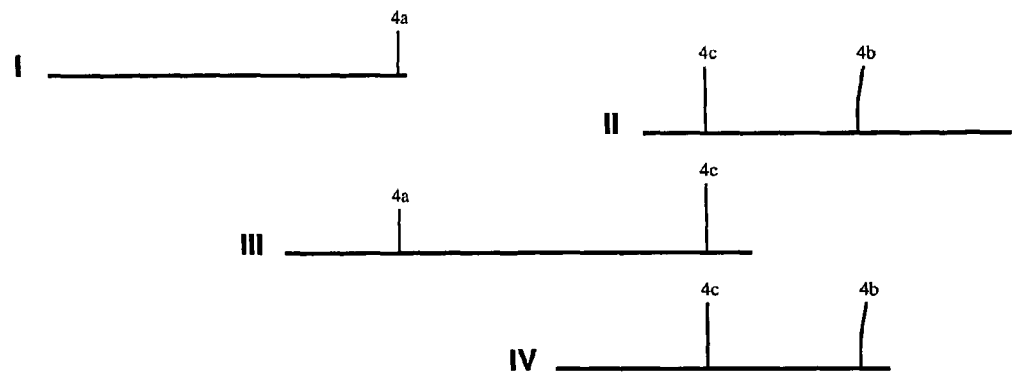
| BAC Clone # | 4 = CA | Concordance | 4 = CA | Discordance | 4 = CA |
|---|---|---|---|---|---|
| I | Singlet 4a | I & III | Singlet & Doublet (4a) | I & II | 4a ≠ 4b, c |
| II | Doublet 4b, 4c | II & III | Doublet & Doublet (4c) | I & IV | 4a ≠ 4b, c |
| III | Doublet 4a, 4c | III & IV | Doublet & Doublet (4c) | | |
| IV | Doublet 4b, 4c | II & IV | Doublet & Doublet (4b, c) | | |
Order of *Drd*I islands in four BAC clones.
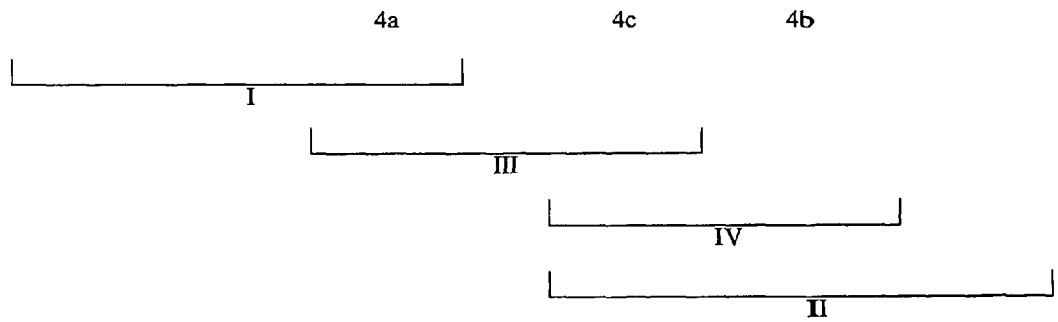
*FIG. 41*

**Overlapping *DrdI* islands in four hypothetical BAC clones: 5GA overhangs**
| BAC Clone # | 5 = GA | Concordance | 5 = GA | Discordance | 5 = GA |
|---|---|---|---|---|---|
| I | Triplet 5a, 5b, 5c | I & III | No overlap | I & II | 5a, b, c ≠ 5d, e |
| II | Doublet 5d, 5e | II & III | No overlap | I & IV | 5a, b, c ≠ 5d |
| III | No sequence | III & IV | No overlap | | |
| IV | Singlet 5d | II & IV | Doublet & Singlet (5d) | | |
Order of *DrdI* islands in four BAC clones.
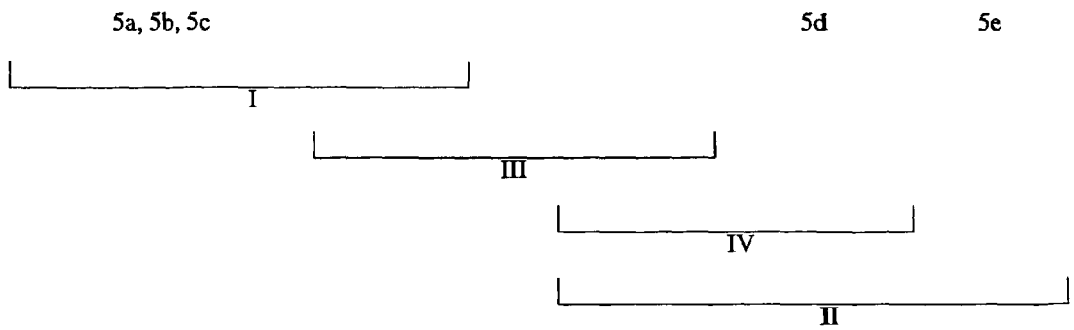
*FIG. 42*

**Overlapping *DrdI* islands in four hypothetical BAC clones: 6 GG overhang**
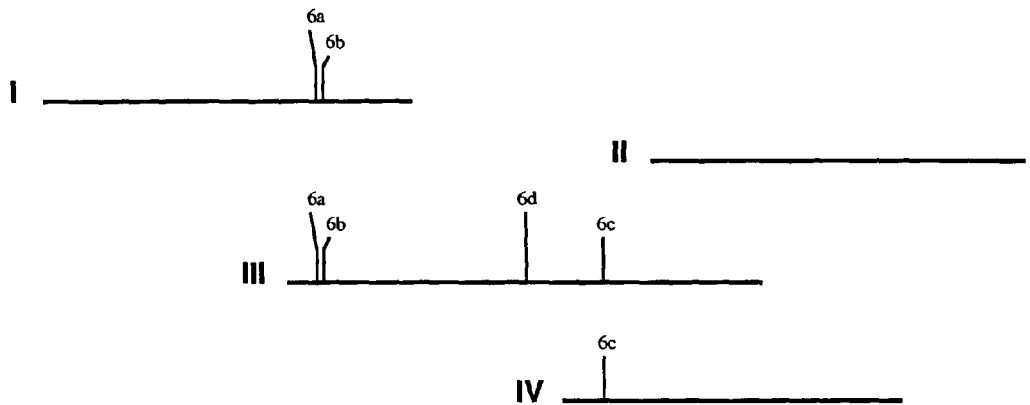
| BAC Clone # | 6 = GG | Concordance | 6 = GG | Discordance | 6 = GG |
|---|---|---|---|---|---|
| I | Doublet 6a, 6b | I & III | Indeterminant | I & II | - |
| II | No sequence | II & III | No overlap | I & IV | 6a, b ≠ 6c |
| III | Multiplet (6a, 6b, 6c, 6d) | III & IV | Indeterminant | | |
| IV | Singlet 6c | II & IV | No overlap | | |
Order of *DrdI* islands in four BAC clones.
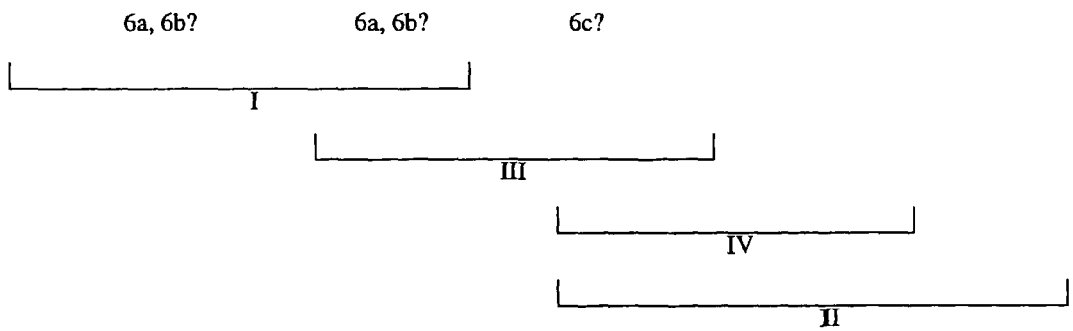
FIG. 43

*DrdI, TaqI* and *MspI* sites in overlapping BACs from 7q31
Contig 1941 (RG253B13, RG013N12, and RG300C03)

DrdI, MspI, TaqI

|  | AG | AC | CA | GA | AA | GG |
|---|---|---|---|---|---|---|
| RG253B13 | 546* | 502 | 559* | 3,419* | 192* | 864 |
|  | 353* | 381* |  |  | 597* | 4,918 |
|  |  |  |  |  |  |  |
| RG013N12 | 546* | 381* | 559* | 3,419* | 192* |  |
|  | 353* | 1,099 | 359 |  | 597* |  |
|  | 1,137† |  | 16† |  | 2,040 |  |
|  |  |  |  |  | 2,328† |  |
|  |  |  |  |  |  |  |
| RG300C03 | 1,1137† | 212 | 16† |  | 2,328† |  |
|  |  | 1,008 |  |  | 224 |  |
|  |  |  |  |  | 1,035 |  |
|  |  |  |  |  |  |  |
|  |  |  |  |  |  |  |
| pBeloBac11 |  |  | 141 | 360 | 66 |  |
|  |  |  |  | 691 |  |  |
|  |  |  |  |  |  |  |

|  | CT | GT | TG | TC | TT | CC |
|---|---|---|---|---|---|---|
| RG253B13 | 1620* | 4497 | 754* | 915* | 1794* | 3641 |
|  | 1631* | 50* |  |  | 296* | 1866 |
|  |  |  |  |  |  |  |
| RG013N12 | 1620* | 50* | 754* | 915* | 1794* |  |
|  | 1631* | 7278 | 1908 | 811 | 296* |  |
|  | 2077† |  | 183† |  | 525 |  |
|  |  |  |  |  | 372† |  |
|  |  |  |  |  |  |  |
| RG300C03 | 2077† | 282 | 183† |  | 372† |  |
|  |  |  |  |  | 1227 |  |
|  |  |  |  |  | 1103 |  |
|  |  |  |  |  |  |  |
|  |  |  |  |  |  |  |
| pBeloBac11 |  |  | 127 | 238 | 145 |  |
|  |  |  |  | 199 |  |  |
|  |  |  |  |  |  |  |

*Drd*I, *Taq*I and *Msp*I sites in overlapping BACs from 7q31
Contig T002144 (RG022J17, RG067E13, RG011J21, RG022C01, and RG043K06)

DrdI/MspI/TaqI

|            | AG     | AC     | CA    | GA     | AA     | GG     |
|------------|--------|--------|-------|--------|--------|--------|
| RG022J17   | 1,215* | 563    |       | 2,977  | 933    |        |
|            |        |        |       | 77*    | 2,608  |        |
|            |        |        |       | 142*   | 71*    |        |
|            |        |        |       | 4,502* | 492*   |        |
|            |        |        |       |        |        |        |
| RG067E13   | 1,215* | 2,001† |       | 77*    | 71*    |        |
|            |        |        |       | 142*   | 492*   |        |
|            |        |        |       | 4,502* |        |        |
|            |        |        |       |        |        |        |
| RG011J21   |        | 2,001† |       | 8      | 6,019‡ | 3,661‡ |
|            |        | 699    | 235   |        |        |        |
|            |        |        |       |        |        |        |
| RG022C01   |        |        |       |        | 6,019‡ | 3,661‡ |
|            |        |        |       |        | 2,043**|        |
|            |        |        |       |        |        |        |
| RG043K06   |        |        | 2,127 | 510    | 2,043**|        |
|            |        |        | 39    |        | 5,578  |        |
|            |        |        | 4     |        |        |        |
|            |        |        |       |        |        |        |
| pBeloBac11 |        |        | 141   | 360    | 66     |        |
|            |        |        |       | 691    |        |        |

DrdI/MspI/TaqI

|  | CT | GT | TG | TC | TT | CC |
|---|---|---|---|---|---|---|
| RG022J17 | 5335* |  | 1433 | 328 | 306 | 6* |
|  |  |  | 6190 | 1427* | 2216 |  |
|  |  |  |  | 663* | 114* |  |
|  |  |  |  | 2311* | 1470* |  |
|  |  |  |  |  |  |  |
| RG067E13 | 5335* | 571† |  | 1427* | 114* | 6* |
|  |  |  |  | 663* | 1470* |  |
|  |  |  |  | 2311* |  |  |
|  |  |  |  |  |  |  |
| RG011J21 | 544‡ | 571† | 4716 | 4298 |  | 2437‡ |
|  |  | 2399 | 2156 |  |  |  |
|  |  |  |  |  |  |  |
| RG022C01 | 544‡ |  |  |  | 5491** | 2437‡ |
|  |  |  |  |  |  |  |
|  |  |  |  |  |  |  |
| RG043K06 |  |  | 19 | 3213 | 5491** |  |
|  |  |  | 1510 |  | 1981 |  |
|  |  |  | 2821 |  |  |  |
|  |  |  |  |  |  |  |
| pBeloBac11 |  |  | 127 | 238 | 145 |  |
|  |  |  |  | 199 |  |  |

*Drd*I, *Taq*I and *Msp*I sites in overlapping BACs from 7q31
Contig T002149 (RG343P13, RG205G13, O68P20, and H-133K23)

DrdI/MspI/TaqI

|  | AG | AC | CA | GA | AA | GG |
|---|---|---|---|---|---|---|
| RG343P13 |  |  | 861 |  | 416 |  |
|  | 157* |  | 4 |  | 426* |  |
|  |  |  |  |  | 52* |  |
|  |  |  |  |  |  |  |
| RG205G13 | 157* | 396† |  |  | 426* |  |
|  |  |  |  |  | 52* |  |
|  |  |  |  |  |  |  |
| O68P20 | 825 | 396† | 155 | 241‡ | 517 | 749‡ |
|  |  |  | 1,178 | 119 |  |  |
|  |  |  | 285 |  |  |  |
|  |  |  | 2,758 |  |  |  |
|  |  |  | 1,161‡ |  |  |  |
|  |  |  |  |  |  |  |
| H_133K23 | 5984 |  | 1,161‡ | 241‡ |  | 749‡ |
|  | 804 |  |  |  |  |  |
|  |  |  |  |  |  |  |
|  |  |  |  |  |  |  |
| pBeloBac11 |  |  | 141 | 360 | 66 |  |
|  |  |  |  | 691 |  |  |

DrdI/MspI/TaqI

| | CT | GT | TG | TC | TT | CC |
|---|---|---|---|---|---|---|
| RG343P13 | 1348 | | 4 | 246 | 144 | |
| | 58* | | | | 110* | |
| | | | | | 45* | |
| | | | | | | |
| RG205G13 | 58* | | | | 110* | |
| | | | | | 45* | |
| | | | | | | |
| O68P20 | 1146 | | 61 | 488‡ | 2438 | 1567‡ |
| | | | 4573 | | 394 | |
| | | | 1456 | | | |
| | | | 1774 | | | |
| | | | 330‡ | | | |
| | | | | | | |
| H_133K23 | | | 330‡ | 488‡ | | 1567‡ |
| | | | | 3335 | | |
| | | | | 1181 | | |
| | | | | | | |
| pBeloBac11 | | | 127 | 238 | 145 | |
| | | | | 199 | | |

DrdI and MseI sites in overlapping BACs from 7q31
  Contig 1941 (RG253B13, RG013N12, and RG300C03)

Drd/MseI

|  | AG | AC | CA | GA | AA | GG |
|---|---|---|---|---|---|---|
| RG253B13 | 546* | 203 | 294 | 36* | 687* | 32 |
|  | 142* | 47* |  |  |  | 935 |
|  |  |  |  |  |  |  |
| RG013N12 | 546* | 47* | 404 | 36* | 687* |  |
|  | 142* | 195 | 277† | 103 | 325 |  |
|  | 39† |  |  |  | 24† |  |
|  |  |  |  |  |  |  |
| RG300C03 | 39† | 132 | 277† |  | 24† |  |
|  |  | 379 |  |  | 190 |  |
|  |  |  |  |  | 14 |  |
|  |  |  |  |  |  |  |
| pBeloBac11 |  |  | 87 | 484 | 344 |  |
|  |  |  |  | 136 |  |  |

DrdI, TaqI and MspI sites in overlapping BACs from 7q31
Contig T002144 (RG022J17, RG067E13, RG011J21, RG022C01, and RG043K06)

DrdI/MseI

|  | AG | AC | CA | GA | AA | GG |
|---|---|---|---|---|---|---|
| RG022J17 | 338* | 109 | 134 | 38 | 19 | 55* |
|  |  |  |  | 586* | 148 |  |
|  |  |  |  | 77* | 273* |  |
|  |  |  |  | 17* |  |  |
|  |  |  |  |  |  |  |
| RG067E13 | 338* | 71† |  | 586* | 273* | 55* |
|  |  |  |  | 77* |  |  |
|  |  |  |  | 17* |  |  |
|  |  |  |  |  |  |  |
| RG011J21 | 92‡ | 71† | 276 | 214 | 48‡ | 42‡ |
|  |  | 30 | 248 |  |  |  |
|  |  |  |  |  |  |  |
|  |  |  |  |  |  |  |
| RG022C01 | 92‡ |  |  |  | 48‡ | 42‡ |
|  |  |  |  |  |  |  |
|  |  |  |  |  |  |  |
| RG043K06 |  |  | 550 | 59 | 80 |  |
|  |  |  | 77 |  |  |  |
|  |  |  | 32 |  |  |  |
| pBeloBac11 |  |  | 87 | 484 | 344 |  |
|  |  |  |  | 136 |  |  |

DrdI/MseI

|  | CT | GT | TG | TC | TT | CC |
|---|---|---|---|---|---|---|
| RG022J17 | 368* |  | 329 | 70 | 33 | 163* |
|  |  |  | 186 | 84* | 182 |  |
|  |  |  |  | 36* | 296* |  |
|  |  |  |  | 57* | 59* |  |
|  |  |  |  |  |  |  |
| RG067E13 | 368* | 161† |  | 84* | 296* | 163* |
|  |  |  |  | 36* | 59* |  |
|  |  |  |  | 57* |  |  |
|  |  |  |  |  |  |  |
| RG011J21 | 41‡ | 161† | 45 | 49 | 270‡ | 101‡ |
|  |  | 46 | 30 |  |  |  |
|  |  |  |  |  |  |  |
| RG022C01 | 41‡ |  |  |  | 270‡ | 101‡ |
|  |  |  |  |  | 29** |  |
|  |  |  |  |  |  |  |
| RG043K06 |  |  | 76 | 12 | 29** |  |
|  |  |  | 35 |  | 65 |  |
|  |  |  | 51 |  |  |  |
|  |  |  |  |  |  |  |
| pBeloBac11 |  |  | 46 | 21 | 420 |  |
|  |  |  |  | 115 |  |  |

***DrdI* and *MseI* sites in overlapping BACs from 7q31.**
    Contig T002149 (RG343P13, RG205G13, O68P20, and H-133K23)

DrdI/MseI

|          | AG    | AC  | CA    | GA   | AA    | GG    |
|----------|-------|-----|-------|------|-------|-------|
| RG343P13 | 1076* |     | 597   |      | 102   |       |
|          |       |     | 184   |      | 648*  |       |
|          |       |     |       |      | 286*  |       |
|          |       |     |       |      |       |       |
| RG205G13 | 1076* | 89† |       |      | 648*  |       |
|          |       |     |       |      | 286*  |       |
|          |       |     |       |      |       |       |
| O68P20   | 59    | 89† | 134   | 21‡  | 26    | 168‡  |
|          |       |     | 62    |      | 63    |       |
|          |       |     | 22    |      |       |       |
|          |       |     | 206‡  |      |       |       |
|          |       |     |       |      |       |       |
| H_133K23 | 155   |     | 206‡  | 21‡  |       | 168‡  |
|          | 36    |     |       |      |       |       |
|          |       |     |       |      |       |       |
| pBeloBac11 |     |     | 87    | 484  | 344   |       |
|          |       |     |       | 136  |       |       |

DrdI/MseI

| | CT | GT | TG | TC | TT | CC |
|---|---|---|---|---|---|---|
| RG343P13 | 41 | | 129 | 73 | 53 | |
| | 53* | | 213 | | 489* | |
| | | | | | | |
| | | | | | | |
| RG205G13 | 53* | 51† | | | 489* | |
| | | | | | | |
| | | | | | | |
| O68P20 | 21 | 51† | 25 | 92‡ | 307 | 78‡ |
| | | | 48 | | 183 | |
| | | | 23 | | | |
| | | | 62 | | | |
| | | | 227‡ | | | |
| | | | | | | |
| H_133K23 | | | 227‡ | 92‡ | | 78‡ |
| | | | | 31 | | |
| | | | | 342 | | |
| | | | | | | |
| pBeloBac11 | | | 46 | 21 | 420 | |
| | | | | 115 | | |

RG253B13, 7q31 Met Oncogene
12 *Drd*I, 86 *Msp*I, and 62 *Taq*I Sites in 171,905 bp

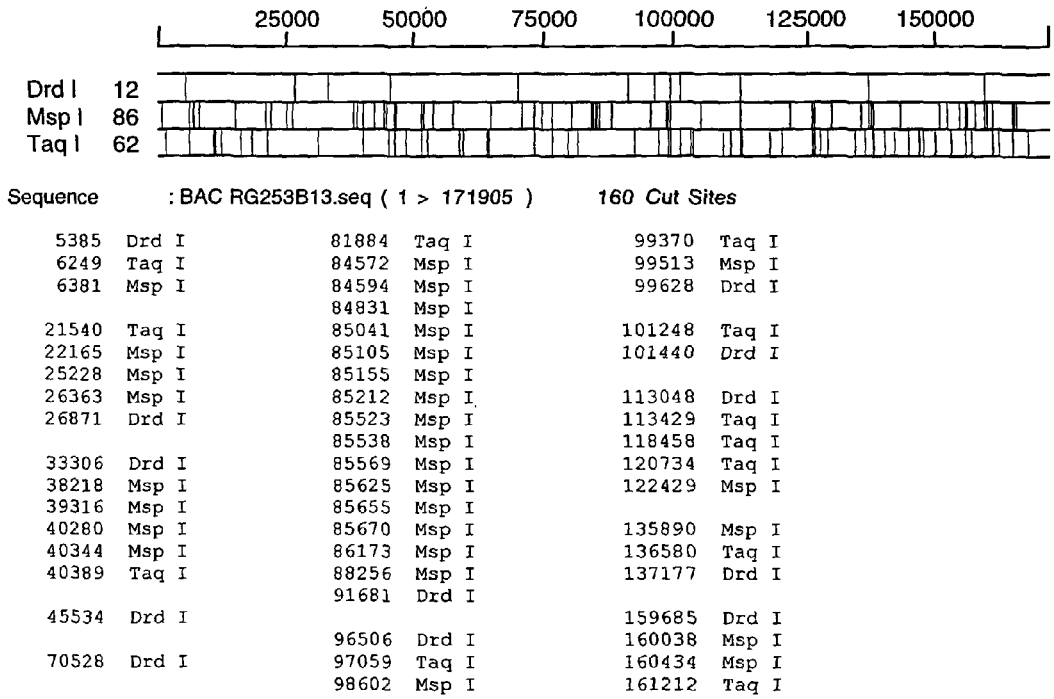

Sequence : BAC RG253B13.seq ( 1 > 171905 )    160 Cut Sites

| | | | | | |
|---|---|---|---|---|---|
| 5385 | Drd I | 81884 | Taq I | 99370 | Taq I |
| 6249 | Taq I | 84572 | Msp I | 99513 | Msp I |
| 6381 | Msp I | 84594 | Msp I | 99628 | Drd I |
| | | 84831 | Msp I | | |
| 21540 | Taq I | 85041 | Msp I | 101248 | Taq I |
| 22165 | Msp I | 85105 | Msp I | 101440 | Drd I |
| 25228 | Msp I | 85155 | Msp I | | |
| 26363 | Msp I | 85212 | Msp I | 113048 | Drd I |
| 26871 | Drd I | 85523 | Msp I | 113429 | Taq I |
| | | 85538 | Msp I | 118458 | Taq I |
| 33306 | Drd I | 85569 | Msp I | 120734 | Taq I |
| 38218 | Msp I | 85625 | Msp I | 122429 | Msp I |
| 39316 | Msp I | 85655 | Msp I | | |
| 40280 | Msp I | 85670 | Msp I | 135890 | Msp I |
| 40344 | Msp I | 86173 | Msp I | 136580 | Taq I |
| 40389 | Taq I | 88256 | Msp I | 137177 | Drd I |
| | | 91681 | Drd I | | |
| 45534 | Drd I | | | 159685 | Drd I |
| | | 96506 | Drd I | 160038 | Msp I |
| 70528 | Drd I | 97059 | Taq I | 160434 | Msp I |
| | | 98602 | Msp I | 161212 | Taq I |

For AA, AC, AG, CA, GA, and GG overhangs

| *Drd*I# | Location | Overhang | Complement | Nearest *Msp*I | Nearest *Taq*I | Fragment Length |
|---|---|---|---|---|---|---|
| 1. | 5,379 | GG* | CC | 6,381 | 6,249 | 864 |
| 2. | 26,865 | GT | AC* | 26,363 | 21,540 | 502 |
| 3. | 33,300 | GG* | CC | 38,218 | 40,389 | 4,918 |
| 4. | 45,528 | AT | AT | | | |
| 5. | 70,522 | AT | AT | | | |
| 6. | 91,675 | TC | GA* | 88,256 | 81,884 | 3,419 |
| 7. | 96,500 | CA* | TG | 98,602 | 97,059 | 559 |
| 8. | 99,622 | CT | AG* | 99,513 | 99,370 | 115 |
| 9. | 101,434 | TT | AA* | | 101,248 | 192 |
| 10. | 113,042 | AC* | GT | 122,429 | 113,429 | 381 |
| 11. | 137,171 | TT | AA* | 135,890 | 136,580 | 597 |
| 12. | 159,679 | AG* | CT | 160,038 | 161,212 | 353 |

* To obtain sequence information on AA, AC, AG, CA, GA, or GG overhangs in the sense direction, the *Drd*I island is amplified using a downstream *Msp*I or *Taq*I site. For such two base sequences on the complementary strand, the *Drd*I island is amplified using an upstream *Msp*I or *Taq*I site.

FIG. 48

PCR amplification of *DrdI* representation for shotgun cloning and generating mapped SNPs.

1. Cut genomic DNAs with *MspI, TaqI* and *DrdI* in the presence of linkers and T4 ligase. Linker for *DrdI* site is phosphorylated, methylated at internal *XmaI* site, and contains a 3' AA overhang. Linker for *MspI* site is phosphorylated, 3' blocked, methylated at internal *XhoI* site, and contains a bubble. Biochemical selection assures that most sites contain linkers.

2. Inactivate T4 ligase and restriction endonucleases at 95°C for 5 min. PCR amplify using unmethylated primers, dNTPs, and *Taq* polymerase. Conditions are optimized to amplify about 35,000 fragments at high yield while minimizing bias in the representation.

3. Cut PCR products with *XmaI* and *XhoI*, separate mixed fragments on an agarose gel, select and purify 200-1,000 bp fragments and clone into the corresponding sites of a standard vector. Sequence inserts to build mapped SNP database.

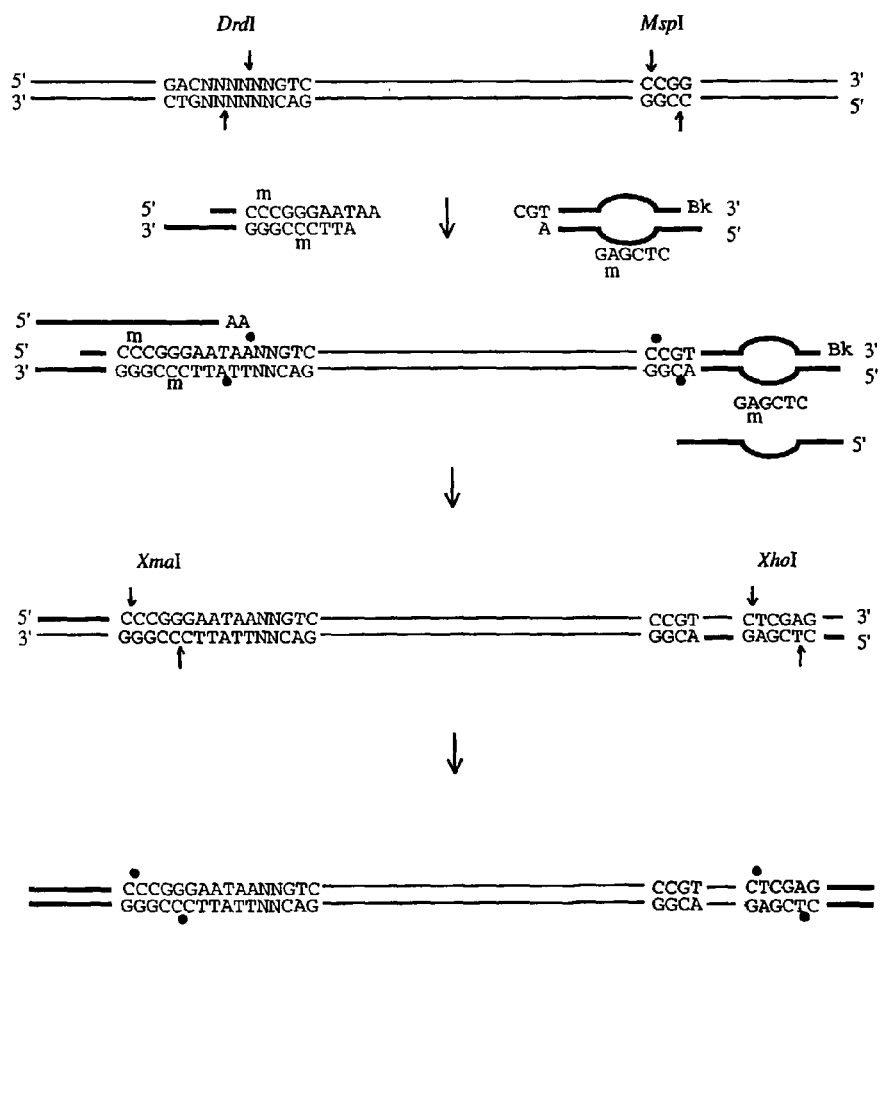

*FIG. 49A*

**PCR amplification of *DrdI* representation for high-throughput SNP detection.**

1. Cut genomic DNA with *MspI*, *TaqI* and *DrdI* in the presence of linkers and T4 ligase. Linker for *DrdI* site is phosphorylated and contains a 3' AA overhang. Linker for *MspI* site is not phosphorylated, and contains a bubble. Biochemical selection assures that most sites contain linkers.

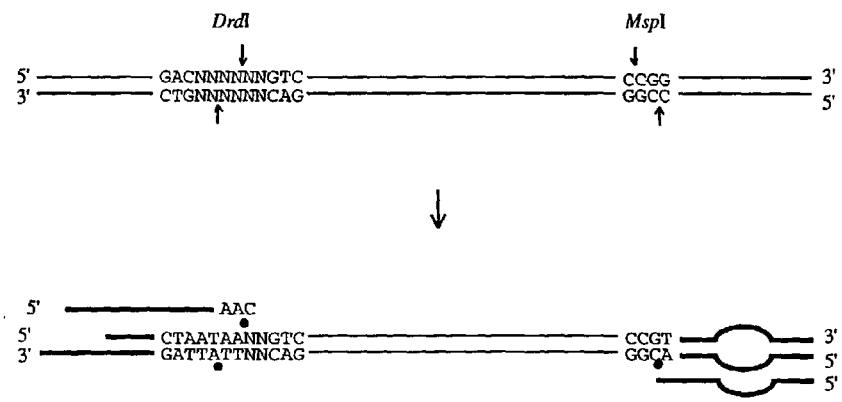

2. Inactivate T4 ligase and restriction endonucleases at 95°C for 5 min. PCR amplify using *DrdI* primer containing a 3' AAC overhang, dNTPs, and *Taq* polymerase. Conditions are optimized to amplify about 9,000 fragments at high yield while minimizing bias in the representation.

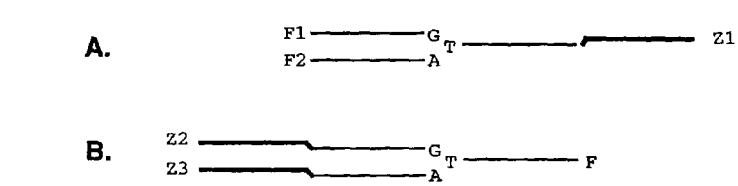

3. Add LDR primers and thermostable ligase to simultaneously detect SNPs at multiple loci. In (A) the common LDR primer contains zip-code Z1, the discriminating primers contain fluorescent labels F1 and F2, after array capture, ratio of F1/F2 determines presence of allele or allele imbalance. In (B) the common LDR primer contains fluorescent label F, the discriminating primers contain zip-codes Z2 and Z3, after array capture, ratio of fluorescence at Z2 and Z3 determines presence of allele or allele imbalance.

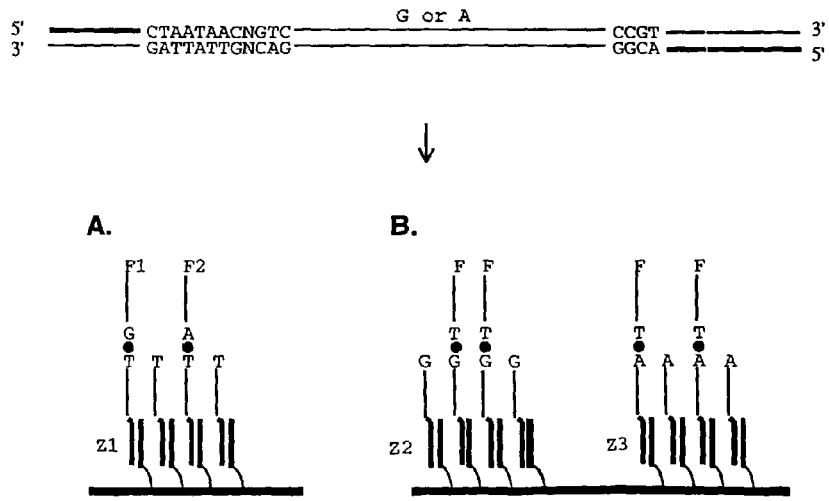

*FIG. 50*

PCR amplification of *DrdI* representation for high-throughput SNP detection.

1. Cut genomic DNA with *MspI*, *TaqI* and *DrdI* in the presence of linkers and T4 ligase. Linker for *DrdI* site is phosphorylated and contains a 3' AA overhang. Linker for *MspI* site is phosphorylated, 3' blocked and contains a bubble. Biochemical selection assures that most sites contain linkers.

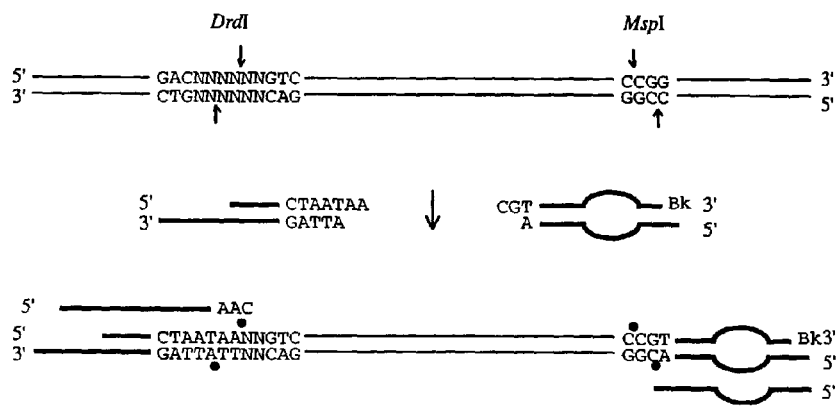

2. Inactivate T4 ligase and restriction endonucleases at 95°C for 5 min. PCR amplify using *DrdI* primer containing a 3' AAC overhang, dNTPs, and *Taq* polymerase. Conditions are optimized to amplify about 9,000 fragments at high yield while minimizing bias in the representation.

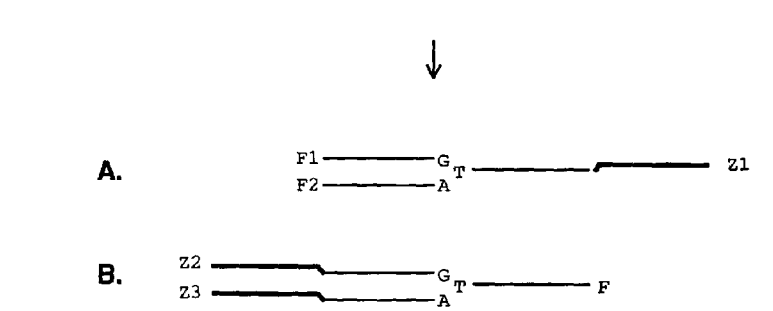

3. Add LDR primers and thermostable ligase to simultaneously detect SNPs at multiple loci. In (A) the common LDR primer contains zip-code Z1, the discriminating primers contain fluorescent labels F1 and F2, after array capture, ratio of F1/F2 determines presence of allele or allele imbalance. In (B) the common LDR primer contains fluorescent label F, the discriminating primers contain zip-codes Z2 and Z3, after array capture, ratio of fluorescence at Z2 and Z3 determines presence of allele or allele imbalance.

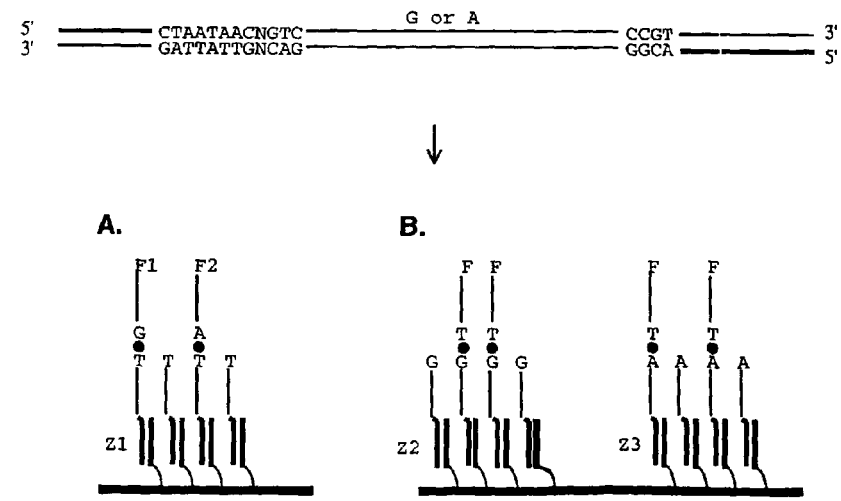

*FIG. 50A*

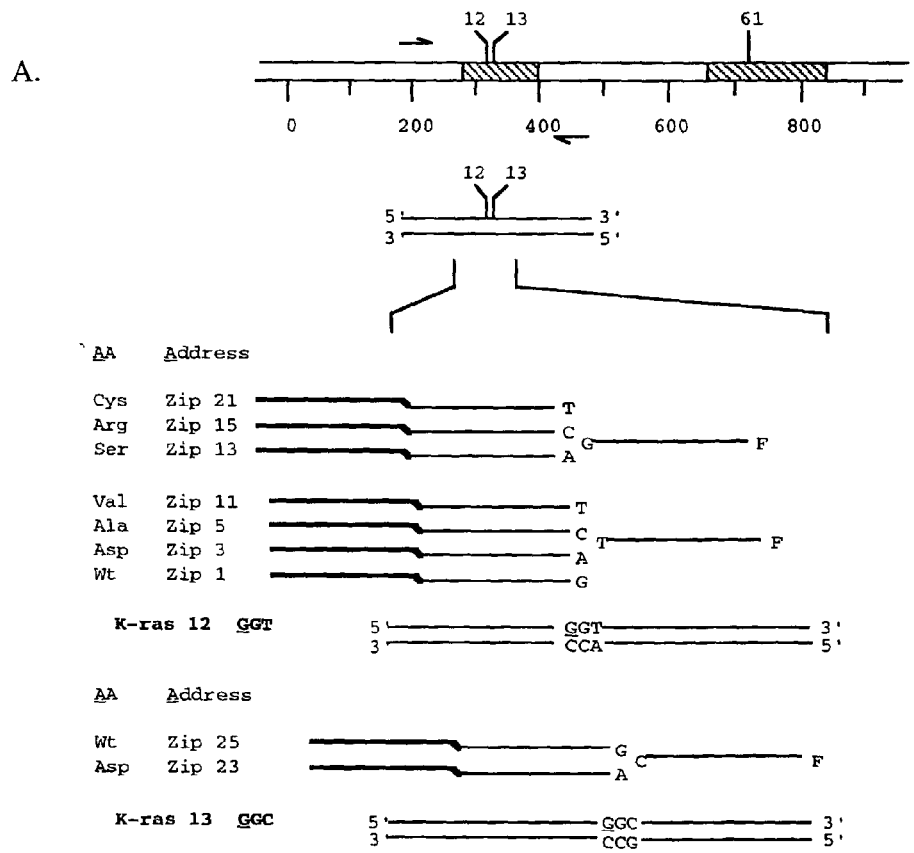
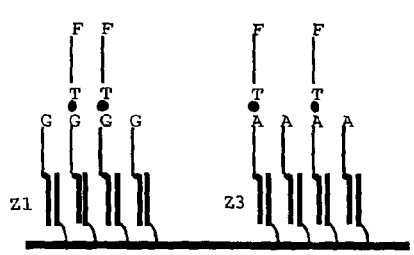
FIG. 52

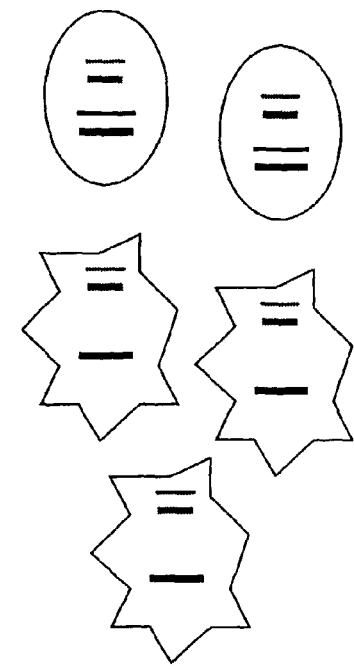
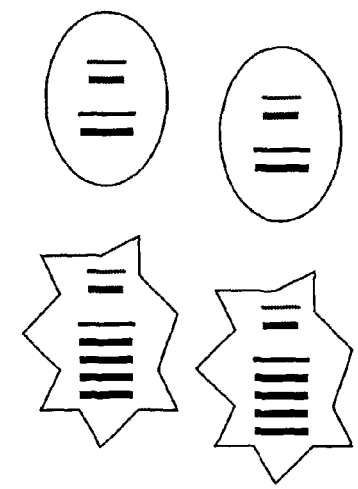
FIG. 55

| Ratio of Normal to | LDR Product (fmol) | | Ratio of LDR Products | |
|---|---|---|---|---|
| Mutant Template | Normal | Mutant | Absolute | Normalized |
| 1:1 | 32.2 | 51.7 | 0.62 | 1 : 1.0 |
| 1:2 | 11.8 | 41.9 | 0.28 | 1 : 2.2 |
| 1:3 | 13.7 | 64.2 | 0.21 | 1 : 3.0 |
| 1:4 | 12.8 | 78.4 | 0.16 | 1 : 3.9 |
| 1:6 | 6.5 | 70.2 | 0.09 | 1 : 6.7 |
| 1:1 | 32.2 | 51.7 | 0.62 | 1.0 : 1 |
| 2:1 | 41.6 | 33.1 | 1.26 | 2.0 : 1 |
| 3:1 | 34.1 | 18.5 | 1.84 | 3.0 : 1 |
| 4:1 | 42.7 | 18.1 | 2.36 | 3.8 : 1 |
| 6:1 | 64.4 | 18.4 | 3.50 | 5.7 : 1 |

PCR/LDR with Addressable Array Capture
A.
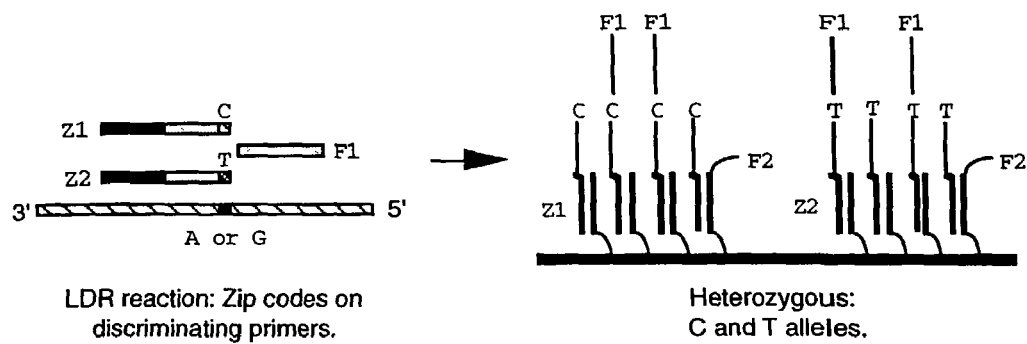
LDR reaction: Zip codes on discriminating primers.
Heterozygous: C and T alleles.
B.
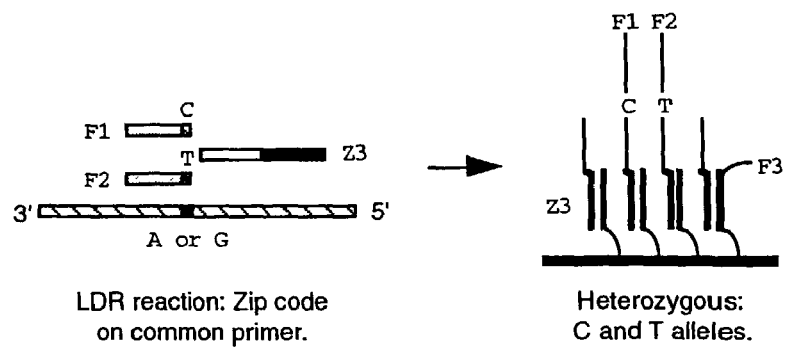
LDR reaction: Zip code on common primer.
Heterozygous: C and T alleles.
FIG. 57

PCR/SNUPE with Addressable Array Capture

A.

SNUPE reaction: Zip code on upstream primer, small percentage labeled with F3. Extend with polymerase and labeled dideoxynucleotides.

Heterozygous: C and T alleles.

PCR/LDR with Gene Array Capture
A.
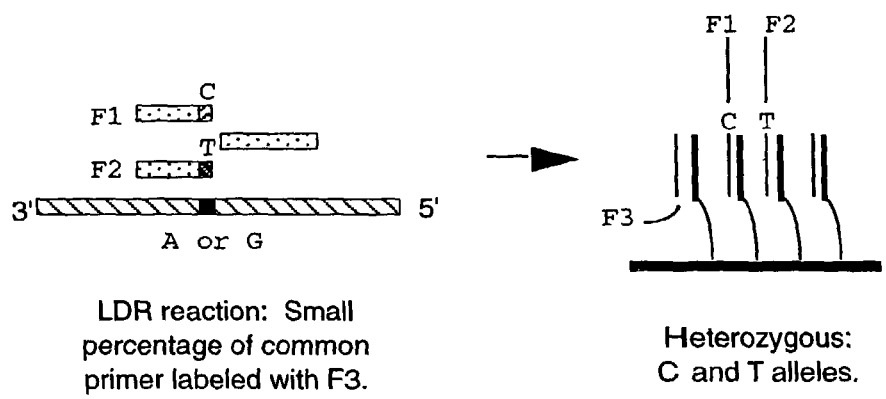
LDR reaction: Small percentage of common primer labeled with F3.
Heterozygous: C and T alleles.
B.
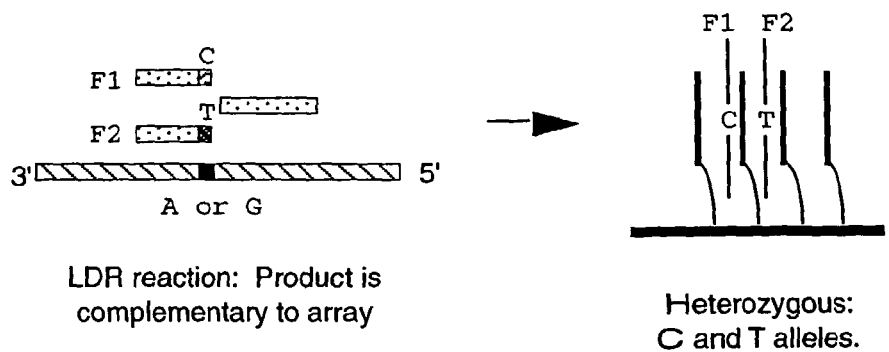
LDR reaction: Product is complementary to array
Heterozygous: C and T alleles.
*FIG. 59*

LDR/PCR with Addressable Array Capture

1. LDR reaction: Universal primer and unique Zip codes on 5' side of discriminating primers, universal primer on 3' side of common primer.

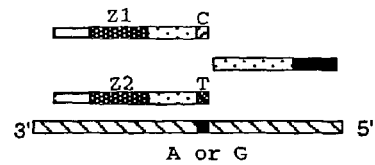

2. PCR reaction: Universal primers amplify multiplex LDR products simultaneously. One primer is fluorescently labeled.

3. Capture: Fluorescently labeled products are captured on addressable array at unique zipcode sequences.

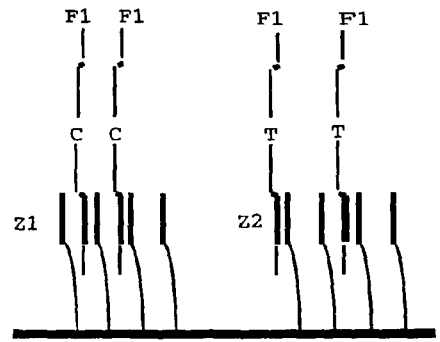

Heterozygous:
C and T alleles.

*FIG. 60*

LDR/PCR with Addressable Array Capture

1. LDR reaction: Universal primer and unique Zip codes on 5' side of discriminating primers, universal primer on 3' side of common primer.

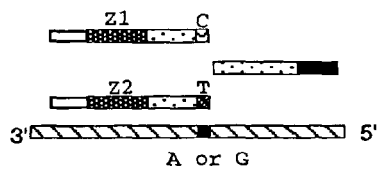

2. PCR reaction: Universal primers amplify multiplex LDR products simultaneously. One primer is fluorescently labeled, while the other contains a 5' phosphate. After PCR amplification, the phosphorylated strand is digested with lambda exonuclease leaving fluorescently labeled single-stranded DNA.

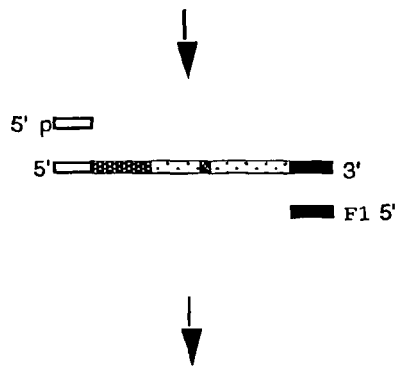

3. Capture: Fluorescently labeled products are captured on addressable array at unique zipcode sequences.

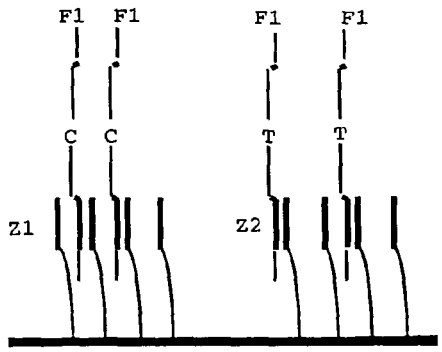

Heterozygous:
C and T alleles.

*FIG. 61*

PCR/LDR with Addressable Array Capture
A.
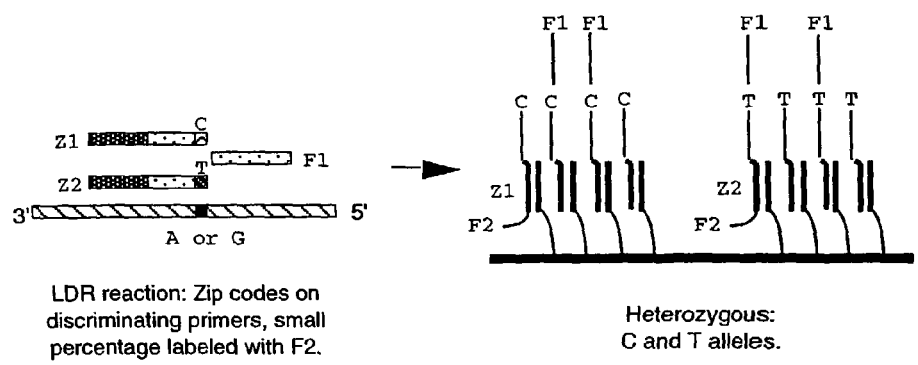
LDR reaction: Zip codes on discriminating primers, small percentage labeled with F2.
Heterozygous: C and T alleles.
B.
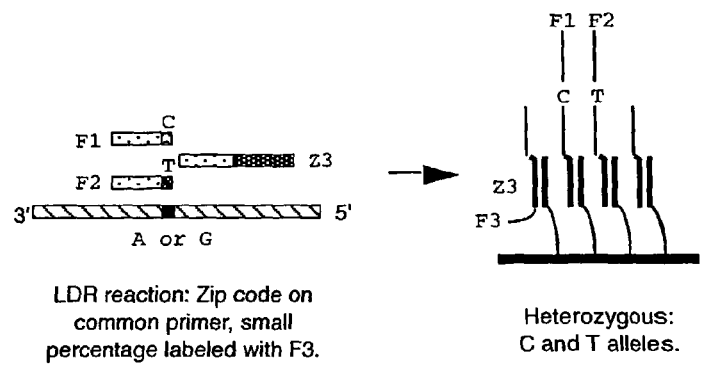
LDR reaction: Zip code on common primer, small percentage labeled with F3.
Heterozygous: C and T alleles.
*FIG. 62*

PCR/LDR with Addressable Array Capture: Detection of gene amplification using zip codes on the discriminating primers.

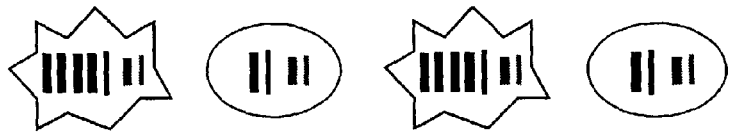

Tumor sample with 50% stromal contamination:

A. Tumor gene alleles: Ratio of C to T alleles = 10 / 4 = 2.5

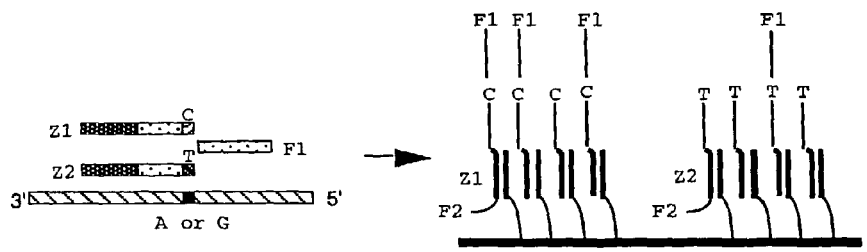

B. Control gene alleles: Ratio of G to A alleles = 4 / 4 = 1.0

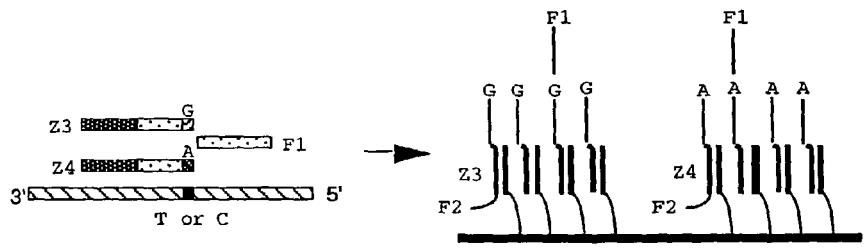

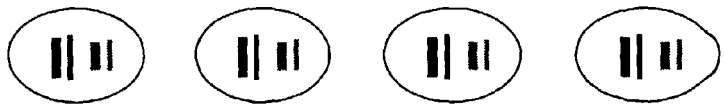

Normal sample with allele balance:

C. Tumor gene alleles: Ratio of C to T alleles = 4 / 4 = 1.0
D. Control gene alleles: Ratio of G to A alleles = 4 / 4 = 1.0

Ratio of Tumor to control allele / normal to control allele:

C : G Tumor / C : G Normal = 10 / 4 / 4 / 4 = 2.5

T : A Tumor / T : A Normal = 4 / 4 / 4 / 4 = 1.0

*FIG. 63*

PCR/LDR with Addressable Array Capture: Detection of gene amplification using zip codes on the common primers.

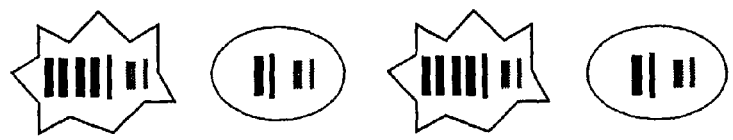

Tumor sample with 50% stromal contamination:

A. Tumor gene alleles: Ratio of C to T alleles = 10 / 4 = 2.5

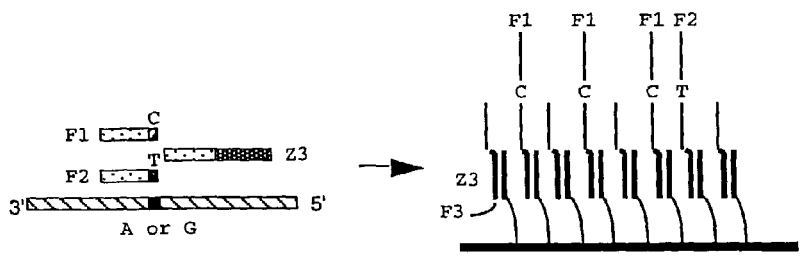

B. Control gene alleles: Ratio of G to A alleles = 4 / 4 = 1.0

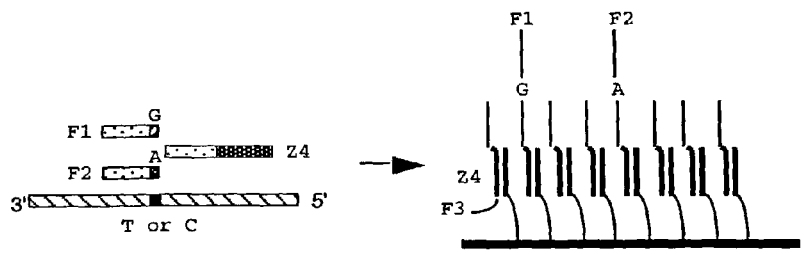

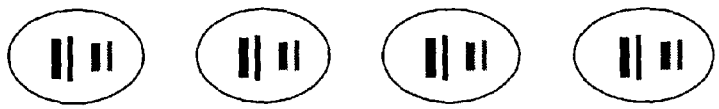

Normal sample with allele balance:

C. Tumor gene alleles: Ratio of C to T alleles = 4 / 4 = 1.0
D. Control gene alleles: Ratio of G to A alleles = 4 / 4 = 1.0

Ratio of Tumor to control allele / normal to control allele:

C : G Tumor / C : G Normal = 10 / 4 / 4 / 4 = 2.5

T : A Tumor / T : A Normal = 4 / 4 / 4 / 4 = 1.0

*FIG. 64*

PCR/LDR with Addressable Array Capture: Detection of loss of heterozygosity using zip codes on the discriminating primers.

Tumor sample with 40% stromal contamination:

A. Tumor gene alleles: Ratio of C to T alleles = 5 / 2 = 2.5

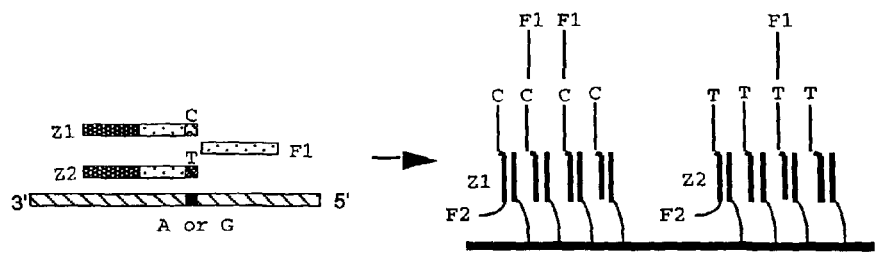

B. Control gene alleles: Ratio of G to A alleles = 5 / 5 = 1.0

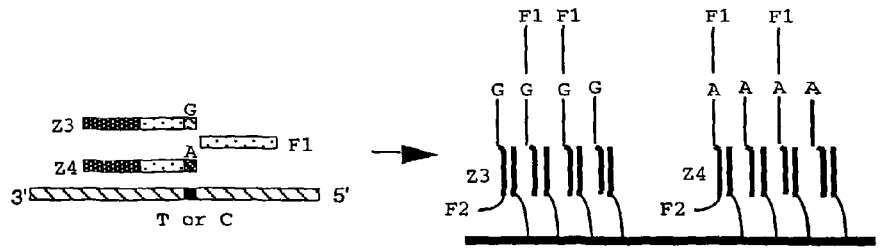

Normal sample with allele balance:

C. Tumor gene alleles: Ratio of C to T alleles = 5 / 5 = 1.0

D. Control gene alleles: Ratio of G to A alleles = 5 / 5 = 1.0

Ratio of Tumor to control allele / normal to control allele:

C : G Tumor / C : G Normal = 5 / 5 / 5 / 5 = 1.0

T : A Tumor / T : A Normal = 2 / 5 / 5 / 5 = 0.4

*FIG. 65*

PCR/LDR with Addressable Array Capture: Detection of loss of heterozygosity using zip codes on the common primers.

Tumor sample with 40% stromal contamination:

A. Tumor gene alleles: Ratio of C to T alleles = 5 / 2 = 2.5

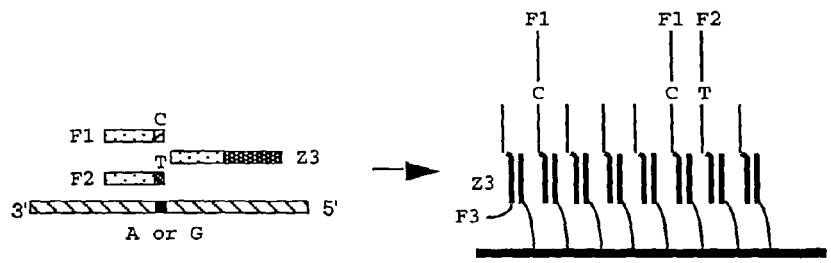

B. Control gene alleles: Ratio of G to A alleles = 5 / 5 = 1.0

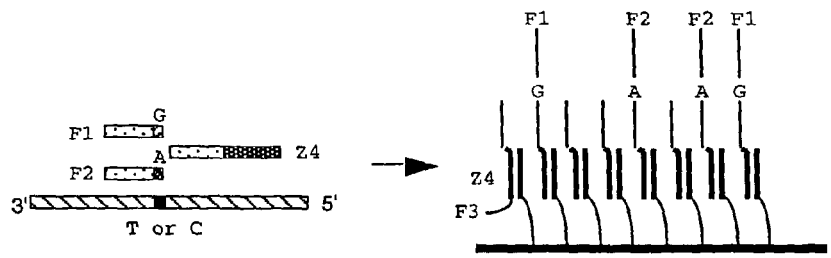

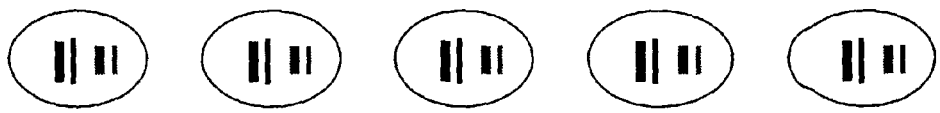

Normal sample with allele balance:

C. Tumor gene alleles: Ratio of C to T alleles = 5 / 5 = 1.0
D. Control gene alleles: Ratio of G to A alleles = 5 / 5 = 1.0

Ratio of Tumor to control allele / normal to control allele:

C : G Tumor / C : G Normal = 5 / 5 / 5 / 5 = 1.0

T : A Tumor / T : A Normal = 2 / 5 / 5 / 5 = 0.4

*FIG. 66*

Detection of gene amplification in tumor samples which contain stromal contamination using zip codes on the discriminating primers.

Tumor samples contains 10,000 tumor gene C alleles, and 4,000 tumor gene T alleles.

F1 for C allele (60% of 10,000)(45% capture at Z1) / F2 (10% of 100,000)(45% capture at Z1)
F1 for C allele (= 2,700) / F2 (= 4,500)
F1 for C allele / F2 = 0.60

F1 for T allele (40% of 4,000)(30% capture at Z2) / F2 (10% of 100,000)(30% capture at Z2)
F1 for T allele (= 480) / F2 ( = 3,000)
F1 for T allele / F2 = 0.16

Normal samples contains 4,000 tumor gene C alleles, and 4,000 tumor gene T alleles.

F1 for C allele (60% of 4,000)(35% capture at Z1) / F2 (10% of 100,000)(35% capture at Z1)
F1 for C allele (= 840) / F2 (= 3,500)
F1 for C allele / F2 = 0.24

F1 for T allele (40% of 4,000)(50% capture at Z2) / F2 (10% of 100,000)(50% capture at Z2)
F1 for T allele (= 800) / F2 ( = 5,000)
F1 for T allele / F2 = 0.16

Tumor sample contains 4,000 control gene G alleles, and 4,000 control gene A alleles.

F1 for G allele (45% of 4,000)(40% capture at Z3) / F2 (10% of 100,000)(40% capture at Z3)
F1 for G allele (= 720) / F2 (= 4,000)
F1 for G allele / F2 = 0.18

F1 for A allele (55% of 4,000)(60% capture at Z4) / F2 (10% of 100,000)(60% capture at Z4)
F1 for A allele (= 1320) / F2 (= 6,000)
F1 for A allele / F2 = 0.22

Normal sample contains 4,000 control gene G alleles, and 4,000 control gene A alleles.

F1 for G allele (45% of 4,000)(55% capture at Z3) / F2 (10% of 100,000)(55% capture at Z3)
F1 for G allele (= 990) / F2 (= 5,500)
F1 for G allele / F2 = 0.18

F1 for A allele (55% of 4,000)(45% capture at Z4) / F2 (10% of 100,000)(45% capture at Z4)
F1 for A allele (= 990) / F2 (=4,500)
F1 for A allele / F2 = 0.22

C : G Tumor / C : G Normal = ( 0.60 / 0.18 ) / (0.24 / 0.18 ) = 2.5
T : A Tumor / T : A Normal = (0.16 / 0.22 ) / (0.16 / 0.22 ) = 1

FIG. 67

Detection of gene amplification in tumor samples which contain stromal contamination using zip codes on the common primers.

Tumor samples contains 10,000 tumor gene C alleles, and 4,000 tumor gene T alleles.

F1 for C allele (60% of 10,000)(55% capture at Z3) / F2 (10% of 100,000)(55% capture at Z3)
F1 for C allele (= 3,300) / F2 (= 5,500)
F1 for C allele / F2 = 0.60

F1 for T allele (40% of 4,000)(55% capture at Z3) / F2 (10% of 100,000)(55% capture at Z3)
F1 for T allele (= 880) / F2 ( = 5,500)
F1 for T allele / F2 = 0.16

Normal samples contains 4,000 tumor gene C alleles, and 4,000 tumor gene T alleles.

F1 for C allele (60% of 4,000)(60% capture at Z3) / F2 (10% of 100,000)(60% capture at Z3)
F1 for C allele (= 1,440) / F2 (= 6,000)
F1 for C allele / F2 = 0.24

F1 for T allele (40% of 4,000)(60% capture at Z3) / F2 (10% of 100,000)(60% capture at Z3)
F1 for T allele (= 960) / F2 ( = 6,000)
F1 for T allele / F2 = 0.16

Tumor sample contains 4,000 control gene G alleles, and 4,000 control gene A alleles.

F1 for G allele (45% of 4,000)(35% capture at Z4) / F2 (10% of 100,000)(35% capture at Z4)
F1 for G allele (= 630) / F2 (= 3,500)
F1 for G allele / F2 = 0.18

F1 for A allele (55% of 4,000)(35% capture at Z4) / F2 (10% of 100,000)(35% capture at Z4)
F1 for A allele (= 770) / F2 (= 3,500)
F1 for A allele / F2 = 0.22

Normal sample contains 4,000 control gene G alleles, and 4,000 control gene A alleles.

F1 for G allele (45% of 4,000)(30% capture at Z4) / F2 (10% of 100,000)(30% capture at Z4)
F1 for G allele (= 540) / F2 (= 3,000)
F1 for G allele / F2 = 0.18

F1 for A allele (55% of 4,000)(30% capture at Z4) / F2 (10% of 100,000)(30% capture at Z4)
F1 for A allele (= 660) / F2 (=3,000)
F1 for A allele / F2 = 0.22

C : G Tumor / C : G Normal = ( 0.60 / 0.18 ) / (0.24 / 0.18 ) = 2.5
T : A Tumor / T : A Normal = (0.16 / 0.22 ) / (0.16 / 0.22 ) = 1

*FIG. 68*

Detection of loss of heterozygosity (LOH) in tumor samples which contain stromal contamination using zip codes on the discriminating primers.

Tumor samples contains 5,000 tumor gene C alleles, and 2,000 tumor gene T alleles.

F1 for C allele (60% of 5,000)(35% capture at Z1) / F2 (10% of 100,000)(35% capture at Z1)
F1 for C allele (= 1,050) / F2 (= 3,500)
F1 for C allele / F2 = 0.30

F1 for T allele (40% of 2,000)(55% capture at Z2) / F2 (10% of 100,000)(55% capture at Z2)
F1 for T allele (= 440) / F2 ( = 5,500)
F1 for T allele / F2 = 0.08

Normal samples contains 5,000 tumor gene C alleles, and 5,000 tumor gene T alleles.

F1 for C allele (60% of 5,000)(30% capture at Z1) / F2 (10% of 100,000)(30% capture at Z1)
F1 for C allele (= 900) / F2 (= 3,000)
F1 for C allele / F2 = 0.30

F1 for T allele (40% of 5,000)(40% capture at Z2) / F2 (10% of 100,000)(40% capture at Z2)
F1 for T allele (= 800) / F2 ( = 4,000)
F1 for T allele / F2 = 0.20

Tumor sample contains 5,000 control gene G alleles, and 5,000 control gene A alleles.

F1 for G allele (45% of 5,000)(45% capture at Z3) / F2 (10% of 100,000)(45% capture at Z3)
F1 for G allele (= 1,012) / F2 (= 4,500)
F1 for G allele / F2 = 0.22

F1 for A allele (55% of 5,000)(50% capture at Z4) / F2 (10% of 100,000)(50% capture at Z4)
F1 for A allele (= 1375) / F2 (= 5,000)
F1 for A allele / F2 = 0.27

Normal sample contains 5,000 control gene G alleles, and 5,000 control gene A alleles.

F1 for G allele (45% of 5,000)(30% capture at Z3) / F2 (10% of 100,000)(30% capture at Z3)
F1 for G allele (= 675) / F2 (= 3,000)
F1 for G allele / F2 = 0.22

F1 for A allele (55% of 5,000)(60% capture at Z4) / F2 (10% of 100,000)(60% capture at Z4)
F1 for A allele (= 1,650) / F2 (=6,000)
F1 for A allele / F2 = 0.27

C : G Tumor / C : G Normal = (0.30 / 0.22 ) / (0.30 / 0.22 ) = 1
T : A Tumor / T : A Normal = (0.08 / 0.27 ) / (0.20 / 0.27 ) = 0.4

*FIG. 69*

Detection of loss of heterozygosity (LOH) in tumor samples which contain stromal contamination using zip codes on the common primers.

Tumor samples contains 5,000 tumor gene C alleles, and 2,000 tumor gene T alleles.

F1 for C allele (60% of 5,000)(60% capture at Z3) / F2 (10% of 100,000)(60% capture at Z3)
F1 for C allele (= 1,800) / F2 (= 6,000)
F1 for C allele / F2 = 0.30

F1 for T allele (40% of 2,000)(60% capture at Z3) / F2 (10% of 100,000)(60% capture at Z3)
F1 for T allele (= 480) / F2 ( = 6,000)
F1 for T allele / F2 = 0.08

Normal samples contains 5,000 tumor gene C alleles, and 5,000 tumor gene T alleles.

F1 for C allele (60% of 5,000)(55% capture at Z3) / F2 (10% of 100,000)(55% capture at Z3)
F1 for C allele (= 1,650) / F2 (= 5,500)
F1 for C allele / F2 = 0.30

F1 for T allele (40% of 5,000)(55% capture at Z3) / F2 (10% of 100,000)(55% capture at Z3)
F1 for T allele (= 1,100) / F2 ( = 5,500)
F1 for T allele / F2 = 0.20

Tumor sample contains 5,000 control gene G alleles, and 5,000 control gene A alleles.

F1 for G allele (45% of 5,000)(40% capture at Z4) / F2 (10% of 100,000)(40% capture at Z4)
F1 for G allele (= 900) / F2 (= 4,000)
F1 for G allele / F2 = 0.22

F1 for A allele (55% of 5,000)(40% capture at Z4) / F2 (10% of 100,000)(40% capture at Z4)
F1 for A allele (= 1,100) / F2 (= 4,000)
F1 for A allele / F2 = 0.27

Normal sample contains 5,000 control gene G alleles, and 5,000 control gene A alleles.

F1 for G allele (45% of 5,000)(45% capture at Z4) / F2 (10% of 100,000)(45% capture at Z4)
F1 for G allele (= 1,012) / F2 (= 4,500)
F1 for G allele / F2 = 0.22

F1 for A allele (55% of 5,000)(45% capture at Z4) / F2 (10% of 100,000)(45% capture at Z4)
F1 for A allele (= 1,237) / F2 (=4,500)
F1 for A allele / F2 = 0.27

C : G Tumor / C : G Normal = (0.30 / 0.22 ) / (0.30 / 0.22 ) = 1
T : A Tumor / T : A Normal = (0.08 / 0.27 ) / (0.20 / 0.27 ) = 0.4

*FIG. 70*

SEQUENCE LISTING

```
<160> NUMBER OF SEQ ID NOS: 212

<210> SEQ ID NO 1
<211> LENGTH: 40
<212> TYPE: DNA
<213> ORGANISM: artificial
<220> FEATURE:
<223> OTHER INFORMATION: probe/primer

<400> SEQUENCE: 1
gattcgatcg tagcgtgtag caagtagcta attcgatcca                40

<210> SEQ ID NO 2
<211> LENGTH: 40
<212> TYPE: DNA
<213> ORGANISM: artificial
<220> FEATURE:
<223> OTHER INFORMATION: probe/primer

<400> SEQUENCE: 2
gattcgatcg tagcgtgtaa caagtagcta attcgatcca                40

<210> SEQ ID NO 3
<211> LENGTH: 80
<212> TYPE: DNA
<213> ORGANISM: artificial
<220> FEATURE:
<223> OTHER INFORMATION: probe/primer

<400> SEQUENCE: 3
tcgtcctcag gaactgaagc tatataatca gttaagtccc tgcttctgat ctcttctgat    60
tttcttctaa gaagagaata                                               80

<210> SEQ ID NO 4
<211> LENGTH: 80
<212> TYPE: DNA
<213> ORGANISM: artificial
<220> FEATURE:
<223> OTHER INFORMATION: probe/primer
```

<400> SEQUENCE: 4
gtgtcaagta aagaagtaca gcagataagt aaaacggaaa aaaataatga aagaattaca    60
aaggaagact aaggaaagag                                                80

<210> SEQ ID NO 5
<211> LENGTH: 80
<212> TYPE: DNA
<213> ORGANISM: artificial
<220> FEATURE:
<223> OTHER INFORMATION: probe/primer

<400> SEQUENCE: 5
aagtctacaa tcaagaggcc aactgattcc atgtctggtg agggtctatt tcctggtgca    60
tagatggctc cttctcactg                                                80

<210> SEQ ID NO 6
<211> LENGTH: 80
<212> TYPE: DNA
<213> ORGANISM: artificial
<220> FEATURE:
<223> OTHER INFORMATION: probe/primer

<400> SEQUENCE: 6
tagtcctcaa tttcaccatg gattaaataa cagaacacag agttactgtg agacttgtgg    60
tagaaaatct ttaattcatt                                                80

<210> SEQ ID NO 7
<211> LENGTH: 80
<212> TYPE: DNA
<213> ORGANISM: artificial
<220> FEATURE:
<223> OTHER INFORMATION: probe/primer

<400> SEQUENCE: 7
gtgtcatcta gctataaatc taaagataat aataaaattg gaaagatttt catcagatag    60
acttttaaca ccaagcttga                                                80

<210> SEQ ID NO 8
<211> LENGTH: 23
<212> TYPE: DNA
<213> ORGANISM: artificial
<220> FEATURE:
<223> OTHER INFORMATION: probe/primer

<400> SEQUENCE: 8
gacacgtcac gtctcgagtc cta                                            23

<210> SEQ ID NO 9
<211> LENGTH: 22
<212> TYPE: DNA
<213> ORGANISM: artificial
<220> FEATURE:
<223> OTHER INFORMATION: probe/primer

<400> SEQUENCE: 9
tgcagtgcaa cactcaggat gc                                             22

<210> SEQ ID NO 10
<211> LENGTH: 23
<212> TYPE: DNA
<213> ORGANISM: artificial
<220> FEATURE:
<223> OTHER INFORMATION: probe/primer

```
<400> SEQUENCE: 10
gacacgtcac gtctcgagtc cta                                          23

<210> SEQ ID NO 11
<211> LENGTH: 22
<212> TYPE: DNA
<213> ORGANISM: artificial
<220> FEATURE:
<223> OTHER INFORMATION: probe/primer

<400> SEQUENCE: 11
cgtaggactc acaacgtgac gt                                           22

<210> SEQ ID NO 12
<211> LENGTH: 22
<212> TYPE: DNA
<213> ORGANISM: artificial
<220> FEATURE:
<223> OTHER INFORMATION: probe/primer

<400> SEQUENCE: 12
cgtaggactc acaacgtgac gt                                           22

<210> SEQ ID NO 13
<211> LENGTH: 26
<212> TYPE: DNA
<213> ORGANISM: artificial
<220> FEATURE:
<223> OTHER INFORMATION: probe/primer

<400> SEQUENCE: 13
gacacgtcac gtctcgagtc ctsasc                                       26

<210> SEQ ID NO 14
<211> LENGTH: 24
<212> TYPE: DNA
<213> ORGANISM: artificial
<220> FEATURE:
<223> OTHER INFORMATION: probe/primer

<400> SEQUENCE: 14
gacacgtcac gtctcgagtc ctac                                         24

<210> SEQ ID NO 15
<211> LENGTH: 23
<212> TYPE: DNA
<213> ORGANISM: artificial
<220> FEATURE:
<223> OTHER INFORMATION: probe/primer

<400> SEQUENCE: 15
gacacgtcac gtctcgagtc ctc                                          23

<210> SEQ ID NO 16
<211> LENGTH: 22
<212> TYPE: DNA
<213> ORGANISM: artificial
<220> FEATURE:
<223> OTHER INFORMATION: probe/primer

<400> SEQUENCE: 16
tgcagtgcaa cactcaggag at                                           22

<210> SEQ ID NO 17
<211> LENGTH: 23
<212> TYPE: DNA
```

```
<213> ORGANISM: artificial
<220> FEATURE:
<223> OTHER INFORMATION: probe/primer

<400> SEQUENCE: 17
gacacgtcac gtctcgagtc ctc                                           23

<210> SEQ ID NO 18
<211> LENGTH: 22
<212> TYPE: DNA
<213> ORGANISM: artificial
<220> FEATURE:
<223> OTHER INFORMATION: probe/primer

<400> SEQUENCE: 18
tagaggactc acaacgtgac gt                                            22

<210> SEQ ID NO 19
<211> LENGTH: 22
<212> TYPE: DNA
<213> ORGANISM: artificial
<220> FEATURE:
<223> OTHER INFORMATION: probe/primer

<400> SEQUENCE: 19
tagaggactc acaacgtgac gt                                            22

<210> SEQ ID NO 20
<211> LENGTH: 26
<212> TYPE: DNA
<213> ORGANISM: artificial
<220> FEATURE:
<223> OTHER INFORMATION: probe/primer

<400> SEQUENCE: 20
gacacgtcac gtctcgagtc ctctaa                                        26

<210> SEQ ID NO 21
<211> LENGTH: 11
<212> TYPE: DNA
<213> ORGANISM: artificial
<220> FEATURE:
<223> OTHER INFORMATION: probe/primer
<220> FEATURE:
<221> NAME/KEY: misc_feature
<222> LOCATION: (4)..(8)
<223> OTHER INFORMATION: n is a, c, g, or t

<400> SEQUENCE: 21
gccnnnnngg c                                                        11

<210> SEQ ID NO 22
<211> LENGTH: 11
<212> TYPE: DNA
<213> ORGANISM: artificial
<220> FEATURE:
<223> OTHER INFORMATION: probe/primer
<220> FEATURE:
<221> NAME/KEY: misc_feature
<222> LOCATION: (4)..(8)
<223> OTHER INFORMATION: n is a, c, g, or t

<400> SEQUENCE: 22
gccnnnnngg c                                                        11

<210> SEQ ID NO 23
<211> LENGTH: 13
<212> TYPE: DNA
```

```
<213> ORGANISM: artificial
<220> FEATURE:
<223> OTHER INFORMATION: probe/primer
<220> FEATURE:
<221> NAME/KEY: misc_feature
<222> LOCATION: (8)..(13)
<223> OTHER INFORMATION: n is a, c, g, or t

<400> SEQUENCE: 23
gctcttcnnn nnn                                                          13

<210> SEQ ID NO 24
<211> LENGTH: 11
<212> TYPE: DNA
<213> ORGANISM: artificial
<220> FEATURE:
<223> OTHER INFORMATION: probe/primer
<220> FEATURE:
<221> NAME/KEY: misc_feature
<222> LOCATION: (4)..(8)
<223> OTHER INFORMATION: n is a, c, g, or t

<400> SEQUENCE: 24
ccannnnntg g                                                            11

<210> SEQ ID NO 25
<211> LENGTH: 18
<212> TYPE: DNA
<213> ORGANISM: artificial
<220> FEATURE:
<223> OTHER INFORMATION: probe/primer

<400> SEQUENCE: 25
gccagtcgga gcatcagg                                                     18

<210> SEQ ID NO 26
<211> LENGTH: 18
<212> TYPE: DNA
<213> ORGANISM: artificial
<220> FEATURE:
<223> OTHER INFORMATION: probe/primer

<400> SEQUENCE: 26
ccccgtggat aagtggat                                                     18

<210> SEQ ID NO 27
<211> LENGTH: 18
<212> TYPE: DNA
<213> ORGANISM: artificial
<220> FEATURE:
<223> OTHER INFORMATION: probe/primer

<400> SEQUENCE: 27
acacggctgc ggcgagcg                                                     18

<210> SEQ ID NO 28
<211> LENGTH: 18
<212> TYPE: DNA
<213> ORGANISM: artificial
<220> FEATURE:
<223> OTHER INFORMATION: probe/primer

<400> SEQUENCE: 28
gccgccgctg ctgctgac                                                     18

<210> SEQ ID NO 29
<211> LENGTH: 35
<212> TYPE: DNA
```

```
<213> ORGANISM: artificial
<220> FEATURE:
<223> OTHER INFORMATION: probe/primer

<400> SEQUENCE: 29
gscscsgscs csgctgctgc tgacggtgtg acgtt                        35

<210> SEQ ID NO 30
<211> LENGTH: 43
<212> TYPE: DNA
<213> ORGANISM: artificial
<220> FEATURE:
<223> OTHER INFORMATION: probe/primer

<400> SEQUENCE: 30
gsascstsgs tscatttgag ggtgatttgt cacactgaaa ggg               43

<210> SEQ ID NO 31
<211> LENGTH: 44
<212> TYPE: DNA
<213> ORGANISM: artificial
<220> FEATURE:
<223> OTHER INFORMATION: probe/primer

<400> SEQUENCE: 31
gsastsasgs tsctgagggt tatctgtcac agatttgagg gtgg              44

<210> SEQ ID NO 32
<211> LENGTH: 41
<212> TYPE: DNA
<213> ORGANISM: artificial
<220> FEATURE:
<223> OTHER INFORMATION: probe/primer

<400> SEQUENCE: 32
csastsasgs tscatgagca acagtttcaa tggccagtcg g                 41

<210> SEQ ID NO 33
<211> LENGTH: 12
<212> TYPE: DNA
<213> ORGANISM: artificial
<220> FEATURE:
<223> OTHER INFORMATION: probe/primer
<220> FEATURE:
<221> NAME/KEY: misc_feature
<222> LOCATION: (4)..(9)
<223> OTHER INFORMATION: n is a, c, g, or t

<400> SEQUENCE: 33
gacnnnnnng tc                                                 12

<210> SEQ ID NO 34
<211> LENGTH: 13
<212> TYPE: DNA
<213> ORGANISM: artificial
<220> FEATURE:
<223> OTHER INFORMATION: probe/primer
<220> FEATURE:
<221> NAME/KEY: misc_feature
<222> LOCATION: (9)..(10)
<223> OTHER INFORMATION: n is a, c, g, or t

<400> SEQUENCE: 34
gacaaaaann gtc                                                13

<210> SEQ ID NO 35
<211> LENGTH: 12
<212> TYPE: DNA
```

```
<213> ORGANISM: artificial
<220> FEATURE:
<223> OTHER INFORMATION: probe/primer
<220> FEATURE:
<221> NAME/KEY: misc_feature
<222> LOCATION: (8)..(9)
<223> OTHER INFORMATION: n is a, c, g, or t

<400> SEQUENCE: 35
gacaaacnng tc                                                          12

<210> SEQ ID NO 36
<211> LENGTH: 12
<212> TYPE: DNA
<213> ORGANISM: artificial
<220> FEATURE:
<223> OTHER INFORMATION: probe/primer
<220> FEATURE:
<221> NAME/KEY: misc_feature
<222> LOCATION: (8)..(9)
<223> OTHER INFORMATION: n is a, c, g, or t

<400> SEQUENCE: 36
gacaaagnng tc                                                          12

<210> SEQ ID NO 37
<211> LENGTH: 12
<212> TYPE: DNA
<213> ORGANISM: artificial
<220> FEATURE:
<223> OTHER INFORMATION: probe/primer
<220> FEATURE:
<221> NAME/KEY: misc_feature
<222> LOCATION: (11)..(12)
<223> OTHER INFORMATION: n is a, c, g, or t

<400> SEQUENCE: 37
tctgggaccc nn                                                          12

<210> SEQ ID NO 38
<211> LENGTH: 12
<212> TYPE: DNA
<213> ORGANISM: artificial
<220> FEATURE:
<223> OTHER INFORMATION: probe/primer

<400> SEQUENCE: 38
gacaaaaaag tc                                                          12

<210> SEQ ID NO 39
<211> LENGTH: 12
<212> TYPE: DNA
<213> ORGANISM: artificial
<220> FEATURE:
<223> OTHER INFORMATION: probe/primer

<400> SEQUENCE: 39 gactttttg tc                                                           12

<210> SEQ ID NO 40
<211> LENGTH: 25
<212> TYPE: DNA
<213> ORGANISM: artificial
<220> FEATURE:
<223> OTHER INFORMATION: probe/primer

<400> SEQUENCE: 40
gaatacccgg gatgactacg tgtaa                                            25
```

```
<210> SEQ ID NO 41
<211> LENGTH: 23
<212> TYPE: DNA
<213> ORGANISM: artificial
<220> FEATURE:
<223> OTHER INFORMATION: probe/primer

<400> SEQUENCE: 41
acacgtagtc atcccgggta ttc                                              23

<210> SEQ ID NO 42
<211> LENGTH: 27
<212> TYPE: DNA
<213> ORGANISM: artificial
<220> FEATURE:
<223> OTHER INFORMATION: probe/primer

<400> SEQUENCE: 42
gaatacccgg gatgactacg tgtsasa                                          27

<210> SEQ ID NO 43
<211> LENGTH: 24
<212> TYPE: DNA
<213> ORGANISM: artificial
<220> FEATURE:
<223> OTHER INFORMATION: probe/primer

<400> SEQUENCE: 43
gatacccggg atgagtacga caac                                             24

<210> SEQ ID NO 44
<211> LENGTH: 22
<212> TYPE: DNA
<213> ORGANISM: artificial
<220> FEATURE:
<223> OTHER INFORMATION: probe/primer

<400> SEQUENCE: 44
tgtcgtactc atcccgggta tc                                               22

<210> SEQ ID NO 45
<211> LENGTH: 26
<212> TYPE: DNA
<213> ORGANISM: artificial
<220> FEATURE:
<223> OTHER INFORMATION: probe/primer

<400> SEQUENCE: 45
gatacccggg atgagtacga casasc                                           26

<210> SEQ ID NO 46
<211> LENGTH: 24
<212> TYPE: DNA
<213> ORGANISM: artificial
<220> FEATURE:
<223> OTHER INFORMATION: probe/primer

<400> SEQUENCE: 46
gatacccggg atgagtacgt caag                                             24

<210> SEQ ID NO 47
<211> LENGTH: 22
<212> TYPE: DNA
<213> ORGANISM: artificial
<220> FEATURE:
<223> OTHER INFORMATION: probe/primer
```

```
<400> SEQUENCE: 47
tgacgtactc atcccgggta tc                                    22

<210> SEQ ID NO 48
<211> LENGTH: 26
<212> TYPE: DNA
<213> ORGANISM: artificial
<220> FEATURE:
<223> OTHER INFORMATION: probe/primer

<400> SEQUENCE: 48
gatacccggg atgagtacgt casasg                                26

<210> SEQ ID NO 49
<211> LENGTH: 25
<212> TYPE: DNA
<213> ORGANISM: artificial
<220> FEATURE:
<223> OTHER INFORMATION: probe/primer

<400> SEQUENCE: 49
gattacccgg gatgactacg tatca                                 25

<210> SEQ ID NO 50
<211> LENGTH: 23
<212> TYPE: DNA
<213> ORGANISM: artificial
<220> FEATURE:
<223> OTHER INFORMATION: probe/primer

<400> SEQUENCE: 50
atacgtagtc atcccgggta atc                                   23

<210> SEQ ID NO 51
<211> LENGTH: 27
<212> TYPE: DNA
<213> ORGANISM: artificial
<220> FEATURE:
<223> OTHER INFORMATION: probe/primer

<400> SEQUENCE: 51
gattacccgg gatgactacg tatscsa                               27

<210> SEQ ID NO 52
<211> LENGTH: 25
<212> TYPE: DNA
<213> ORGANISM: artificial
<220> FEATURE:
<223> OTHER INFORMATION: probe/primer

<400> SEQUENCE: 52
gattacccgg gatgactacg tatga                                 25

<210> SEQ ID NO 53
<211> LENGTH: 27
<212> TYPE: DNA
<213> ORGANISM: artificial
<220> FEATURE:
<223> OTHER INFORMATION: probe/primer

<400> SEQUENCE: 53
gattacccgg gatgactacg tatsgsa                               27

<210> SEQ ID NO 54
<211> LENGTH: 25
<212> TYPE: DNA
```

```
<213> ORGANISM: artificial
<220> FEATURE:
<223> OTHER INFORMATION: probe/primer

<400> SEQUENCE: 54
gattacccgg gatgactacg tatgg                                          25

<210> SEQ ID NO 55
<211> LENGTH: 27
<212> TYPE: DNA
<213> ORGANISM: artificial
<220> FEATURE:
<223> OTHER INFORMATION: probe/primer

<400> SEQUENCE: 55
gattacccgg gtagactacg tatsgsg                                        27

<210> SEQ ID NO 56
<211> LENGTH: 23
<212> TYPE: DNA
<213> ORGANISM: artificial
<220> FEATURE:
<223> OTHER INFORMATION: probe/primer

<400> SEQUENCE: 56
gacacgtcac gtctcgagtc cta                                            23

<210> SEQ ID NO 57
<211> LENGTH: 22
<212> TYPE: DNA
<213> ORGANISM: artificial
<220> FEATURE:
<223> OTHER INFORMATION: probe/primer

<400> SEQUENCE: 57
cgtaggactc acaacgtgac gt                                             22

<210> SEQ ID NO 58
<211> LENGTH: 22
<212> TYPE: DNA
<213> ORGANISM: artificial
<220> FEATURE:
<223> OTHER INFORMATION: probe/primer

<400> SEQUENCE: 58
cgtaggactc acaacgtgac gt                                             22

<210> SEQ ID NO 59
<211> LENGTH: 26
<212> TYPE: DNA
<213> ORGANISM: artificial
<220> FEATURE:
<223> OTHER INFORMATION: probe/primer

<400> SEQUENCE: 59
gacacgtcac gtctcgagtc ctsasc                                         26

<210> SEQ ID NO 60
<211> LENGTH: 24
<212> TYPE: DNA
<213> ORGANISM: artificial
<220> FEATURE:
<223> OTHER INFORMATION: probe/primer

<400> SEQUENCE: 60
gacacgtcac gtctcgagtc ctac                                           24
```

```
<210> SEQ ID NO 61
<211> LENGTH: 25
<212> TYPE: DNA
<213> ORGANISM: artificial
<220> FEATURE:
<223> OTHER INFORMATION: probe/primer

<400> SEQUENCE: 61
gaatacaagg gatgactacg tgtaa                                             25

<210> SEQ ID NO 62
<211> LENGTH: 23
<212> TYPE: DNA
<213> ORGANISM: artificial
<220> FEATURE:
<223> OTHER INFORMATION: probe/primer

<400> SEQUENCE: 62
acacgtagtc atcccgggta ttc                                               23

<210> SEQ ID NO 63
<211> LENGTH: 27
<212> TYPE: DNA
<213> ORGANISM: artificial
<220> FEATURE:
<223> OTHER INFORMATION: probe/primer

<400> SEQUENCE: 63
gaatacccgg gatgactacg tgtsasa                                           27

<210> SEQ ID NO 64
<211> LENGTH: 24
<212> TYPE: DNA
<213> ORGANISM: artificial
<220> FEATURE:
<223> OTHER INFORMATION: probe/primer

<400> SEQUENCE: 64
gatacaaggg atgagtacga caac                                              24

<210> SEQ ID NO 65
<211> LENGTH: 22
<212> TYPE: DNA
<213> ORGANISM: artificial
<220> FEATURE:
<223> OTHER INFORMATION: probe/primer

<400> SEQUENCE: 65
tgtcgtactc atcccgggta tc                                                22

<210> SEQ ID NO 66
<211> LENGTH: 26
<212> TYPE: DNA
<213> ORGANISM: artificial
<220> FEATURE:
<223> OTHER INFORMATION: probe/primer

<400> SEQUENCE: 66
gatacccggg atgagtacga casasc                                            26

<210> SEQ ID NO 67
<211> LENGTH: 24
<212> TYPE: DNA
<213> ORGANISM: artificial
<220> FEATURE:
<223> OTHER INFORMATION: probe/primer
```

-continued

<400> SEQUENCE: 67
gatacaaggg atgagtacgt caag                                      24

<210> SEQ ID NO 68
<211> LENGTH: 22
<212> TYPE: DNA
<213> ORGANISM: artificial
<220> FEATURE:
<223> OTHER INFORMATION: probe/primer

<400> SEQUENCE: 68
tgacgtactc atcccgggta tc                                        22

<210> SEQ ID NO 69
<211> LENGTH: 26
<212> TYPE: DNA
<213> ORGANISM: artificial
<220> FEATURE:
<223> OTHER INFORMATION: probe/primer

<400> SEQUENCE: 69
gatacccggg atgagtacgt casasg                                    26

<210> SEQ ID NO 70
<211> LENGTH: 25
<212> TYPE: DNA
<213> ORGANISM: artificial
<220> FEATURE:
<223> OTHER INFORMATION: probe/primer

<400> SEQUENCE: 70
gattacaagg gatgactacg tatca                                     25

<210> SEQ ID NO 71
<211> LENGTH: 23
<212> TYPE: DNA
<213> ORGANISM: artificial
<220> FEATURE:
<223> OTHER INFORMATION: probe/primer

<400> SEQUENCE: 71
atacgtagtc atcccgggta atc                                       23

<210> SEQ ID NO 72
<211> LENGTH: 27
<212> TYPE: DNA
<213> ORGANISM: artificial
<220> FEATURE:
<223> OTHER INFORMATION: probe/primer

<400> SEQUENCE: 72
gattacccgg gatgactacg tatscsa                                   27

<210> SEQ ID NO 73
<211> LENGTH: 25
<212> TYPE: DNA
<213> ORGANISM: artificial
<220> FEATURE:
<223> OTHER INFORMATION: probe/primer

<400> SEQUENCE: 73
gattacaagg gatgactacg tatga                                     25

<210> SEQ ID NO 74
<211> LENGTH: 27
<212> TYPE: DNA

```
<213> ORGANISM: artificial
<220> FEATURE:
<223> OTHER INFORMATION: probe/primer

<400> SEQUENCE: 74
gattacccgg gatgactacg tatsgsa                                  27

<210> SEQ ID NO 75
<211> LENGTH: 25
<212> TYPE: DNA
<213> ORGANISM: artificial
<220> FEATURE:
<223> OTHER INFORMATION: probe/primer

<400> SEQUENCE: 75
gattacaagg gatgactacg tatgg                                    25

<210> SEQ ID NO 76
<211> LENGTH: 27
<212> TYPE: DNA
<213> ORGANISM: artificial
<220> FEATURE:
<223> OTHER INFORMATION: probe/primer

<400> SEQUENCE: 76
gattacccgg gtagactacg tatsgsg                                  27

<210> SEQ ID NO 77
<211> LENGTH: 17
<212> TYPE: DNA
<213> ORGANISM: artificial
<220> FEATURE:
<223> OTHER INFORMATION: probe/primer

<400> SEQUENCE: 77
tagactgcgt actctaa                                             17

<210> SEQ ID NO 78
<211> LENGTH: 24
<212> TYPE: DNA
<213> ORGANISM: artificial
<220> FEATURE:
<223> OTHER INFORMATION: probe/primer

<400> SEQUENCE: 78
agagtacgca gtctacgact cagg                                     24

<210> SEQ ID NO 79
<211> LENGTH: 26
<212> TYPE: DNA
<213> ORGANISM: artificial
<220> FEATURE:
<223> OTHER INFORMATION: probe/primer

<400> SEQUENCE: 79
cctgagtcgt agactgcgta ctctaa                                   26

<210> SEQ ID NO 80
<211> LENGTH: 26
<212> TYPE: DNA
<213> ORGANISM: artificial
<220> FEATURE:
<223> OTHER INFORMATION: probe/primer

<400> SEQUENCE: 80
cctgagtcgt agactgcgta ctctaa                                   26
```

```
<210> SEQ ID NO 81
<211> LENGTH: 17
<212> TYPE: DNA
<213> ORGANISM: artificial
<220> FEATURE:
<223> OTHER INFORMATION: probe/primer

<400> SEQUENCE: 81
tagactgcgt actctac                                                    17

<210> SEQ ID NO 82
<211> LENGTH: 26
<212> TYPE: DNA
<213> ORGANISM: artificial
<220> FEATURE:
<223> OTHER INFORMATION: probe/primer

<400> SEQUENCE: 82
cctgagtcgt agactgcgta ctctac                                          26

<210> SEQ ID NO 83
<211> LENGTH: 26
<212> TYPE: DNA
<213> ORGANISM: artificial
<220> FEATURE:
<223> OTHER INFORMATION: probe/primer

<400> SEQUENCE: 83
cctgagtcgt agactgcgta ctctac                                          26

<210> SEQ ID NO 84
<211> LENGTH: 17
<212> TYPE: DNA
<213> ORGANISM: artificial
<220> FEATURE:
<223> OTHER INFORMATION: probe/primer

<400> SEQUENCE: 84
tagactgcgt actcaag                                                    17

<210> SEQ ID NO 85
<211> LENGTH: 26
<212> TYPE: DNA
<213> ORGANISM: artificial
<220> FEATURE:
<223> OTHER INFORMATION: probe/primer

<400> SEQUENCE: 85
actgagtcgt agactgcgta ctcaag                                          26

<210> SEQ ID NO 86
<211> LENGTH: 24
<212> TYPE: DNA
<213> ORGANISM: artificial
<220> FEATURE:
<223> OTHER INFORMATION: probe/primer

<400> SEQUENCE: 86
tgagtacgca gtctacgact cagt                                            24

<210> SEQ ID NO 87
<211> LENGTH: 26
<212> TYPE: DNA
<213> ORGANISM: artificial
<220> FEATURE:
<223> OTHER INFORMATION: probe/primer
```

```
<400> SEQUENCE: 87
actgagtcgt agactgcgta ctcaag                                              26

<210> SEQ ID NO 88
<211> LENGTH: 26
<212> TYPE: DNA
<213> ORGANISM: artificial
<220> FEATURE:
<223> OTHER INFORMATION: probe/primer

<400> SEQUENCE: 88
actgagtcgt agactgcgta ctcaag                                              26

<210> SEQ ID NO 89
<211> LENGTH: 17
<212> TYPE: DNA
<213> ORGANISM: artificial
<220> FEATURE:
<223> OTHER INFORMATION: probe/primer

<400> SEQUENCE: 89
tagactgcgt actctca                                                        17

<210> SEQ ID NO 90
<211> LENGTH: 26
<212> TYPE: DNA
<213> ORGANISM: artificial
<220> FEATURE:
<223> OTHER INFORMATION: probe/primer

<400> SEQUENCE: 90
actgagtcgt agactgcgta ctctca                                              26

<210> SEQ ID NO 91
<211> LENGTH: 24
<212> TYPE: DNA
<213> ORGANISM: artificial
<220> FEATURE:
<223> OTHER INFORMATION: probe/primer

<400> SEQUENCE: 91
agagtacgca gtctacgact cagt                                                24

<210> SEQ ID NO 92
<211> LENGTH: 26
<212> TYPE: DNA
<213> ORGANISM: artificial
<220> FEATURE:
<223> OTHER INFORMATION: probe/primer

<400> SEQUENCE: 92
actgagtcgt agactgcgta ctctca                                              26

<210> SEQ ID NO 93
<211> LENGTH: 26
<212> TYPE: DNA
<213> ORGANISM: artificial
<220> FEATURE:
<223> OTHER INFORMATION: probe/primer

<400> SEQUENCE: 93
actgagtcgt agactgcgta ctctca                                              26

<210> SEQ ID NO 94
<211> LENGTH: 17
<212> TYPE: DNA
```

```
<213> ORGANISM: artificial
<220> FEATURE:
<223> OTHER INFORMATION: probe/primer

<400> SEQUENCE: 94
tagactgcgt actctga                                                    17

<210> SEQ ID NO 95
<211> LENGTH: 26
<212> TYPE: DNA
<213> ORGANISM: artificial
<220> FEATURE:
<223> OTHER INFORMATION: probe/primer

<400> SEQUENCE: 95
actgagtcgt agactgcgta ctctga                                          26

<210> SEQ ID NO 96
<211> LENGTH: 26
<212> TYPE: DNA
<213> ORGANISM: artificial
<220> FEATURE:
<223> OTHER INFORMATION: probe/primer

<400> SEQUENCE: 96
actgagtcgt agactgcgta ctctga                                          26

<210> SEQ ID NO 97
<211> LENGTH: 17
<212> TYPE: DNA
<213> ORGANISM: artificial
<220> FEATURE:
<223> OTHER INFORMATION: probe/primer

<400> SEQUENCE: 97
tagactgcgt actatgg                                                    17

<210> SEQ ID NO 98
<211> LENGTH: 24
<212> TYPE: DNA
<213> ORGANISM: artificial
<220> FEATURE:
<223> OTHER INFORMATION: probe/primer

<400> SEQUENCE: 98
atagtacgca gtctacgact cagt                                            24

<210> SEQ ID NO 99
<211> LENGTH: 26
<212> TYPE: DNA
<213> ORGANISM: artificial
<220> FEATURE:
<223> OTHER INFORMATION: probe/primer

<400> SEQUENCE: 99
actgagtcgt agactgcgta ctatgg                                          26

<210> SEQ ID NO 100
<211> LENGTH: 26
<212> TYPE: DNA
<213> ORGANISM: artificial
<220> FEATURE:
<223> OTHER INFORMATION: probe/primer

<400> SEQUENCE: 100
actgagtcgt agactgcgta ctatgg                                          26
```

<210> SEQ ID NO 101
<211> LENGTH: 22
<212> TYPE: DNA
<213> ORGANISM: artificial
<220> FEATURE:
<223> OTHER INFORMATION: probe/primer

<400> SEQUENCE: 101
cattcaggac ctggattggc ga                                          22

<210> SEQ ID NO 102
<211> LENGTH: 24
<212> TYPE: DNA
<213> ORGANISM: artificial
<220> FEATURE:
<223> OTHER INFORMATION: probe/primer

<400> SEQUENCE: 102
tcgccaatcc aggtcctgaa tgtt                                        24

<210> SEQ ID NO 103
<211> LENGTH: 24
<212> TYPE: DNA
<213> ORGANISM: artificial
<220> FEATURE:
<223> OTHER INFORMATION: probe/primer

<400> SEQUENCE: 103
tcgccaatcc aggtcctgaa tgcc                                        24

<210> SEQ ID NO 104
<211> LENGTH: 28
<212> TYPE: DNA
<213> ORGANISM: artificial
<220> FEATURE:
<223> OTHER INFORMATION: probe/primer

<400> SEQUENCE: 104
attatcgcca atccaggtcc tgaatgct                                    28

<210> SEQ ID NO 105
<211> LENGTH: 32
<212> TYPE: DNA
<213> ORGANISM: artificial
<220> FEATURE:
<223> OTHER INFORMATION: probe/primer

<400> SEQUENCE: 105
attaattatc gccaatccag gtcctgaatg tc                               32

<210> SEQ ID NO 106
<211> LENGTH: 26
<212> TYPE: DNA
<213> ORGANISM: artificial
<220> FEATURE:
<223> OTHER INFORMATION: probe/primer

<400> SEQUENCE: 106
ctgagtcgta gactgcgtac tctcat                                      26

<210> SEQ ID NO 107
<211> LENGTH: 26
<212> TYPE: DNA
<213> ORGANISM: artificial
<220> FEATURE:
<223> OTHER INFORMATION: probe/primer

```
<400> SEQUENCE: 107
ctgagtcgta gactgcgtac tctcag                                              26

<210> SEQ ID NO 108
<211> LENGTH: 26
<212> TYPE: DNA
<213> ORGANISM: artificial
<220> FEATURE:
<223> OTHER INFORMATION: probe/primer

<400> SEQUENCE: 108
ctgagtcgta gactgcgtac tcaaga                                              26

<210> SEQ ID NO 109
<211> LENGTH: 26
<212> TYPE: DNA
<213> ORGANISM: artificial
<220> FEATURE:
<223> OTHER INFORMATION: probe/primer

<400> SEQUENCE: 109
ctgagtcgta gactgcgtac tcaagc                                              26

<210> SEQ ID NO 110
<211> LENGTH: 27
<212> TYPE: DNA
<213> ORGANISM: artificial
<220> FEATURE:
<223> OTHER INFORMATION: probe/primer

<400> SEQUENCE: 110
ctgagtcgta gactgcgtac tcaagat                                             27

<210> SEQ ID NO 111
<211> LENGTH: 27
<212> TYPE: DNA
<213> ORGANISM: artificial
<220> FEATURE:
<223> OTHER INFORMATION: probe/primer

<400> SEQUENCE: 111
ctgagtcgta gactgcgtac tcaagag                                             27

<210> SEQ ID NO 112
<211> LENGTH: 27
<212> TYPE: DNA
<213> ORGANISM: artificial
<220> FEATURE:
<223> OTHER INFORMATION: probe/primer

<400> SEQUENCE: 112
ctgagtcgta gactgcgtac tctcatg                                             27

<210> SEQ ID NO 113
<211> LENGTH: 27
<212> TYPE: DNA
<213> ORGANISM: artificial
<220> FEATURE:
<223> OTHER INFORMATION: probe/primer

<400> SEQUENCE: 113
ctgagtcgta gactgcgtac tctcagt                                             27

<210> SEQ ID NO 114
<211> LENGTH: 22
<212> TYPE: DNA
```

-continued

<210> SEQ ID NO 114
<211> LENGTH: 22
<212> TYPE: DNA
<213> ORGANISM: artificial
<220> FEATURE:
<223> OTHER INFORMATION: probe/primer

<400> SEQUENCE: 114
ggagcacgct atcccgttag ac                                              22

<210> SEQ ID NO 115
<211> LENGTH: 21
<212> TYPE: DNA
<213> ORGANISM: artificial
<220> FEATURE:
<223> OTHER INFORMATION: probe/primer

<400> SEQUENCE: 115
cgctgccaac taccgcacat c                                               21

<210> SEQ ID NO 116
<211> LENGTH: 44
<212> TYPE: DNA
<213> ORGANISM: artificial
<220> FEATURE:
<223> OTHER INFORMATION: probe/primer

<400> SEQUENCE: 116
ggagcacgct atcccgttag acccctgcaa tgactcccca tttc                      44

<210> SEQ ID NO 117
<211> LENGTH: 43
<212> TYPE: DNA
<213> ORGANISM: artificial
<220> FEATURE:
<223> OTHER INFORMATION: probe/primer

<400> SEQUENCE: 117
cgctgccaac taccgcacat cagtagggct ggggcatcag aac                       43

<210> SEQ ID NO 118
<211> LENGTH: 21
<212> TYPE: DNA
<213> ORGANISM: artificial
<220> FEATURE:
<223> OTHER INFORMATION: probe/primer

<400> SEQUENCE: 118
agcttcagac acaccaggca c                                               21

<210> SEQ ID NO 119
<211> LENGTH: 26
<212> TYPE: DNA
<213> ORGANISM: artificial
<220> FEATURE:
<223> OTHER INFORMATION: probe/primer

<400> SEQUENCE: 119
atttagttct tccttcttgc ctctgc                                          26

<210> SEQ ID NO 120
<211> LENGTH: 47
<212> TYPE: DNA
<213> ORGANISM: artificial
<220> FEATURE:
<223> OTHER INFORMATION: probe/primer

<400> SEQUENCE: 120
ggagcacgct atcccgttag acattgtgga agacagtgtg gtgattc                   47

<210> SEQ ID NO 121
<211> LENGTH: 46
<212> TYPE: DNA
<213> ORGANISM: artificial
<220> FEATURE:
<223> OTHER INFORMATION: probe/primer

<400> SEQUENCE: 121
cgctgccaac taccgcacat ccatggcata tatgtgccac attttc        46

<210> SEQ ID NO 122
<211> LENGTH: 23
<212> TYPE: DNA
<213> ORGANISM: artificial
<220> FEATURE:
<223> OTHER INFORMATION: probe/primer

<400> SEQUENCE: 122
aagcatgctg ctgtaaagac aca        23

<210> SEQ ID NO 123
<211> LENGTH: 29
<212> TYPE: DNA
<213> ORGANISM: artificial
<220> FEATURE:
<223> OTHER INFORMATION: probe/primer

<400> SEQUENCE: 123
tgcacatgta tgtttattgc agcactatt        29

<210> SEQ ID NO 124
<211> LENGTH: 46
<212> TYPE: DNA
<213> ORGANISM: artificial
<220> FEATURE:
<223> OTHER INFORMATION: probe/primer

<400> SEQUENCE: 124
ggagcacgct atcccgttag acgtgttagc caggatggtc tccatc        46

<210> SEQ ID NO 125
<211> LENGTH: 46
<212> TYPE: DNA
<213> ORGANISM: artificial
<220> FEATURE:
<223> OTHER INFORMATION: probe/primer

<400> SEQUENCE: 125
cgctgccaac taccgcacat ccatgggtgg ggtaacagaa agaaac        46

<210> SEQ ID NO 126
<211> LENGTH: 23
<212> TYPE: DNA
<213> ORGANISM: artificial
<220> FEATURE:
<223> OTHER INFORMATION: probe/primer

<400> SEQUENCE: 126
gacaattatc ctgatttggg acc        23

<210> SEQ ID NO 127
<211> LENGTH: 25
<212> TYPE: DNA
<213> ORGANISM: artificial
<220> FEATURE:
<223> OTHER INFORMATION: probe/primer

```
<400> SEQUENCE: 127
ttaccttcag atggttttcc ctcct                                        25

<210> SEQ ID NO 128
<211> LENGTH: 46
<212> TYPE: DNA
<213> ORGANISM: artificial
<220> FEATURE:
<223> OTHER INFORMATION: probe/primer

<400> SEQUENCE: 128
ggagcacgct atcccgttag actagtgtct agggatagag gagaac                 46

<210> SEQ ID NO 129
<211> LENGTH: 46
<212> TYPE: DNA
<213> ORGANISM: artificial
<220> FEATURE:
<223> OTHER INFORMATION: probe/primer

<400> SEQUENCE: 129
cgctgccaac taccgcacat cctcctgaca ttatggagag ccttac                 46

<210> SEQ ID NO 130
<211> LENGTH: 25
<212> TYPE: DNA
<213> ORGANISM: artificial
<220> FEATURE:
<223> OTHER INFORMATION: probe/primer

<400> SEQUENCE: 130
aatgccacac ttcagatttt gatac                                        25

<210> SEQ ID NO 131
<211> LENGTH: 25
<212> TYPE: DNA
<213> ORGANISM: artificial
<220> FEATURE:
<223> OTHER INFORMATION: probe/primer

<400> SEQUENCE: 131
ttgcaggatc ctatttctgg cacta                                        25

<210> SEQ ID NO 132
<211> LENGTH: 22
<212> TYPE: DNA
<213> ORGANISM: artificial
<220> FEATURE:
<223> OTHER INFORMATION: probe/primer

<400> SEQUENCE: 132
ggagcacgct atcccgttag ac                                           22

<210> SEQ ID NO 133
<211> LENGTH: 21
<212> TYPE: DNA
<213> ORGANISM: artificial
<220> FEATURE:
<223> OTHER INFORMATION: probe/primer

<400> SEQUENCE: 133
cgctgccaac taccgcacat c                                            21

<210> SEQ ID NO 134
<211> LENGTH: 50
<212> TYPE: DNA
```

```
<213> ORGANISM: artificial
<220> FEATURE:
<223> OTHER INFORMATION: probe/primer

<400> SEQUENCE: 134
ggagcacgct atcccgttag acggacttct ccccactaca acatagattc          50

<210> SEQ ID NO 135
<211> LENGTH: 49
<212> TYPE: DNA
<213> ORGANISM: artificial
<220> FEATURE:
<223> OTHER INFORMATION: probe/primer

<400> SEQUENCE: 135
cgctgccaac taccgcacat ctttatcagc aacatgaaaa cagactaac            49

<210> SEQ ID NO 136
<211> LENGTH: 28
<212> TYPE: DNA
<213> ORGANISM: artificial
<220> FEATURE:
<223> OTHER INFORMATION: probe/primer

<400> SEQUENCE: 136
tgtggaattt atcatttaat ttagcttc                                    28

<210> SEQ ID NO 137
<211> LENGTH: 28
<212> TYPE: DNA
<213> ORGANISM: artificial
<220> FEATURE:
<223> OTHER INFORMATION: probe/primer

<400> SEQUENCE: 137
agtgaaccgt tctttccaga ttattttg                                    28

<210> SEQ ID NO 138
<211> LENGTH: 48
<212> TYPE: DNA
<213> ORGANISM: artificial
<220> FEATURE:
<223> OTHER INFORMATION: probe/primer

<400> SEQUENCE: 138
ggagcacgct atcccgttag acagaataga atgcttgcaa ttgatcac             48

<210> SEQ ID NO 139
<211> LENGTH: 47
<212> TYPE: DNA
<213> ORGANISM: artificial
<220> FEATURE:
<223> OTHER INFORMATION: probe/primer

<400> SEQUENCE: 139
cgctgccaac taccgcacat catgtcaatt tgttggggtt atacaac              47

<210> SEQ ID NO 140
<211> LENGTH: 25
<212> TYPE: DNA
<213> ORGANISM: artificial
<220> FEATURE:
<223> OTHER INFORMATION: probe/primer

<400> SEQUENCE: 140
aaaaaggagg gtgacagtga acctg                                       25
```

```
<210> SEQ ID NO 141
<211> LENGTH: 28
<212> TYPE: DNA
<213> ORGANISM: artificial
<220> FEATURE:
<223> OTHER INFORMATION: probe/primer

<400> SEQUENCE: 141
gaggtaaaat tcaacaattc atttgctt                                          28

<210> SEQ ID NO 142
<211> LENGTH: 48
<212> TYPE: DNA
<213> ORGANISM: artificial
<220> FEATURE:
<223> OTHER INFORMATION: probe/primer

<400> SEQUENCE: 142
ggagcacgct atcccgttag acgtgcagac aagagaatgt caagtttc                    48

<210> SEQ ID NO 143
<211> LENGTH: 48
<212> TYPE: DNA
<213> ORGANISM: artificial
<220> FEATURE:
<223> OTHER INFORMATION: probe/primer

<400> SEQUENCE: 143
cgctgccaac taccgcacat cagaggctgg aaaaataaat ccaataca                    48

<210> SEQ ID NO 144
<211> LENGTH: 23
<212> TYPE: DNA
<213> ORGANISM: artificial
<220> FEATURE:
<223> OTHER INFORMATION: probe/primer

<400> SEQUENCE: 144
gatcagaaac cacaggaaat ttg                                               23

<210> SEQ ID NO 145
<211> LENGTH: 22
<212> TYPE: DNA
<213> ORGANISM: artificial
<220> FEATURE:
<223> OTHER INFORMATION: probe/primer

<400> SEQUENCE: 145
atttatgcca gccctgcatc cc                                                22

<210> SEQ ID NO 146
<211> LENGTH: 27
<212> TYPE: DNA
<213> ORGANISM: artificial
<220> FEATURE:
<223> OTHER INFORMATION: probe/primer

<400> SEQUENCE: 146
ctgagtcgta gactgcgtac tctagat                                           27

<210> SEQ ID NO 147
<211> LENGTH: 27
<212> TYPE: DNA
<213> ORGANISM: artificial
<220> FEATURE:
<223> OTHER INFORMATION: probe/primer
```

```
<400> SEQUENCE: 147
ctgagtcgta gactgcgtac tctagag                                27

<210> SEQ ID NO 148
<211> LENGTH: 27
<212> TYPE: DNA
<213> ORGANISM: artificial
<220> FEATURE:
<223> OTHER INFORMATION: probe/primer

<400> SEQUENCE: 148
ctgagtcgta gactgcgtac tctcatg                                27

<210> SEQ ID NO 149
<211> LENGTH: 27
<212> TYPE: DNA
<213> ORGANISM: artificial
<220> FEATURE:
<223> OTHER INFORMATION: probe/primer

<400> SEQUENCE: 149
ctgagtcgta gactgcgtac tctcagt                                27

<210> SEQ ID NO 150
<211> LENGTH: 22
<212> TYPE: DNA
<213> ORGANISM: artificial
<220> FEATURE:
<223> OTHER INFORMATION: probe/primer

<400> SEQUENCE: 150
ggagcacgct atcccgttag ac                                     22

<210> SEQ ID NO 151
<211> LENGTH: 21
<212> TYPE: DNA
<213> ORGANISM: artificial
<220> FEATURE:
<223> OTHER INFORMATION: probe/primer

<400> SEQUENCE: 151
cgctgccaac taccgcacat c                                      21

<210> SEQ ID NO 152
<211> LENGTH: 48
<212> TYPE: DNA
<213> ORGANISM: artificial
<220> FEATURE:
<223> OTHER INFORMATION: probe/primer

<400> SEQUENCE: 152
ggagcacgct atcccgttag acgatgagct tacacaggca ctgattac         48

<210> SEQ ID NO 153
<211> LENGTH: 48
<212> TYPE: DNA
<213> ORGANISM: artificial
<220> FEATURE:
<223> OTHER INFORMATION: probe/primer

<400> SEQUENCE: 153
cgctgccaac taccgcacat ctattggtga ctgatgaaaa tgtcaaac         48

<210> SEQ ID NO 154
<211> LENGTH: 29
<212> TYPE: DNA
```

```
<213> ORGANISM: artificial
<220> FEATURE:
<223> OTHER INFORMATION: probe/primer

<400> SEQUENCE: 154
tgtcaagaaa gtgtatttag cttacaaac                                29

<210> SEQ ID NO 155
<211> LENGTH: 29
<212> TYPE: DNA
<213> ORGANISM: artificial
<220> FEATURE:
<223> OTHER INFORMATION: probe/primer

<400> SEQUENCE: 155
tattaacagc ctgttttacc ctacttttg                                29

<210> SEQ ID NO 156
<211> LENGTH: 47
<212> TYPE: DNA
<213> ORGANISM: artificial
<220> FEATURE:
<223> OTHER INFORMATION: probe/primer

<400> SEQUENCE: 156
ggagcacgct atcccgttag acgcacctta tcttggcttt tctattc            47

<210> SEQ ID NO 157
<211> LENGTH: 48
<212> TYPE: DNA
<213> ORGANISM: artificial
<220> FEATURE:
<223> OTHER INFORMATION: probe/primer

<400> SEQUENCE: 157
cgctgccaac taccgcacat caagcatatt acatcatgtc atcacttc           48

<210> SEQ ID NO 158
<211> LENGTH: 22
<212> TYPE: DNA
<213> ORGANISM: artificial
<220> FEATURE:
<223> OTHER INFORMATION: probe/primer

<400> SEQUENCE: 158
ttcgtttctc tttatccaca cc                                       22

<210> SEQ ID NO 159
<211> LENGTH: 30
<212> TYPE: DNA
<213> ORGANISM: artificial
<220> FEATURE:
<223> OTHER INFORMATION: probe/primer

<400> SEQUENCE: 159
atgggaaatg tcttttacaa tgtacataac                               30

<210> SEQ ID NO 160
<211> LENGTH: 45
<212> TYPE: DNA
<213> ORGANISM: artificial
<220> FEATURE:
<223> OTHER INFORMATION: probe/primer

<400> SEQUENCE: 160
ggagcacgct atcccgttag accagccatg tgattccctg tgtac              45
```

```
<210> SEQ ID NO 161
<211> LENGTH: 45
<212> TYPE: DNA
<213> ORGANISM: artificial
<220> FEATURE:
<223> OTHER INFORMATION: probe/primer

<400> SEQUENCE: 161
cgctgccaac taccgcacat cctgcattgt acaatgcatg catac            45

<210> SEQ ID NO 162
<211> LENGTH: 36
<212> TYPE: DNA
<213> ORGANISM: artificial
<220> FEATURE:
<223> OTHER INFORMATION: probe/primer

<400> SEQUENCE: 162
aaatataaac taaatgaatc aaagatagag tgaatg                      36

<210> SEQ ID NO 163
<211> LENGTH: 24
<212> TYPE: DNA
<213> ORGANISM: artificial
<220> FEATURE:
<223> OTHER INFORMATION: probe/primer

<400> SEQUENCE: 163
tatgcatgca ttgtacaatg cagg                                   24

<210> SEQ ID NO 164
<211> LENGTH: 47
<212> TYPE: DNA
<213> ORGANISM: artificial
<220> FEATURE:
<223> OTHER INFORMATION: probe/primer

<400> SEQUENCE: 164
ggagcacgct atcccgttag acttctgata gagtcgtttt gtgcttc          47

<210> SEQ ID NO 165
<211> LENGTH: 46
<212> TYPE: DNA
<213> ORGANISM: artificial
<220> FEATURE:
<223> OTHER INFORMATION: probe/primer

<400> SEQUENCE: 165
cgctgccaac taccgcacat ccattttagg atctgggaag cattac           46

<210> SEQ ID NO 166
<211> LENGTH: 21
<212> TYPE: DNA
<213> ORGANISM: artificial
<220> FEATURE:
<223> OTHER INFORMATION: probe/primer

<400> SEQUENCE: 166
tttttcctcc catccaaatt c                                      21

<210> SEQ ID NO 167
<211> LENGTH: 25
<212> TYPE: DNA
<213> ORGANISM: artificial
<220> FEATURE:
<223> OTHER INFORMATION: probe/primer
```

```
<400> SEQUENCE: 167 agagaccccta gaattctagc gatgg                                    25

<210> SEQ ID NO 168
<211> LENGTH: 22
<212> TYPE: DNA
<213> ORGANISM: artificial
<220> FEATURE:
<223> OTHER INFORMATION: probe/primer

<400> SEQUENCE: 168
ggagcacgct atcccgttag ac                                        22

<210> SEQ ID NO 169
<211> LENGTH: 21
<212> TYPE: DNA
<213> ORGANISM: artificial
<220> FEATURE:
<223> OTHER INFORMATION: probe/primer

<400> SEQUENCE: 169
cgctgccaac taccgcacat c                                         21

<210> SEQ ID NO 170
<211> LENGTH: 44
<212> TYPE: DNA
<213> ORGANISM: artificial
<220> FEATURE:
<223> OTHER INFORMATION: probe/primer

<400> SEQUENCE: 170
ggagcacgct atcccgttag acccttggaa agcaggtgca aatc                44

<210> SEQ ID NO 171
<211> LENGTH: 48
<212> TYPE: DNA
<213> ORGANISM: artificial
<220> FEATURE:
<223> OTHER INFORMATION: probe/primer

<400> SEQUENCE: 171
cgctgccaac taccgcacat caaataacaa ctgcattact ccatcatc            48

<210> SEQ ID NO 172
<211> LENGTH: 25
<212> TYPE: DNA
<213> ORGANISM: artificial
<220> FEATURE:
<223> OTHER INFORMATION: probe/primer

<400> SEQUENCE: 172
aatgaaaaaa tccaatattg gtctg                                     25

<210> SEQ ID NO 173
<211> LENGTH: 30
<212> TYPE: DNA
<213> ORGANISM: artificial
<220> FEATURE:
<223> OTHER INFORMATION: probe/primer

<400> SEQUENCE: 173
tgtgtgaaag tgtaaatgta tacgtgtatg                                30

<210> SEQ ID NO 174
<211> LENGTH: 45
<212> TYPE: DNA
```

```
<213> ORGANISM: artificial
<220> FEATURE:
<223> OTHER INFORMATION: probe/primer

<400> SEQUENCE: 174
ggagcacgct atcccgttag acctgtcaag cagggaattg gatac          45

<210> SEQ ID NO 175
<211> LENGTH: 47
<212> TYPE: DNA
<213> ORGANISM: artificial
<220> FEATURE:
<223> OTHER INFORMATION: probe/primer

<400> SEQUENCE: 175
cgctgccaac taccgcacat ccctttctga tttcagttgc tagtttc        47

<210> SEQ ID NO 176
<211> LENGTH: 21
<212> TYPE: DNA
<213> ORGANISM: artificial
<220> FEATURE:
<223> OTHER INFORMATION: probe/primer

<400> SEQUENCE: 176
gagaccaaac cagggagaaa g                                    21

<210> SEQ ID NO 177
<211> LENGTH: 29
<212> TYPE: DNA
<213> ORGANISM: artificial
<220> FEATURE:
<223> OTHER INFORMATION: probe/primer

<400> SEQUENCE: 177
tacagagaga gagcaaagag agttcagac                            29

<210> SEQ ID NO 178
<211> LENGTH: 44
<212> TYPE: DNA
<213> ORGANISM: artificial
<220> FEATURE:
<223> OTHER INFORMATION: probe/primer

<400> SEQUENCE: 178
ggagcacgct atcccgttag actggaggtc ctagccagag caac           44

<210> SEQ ID NO 179
<211> LENGTH: 47
<212> TYPE: DNA
<213> ORGANISM: artificial
<220> FEATURE:
<223> OTHER INFORMATION: probe/primer

<400> SEQUENCE: 179
cgctgccaac taccgcacat cggtattgcc tttctgattt agctttc        47

<210> SEQ ID NO 180
<211> LENGTH: 20
<212> TYPE: DNA
<213> ORGANISM: artificial
<220> FEATURE:
<223> OTHER INFORMATION: probe/primer

<400> SEQUENCE: 180
agcccaaaag ctccttcagc                                      20
```

<210> SEQ ID NO 181
<211> LENGTH: 28
<212> TYPE: DNA
<213> ORGANISM: artificial
<220> FEATURE:
<223> OTHER INFORMATION: probe/primer

<400> SEQUENCE: 181
tgataaacaa cttcagcaaa gtttcagg                                28

<210> SEQ ID NO 182
<211> LENGTH: 12
<212> TYPE: DNA
<213> ORGANISM: artificial
<220> FEATURE:
<223> OTHER INFORMATION: probe/primer
<220> FEATURE:
<221> NAME/KEY: misc_feature
<222> LOCATION: (4)..(9)
<223> OTHER INFORMATION: n is a, c, g, or t

<400> SEQUENCE: 182
gacnnnnnng tc                                                 12

<210> SEQ ID NO 183
<211> LENGTH: 12
<212> TYPE: DNA
<213> ORGANISM: artificial
<220> FEATURE:
<223> OTHER INFORMATION: probe/primer
<220> FEATURE:
<221> NAME/KEY: misc_feature
<222> LOCATION: (4)..(9)
<223> OTHER INFORMATION: n is a, c, g, or t

<400> SEQUENCE: 183
ctgnnnnnnc ag                                                 12

<210> SEQ ID NO 184
<211> LENGTH: 12
<212> TYPE: DNA
<213> ORGANISM: artificial
<220> FEATURE:
<223> OTHER INFORMATION: probe/primer
<220> FEATURE:
<221> NAME/KEY: misc_feature
<222> LOCATION: (8)..(9)
<223> OTHER INFORMATION: n is a, c, g, or t

<400> SEQUENCE: 184
ctaataanng tc                                                 12

<210> SEQ ID NO 185
<211> LENGTH: 12
<212> TYPE: DNA
<213> ORGANISM: artificial
<220> FEATURE:
<223> OTHER INFORMATION: probe/primer
<220> FEATURE:
<221> NAME/KEY: misc_feature
<222> LOCATION: (8)..(9)
<223> OTHER INFORMATION: n is a, c, g, or t

<400> SEQUENCE: 185
gattattnnc ag                                                 12

<210> SEQ ID NO 186
<211> LENGTH: 12
<212> TYPE: DNA

-continued

<213> ORGANISM: Artificial
<220> FEATURE:
<223> OTHER INFORMATION: probe/primer
<220> FEATURE:
<221> NAME/KEY: misc_feature
<222> LOCATION: (8)..(9)
<223> OTHER INFORMATION: n is a, c, g, t or u

<400> SEQUENCE: 186
cuaauaanng tc                                                          12

<210> SEQ ID NO 187
<211> LENGTH: 11
<212> TYPE: DNA
<213> ORGANISM: artificial
<220> FEATURE:
<223> OTHER INFORMATION: probe/primer
<220> FEATURE:
<221> NAME/KEY: misc_feature
<222> LOCATION: (4)..(8)
<223> OTHER INFORMATION: n is a, c, g, or t

<400> SEQUENCE: 187
gccnnnnngg c                                                           11

<210> SEQ ID NO 188
<211> LENGTH: 11
<212> TYPE: DNA
<213> ORGANISM: artificial
<220> FEATURE:
<223> OTHER INFORMATION: probe/primer
<220> FEATURE:
<221> NAME/KEY: misc_feature
<222> LOCATION: (4)..(8)
<223> OTHER INFORMATION: n is a, c, g, or t

<400> SEQUENCE: 188
cggnnnnncc g                                                           11

<210> SEQ ID NO 189
<211> LENGTH: 11
<212> TYPE: DNA
<213> ORGANISM: artificial
<220> FEATURE:
<223> OTHER INFORMATION: probe/primer
<220> FEATURE:
<221> NAME/KEY: misc_feature
<222> LOCATION: (8)..(8)
<223> OTHER INFORMATION: n is a, c, g, or t

<400> SEQUENCE: 189
ctaatacngg c                                                           11

<210> SEQ ID NO 190
<211> LENGTH: 11
<212> TYPE: DNA
<213> ORGANISM: artificial
<220> FEATURE:
<223> OTHER INFORMATION: probe/primer
<220> FEATURE:
<221> NAME/KEY: misc_feature
<222> LOCATION: (8)..(8)
<223> OTHER INFORMATION: n is a, c, g, or t

<400> SEQUENCE: 190
gattatgncc g                                                           11

<210> SEQ ID NO 191
<211> LENGTH: 11
<212> TYPE: RNA

```
<213> ORGANISM: artificial
<220> FEATURE:
<223> OTHER INFORMATION: probe/primer
<220> FEATURE:
<221> NAME/KEY: misc_feature
<222> LOCATION: (8)..(8)
<223> OTHER INFORMATION: n is a, c, g, or u

<400> SEQUENCE: 191
cuaauacngg c                                                         11

<210> SEQ ID NO 192
<211> LENGTH: 11
<212> TYPE: DNA
<213> ORGANISM: artificial
<220> FEATURE:
<223> OTHER INFORMATION: probe/primer
<220> FEATURE:
<221> NAME/KEY: misc_feature
<222> LOCATION: (8)..(8)
<223> OTHER INFORMATION: n is a, c, g, or t

<400> SEQUENCE: 192
gattatgncc g                                                         11

<210> SEQ ID NO 193
<211> LENGTH: 11
<212> TYPE: DNA
<213> ORGANISM: artificial
<220> FEATURE:
<223> OTHER INFORMATION: probe/primer
<220> FEATURE:
<221> NAME/KEY: misc_feature
<222> LOCATION: (4)..(4)
<223> OTHER INFORMATION: n is a, c, g, or t

<400> SEQUENCE: 193
gccntactta g                                                         11

<210> SEQ ID NO 194
<211> LENGTH: 11
<212> TYPE: DNA
<213> ORGANISM: artificial
<220> FEATURE:
<223> OTHER INFORMATION: probe/primer
<220> FEATURE:
<221> NAME/KEY: misc_feature
<222> LOCATION: (4)..(4)
<223> OTHER INFORMATION: n is a, c, g, or t

<400> SEQUENCE: 194
cggnatgaat c                                                         11

<210> SEQ ID NO 195
<211> LENGTH: 11
<212> TYPE: DNA
<213> ORGANISM: artificial
<220> FEATURE:
<223> OTHER INFORMATION: probe/primer
<220> FEATURE:
<221> NAME/KEY: misc_feature
<222> LOCATION: (7)..(8)
<223> OTHER INFORMATION: n is a, c, g, or t

<400> SEQUENCE: 195
ctaaacnggc c                                                         11

<210> SEQ ID NO 196
<211> LENGTH: 11
<212> TYPE: DNA
```

```
<213> ORGANISM: artificial
<220> FEATURE:
<223> OTHER INFORMATION: probe/primer
<220> FEATURE:
<221> NAME/KEY: misc_feature
<222> LOCATION: (7)..(8)
<223> OTHER INFORMATION: n is a, c, g, or t

<400> SEQUENCE: 196
gatttgnncc g                                                              11

<210> SEQ ID NO 197
<211> LENGTH: 11
<212> TYPE: DNA
<213> ORGANISM: artificial
<220> FEATURE:
<223> OTHER INFORMATION: probe/primer
<220> FEATURE:
<221> NAME/KEY: misc_feature
<222> LOCATION: (8)..(11)
<223> OTHER INFORMATION: n is a, c, g, or t

<400> SEQUENCE: 197
gctcttcnnn n                                                              11

<210> SEQ ID NO 198
<211> LENGTH: 11
<212> TYPE: DNA
<213> ORGANISM: artificial
<220> FEATURE:
<223> OTHER INFORMATION: probe/primer
<220> FEATURE:
<221> NAME/KEY: misc_feature
<222> LOCATION: (8)..(11)
<223> OTHER INFORMATION: n is a, c, g, or t

<400> SEQUENCE: 198
cgagaagnnn n                                                              11

<210> SEQ ID NO 199
<211> LENGTH: 11
<212> TYPE: DNA
<213> ORGANISM: artificial
<220> FEATURE:
<223> OTHER INFORMATION: probe/primer

<400> SEQUENCE: 199
ctaatacaat g                                                              11

<210> SEQ ID NO 200
<211> LENGTH: 11
<212> TYPE: DNA
<213> ORGANISM: artificial
<220> FEATURE:
<223> OTHER INFORMATION: probe/primer

<400> SEQUENCE: 200
gattatgtta c                                                              11

<210> SEQ ID NO 201
<211> LENGTH: 11
<212> TYPE: DNA
<213> ORGANISM: artificial
<220> FEATURE:
<223> OTHER INFORMATION: probe/primer
<220> FEATURE:
<221> NAME/KEY: misc_feature
<222> LOCATION: (8)..(8)
<223> OTHER INFORMATION: n is a, c, g, or t
```

```
<400> SEQUENCE: 201
cgagaagnta c                                                         11

<210> SEQ ID NO 202
<211> LENGTH: 11
<212> TYPE: RNA
<213> ORGANISM: artificial
<220> FEATURE:
<223> OTHER INFORMATION: probe/primer

<400> SEQUENCE: 202
cuaauacaau g                                                         11

<210> SEQ ID NO 203
<211> LENGTH: 11
<212> TYPE: DNA
<213> ORGANISM: artificial
<220> FEATURE:
<223> OTHER INFORMATION: probe/primer

<400> SEQUENCE: 203
gattatgtta c                                                         11

<210> SEQ ID NO 204
<211> LENGTH: 11
<212> TYPE: DNA
<213> ORGANISM: artificial
<220> FEATURE:
<223> OTHER INFORMATION: probe/primer
<220> FEATURE:
<221> NAME/KEY: misc_feature
<222> LOCATION: (8)..(8)
<223> OTHER INFORMATION: n is a, c, g, or t

<400> SEQUENCE: 204
gctcttcnat g                                                         11

<210> SEQ ID NO 205
<211> LENGTH: 11
<212> TYPE: DNA
<213> ORGANISM: artificial
<220> FEATURE:
<223> OTHER INFORMATION: probe/primer
<220> FEATURE:
<221> NAME/KEY: misc_feature
<222> LOCATION: (8)..(8)
<223> OTHER INFORMATION: n is a, c, g, or t

<400> SEQUENCE: 205
cgagaagnta c                                                         11

<210> SEQ ID NO 206
<211> LENGTH: 16
<212> TYPE: DNA
<213> ORGANISM: artificial
<220> FEATURE:
<223> OTHER INFORMATION: probe/primer
<220> FEATURE:
<221> NAME/KEY: misc_feature
<222> LOCATION: (12)..(13)
<223> OTHER INFORMATION: n is a, c, g, or t

<400> SEQUENCE: 206
cccgggaata anngtc                                                    16

<210> SEQ ID NO 207
<211> LENGTH: 16
<212> TYPE: DNA
```

```
<213> ORGANISM: artificial
<220> FEATURE:
<223> OTHER INFORMATION: probe/primer
<220> FEATURE:
<221> NAME/KEY: misc_feature
<222> LOCATION: (12)..(13)
<223> OTHER INFORMATION: n is a, c, g, or t

<400> SEQUENCE: 207
gggcccttat tnncag                                                     16

<210> SEQ ID NO 208
<211> LENGTH: 11
<212> TYPE: DNA
<213> ORGANISM: artificial
<220> FEATURE:
<223> OTHER INFORMATION: probe/primer

<400> SEQUENCE: 208
cccgggaata a                                                          11

<210> SEQ ID NO 209
<211> LENGTH: 12
<212> TYPE: DNA
<213> ORGANISM: artificial
<220> FEATURE:
<223> OTHER INFORMATION: probe/primer
<220> FEATURE:
<221> NAME/KEY: misc_feature
<222> LOCATION: (8)..(9)
<223> OTHER INFORMATION: n is a, c, g, or t

<400> SEQUENCE: 209
ctaataanng tc                                                         12

<210> SEQ ID NO 210
<211> LENGTH: 12
<212> TYPE: DNA
<213> ORGANISM: artificial
<220> FEATURE:
<223> OTHER INFORMATION: probe/primer
<220> FEATURE:
<221> NAME/KEY: misc_feature
<222> LOCATION: (8)..(9)
<223> OTHER INFORMATION: n is a, c, g, or t

<400> SEQUENCE: 210
gattattnnc ag                                                         12

<210> SEQ ID NO 211
<211> LENGTH: 12
<212> TYPE: DNA
<213> ORGANISM: artificial
<220> FEATURE:
<223> OTHER INFORMATION: probe/primer
<220> FEATURE:
<221> NAME/KEY: misc_feature
<222> LOCATION: (9)..(9)
<223> OTHER INFORMATION: n is a, c, g, or t

<400> SEQUENCE: 211
gattattgng ag                                                         12

<210> SEQ ID NO 212
<211> LENGTH: 10
<212> TYPE: DNA
<213> ORGANISM: artificial
<220> FEATURE:
<223> OTHER INFORMATION: probe/primer
<220> FEATURE:
```

-continued

```
<221> NAME/KEY: misc_feature
<222> LOCATION: (4)..(7)
<223> OTHER INFORMATION: n is a, c, g, or t

<400> SEQUENCE: 212 cacnnnngtg                                                                10
```

ACCELERATING IDENTIFICATION OF SINGLE NUCLEOTIDE POLYMORPHISMS AND ALIGNMENT OF CLONES IN GENOMIC SEQUENCING

This application is a continuation-in-part of U.S. patent application Ser. No. 09/478,189, filed on Jan. 5, 2000, now U.S. Pat. No. 6,534,293 B1, and claims the benefit of U.S. Provisional Patent Application Ser. No. 60/114,881, filed on Jan. 6, 1999, which are hereby incorporated by reference in their entirety.

The present invention was made with funding from National Institutes of Health Grant No. GM38839 and National Institutes of Health Grant No. 5R01CA81467-3. The United Stated Government may have certain rights in this invention.

FIELD OF THE INVENTION

The present invention is directed to accelerating identification of single nucleotide polymorphisms and an alignment of clone in genomic sequencing.

BACKGROUND OF THE INVENTION

Introduction to Applications of SNPS

Accumulation of genetic changes affecting cell cycle control, cell differentiation, apoptosis, and DNA replication and repair lead to carcinogenesis (Bishop, J. M., "Molecular Themes In Oncogenesis," *Cell*, 64(2):235-48 (1991)). DNA alterations include large deletions which inactivate tumor supressor genes, amplification to increase expression of oncogenes, and most commonly single nucleotide mutations or polymorphisms which impair gene expression or gene function or predispose an individual to further genomic instability (Table 1).

allele amplification in multiple genes. Single nucleotide polymorphisms ("SNP"s) are potentially powerful genetic markers for early detection, diagnosis, and staging of human cancers.

Identification of DNA sequence polymorphisms is the cornerstone of modern genome mapping. Initially, maps were created using RFLP markers (Botstein, D., et al., "Construction Of A Genetic Linkage Map In Man Using Restriction Fragment Length Polymorphisms," *Amer. J. Hum. Genet.*, 32:314-331 (1980)), and later by the more polymorphic dinucleotide repeat sequences (Weber, J. L. et al., "Abundant Class Of Human DNA Polymorphisms Which Can Be Typed Using The Polymerase Chain Reaction," *Amer. J. Hum. Genet.*, 44:388-396 (1989) and Reed, P. W., et al., "Chromosome-Specific Microsatellite Sets For Fluorescence-Based, Semi-Automated Genome Mapping," *Nat Genet*, 7(3): 390-5 (1994)). Such sequence polymorphisms may also be used to detect inactivation of tumor suppressor genes via LOH and activation of oncogenes via amplification. These genomic changes are currently being analyzed using conventional Southern hybridizations, competitive PCR, real-time PCR, microsatellite marker analysis, and comparative genome hybridization (CGH) (Ried, T., et al., "Comparative Genomic Hybridization Reveals A Specific Pattern Of Chromosomal Gains And Losses During The Genesis Of Colorectal Tumors," *Genes, Chromosomes & Cancer*, 15(4):234-45 (1996), Kallioniemi, et al., "ERBB2 Amplification In Breast Cancer Analyzed By Fluorescence In Situ Hybridization," *Proc Natl Acad Sci USA*, 89(12):5321-5 (1992), Kallioniemi, et al., "Comparative Genomic Hybridization: A Rapid New Method For Detecting And Mapping DNA Amplification In Tumors," *Semin Cancer Biol*, 4(1):41-6 (1993), Kallioniemi, et al., "Detection And Mapping Of Amplified DNA Sequences In Breast Cancer By Comparative Genomic Hybridization," *Proc Natl Acad Sci USA*, 91(6):2156-60

TABLE 1

Genetic Alterations Commonly Found in the Human Genome

| Type of Alteration | Possible Causes of Alteration | Possible Consequences of Alteration | Detection of Alteration |
|---|---|---|---|
| Single nucleotide polymorphism (SNP) | Inherited variation Methylation Carcinogens Defective repair genes | Silent does not alter function Missense: alters gene function Nonsense: truncates gene | DNA sequencing SSCP, DGGE, CDGE Protein truncation Mismatch cleavage |
| Microsatellite instability (MIN) | Defective DNA repair genes Carcinogens | Frameshift truncates gene | Microsatellite Analysis |
| Large deletions | Defective DNA repair genes Defective DNA replication genes Illegitimate recombination Double strand break | Loss of gene function | Loss of heterozygosity CGH SNP analysis |
| DNA amplifications | Defective DNA repair genes Defective DNA replication genes Illegitimate recombination | Overexpression of gene | Competitive PCR CGH SNP analysis |
| Others: Methylation, Translocation | Defective methylase genes Double strand break | Gene silencing or overexpression, creation of chimeric protein | Endonuclease digestion PCR, FISH |

Rapid detection of germline mutations in individuals at risk and accurate characterization of genetic changes in individual tumors would provide opportunities to improve early detection, prevention, prognosis, and specific treatment. However, genetic detection poses the problem of identifying a predisposing polymorphism in the germline or an index mutation in a pre-malignant lesion or early cancer that may be present at many potential sites in many genes. Furthermore, quantification of allele copy number is necessary to detect gene amplification and deletion. Therefore, technologies are urgently needed that can rapidly detect mutation, allele deletion, and (1994), Kallioniemi, et al., "Identification Of Gains And Losses Of DNA Sequences In Primary Bladder Cancer By Comparative Genomic Hybridization," *Genes Chromosom Cancer*, 12(3):213-9 (1995), Schwab, M., et al., "Amplified DNA With Limited Homology To Myc Cellular Oncogene Is Shared By Human Neuroblastoma Cell Lines And A Neuroblastoma Tumour," *Nature*, 305(5931):245-8 (1983), Solomon, E., et al., "Chromosome 5 Allele Loss In Human Colorectal Carcinomas," *Nature*, 328(6131):616-9 (1987), Law, D. J., et al., "Concerted Nonsyntenic Allelic Loss In Human Colorectal Carcinoma," *Science*, 241(4868):961-5

(1988), Frye, R. A., et al., "Detection Of Amplified Oncogenes By Differential Polymerase Chain Reaction," *Oncogene*, 4(9):1153-7 (1989), Neubauer, A., et al., "Analysis Of Gene Amplification In Archival Tissue By Differential Polymerase Chain Reaction," *Oncogene*, 7(5):1019-25 (1992), Chiang, P. W., et al., "Use Of A Fluorescent-PCR Reaction To Detect Genomic Sequence Copy Number And Transcriptional Abundance," *Genome Research*, 6(10):1013-26 (1996), Heid, C. A., et al., "Real Time Quantitative PCR," *Genome Research*, 6(10):986-94 (1996), Lee, H. H., et al., "Rapid Detection Of Trisomy 21 By Homologous Gene Quantitative PCR (HGQ-PCR)," *Human Genetics*, 99(3):364-7 (1997), Boland, C. R., et al., "Microallelotyping Defines The Sequence And Tempo Of Allelic Losses At Tumour Suppressor Gene Loci During Colorectal Cancer Progression," *Nature Medicine*, 1(9):902-9 (1995), Cawkwell, L., et al., "Frequency Of Allele Loss Of DCC, p53, RBI, WT1, NF1, NM23 And APC/MCC In Colorectal Cancer Assayed By Fluorescent Multiplex Polymerase Chain Reaction," *Br J Cancer,* 70(5):813-8 (1994), and Hampton, G. M., et al., "Simultaneous Assessment Of Loss Of Heterozygosity At Multiple Microsatellite Loci Using Semi-Automated Fluorescence-Based Detection: Subregional Mapping Of Chromosome 4 In Cervical Carcinoma," *Proceedings of the National Academy of Sciences of the United States of America*, 93(13):6704-9 (1996)). Competitive and real-time PCR are considerably faster and require less material than Southern hybridization, although neither technique is amenable to multiplexing. Current multiplex microsatellite marker approaches require careful attention to primer concentrations and amplification conditions. While PCR products may be pooled in sets, this requires an initial run on agarose gels to approximate the amount of DNA in each band (Reed, P. W., et al., "Chromosome-Specific Microsatellite Sets For Fluorescence-Based, Semi-Automated Genome Mapping," *Nat Genet*, 7(3): 390-5 (1994), and Hampton, G. M., et al., "Simultaneous Assessment Of Loss Of Heterozygosity At Multiple Microsatellite Loci Using Semi-Automated Fluorescence-Based Detection: Subregional Mapping Of Chromosome 4 In Cervical Carcinoma," *Proc. Nat'l. Acad. Sci. USA,* 93(13):6704-9 (1996)). CGH provides a global assessment of LOH and amplification, but with a resolution range of about 20 Mb. To improve gene mapping and discovery, new techniques are urgently needed to allow for simultaneous detection of multiple genetic alterations.

Amplified fragment length polymorphism ("AFLP") technology is a powerful DNA fingerprinting technique originally developed to identify plant polymorphisms in genomic DNA. It is based on the selective amplification of restriction fragments from a total digest of genomic DNA.

The original technique involved three steps: (1) restriction of the genomic DNA, i.e. with EcoRI and MseI, and ligation of oligonucleotide adapters, (2) selective amplification of a subset of all the fragments in the total digest using primers which reached in by from 1 to 3 bases, and (3) gel-based analysis of the amplified fragments. Janssen, et al., "Evaluation of the DNA Fingerprinting Method AFLP as an New Tool in Bacterial Taxonomy," *Microbiology,* 142(Pt 7):1881-93 (1996); Thomas, et al., "Identification of Amplified Restriction Fragment Polymorphism (AFLP) Markers Tightly Linked to the Tomato Cf-9 Gene for Resistance to *Cladosporium fulvum,*". *Plant J,* 8(5):785-94 (1995); Vos, et al., "AFLP: A New Technique for DNA Fingerprinting," *Nucleic Acids Res,* 23(21):4407-14 (1995); Bachem, et al., "Visualization of Differential Gene Expression Using a Novel Method of RNA Fingerprinting Based on AFLP: Analysis of Gene Expression During Potato Tuber Development," *Plant J,* 9(5):745-53 (1996); and Meksem, et al., "A High-Resolution Map of the Vicinity of the R1 Locus on Chromosome V of Potato Based on RFLP and AFLP Markers," *Mol Gen Genet,* 249(1):74-81 (1995), which are hereby incorporated by reference.

AFLP differs substantially from the present invention because it: (i) uses palindromic enzymes, (ii) amplifies both desired EcoRI-MseI as well as unwanted MseI-MseI fragments, and (iii) does not identify both alleles when a SNP destroys a pre-existing restriction site. Further, AFLP does not identify SNPs which are outside restriction sites. AFLP does not, and was not designed to create a map of a genome.

Representational Difference Analysis (RDA) was developed by N. Lisitsyn and M. Wigler to isolate the differences between two genomes (Lisitsyn, et al., "Cloning the Differences Between Two Complex Genomes," *Science*, 259:946-951 (1993), Lisitsyn, et al., "Direct Isolation of Polymorphic Markers Linked to a Trait by Genetically Directed Representational Difference Analysis," *Nat Genet,* 6(1):57-63 (1994); Lisitsyn, et al., "Comparative Genomic Analysis of Tumors: Detection of DNA Losses and Amplification," *Proc Natl Acad Sci USA,* 92(1):151-5 (1995); Thiagalingam, et al., "Evaluation of the FHIT Gene in Colorectal Cancers," *Cancer Res,* 56(13):2936-9 (1996), Li, et al., "PTEN, a Putative Protein Tyrosine Phosphatase Gene Mutated in Human Brain, Breast, and Prostate Cancer," *Science,* 275(5308):1943-7 (1997); and Schutte, et al., "Identification by Representational Difference Analysis of a Homozygous Deletion in Pancreatic Carcinoma That Lies Within the BRCA2 Region," *Proc Natl Acad Sci USA,* 92(13):5950-4 (1995). The system was developed in which subtractive and kinetic enrichment was used to purify restriction endonuclease fragments present in one DNA sample, but not in another. The representational part is required to reduce the complexity of the DNA and generates "amplicons". This allows isolation of probes that detect viral sequences in human DNA, polymorphisms, loss of heterozygosities, gene amplifications, and genome rearrangements.

The principle is to subtract "tester" amplicons from an excess of "driver" amplicons. When the tester DNA is tumor DNA and the driver is normal DNA, one isolates gene amplifications. When the tester DNA is normal DNA and the driver is tumor DNA, one isolates genes which lose function (i.e. tumor suppressor genes).

A brief outline of the procedure is provided herein: (i) cleave both tester and driver DNA with the same restriction endonuclease, (ii) ligate unphosphorylated adapters to tester DNA, (iii) mix a 10-fold excess of driver to tester DNA, melt and hybridize, (iv) fill in ends, (v) add primer and PCR amplify, (vi) digest ssDNA with mung bean nuclease, (vii) PCR amplify, (viii) repeat steps (i) to (vii) for 2-3 rounds, (ix) clone fragments and sequence.

RDA differs substantially from the present invention because it: (i) is a very complex procedure, (ii) is used to identify only a few differences between a tester and driver sample, and (iii) does not identify both alleles when a SNP destroys a pre-existing restriction site. Further, RDA does not identify SNPs which are outside restriction sites. RDA does not, and was not designed to create a map of a genome.

The advent of DNA arrays has resulted in a paradigm shift in detecting vast numbers of sequence variation and gene expression levels on a genomic scale (Pease, A. C., et al., "Light-Generated Oligonucleotide Arrays For Rapid DNA Sequence Analysis," *Proc Natl Acad Sci USA,* 91(11):5022-6 (1994), Lipshutz, R. J., et al., "Using Oligonucleotide Probe Arrays To Access Genetic Diversity," *Biotechniques,* 19(3): 442-7 (1995), Eggers, M., et al., "A Microchip For Quantitative Detection Of Molecules Utilizing Luminescent And Radioisotope Reporter Groups," *Biotechniques,* 17(3):516-25 (1994), Guo, Z., et al., "Direct Fluorescence Analysis Of Genetic Polymorphisms By Hybridization With Oligonucleotide Arrays On Glass Supports," *Nucleic Acids Res,* 22(24):5456-65 (1994), Beattie, K. L., et al., "Advances In Genosensor Research," *Clinical Chemistry,* 41(5):700-6 (1995), Hacia, J. G., et al., "Detection Of Heterozygous Mutations In BRCA1 Using High Density Oligonucleotide Arrays And Two-Colour Fluorescence Analysis," *Nature Genetics,* 14(4):441-7 (1996), Chee, M., et al., "Accessing Genetic Information With High-Density DNA Arrays," *Science,* 274(5287):610-4 (1996), Cronin, M. T., et al., "Cystic Fibrosis Mutation Detection By Hybridization To Light-Generated DNA Probe Arrays," *Hum Mutat,* 7(3):244-55 (1996), Drobyshev, A., et al., "Sequence Analysis By Hybridization With Oligonucleotide Microchip: Identification Of Beta-Thalassemia Mutations," *Gene,* 188(1):45-52 (1997), Kozal, M. J., et al., "Extensive Polymorphisms Observed In HIV-1 Clade B Protease Gene Using High-Density Oligonucleotide Arrays," *Nature Medicine,* 2(7):753-9 (1996), Yershov, G., et al., "DNA Analysis And Diagnostics On Oligonucleotide Microchips," *Proc Natl Acad Sci USA,* 93(10):4913-8 (1996), DeRisi, J., et al., "Use Of A CDNA Microarray To Analyse Gene Expression Patterns In Human Cancer," *Nature Genetics,* 14(4):457-60 (1996), Schena, M., et al., "Parallel Human Genome Analysis: Microarray-Based Expression Monitoring Of 1000 Genes," *Proc. Nat'l. Acad. Sci. USA,* 93(20):10614-9 (1996), Shalon, D., et al., "A DNA Microarray System For Analyzing Complex DNA Samples Using Two-Color Fluorescent Probe Hybridization," *Genome Research,* 6(7):639-45 (1996)). Determining deletions, amplifications, and mutations at the DNA level will complement the information obtained from expression profiling of tumors (DeRisi, J., et al., "Use Of A cDNA Microarray To Analyse Gene Expression Patterns In Human Cancer," *Nature Genetics,* 14(4):457-60 (1996), and Zhang, L., et al., "Gene Expression Profiles In Normal And Cancer Cells," *Science,* 276:1268-1272 (1997)). DNA chips designed to distinguish single nucleotide differences are generally based on the principle of "sequencing by hybridization" (Lipshutz, R. J., et al., "Using Oligonucleotide Probe Arrays To Access Genetic Diversity," *Biotechniques,* 19(3):442-7 (1995), Eggers, M., et al., "A Microchip For Quantitative Detection Of Molecules Utilizing Luminescent And Radioisotope Reporter Groups," *Biotechniques,* 17(3):516-25 (1994), Guo, Z., et al., "Direct Fluorescence Analysis Of Genetic Polymorphisms By Hybridization With Oligonucleotide Arrays On Glass Supports," *Nucleic Acids Res,* 22(24):5456-65 (1994), Beattie, K. L., et al., "Advances In Genosensor Research," *Clinical Chemistry,* 41(5):700-6 (1995), Hacia, J. G., et al., "Detection Of Heterozygous Mutations In BRCA1 Using High Density Oligonucleotide Arrays And Two-Colour Fluorescence Analysis," *Nature Genetics,* 14(4):441-7 (1996), Chee, M., et al., "Accessing Genetic Information With High-Density DNA Arrays," *Science,* 274(5287):610-4 (1996), Cronin, M. T., et al., "Cystic Fibrosis Mutation Detection By Hybridization To Light-Generated DNA Probe Arrays," *Hum Mutat,* 7(3):244-55 (1996), Drobyshev, A., et al., "Sequence Analysis By Hybridization With Oligonucleotide Microchip: Identification Of Beta-Thalassemia Mutations," *Gene,* 188(1):45-52 (1997), Kozal, M. J., et al., "Extensive Polymorphisms Observed In HIV-1 Clade B Protease Gene Using High-Density Oligonucleotide Arrays," *Nature Medicine,* 2(7):753-9 (1996), and Yershov, G., et al., "DNA Analysis And Diagnostics On Oligonucleotide Microchips," *Proc Natl Acad Sci USA,* 93(10):4913-8 (1996)), or polymerase extension of arrayed primers (Nikiforov, T. T., et al., "Genetic Bit Analysis: A Solid Phase Method For Typing Single Nucleotide Polymorphisms," *Nucleic Acids Research,* 22(20):4167-75 (1994), Shumaker, J. M., et al., "Mutation Detection By Solid Phase Primer Extension," *Human Mutation,* 7(4):346-54 (1996), Pastinen, T., et al., "Minisequencing: A Specific Tool For DNA Analysis And Diagnostics On Oligonucleotide Arrays," *Genome Research,* 7(6):606-14 (1997), and Lockley, A. K., et al., "Colorimetric Detection Of Immobilised PCR Products Generated On A Solid Support," *Nucleic Acids Research,* 25(6):1313-4 (1997) (See Table 2)). While DNA chips can confirm a known sequence, similar hybridization profiles create ambiguities in distinguishing heterozygous from homozygous alleles (Eggers, M., et al., "A Microchip For Quantitative Detection Of Molecules Utilizing Luminescent And Radioisotope Reporter Groups," *Biotechniques,* 17(3):516-25 (1994), Beattie, K. L., et al., "Advances In Genosensor Research," *Clinical Chemistry,* 41(5):700-6 (1995), Chee, M., et al., "Accessing Genetic Information With High-Density DNA Arrays," *Science,* 274(5287):610-4 (1996), Kozal, M. J., et al., "Extensive Polymorphisms Observed In HIV-1 Clade B Protease Gene Using High-Density Oligonucleotide Arrays," *Nature Medicine,* 2(7):753-9 (1996), and Southern, E. M., "DNA Chips: Analysing Sequence By Hybridization To Oligonucleotides On A Large Scale," *Trends in Genetics,* 12(3):110-5 (1996)). Attempts to overcome this problem include using two-color fluorescence analysis (Hacia, J. G., et al., "Detection Of Heterozygous Mutations In BRCA1 Using High Density Oligonucleotide Arrays And Two-Colour Fluorescence Analysis," *Nature Genetics,* 14(4):441-7 (1996)), 40 overlapping addresses for each known polymorphism (Cronin, M. T., et al., "Cystic Fibrosis Mutation Detection By Hybridization To Light-Generated DNA Probe Arrays," *Hum Mutat,* 7(3):244-55 (1996)), nucleotide analogues in the array sequence (Guo, Z., et al., "Enhanced Discrimination Of Single Nucleotide Polymorphisms By Artificial Mismatch Hybridization," *Nature Biotech.,* 15:331-335 (1997)), or adjacent co-hybridized oligonucleotides (Drobyshev, A., et al., "Sequence Analysis By Hybridization With Oligonucleotide Microchip: Identification Of Beta-Thalassemia Mutations," *Gene,* 188(1):45-52 (1997) and Yershov, G., et al., "DNA Analysis And Diagnostics On Oligonucleotide Microchips," *Proc Natl Acad Sci USA,* 93(10):4913-8 (1996)). In a side-by-side comparison, nucleotide discrimination using the hybridization chips fared an order of magnitude worse than using primer extension (Pastinen, T., et al., "Minisequencing: A Specific Tool For DNA Analysis And Diagnostics On Oligonucleotide Arrays," *Genome Research,* 7(6):606-14 (1997)). Nevertheless, solid phase primer extension also generates false positive signals from mononucleotide repeat sequences, template-dependent errors, and template-independent errors (Nikiforov, T. T., et al., "Genetic Bit Analysis: A Solid Phase Method For Typing Single Nucleotide Polymorphisms," *Nucl. Acids Res.,* 22(20):4167-75 (1994) and Shumaker, J. M., et al., "Mutation Detection By Solid Phase Primer Extension," *Human Mutation,* 7(4):346-54 (1996)).

Over the past few years, an alternate strategy in DNA array design has been pursued. Combined with solution-based polymerase chain reaction/ligase detection assay (PCR/LDR) this array allows for accurate quantification of each SNP allele (See Table 2).

TABLE 2

Comparison of high-throughput techniques to quantify known SNPs in clinical samples.

| Technique | Advantages | Disadvantages |
|---|---|---|
| Hybridization on DNA array | 1) High density: up to 135,000 addresses.<br>2) Scan for SNPs in thousands of loci.<br>3) Detects small insertions/deletions | 1) Specificity determined by hybridization difficult to distinguish all SNPs.<br>difficult to quantify allelic imbalance<br>2) Each new DNA target requires a new array |
| Mini-sequencing (SNuPE) on DNA array | 1) Uses high fidelity polymerase extension minimizes false positive signal.<br>2) Potential for single-tube assay | 1) Cannot detect small insertions/deletions.<br>2) Each new DNA target requires a new array. |
| PCR/LDR with zip-code capture on universal DNA array | 1) Uses high fidelity thermostable ligase; minimizes false positive signal.<br>2) Separates SNP identification from signal capture; avoids problems of false hybridization<br>3) Quantify gene amplifications and deletions.<br>4) Universal array works for all gene targets. | 1) Requires synthesis of many ligation primers |

For high throughput detection of specific multiplexed LDR products, unique addressable array-specific sequences on the LDR probes guide each LDR product to a designated address on a DNA array, analogous to molecular tags developed for bacterial and yeast genetics genetics (Hensel, M., et al., "Simultaneous Identification Of Bacterial Virulence Genes By Negative Selection," Science, 269(5222):400-3 (1995) and Shoemaker, D. et al., "Quantitative Phenotypic Analysis Of Yeast Deletion Mutants Using A Highly Parallel Molecular Bar-Coding Strategy," Nat Genet, 14(4):450-6 (1996)). The specificity of this reaction is determined by a thermostable ligase which allows detection of (i) dozens to hundreds of polymorphisms in a single-tube multiplex format, (ii) small insertions and deletions in repeat sequences, and (iii) low level polymorphisms in a background of normal DNA. By uncoupling polymorphism identification from hybridization, each step may be optimized independently, thus allowing for quantitative assessment of allele imbalance even in the presence of stromal cell contamination. This approach has the potential to rapidly identify multiple gene deletions and amplifications associated with tumor progression, as well as lead to the discovery of new oncogenes and tumor suppressor genes. Further, the ability to score hundreds to thousands of SNPs has utility in linkage studies (Nickerson, D. A., et al., "Identification Of Clusters Of Biallelic Polymorphic Sequence-Tagged Sites (pSTSs) That Generate Highly Informative And Automatable Markers For Genetic Linkage Mapping," Genomics, 12(2):377-87 (1992), Lin, Z., et al., "Multiplex Genotype Determination At A Large Number Of Gene Loci," Proc Natl Acad Sci USA, 93(6):2582-7 (1996), Fanning, G. C., et al., "Polymerase Chain Reaction Haplotyping Using 3' Mismatches In The Forward And Reverse Primers: Application To The Biallelic Polymorphisms Of Tumor Necrosis Factor And Lymphotoxin Alpha," Tissue Antigens, 50(1):23-31 (1997), and Kruglyak, L., "The Use of a Genetic Map of Biallelic Markers in Linkage Studies," Nature Genetics, 17:21-24 (1997)), human identification (Delahunty, C., et al., "Testing The Feasibility Of DNA Typing For Human Identification By PCR And An Oligonucleotide Ligation Assay," Am. J. Hum. Gen., 58(6):1239-46 (1996) and Belgrader, P., et al., "A Multiplex PCR-Ligase Detection Reaction Assay For Human Identity Testing," Gen. Sci. & Tech., 1:77-87 (1996)), and mapping complex human diseases using association studies where SNPs are identical by decent (Collins, F. S., "Positional Cloning Moves From Perditional To Traditional," Nat Genet, 9(4):347-50 (1995), Lander, E. S., "The New Genomics: Global Views Of Biology," Science, 274(5287):536-9 (1996), Risch, N. et al., "The Future Of Genetic Studies Of Complex Human Diseases," Science, 273 (5281):1516-7 (1996), Cheung, V. G. et al., "Genomic Mismatch Scanning Identifies Human Genomic DNA Shared Identical By Descent," Genomics, 47(1):1-6 (1998), Heung, V. G., et al., "Linkage-Disequilibrium Mapping Without Genotyping," Nat Genet, 18(3):225-230 (1998), and McAllister, L., et al., "Enrichment For Loci Identical-By-Descent Between Pairs Of Mouse Or Human Genomes By Genomic Mismatch Scanning," Genomics, 47(1):7-11 (1998)).

For 85% of epithelial cancers, loss of heterozygosity and gene amplification are the most frequently observed changes which inactivate the tumor suppressor genes and activate the oncogenes. Southern hybridizations, competitive PCR, real time PCR, microsatellite marker analysis, and comparative genome hybridization (CGH) have all been used to quantify changes in chromosome copy number (Ried, T., et al., "Comparative Genomic Hybridization Reveals A Specific Pattern Of Chromosomal Gains And Losses During The Genesis Of Colorectal Tumors," Genes, Chromosomes & Cancer, 15(4): 234-45 (1996), Kallioniemi, et al., "ERBB2 Amplification In Breast Cancer Analyzed By Fluorescence In Situ Hybridization," Proc Natl Acad Sci USA, 89(12):5321-5 (1992), Kallioniemi, et al., "Comparative Genomic Hybridization: A Rapid New Method For Detecting And Mapping DNA Amplification In Tumors," Semin Cancer Biol, 4(1):41-6 (1993), Kallioniemi, et al., "Detection And Mapping Of Amplified DNA Sequences In Breast Cancer By Comparative Genomic Hybridization," Proc Natl Acad Sci USA, 91(6): 2156-60 (1994), Kallioniemi, et al., "Identification Of Gains And Losses Of DNA Sequences In Primary Bladder Cancer By Comparative Genomic Hybridization," Genes Chromosom Cancer, 12(3):213-9 (1995), Schwab, M., et al., "Amplified DNA With Limited Homology To Myc Cellular Oncogene Is Shared By Human Neuroblastoma Cell Lines And A Neuroblastoma Tumour," Nature, 305(5931):245-8 (1983), Solomon, E., et al., "Chromosome 5 Allele Loss In Human Colorectal Carcinomas," Nature, 328(6131):616-9 (1987), Law, D. J., et al., "Concerted Nonsyntenic Allelic Loss In Human Colorectal Carcinoma," Science, 241(4868):961-5 (1988), Frye, R. A., et al., "Detection Of Amplified Oncogenes By Differential Polymerase Chain Reaction," Oncogene, 4(9):1153-7 (1989), Neubauer, A., et al., "Analysis Of Gene Amplification In Archival Tissue By Differential Polymerase Chain Reaction," Oncogene, 7(5):1019-25 (1992), Chiang, P. W., et al., "Use Of A Fluorescent-PCR Reaction To Detect Genomic Sequence Copy Number And Transcriptional Abundance," Genome Research, 6(10):1013-26 (1996), Heid, C. A., et al., "Real Time Quantitative PCR," Genome Research, 6(10):986-94 (1996), Lee, H. H., et al., "Rapid Detection Of Trisomy 21 By Homologous Gene Quantitative PCR (HGQ-PCR)," *Human Genetics*, 99(3):364-7 (1997), Boland, C. R., et al., "Microallelotyping Defines The Sequence And Tempo Of Allelic Losses At Tumour Suppressor Gene Loci During Colorectal Cancer Progression," *Nature Medicine*, 1(9):902-9 (1995), Cawkwell, L., et al., "Frequency Of Allele Loss Of DCC, p53, RBI, WT1, NF1, NM23 And APC/MCC In Colorectal Cancer Assayed By Fluorescent Multiplex Polymerase Chain Reaction," *Br J Cancer*, 70(5):813-8 (1994), and Hampton, G. M., et al., "Simultaneous Assessment Of Loss Of Heterozygosity At Multiple Microsatellite Loci Using Semi-Automated Fluorescence-Based Detection: Subregional Mapping Of Chromosome 4 In Cervical Carcinoma," *Proc. Nat'l. Acad. Sci. USA*, 93(13):6704-9 (1996)). Recently, a microarray of consecutive BACs from the long arm of chromosome 20 has been used to accurately quantify 5 regions of amplification and one region of LOH associated with development of breast cancer. This area was previously thought to contain only 3 regions of amplification (Tanner, M. et al., "Independent Amplification And Frequent Co-Amplification Of Three Nonsyntenic Regions On The Long Arm Of Chromosome 20 In Human Breast Cancer," *Cancer Research*, 56(15):3441-5 (1996)). Although this approach will yield valuable information from cell lines, it is not clear it will prove equivalent when starting with microdissected tissue which require PCR amplification. Competitive and real time PCR approaches require careful optimization to detect 2-fold differences (Frye, R. A., et al., "Detection Of Amplified Oncogenes By Differential Polymerase Chain Reaction," *Oncogene*, 4(9): 1153-7 (1989), Neubauer, A., et al., "Analysis Of Gene Amplification In Archival Tissue By Differential Polymerase Chain Reaction," Oncogene, 7(5):1019-25 (1992), Chiang, P. W., et al., "Use Of A Fluorescent-PCR Reaction To Detect Genomic Sequence Copy Number And Transcriptional Abundance," *Genome Research*, 6(10):1013-26 (1996), Heid, C. A., et al., "Real Time Quantitative PCR," *Genome Research*, 6(10):986-94 (1996), and Lee, H. H., et al., "Rapid Detection Of Trisomy 21 By Homologous Gene Quantitative PCR (HGQ-PCR)," *Human Genetics*, 99(3):364-7 (1997)). Unfortunately, stromal contamination may reduce the ratio between tumor and normal chromosome copy number to less than 2-fold. By using a quantitative SNP-DNA array detection, each allele can be distinguished independently, thus reducing the effect of stromal contamination in half. Further by comparing the ratio of allele-specific LDR product formed from a tumor to control gene between a tumor and normal sample, it may be possible to distinguish gene amplification from loss of heterozygosity at multiple loci in a single reaction.

Using PCR/LDR to Detect SNPs.

The ligase detection reaction ("LDR") is ideal for multiplexed discrimination of single-base mutations or polymorphisms (Barany, F., et al., "Cloning, Overexpression, And Nucleotide Sequence Of A Thermostable DNA Ligase Gene," *Gene*, 109:1-11 (1991), Barany, F., "Genetic Disease Detection And DNA Amplification Using Cloned Thermostable Ligase," *Proc. Natl. Acad. Sci. USA*, 88:189-193 (1991), and Barany, F., "The Ligase Chain Reaction (LCR) In A PCR World," *PCR Methods and Applications*, 1:5-16 (1991)). Since there is no polymerization step, several probe sets can ligate along a gene without interference. The optimal multiplex detection scheme involves a primary PCR amplification, followed by either LDR (two probes, same strand) or ligase chain reaction ("LCR") (four probes, both strands) detection. This approach has been successfully applied for simultaneous multiplex detection of 61 cystic fibrosis alleles (Grossman, P. D., et al., "High-Density Multiplex Detection Of Nucleic Acid Sequences: Oligonucleotide Ligation Assay And Sequence-Coded Separation," *Nucleic Acids Res.*, 22:4527-4534 (1994) and Eggerding, F. A., et al., "Fluorescence-Based Oligonucleotide Ligation Assay For Analysis Of Cystic Fibrosis Transmembrane Conductance Regulator Gene Mutations," *Human Mutation*, 5:153-165 (1995)), 6 hyperkalemic periodic paralysis alleles (Feero, W. T., et al., "Hyperkalemic Periodic Paralysis: Rapid Molecular Diagnosis And Relationship Of Genotype To Phenotype In 12 Families," *Neurology*, 43:668-673 (1993)), and 20 21-hydroxylase deficiency alleles (Day, D., et al., "Detection Of Steroid 21 Hydroxylase Alleles Using Gene-Specific PCR And A Multiplexed Ligation Detection Reaction," *Genomics*, 29:152-162 (1995) and Day, D. J., et al., "Identification Of Non-Amplifying CYP21 Genes When Using PCR-Based Diagnosis Of 21-Hydroxylase Deficiency In Congenital Adrenal Hyperplasia (CAH) Affected Pedigrees," *Hum Mol Genet*, 5(12):2039-48 (1996)).

21-hydroxylase deficiency has the highest carrier rate of any genetic disease, with 6% of Ashkenazi Jews being carriers. Approximately 95% of mutations causing 21-hydroxylase deficiency are the result of recombinations between an inactive pseudogene termed CYP21P and the normally active gene termed CYP21, which share 98% sequence homology (White, P. C., et al., "Structure Of Human Steroid 21-Hydroxylase Genes," *Proc. Natl. Acad. Sci. USA*, 83:5111-5115 (1986)). PCR/LDR was developed to rapidly determine heterozygosity or homozygosity for any of the 10 common apparent gene conversions in CYP21. By using allele-specific PCR, defined regions of CYP21 are amplified without amplifying the CYP21P sequence. The presence of wild-type or pseudogene mutation is subsequently determined by fluorescent LDR. Discriminating oligonucleotides complementary to both CYP21 and CYP21P are included in equimolar amounts in a single reaction tube so that a signal for either active gene, pseudogene, or both is always obtained. PCR/LDR genotyping (of 82 samples) was able to readily type compound heterozygotes with multiple gene conversions in a multiplexed reaction, and was in complete agreement with direct sequencing/ASO analysis. This method was able to distinguish insertion of a single T nucleotide into a $(T)_7$ tract, which cannot be achieved by allele-specific PCR alone (Day, D., et al., "Detection Of Steroid 21 Hydroxylase Alleles Using Gene-Specific PCR And A Multiplexed Ligation Detection Reaction," *Genomics*, 29:152-162 (1995)). A combination of PCR/LDR and microsatellite analysis revealed some unusual cases of PCR allele dropout (Day, D. J., et al., "Identification Of Non-Amplifying CYP21 Genes When Using PCR-Based Diagnosis Of 21-Hydroxylase Deficiency In Congenital Adrenal Hyperplasia (CAH) Affected Pedigrees," *Hum Mol Genet*, 5(12):2039-48 (1996)). The LDR approach is a single-tube reaction which enables multiple samples to be analyzed on a single polyacrylamide gel.

A PCR/LDR assay has been developed to detect germline mutations, found at high frequency (3% total), in BRCA1 and BRCA2 genes in the Jewish population. The mutations are: BRCA1, exon 2 185delAG; BRCA1, exon 20 5382insC; BRCA2, exon 11 6174delT. These mutations are more difficult to detect than most germline mutations, as they involve slippage in short repeat regions. A preliminary screening of 20 samples using multiplex PCR of three exons and LDR of six alleles in a single tube assay has successfully detected the three Ashkenazi BRCA1 and BRCA2 mutations.

Multiplexed PCR for Amplifying Many Regions of Chromosomal DNA Simultaneously.

A coupled multiplex PCR/PCR/LDR assay was developed to identify armed forces personnel. Several hundred SNPs in known genes with heterozygosities, >0.4 are currently listed.

Twelve of these were amplified in a single PCR reaction as follows: Long PCR primers were designed to have gene-specific 3' ends and 5' ends complementary to one of two sets of PCR primers. The upstream primers were synthesized with either FAM- or TET-fluorescent labels. These 24 gene-specific primers were pooled and used at low concentration in a 15 cycle PCR. After this, the two sets of primers were added at higher concentrations and the PCR was continued for an additional 25 cycles. The products were separated on an automated ABD 373A DNA Sequencer. The use of these primers produces similar amounts of multiplexed products without the need to carefully adjust gene-specific primer concentrations or PCR conditions (Belgrader, P., et al., "A Multiplex PCR-Ligase Detection Reaction Assay For Human Identity Testing," Genome Science and Technology, 1:77-87 (1996)). In a separate experiment, non-fluorescent PCR products were diluted into an LDR reaction containing 24 fluorescently labeled allele-specific LDR probes and 12 adjacent common LDR probes, with products separated on an automated DNA sequencer. LDR probe sets were designed in two ways: (i) allele-specific FAM- or TET-labeled LDR probes of uniform length, or (ii) allele-specific HEX-labeled LDR probes differing in length by two bases. A comparison of LDR profiles of several individuals demonstrated the ability of PCR/LDR to distinguish both homozygous and heterozygous genotypes at each locus (Id.). The use of PCR/PCR in human identification to simultaneously amplify 26 loci has been validated (Lin, Z., et al., "Multiplex Genotype Determination At A Large Number Of Gene Loci," *Proc Natl Acad Sci USA*, 93(6):2582-7 (1996)), or ligase based detection to distinguish 32 alleles although the latter was in individual reactions (Nickerson, D. A., et al., "Identification Of Clusters Of Biallelic Polymorphic Sequence-Tagged Sites (pSTSs) That Generate Highly Informative And Automatable Markers For Genetic Linkage Mapping," *Genomics*, 12(2):377-87 (1992)). This study validates the ability to multiplex both PCR and LDR reactions in a single tube, which is a prerequisite for developing a high throughput method to simultaneously detect SNPs throughout the genome.

For the PCR/PCR/LDR approach, two long PCR primers are required for each SNP analyzed. A method which reduces the need for multiple PCR primers would give significant savings in time and cost of a large-scale SNP analysis. The present invention is directed to achieving this objective.

SUMMARY OF THE INVENTION

The present invention is directed to a method of assembling genomic maps of an organism's DNA or portions thereof. A library of an organism's DNA is provided where the individual genomic segments or sequences are found on more than one clone in the library. Representations of the genome are created, and nucleic acid sequence information is generated from the representations. The sequence information is analyzed to determine clone overlap from a representation. The clone overlap and sequence information from different representations is combined to assemble a genomic map of the organism.

As explained in more detail infra, the representation can be created by selecting a subpopulation of genomic segments out of a larger set of the genomic segments in that clone. In particular, this is achieved by first subjecting an individual clone to a first restriction endonuclease under conditions effective to cleave DNA from the individual clone so that a degenerate overhang is created in the clone. Non-palindromic complementary linker adapters are added to the overhangs in the presence of ligase and the first restriction endonuclease to select or amplify particular fragments from the first restriction endonuclease digested clone as a representation. As a result, sufficient linker-genomic fragment products are formed to allow determination of a DNA sequence adjacent to the overhang. Although a number of first restriction endonucleases are suitable for use in this process, it is particularly desirable to use the enzyme DrdI to create the representation which comprises what are known as DrdI islands (i.e. the genomic segments which are produced when DrdI cleaves the genomic DNA in the clones).

The procedure is amenable to automation and requires just a single extra reaction (simultaneous cleavage/ligation) compared to straight dideoxy sequencing. Use of from 4 to 8 additional linker adapters/primers is compatible with microtiter plate format for delivery of reagents. A step which destroys the primers after the PCR amplification allows for direct sequencing without purifying the PCR products.

A method is provided for analyzing sequencing data allowing for assignment of overlap between two or more clones. The method deconvolutes singlet, doublet, and triplet sequencing runs allowing for interpretation of the data. For sequencing runs which are difficult to interpret, sequencing primers containing an additional one or two bases on the 3' end will generate a readable sequence. As an alternative to deconvoluting doublet and triplet sequencing runs, other enzymes may be used to create short representational fragments. Such fragments may be differentially enriched via ultrafiltration to provide dominant signal, or, alternatively, their differing length provides unique sequence signatures on a full length sequencing run.

About 200,000 to 300,000 Drd Islands are predicted in the human genome. The DrdI Islands are a representation of $1/15^{th}$ to $1/10^{th}$ of the genome. With an average BAC size of 100-150 kb, a total of 20,000 to 30,000 BAC clones would cover the human genome, or 150,000 clones would provide 5-fold coverage. Using the DrdI island approach, 4-6 sequencing runs are required for a total of 600,000 to 900,000 sequencing reactions. New automated capillary sequencing machines (Perkin Elmer 3700 machine) can run 2,304 short (80-100 bp) sequencing reads per day. Thus, the DrdI approach for overlapping all BAC clones providing a 5-fold coverage of the human genome would require only 39 days using 10 of the new DNA sequencing machines.

The above approach will provide a highly organized contig of the entire genome for just under a million sequencing reactions, or about $1/70^{th}$ of the effort required by just random clone overlap. Subsequently, random sequencing will fill in the sequence information between DrdI islands. Since the islands are anchored in the contig, this will result in a 2- to 4-fold reduction in the amount of sequencing necessary to obtain a complete sequence of the genome.

Single nucleotide polymorphisms or SNPs have been proposed as valuable tools for gene mapping and discovering genes associated with common diseases. The present invention provides a rapid method to find mapped single nucleotide polymorphisms within genomes. A representation of the genomes of multiple individuals is cloned into a common vector. Sequence information generated from representational library is analyzed to determine single nucleotide polymorphisms.

The present invention provides a method for large scale detection of single nucleotide polymorphisms ("SNP"s) on a DNA array. This method involves creating a representation of a genome from a clinical sample. A plurality of oligonucleotide probe sets are provided with each set characterized by (a) a first oligonucleotide probe, having a target-specific portion and an addressable array-specific portion, and (b) a second oligonucleotide probe, having a target-specific portion and a detectable reporter label. The oligonucleotide probes in a particular set are suitable for ligation together when hybridized adjacent to one another on a corresponding target nucleotide sequence, but have a mismatch which interferes with such ligation when hybridized to any other nucleotide sequence present in the representation of the sample. A mixture is formed by blending the sample, the plurality of oligonucleotide probe sets, and a ligase. The mixture is subjected to one or more ligase detection reaction ("LDR") cycles comprising a denaturation treatment, where any hybridized oligonucleotides are separated from the target nucleotide sequences, and a hybridization treatment, where the oligonucleotide probe sets hybridize at adjacent positions in a base-specific manner to their respective target nucleotide sequences, if present in the sample, and ligate to one another to form a ligation product sequence containing (a) the addressable array-specific portion, (b) the target-specific portions connected together, and (c) the detectable reporter label. The oligonucleotide probe sets may hybridize to nucleotide sequences in the sample other than their respective target but do not ligate together due to a presence of one or more mismatches and individually separate during the denaturation treatment. A solid support with different capture oligonucleotides immobilized at particular sites is provided where the capture oligonucleotides have nucleotide sequences complementary to the addressable array-specific portions. After subjecting the mixture to one or more ligase detection reaction cycles, the mixture is contacted with the solid support under conditions effective to hybridize the addressable array-specific portions to the capture oligonucleotides in a base-specific manner. As a result, the addressable array-specific portions are captured on the solid support at the site with the complementary capture oligonucleotide. Finally the reporter labels of ligation product sequences captured to the solid support at particular sites are detected which indicates the presence of single nucleotide polymorphisms.

It has been estimated that 30,000 to 300,000 SNPs will be needed to map the positions of genes which influence the major multivariate diseases in defined populations using association methods. Since the above SNP database is connected to a closed map of the entire genome, new genes may be rapidly discovered. Further, the representative PCR/LDR/universal array may be used to quantify allele imbalance. This allows for use of SNPs to discover new tumor suppressor genes, which undergo loss of heterozygosity, or oncogenes, which undergo amplification, in various cancers.

BRIEF DESCRIPTION OF THE DRAWINGS

FIG. 2 is a schematic drawing of a first embodiment for sequencing restriction enzyme generated representations.

FIG. 4 is a schematic drawing for DNA sequencing directly from PCR amplified DNA without primer interference.

FIG. 5 is a schematic drawing showing another embodiment of the DrdI island sequencing technique (including the nucleotide sequences of GACNNNNNNGTC (SEQ ID NO: 182) CTGNNNNNNCAG (SEQ ID NO: 183) CTAATAANNGTC (SEQ ID NO: 184) GATTATTNNCAG (SEQ ID NO: 185) and CUAAUAANNGTC (SEQ ID NO: 186), with N being A, C, G, or T in SEQ ID NOs: 182-185 and N being A, C, G, T, or U in SEQ ID NO: 186) of the present invention.

FIG. 6 is a schematic drawing showing a further alternative embodiment of sequencing DrdI islands in random BAC clones using PCR amplification (including the nucleotide sequences of GACNNNNNNGTC (SEQ ID NO: 182), CTGNNNNNNCAG (SEQ ID NO: 183), CTAATAANNGTC (SEQ ID NO: 184), GATTATTNNCAG (SEQ ID NO: 185), and CUAAUAANNGTC (SEQ ID NO: 186), with N being A, C, G, or T in SEQ ID NOs: 182-185 and N being A C G T or U in SEQ ID NO: 186).

FIG. 7 shows the three degrees of specificity in amplifying a DrdI representation (including the nucleotide sequences of CTAATAANNGTC (SEQ ID NO: 184) and GATTATTNNCAG (SEQ ID NO: 185), where N is A, C, G, or T).

FIG. 9 shows the SapI site frequencies per 40 kb in the Met Oncogene BAC from the 7q31 chromosome. The locations of the 25 SapI sites in a 171,905 bp clone are shown pictorially and in tabular form, indicating the type of overhang and the complement to that overhang. The number of sites with the 3' overhang having the same last 2 bases within the BAC clone used exactly once—singlets (i.e. @) is 5 of such SapI sites. The number of sites with the 3' overhang having the same last 2 bases within the BAC clone used exactly twice—doublets (i.e. #) is 10 of such SapI sites. The number of sites with the 3' overhang having the same last 2 bases within the BAC clone used more than twice (i.e. X) is 3 of such SapI sites.

FIG. 10 shows the DrdI and BglI site frequencies per 40 kb in the HMG Oncogene BAC from the 7q31 chromosome. The locations of the 11 DrdI and 12 BglI sites in a 165,608 bp clone are shown pictorially and in tabular form, indicating the type of overhang and the complement to that overhang. For this clone, per 40 kb, the unique sites (i.e. singlets) are as follows: 1.2 of such unique DrdI sites and 3.9 of such unique BglI sites. In this clone, per 40 kb, the sites with the 3' overhang having the same last 2 bases—doublets (i.e. *) are as follows: 1.2 of such DrdI sites and 2.0 of such BglI sites. The number of palindromic overhangs not used (i.e. ^) is as follows: 1 overhang for DrdI and 0 overhangs for BglI. The number of sites with the 3' overhang having the same last 2 bases within the BAC clone used exactly once—singlets (i.e. @) is as follows: 3 of such DrdI sites and 5 of such BglI sites.

Figure 1:
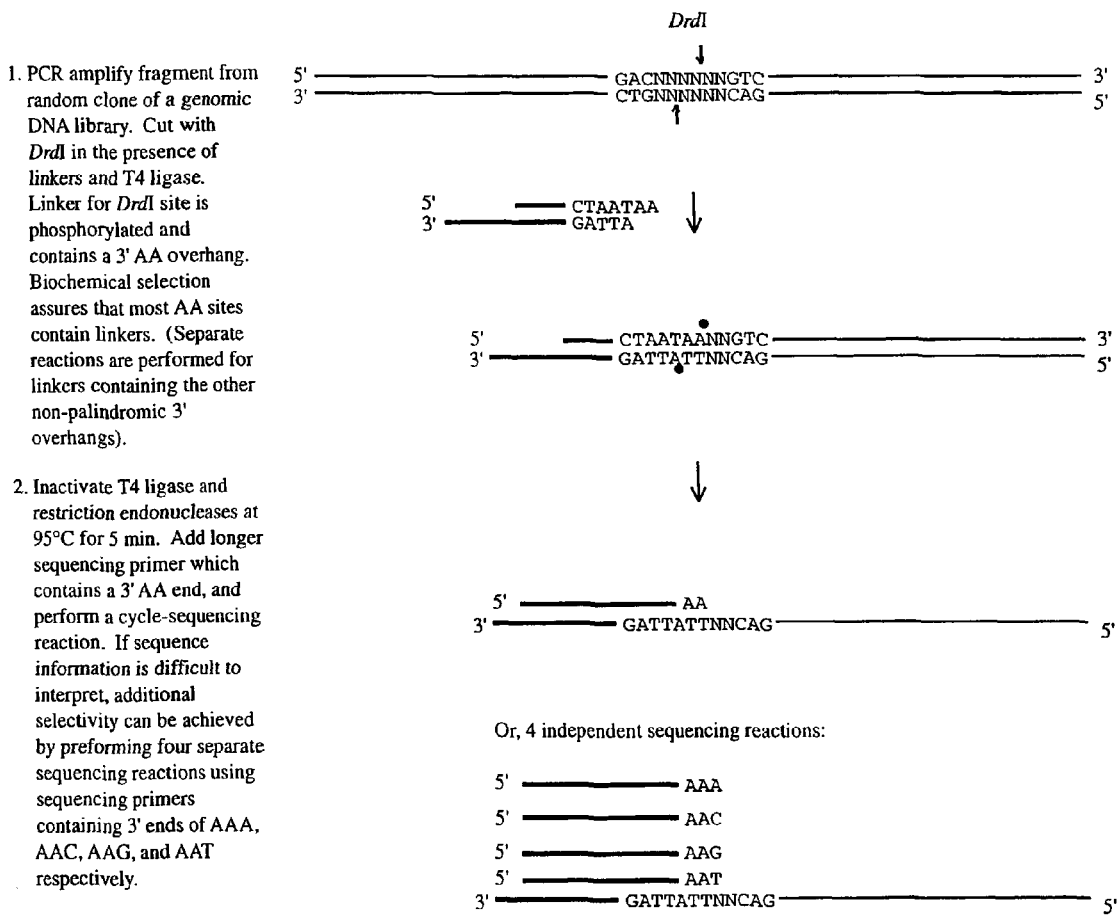
FIG. 1 is a schematic drawing showing the sequencing of DrdI islands in random plasmid or cosmid clones (including the nucleotide sequences of GACNNNNNNGTC (SEQ ID NO: 182), CTGNNNNNNCAG (SEQ ID NO: 183), CTAATAANNGTC (SEQ ID NO: 184) and GATTATTNNCAG (SEQ ID NO: 185) where N is A, C, G, or T) in accordance with the present invention.

The number of sites with the 3' overhang having the same last 2 bases within the BAC clone used exactly twice—doublets (i.e. #) is as follows: 2 of such DrdI sites and 4 of such BglI sites. The number of sites with the 3' overhang having the same last 2 bases within the BAC clone used more than twice (i.e. X) is as follows: 1 of such DrdI sites and 3 of such BglI sites.

FIG. 11 shows the SapI site frequencies per 40 kb in the HMG Oncogene BAC from the 7q31 chromosome with the locations of the 12 SapI sites in a 165,608 bp clone being shown in pictorial and tabular form, indicating the type of overhang and the complement to that overhang. The number of sites with the 3' overhang having the same last 2 bases within the BAC clone used exactly once—singlets (i.e. @) is 4 of such SapI sites. The number of sites with the 3' overhang having the same last 2 bases within the BAC clone used exactly twice—doublets (i.e. #) is 1 of such SapI sites. The number of sites with the 3' overhang having the same last 2 bases with BAC in the clone used more than twice (i.e. X) is 2 of such SapI sites.

FIG. 12 shows the DrdI and BglI site frequencies per 40 kb in the Pendrin Oncogene BAC from the 7q31 chromosome with the locations of the 10 DrdI and 17 BglI sites in a 97,943 bp clone being shown in pictorial and tabular form, indicating the type of overhang, and the complement to that overhang. For this clone, per 40 kb, the unique sites are as follows: 1.3 of such unique DrdI sites and 5.0 of such unique BglI sites. In this clone, per 40 kb, the sites with the 3' overhang having the same last 2 bases—doublets (i.e. *) are as follows: 2.1 of such DrdI sites and 9.2 of such BglI sites. The number of palindromic overhangs not used (i.e. ^) is as follows: 2 overhangs for DrdI and 0 overhangs for BglI. The number of sites with the 3' overhang having the same last 2 bases within the BAC clone used exactly once—singlets (i.e. @) is as follows: 3 of such DrdI sites and 1 of such BglI sites. The number of sites with the 3' overhang having the same last 2 bases within the BAC clone used exactly twice—doublets (i.e. #) is as follows: 1 of such DrdI sites and 5 of such BglI sites. The number of sites with the 3' overhang having the same last 2 bases within the BAC clone used more than twice (i.e. X) is as follows: 1 of such DrdI sites and 7 of such BglI sites.

FIG. 13 shows the SapI site frequencies per 40 kb in the Pendrin gene BAC from the 7q31 chromosome with the locations of the 14 SapI sites in a 97,943 bp clone being shown in pictorial and tabular form, indicating the type of overhang and the complement to that overhang. The number of sites with the 3' overhang having the same last 2 bases within the BAC clone used exactly once—singlets (i.e. @) is 7 of such SapI sites. The number of sites with the 3' overhang having the same last 2 bases within the BAC clone used exactly twice—doublets (i.e. #) is 2 of such SapI sites. The number of sites with the 3' overhang having the same last 2 bases within the BAC clone used more than twice (i.e. X) is 1 of such SapI sites.

FIG. 14 shows the DrdI and BglI site frequencies per 40 kb in the alpha2(I) collagen BAC from the 7q31 chromosome with the locations of the 11 DrdI and 15 BglI sites in a 116,466 bp clone being in pictorial and tabular form, indicating the type of overhang and the complement to that overhang. For this clone, per 40 kb, the unique sites are as follows: 1.4 of such unique DrdI sites and 3.1 of such unique BglI sites. In this clone, per 40 kb, the sites with the 3' overhang having the same last 2 bases—doublets (i.e. *) are as follows: 2.1 of such DrdI sites and 7.2 of such BglI sites. The number of palindromic overhangs not used (i.e. ^) is as follows: 1 overhang for DrdI and 0 overhangs for BglI. The number of sites with the 3' overhang having the same last 2 bases within the BAC clone used exactly once—singlets (i.e. @) is as follows: 2 of such DrdI sites and 4 of such BglI sites. The number of sites with the 3' overhang having the same last 2 bases within the BAC clone used exactly twice—doublets (i.e. #) is as follows: 4 of such DrdI sites and 7 of such BglI sites. The number of sites with the 3' overhang having the same last 2 bases within the BAC clone used more than twice (i.e. X) is as follows: 0 of such DrdI sites and 3 of such BglI sites.

FIG. 15 shows the SapI site frequencies per 40 kb in the alpha2(I) collagen BAC from the 7q31 chromosome with the locations of the 18 SapI sites in a 116,466 bp clone being in pictorial and tabular form, indicating the 18 SapI site locations, the type of overhang, and the complement to that overhang. The number of sites with the 3' overhang having the same last 2 bases within the BAC clone used exactly once—singlets (i.e. @) is 4 of such SapI sites. The number of sites with the 3' overhang having the same last 2 bases within the BAC clone used exactly twice—doublets (i.e. #) is 3 of such SapI sites. The number of sites with the 3' overhang having the same last 2 bases within the BAC clone used more than twice (i.e. X) is 2 of such SapI sites.

Figure 16:
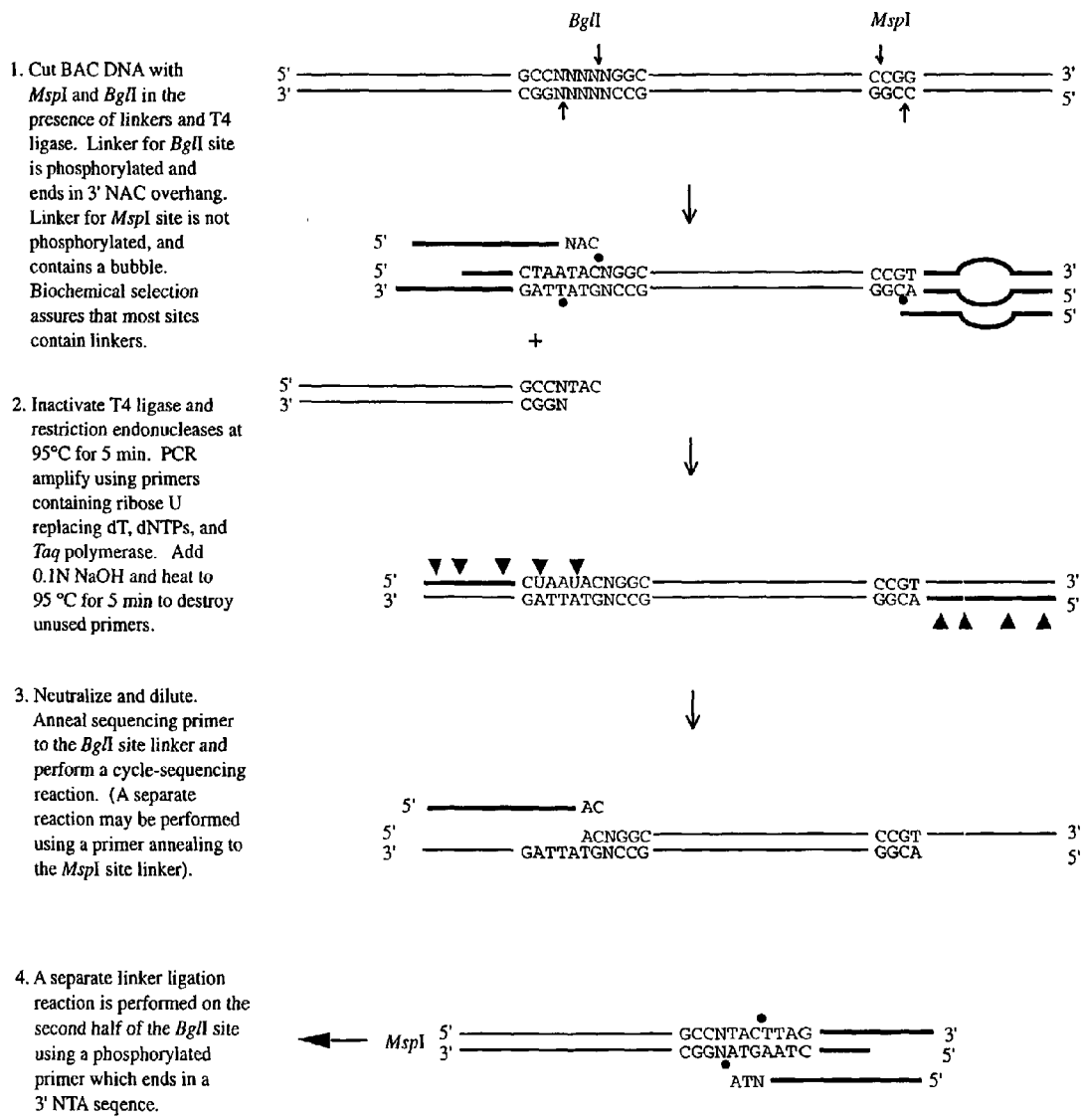

FIG. 16 is a schematic drawing showing the sequencing of BglI islands in random BAC clones (including the nucleotide sequences of GCCNNNNNGGC (SEQ ID NO: 187), CGGNNNNNCCG (SEQ ID NO: 188), CTAATACNGGC (SEQ ID NO: 189), GATTATGNCCG (SEQ ID NO: 190) CUAAUACNGGC (SEQ ID NO: 191) GATTATGNCCG (SEQ ID NO: 192), GCCNTACTTAG (SEQ ID NO: 193), and CGGNATGAATC (SEQ ID NO: 194), with N being A, C, G, or T in SEQ ID NOs: 187-190, 192-193 and with N being A, C, G, or U in SEQ ID NO: 191 SEQ. ID. No. 187 194) in accordance with the present invention.

FIG. 16A is a schematic drawing showing the sequencing of BglI islands in random BAC clones using PCR amplification (including the nucleotide sequences of GCCNNNNNGGC (SEQ ID NO: 187), CGGNNNNNCCG (SEQ ID NO: 188), CUAAUACNGGC (SEQ ID NO: 191), CTAAACNNGGC (SEQ ID NO: 195) and GATTTGNNCCG (SEQ ID NO: 196), with N being A, C, G, or T in SEQ ID NOs: 187, 188, 191, 195, 196 and with N being A, C, G, or U in SEQ ID NO: 191).

Figure 17:
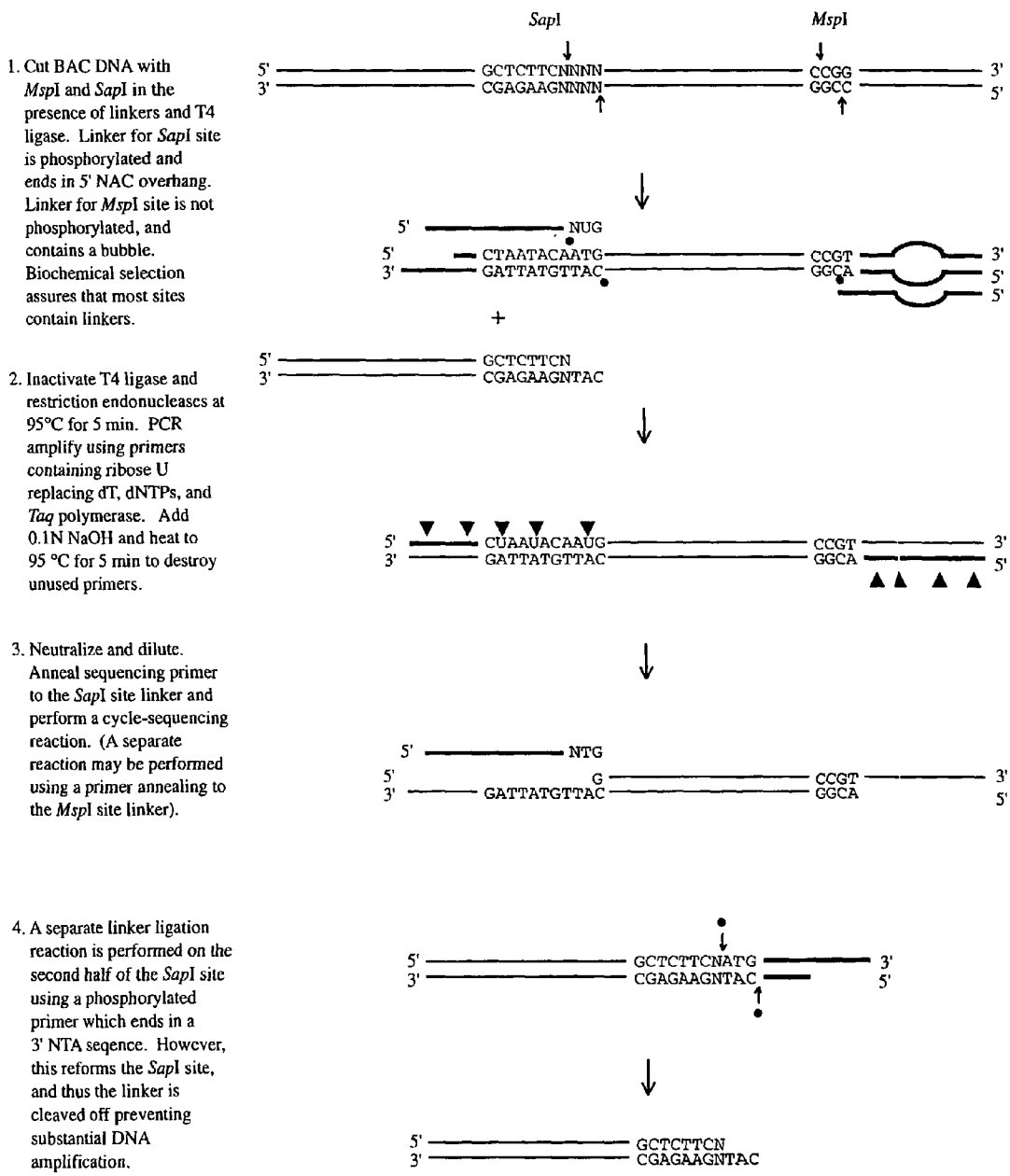

FIG. 17 is a schematic drawing showing the sequencing of SapI islands in random BAC clones (including the nucleotide sequences of GCTCTTCNNNN (SEQ ID NO: 197), CGAGAAGNNNN (SEQ ID NO: 198), CTAATACAATG (SEQ ID NO: 199), GATTATGTTAC (SEQ ID NO: 200), CGAGAAGNTAC (SEQ ID NO: 201), CUAAUACAAUG (SEQ ID NO: 202), GATTATGTTAC (SEQ ID NO: 203), and GCTCTTCNATG (SEQ ID. NO: 204), with N being A, C, G, or T in SEQ ID NOs: 197-198, 201, and 204 in accordance with the present invention.

FIG. 17A shows the probabilities of two or more singlets or doublets of DrdI, SapI, or BglI sites in BAC clones containing 2 to 36 sites.

FIG. 18 shows the alignment of BAC clone sequences, which are concordant and discordant, from DrdI sites (including the nucleotide sequences of TCGTCCTCAGGAACT-GAAGCTATATAATCAGTTAAGTCCCT-GCTTCTGATCTCTTC TGATTTTCTTCTAAGAAGAGAATA (SEQ ID NO: 3), GTGTCAAGTAAAGAAGTACAGCA-GATAAGTAAAACGGAA AAAAATAATGAAAG AAT-TACAAAGGAAGACTAAGGAAAGAG (SEQ ID NO: 4) AAGTCTACAATCAAGAGGCCAACTGAT-TCCATGTCTGGTGAGGGTCTA TTTCCTG GTGCATA-GATGGCTCCTTCTCACTG (SEQ ID NO: 5), TAGTCCT-CAATTTCACCATGGATTAAATAACAGAACACAGA GTTACTGTGAGACT TGTGGTAGAAAATCTTTAATTCATT (SEQ ID NO: 6), and GTGTCATCTAGCTATAAATCTAAAGATAATAATAAAATTGGGAAAGATTTTCATCAGATAGACTTTTAACACCAAGCTTGA (SEQ ID NO: 7).

FIGS. 19A-19D show DrdI/MseI fragments in approximately 2 MB of human DNA. The average fragment size is about 125 bp, with most fragments being under 600 bp.

FIGS. 20A-20D show DrdI/MspI/TaqI fragments in approximately 2 MB of human DNA. The average fragment size is about 1,000 bp, with most fragments being over 600 bp.

FIG. 21 shows how 4 unique singlet DrdI sequences are determined from 2 overlapping doublet BAC clone sequences (including the nucleotide sequences of TCGTCCTCAGGAACTGAAGCTATATAATCAGTTAAGTCCCTGCTTCTGATCTCTTC TGATTTTCTTCTAAGAAGAGAATA (SEQ ID NO: 3), GTGTCAAGTAAAGAAGTACAGCAGATAAGTAAAACGGAAAAAAATAATGAAAG AATTACAAAGGAAGACTAAGGAAAGAG (SEQ ID NO: 4) AAGTCTACAATCAAGAGGCCAACTGATTCCATGTCTGGTGAGGGTCTATTTCCTG GTGCATAGATGGCTCCTTCTCACTG (SEQ ID NO: 5), and TAGTCCTCAATTTCACCATGGATTAAATAACAGAACACA GAGTTACTGTGAGACT TGTGGTAGAAAATCTTTAATTCATT (SEQ ID NO: 6).

FIG. 22 shows how 3 unique singlet DrdI sequences are determined from overlapping doublet and triplet BAC clone sequences (including the nucleotide sequences of TCGTCCTCAGGAACTGAAGCTATATAATCAGTTAAGTCCCTGCTTCTGATCTCTTC TGATTTTCTTCTAAGAAGAGAATA (SEQ ID NO: 3), GTGTCAAGTAAAGAAGTACAGCAGATAAGTAAAACGGAAAAAAATAATGAAAG AATTACAAAGGAAGACTAAGGAAAGAG (SEQ ID NO: 4) AAGTCTACAATCAAGAGGCCAACTGATTCCATGTCTGGTGAGGGTCTATTTCCTG GTGCATAGATGGCTCCTTCTCACTG (SEQ ID NO: 5), TAGTCCTCAATTTCACCATGGATTAAATAACAGAACACA GAGTTACTGTGAGACT TGTGGTAGAAAATCTTTAATTCATT (SEQ ID NO: 6), and GTGTCATCTAGCTATAAATCTAAAGATAATAATAAAATTGGGAAAGATTTTCATCAGATAGACTTTTAACACCAAGCTTGA (SEQ ID NO: 7).

FIG. 23 shows the BglI, DrdI, and SapI sites in the pBeloBAC11 cloning vector.

Figure 24:
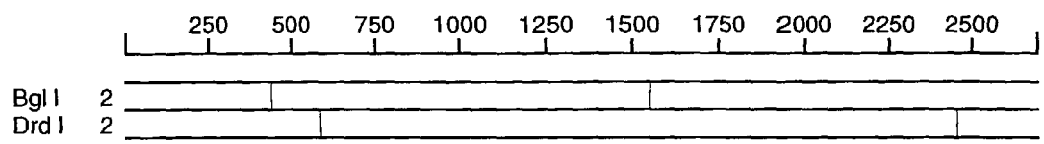

FIG. 24 shows the BglI, DrdI, and SapI sites in the pUC19 cloning vector.

Figure 25:
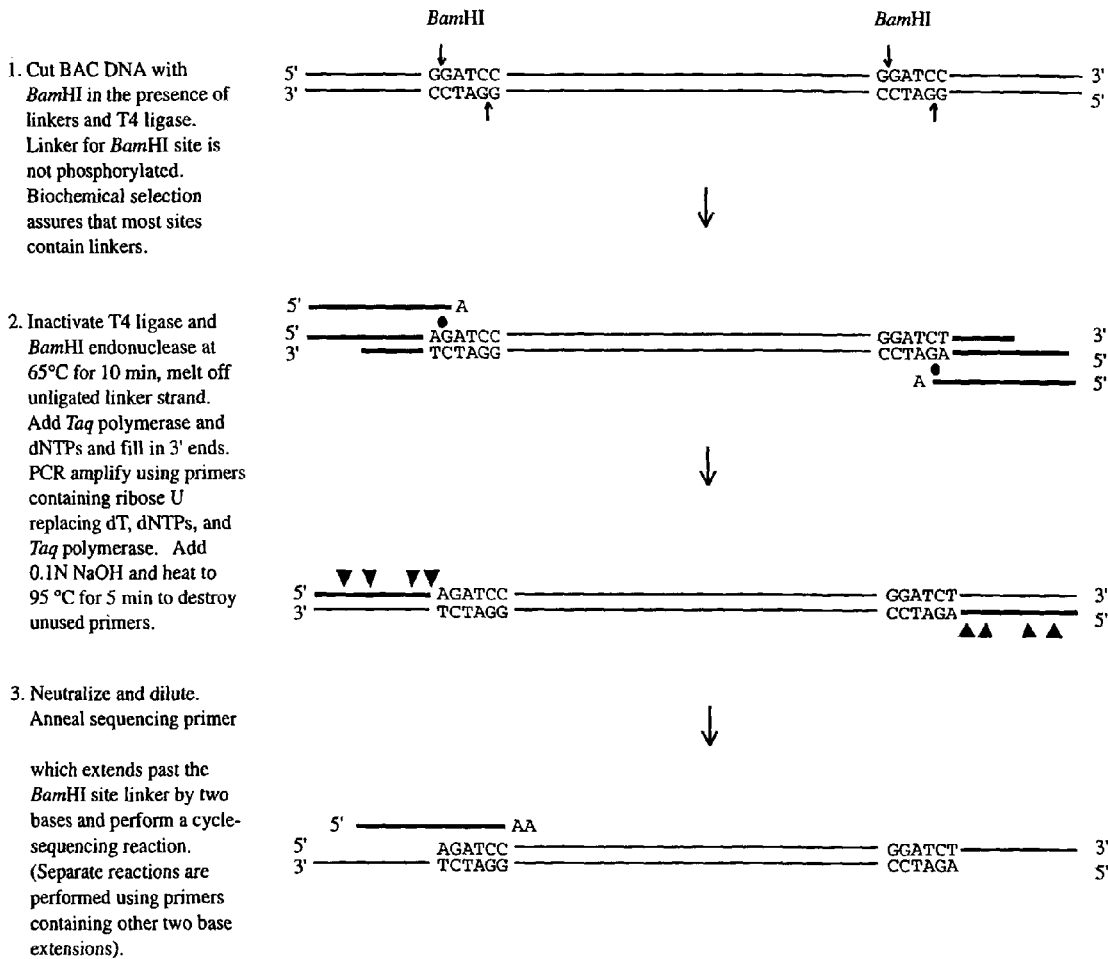

FIG. 25 is a schematic drawing showing the sequencing of BamHI islands in random BAC clones.

Figure 26B:
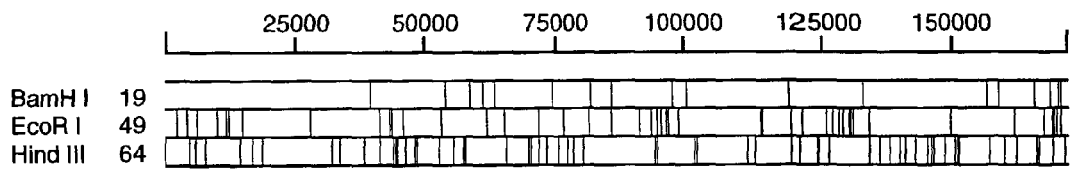

FIGS. 26A-26B show the EcoRI, HindIII, and BamIII site frequencies for the Met Oncogene in a sequenced BAC clone from the 7q31 chromosome. There are 19 BamHI sites, 49 EcoRI sites, and the 64 HindIII sites within 171,905 bp clone as shown. The number of BamHI sites that are the same where the 2 bases next to the site within the BAC clone are used exactly once—a singlet (i.e. @) is 6. The number of BamHI sites that are the same where the 2 bases next to the site within the BAC clone are used exactly twice—a doublet (i.e. #) is 2. The number of BamHI sites that are the same where the 2 bases next to the site within the BAC clone are used more than once is 2.

FIGS. 27A-27C show the AvrII, NheI, and SpeI site frequencies for the Met Oncogene in a sequenced BAC clone from the 7q31 chromosome. There are the 25 AvrII sites, 22 NheI sites, and the 21 SpeI sites within the 171,905 bp clone shown. The number of AvrII sites that are the same where the 2 bases next to the site within the BAC clone are used exactly once—a singlet (i.e. @) is 5. The number of AvrII sites that are the same where the 2 bases next to the site within the BAC clone are used exactly twice—a doublet (i.e. #) is 2. The number of AvrII sites that are the same where the 2 bases next to the site within the BAC clone are used more than once is 3. The number of NheI sites that are the same where the 2 bases next to the site within the BAC clone are used exactly once—a singlet (i.e. @) is 3. The number of NheI sites that are the same where the 2 bases next to the site within the BAC clone are used exactly twice—a doublet (i.e. #) is 3. The number of NheI sites that are the same where the 2 bases next to the site within the BAC clone are used more than once is 3. The number of SpeI sites that are the same where the 2 bases next to the site within the BAC clone are used exactly once—a singlet (i.e. @) is 3. The number of AvrII sites that are the same where the 2 bases next to the site within the BAC clone are used exactly twice—a doublet (i.e. #) is 3. The number of AvrII sites that are the same where the 2 bases next to the site within the BAC clone are used more than once is 3.

Figure 28:
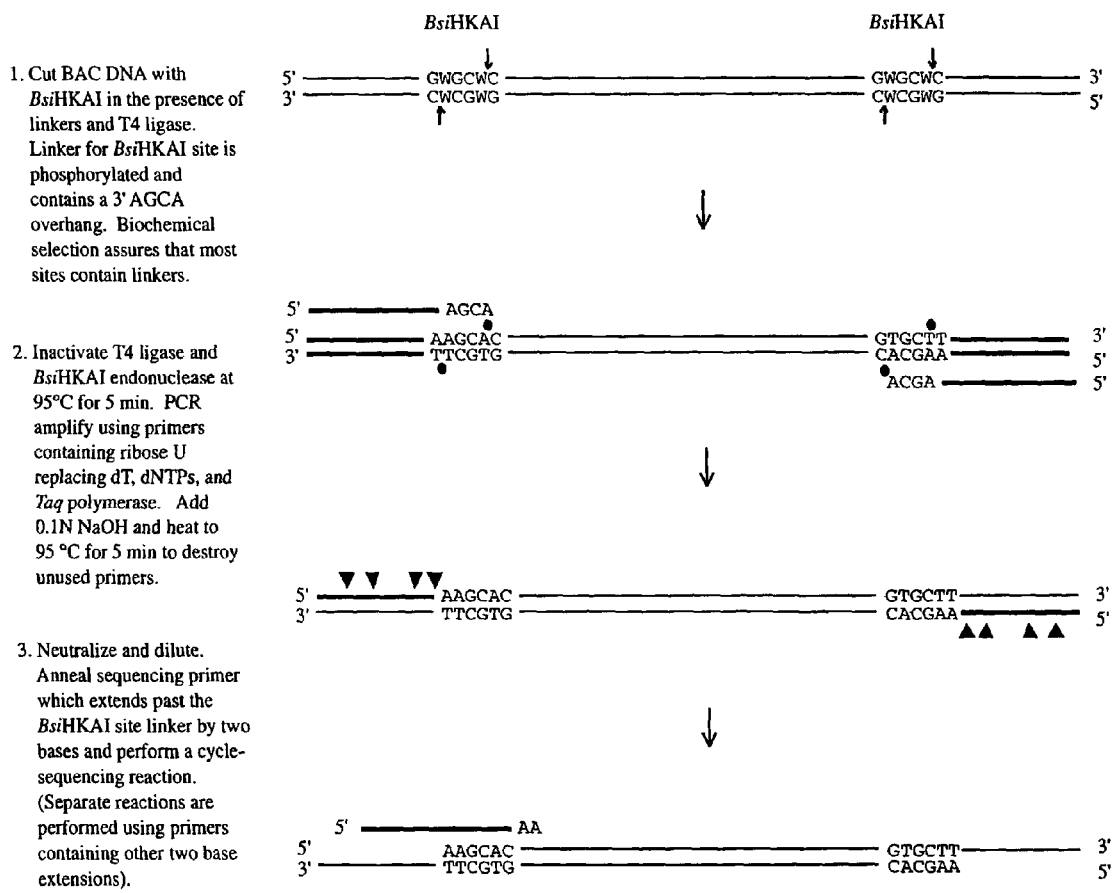

FIG. 28 is a schematic drawing showing the sequencing of BsiHKAI islands in random BAC clones.

Figure 29B:
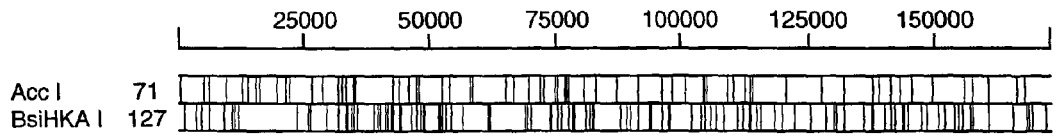

FIGS. 29A-29B show the AccI and BsiHKAI site frequencies for the Met Oncogene in a sequenced BAC clone from the 7q31 chromosome. 71 AccI sites and 127 BsiHKAI sites within 171,905 bp clone are shown. The number of AccI sites that are the same where the 2 bases next to the site within the BAC clone are used exactly once—a singlet (i.e. @) is 4. The number of AccI sites that are the same where the 2 bases next to the site within the BAC clone are used exactly twice—a doublet (i.e. #) is 2. The number of AccI sites that are the same where the 2 bases next to the site within the BAC clone are used more than once is 0. The number of BsiHKAI sites that are the same where the 2 bases next to the site within the BAC clone are used exactly once—a singlet (i.e. @) is 6. The number of BsiHKAI sites that are the same where the 2 bases next to the site within the BAC clone are used exactly twice—a doublet (i.e. #) is 3. The number of BsiHKAI sites that are the same where the 2 bases next to the site within the BAC clone are used more than twice is 0.

Figure 30:
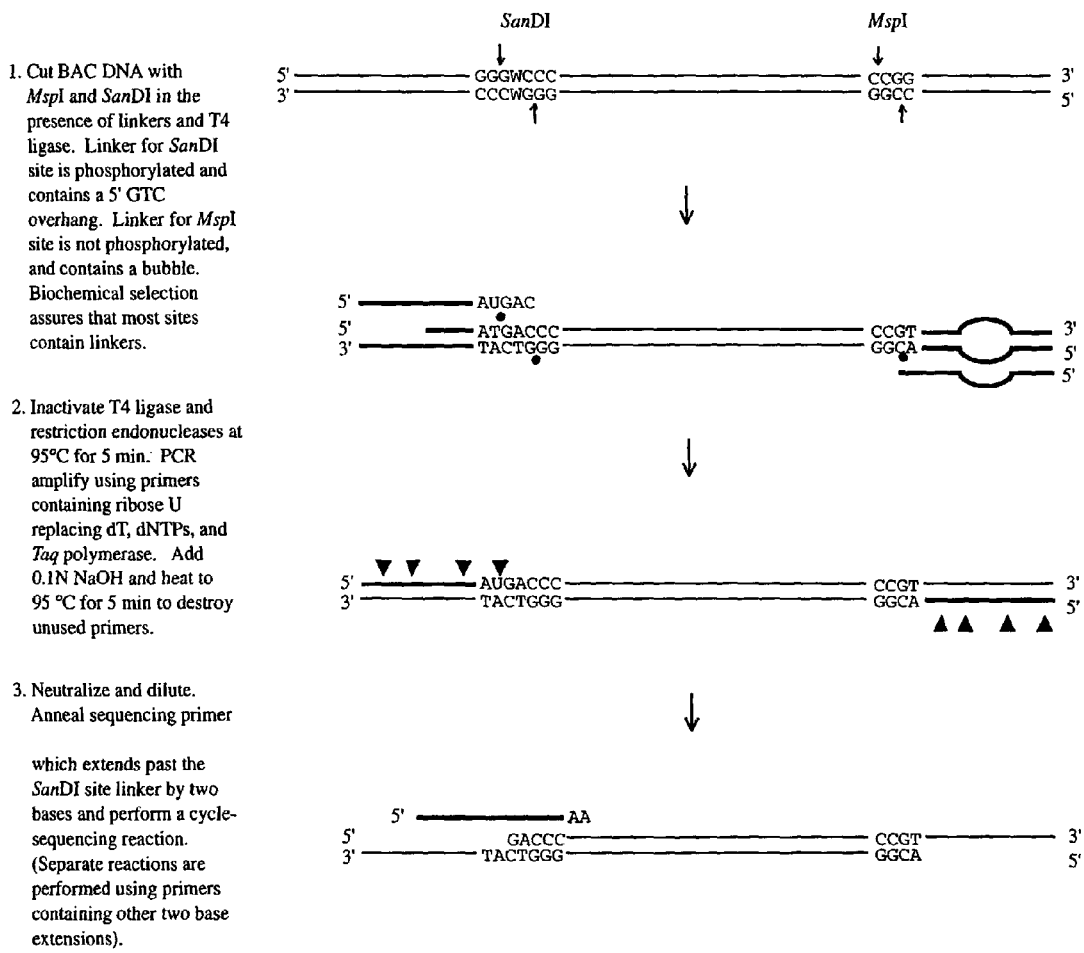

FIG. 30 is a schematic drawing showing the sequencing of SanDI islands in random BAC clones.

Figure 31B:
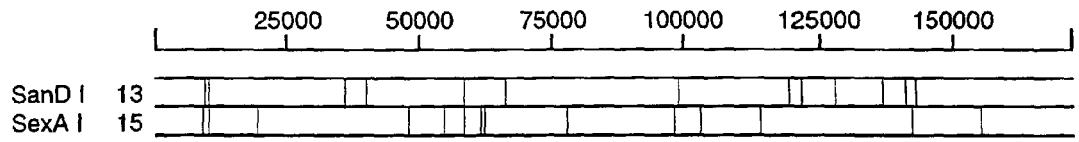

FIGS. 31A-31B show the SanDI and SexAI site frequencies for the Met Oncogene in a sequenced BAC clone from the 7q31 chromosome. There are 13 SanDI sites and 15 SexAI within the 171,905 bp clone. The number of SanDI sites that are the same where the 2 bases next to the site within the BAC clone are used exactly once—a singlet (i.e. @) is 3. The number of SanDI sites that are the same where the 2 bases next to the site within the BAC clone are used exactly twice—a doublet (i.e. #) is 5. The number of SanDI sites that are the same where the 2 bases next to the site within the BAC clone are used more than once is 0. The number of SexAI sites that are the same where the 2 bases next to the site within the BAC clone are used exactly once—a singlet (i.e. @) is 8. The number of SexAI sites that are the same where the 2 bases next to the site within the BAC clone are used exactly twice—a doublet (i.e. #) is 2. The number of SexAI sites that are the same where the 2 bases next to the site within the BAC clone are used more than twice is 1.

Figure 32:
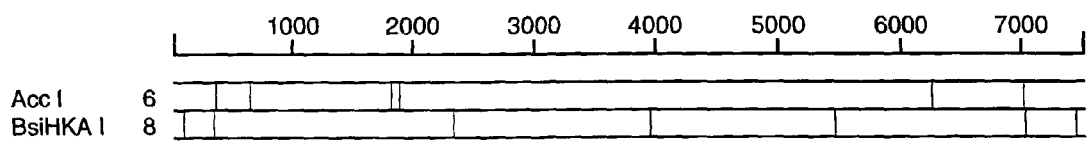

FIG. 32 shows the AccI and BsiHKAI sites in the pBeloBAC11 cloning vector. There are 6 AccI sites and 8 BsiHKAI sites.

FIG. 33 shows the AvrII, BamHI, NheI, and SpeI sites in the pBeloBAC11 cloning vector.

Figure 34:
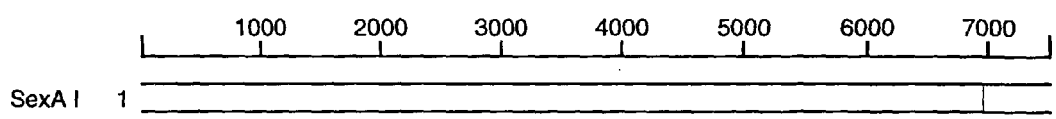
Figure 35A:
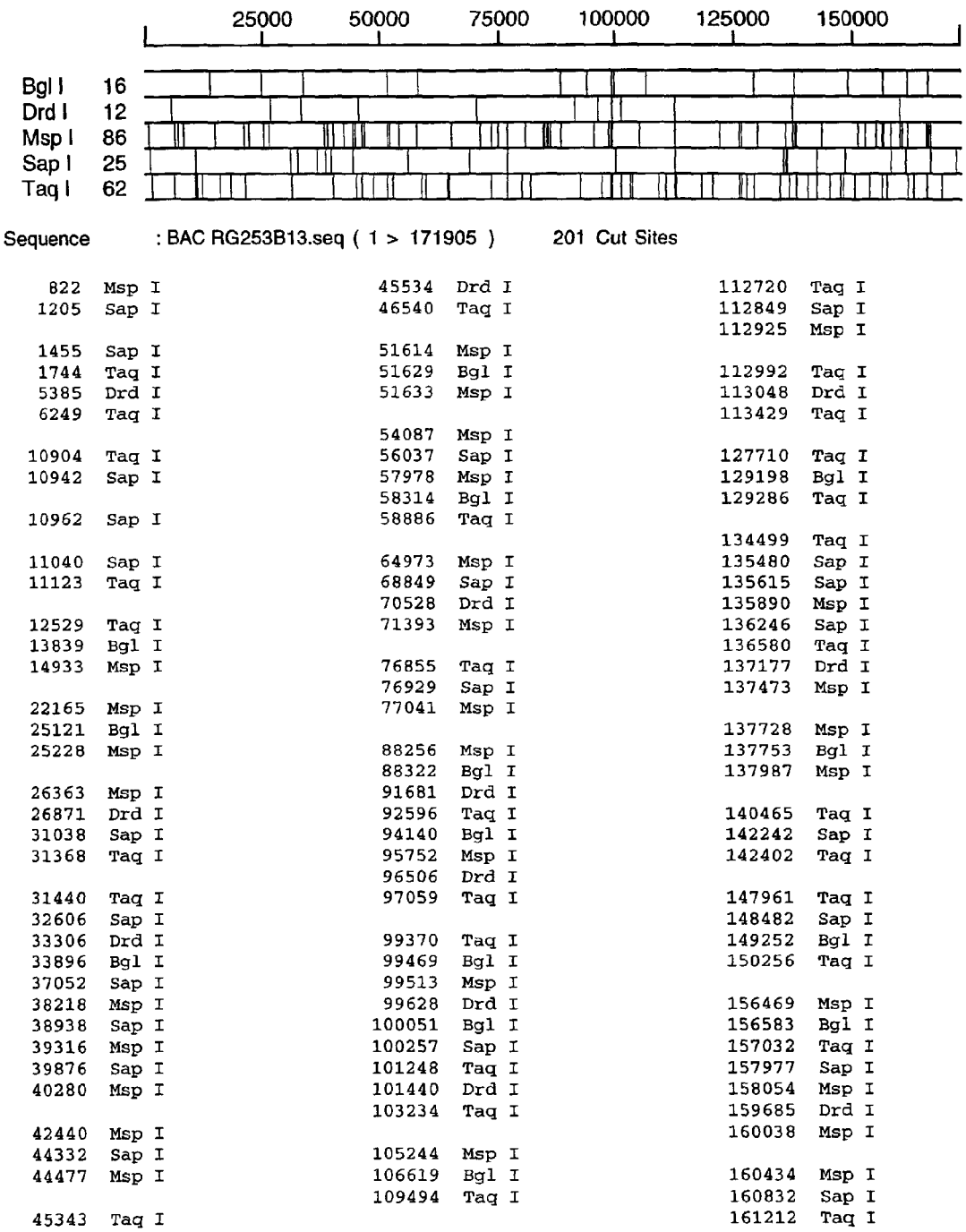

FIG. 34 shows the SanDI and SexAI sites in the pBeloBAC11 cloning vector.

FIGS. 35A-35G show the DrdI, BglI, SapI, TaqI, and MspI sites in a sequenced BAC cloning vector from the 7q31 chromosome. There are 12 DrdI sites, 16 BglI sites, 25 SapI sites, 63 TaqI sites, and 86 MspI sites in the 171,905 base pairs.

FIG. 36 shows the three degrees of specificity in amplifying a BglI representation (including the nucleotide sequences of CTAAACNNGGC (SEQ ID NO: 195) and GATTTGNNCCG (SEQ ID NO: 196), where N is A, C, G, or T).

Figure 37:
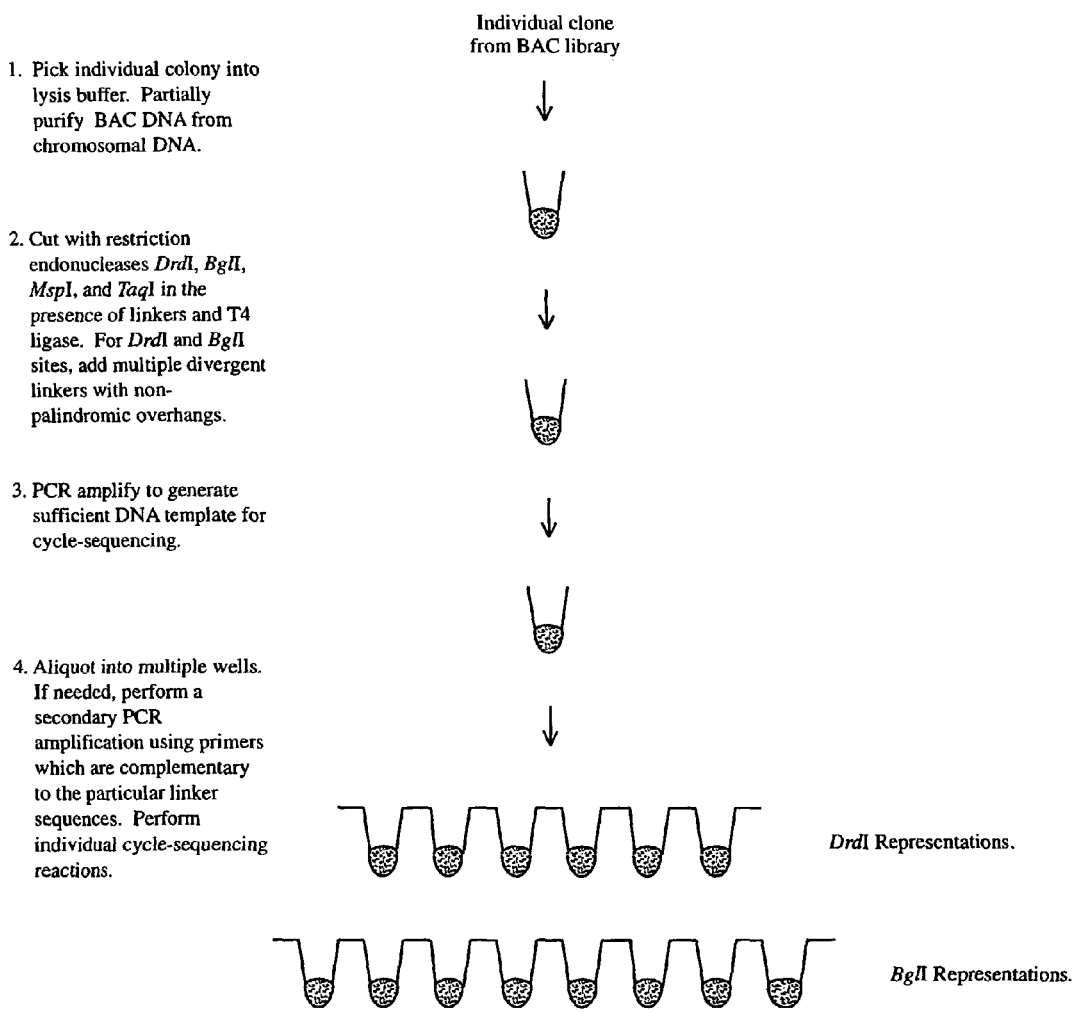

FIG. 37 shows Scheme 1 for sequencing for DrdI and BglI representations of individual BAC clones.

FIG. 38 shows overlapping DrdI islands in four hypothetical BAC clones using AA overhangs.

FIG. 39 shows overlapping DrdI islands in four hypothetical BAC clones using AC overhangs.

FIG. 40 shows overlapping DrdI islands in four hypothetical BAC clones using AG overhangs.

FIG. 41 shows overlapping DrdI islands in four hypothetical BAC clones using CA overhangs.

FIG. 42 shows overlapping DrdI islands in four hypothetical BAC clones using GA overhangs.

FIG. 43 shows overlapping DrdI islands in four hypothetical BAC clones using GG overhangs.

Figure 44:
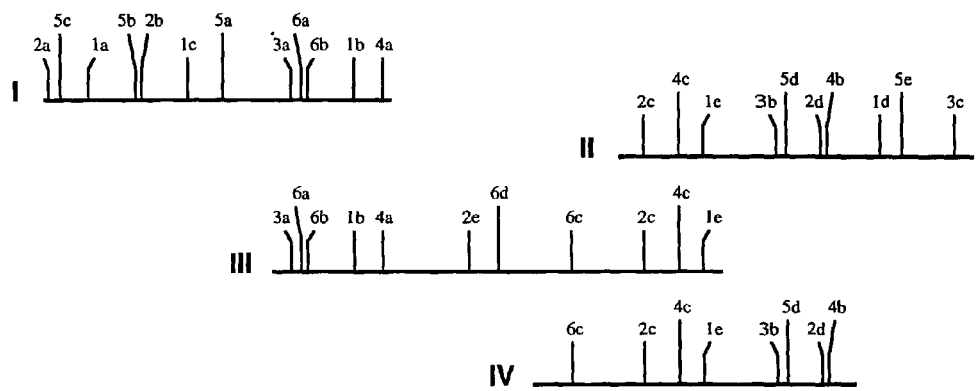

FIG. 44 shows overlapping DrdI islands in four hypothetical BAC clones using AA, AC, AG, CA, GA, and GG overhangs.

Figure 45:
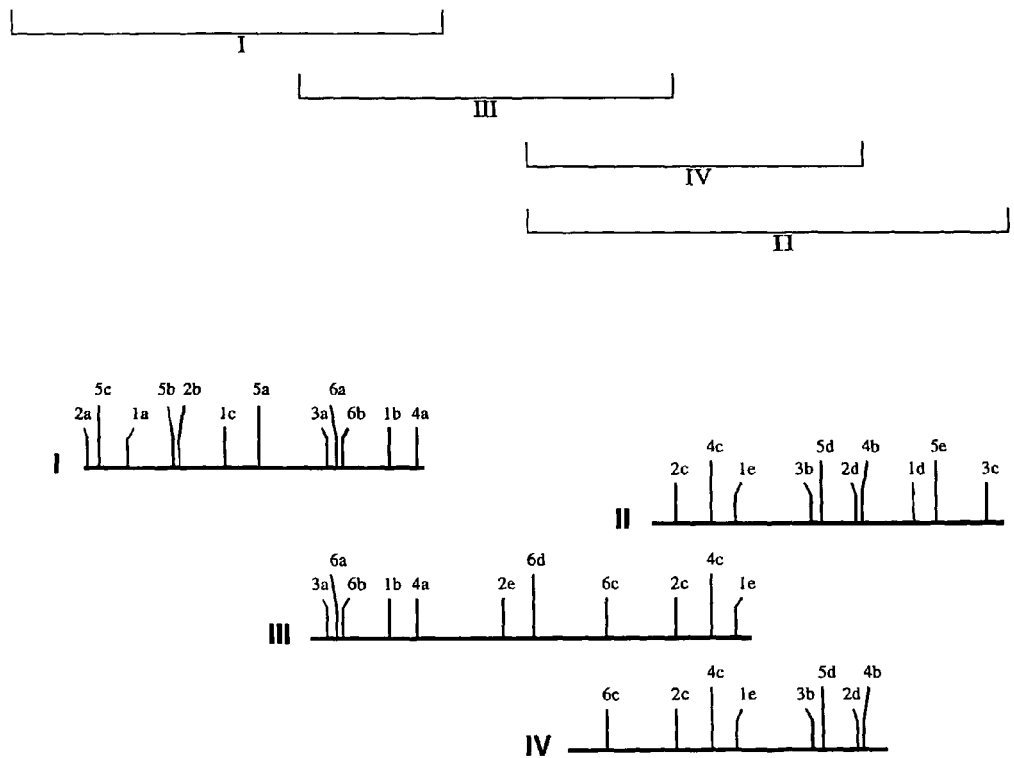

FIG. 45 shows the alignment of the four hypothetical BAC clones based upon on the unique and overlapping DrdI islands depicted in FIGS. 38 to 44.

FIGS. 46A-46E show the sizes of representational fragments generated by DrdI, TaqI and MspI digestion in overlapping BACs from 7q31. When such fragments are amplified using linker ligation/PCR amplification, they will contain approximately 25 additional bases on each side. Sizes of fragments were determined from 3 separate contigs on 7q31 known as contig 1941 (BACs RG253B13, RG013N12, and RG300C03), contig T002144 (BACs RG022J17, RG067E13, RG011J21, RG022C01, and RG043K06), and contig T002149 (RG343P13, RG205G13, O68P20, and H_133K23). Overlaps between BACs in contig 1941 are indicated by the following symbols: RG253B13/RG013N12=*, RG013N12/R RG300C03=†. Overlaps between BACs in contig T002144 are indicated by the following symbols: RG022J17/RG067E13=*, RG067E13/RG011J21=†, RG011J21/RG022C01=‡, and RG022C01/RG043K06=**. Overlaps between BACs in contig T002149 are indicated by the following symbols: RG343P13/RG205G13=*, RG205G13/O68P20=†, and O68P20/H_133K23=‡.

FIGS. 47A-47E show the sizes of representational fragments generated by DrdI and MseI digestion in overlapping BACs from 7q31. When such fragments are amplified using linker ligation/PCR amplification, they will contain approximately 25 additional bases on each side. Sizes of fragments were determined from 3 separate contigs on 7q31 known as contig 1941 (BACs RG253B13, RG013N12, and RG300C03), contig T002144 (BACs RG022J17, RG067E13, RG011J21, RG022C01, and RG043K06), and contig T002149 (RG343P13, RG205G13, O68P20, and H_133K23). Overlaps between BACs in contig 1941 are indicated by the following symbols: RG253B13/RG013N12=*, RG013N12/R RG300C03=†. Overlaps between BACs in contig T002144 are indicated by the following symbols: RG022J17/RG067E13=*, RG067E13/RG011J21=‡, RG011J21/RG022C01=‡, and RG022C01/RG043K06=**. Overlaps between BACs in contig T002149 are indicated by the following symbols: RG343P13/RG205G13=*, RG205G13/O68P20=†, and O68P20/H_133K23=‡.

FIG. 48 shows the DrdI, TaqI, and MspI sites in 4 sequenced BAC clones from a 7q31c chromosome as well as the location and identities of the AA, AC, AG, CA, GA, and GG overhangs and their overhangs.

Figure 49:
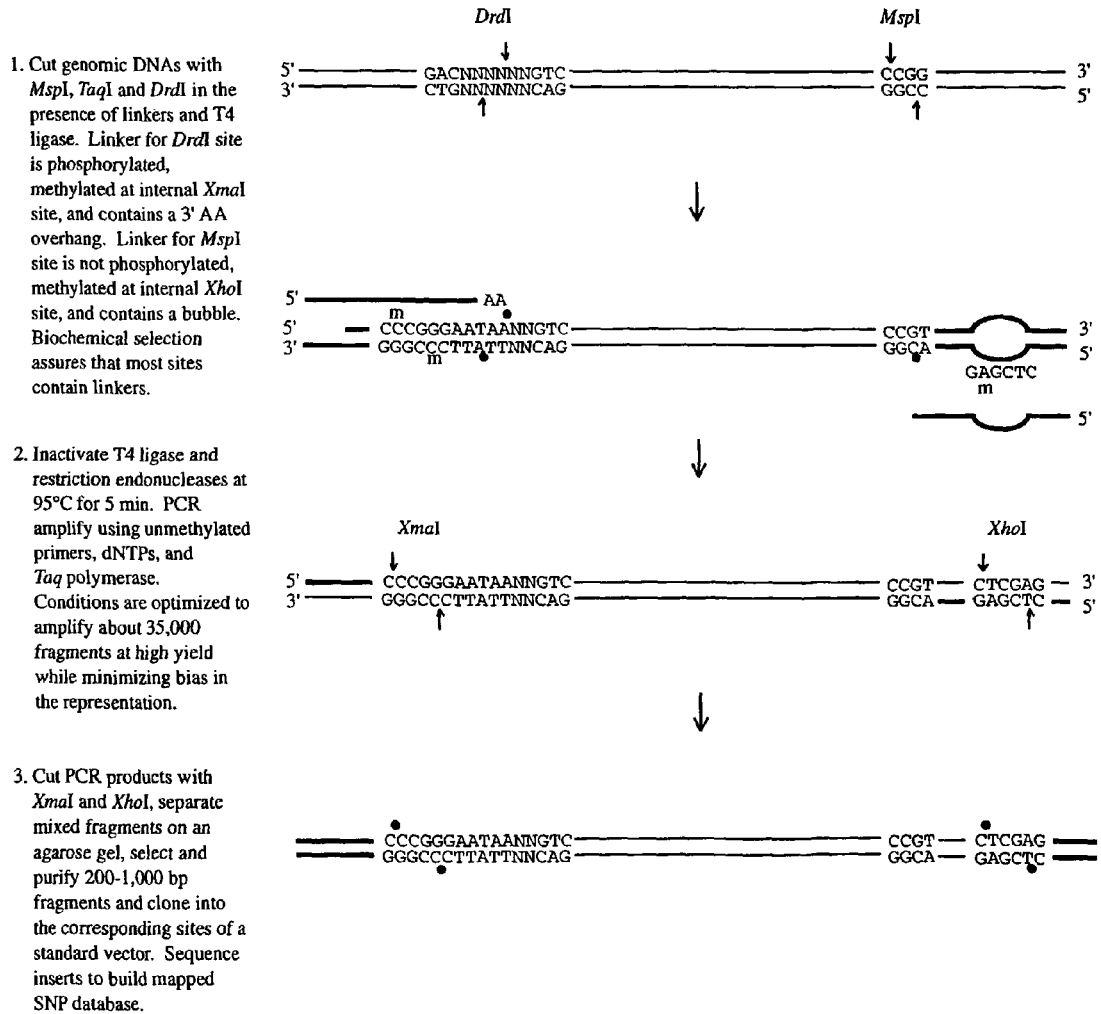

FIG. 49 is a schematic drawing showing the PCR amplification of a DrdI representation for shotgun cloning and generating mapped SNPs (including the nucleotide sequences of GACNNNNNNGTC (SEQ ID NO: 182), CTGNNNNNNCAG (SEQ ID NO: 183), CCCGGGAATAANNGTC (SEQ ID NO: 206), and GGGCCCTTATTNNCAG (SEQ ID NO: 207), where N is A, C, G, or T SEQ. ID. No. 182 183, 206 207).

FIG. 49A is a schematic drawing of the PCR amplification of a DrdI representation for shotgun cloning and generating mapped SNPs (including the nucleotide sequences of GACNNNNNNGTC (SEQ ID NO: 182), CTGNNNNNNCAG (SEQ ID NO: 183) CCCGGGAATAANNGTC (SEQ ID NO: 206) GGGCCCTTATTNNCAG (SEQ ID NO: 207), and CCCGGGAATAA (SEQ ID NO: 208), where N is A, C, G, or T).

FIG. 50 is a schematic drawing showing the PCR amplification of a DrdI representation for high-throughput SNP detection (including the nucleotide sequences of GAC GTC (SEQ ID NO: 182), CTG CAG (SEQ. ID. NO: 183), CTAATAANNGTC (SEQ ID NO: 209) and GATTATTNNCAG (SEQ ID NO: 210) and GATTATTGNGAG (SEQ ID NO: 211), where N is A, C, G, or T).

FIG. 50A is an alternative schematic drawing showing the PCR amplification of a DrdI representation for high-throughput SNP detection.

FIGS. 51A-B show the quantitative detection of G12V mutation of the K-ras gene using two LDR probes in the presence of 10 micrograms of salmon sperm DNA. FIG. 51A is a graph showing the amount of LDR product formed is a linear function of K-ras mutant DNA template, even at very low amounts of template. FIG. 51B is a log-log graph of amount of LDR product formed for various amount of K-ras mutant DNA in a 20 µl LDR reaction. The amount of LDR product formed with 2.5 pM (50 amol) to 3 nM (60 fmol) of mutant K-ras template was determined in duplicate using fluorescent probes on an ABD 373 DNA sequencer.

FIGS. 52A-B show a scheme for PCR/LDR detection of mutations in codons 12 and 13 of K-ras. using an addressable array. FIG. 52A shows a schematic representation of chromosomal DNA containing the K-ras gene. Exons are shaded and the position of codons 12 and 13 are shown. Exon-specific primers were used to selectively amplify K-ras DNA flanking codons 12 and 13. Probes were designed for LDR detection of seven possible mutations in these two codons. Discriminating LDR probes contained a complement to an address sequence on the 5' end and the discriminating base on the 3' end. Common LDR probes were phosphorylated on the 5' end and contained a fluorescent label on the 3' end. FIG. 52B shows the presence and type of mutation is determined by hybridizing the contents of an LDR reaction to an addressable DNA array. The capture oligonucleotides on the array have sequences which are designed to be sufficiently different, so that only probes containing the correct complement to a given capture oligonucleotide remain bound at that address. In the LDR reaction, only a portion of the hybrid probe is ligated to its adjacent common fluorescently labeled probe (in the presence of the correct target). Thus, for every hybridization, an identical quantity of addressable array-specific portion competes for hybridization to each address. This feature allows for simultaneous identification and quantification of LDR signal.

Figure 53:
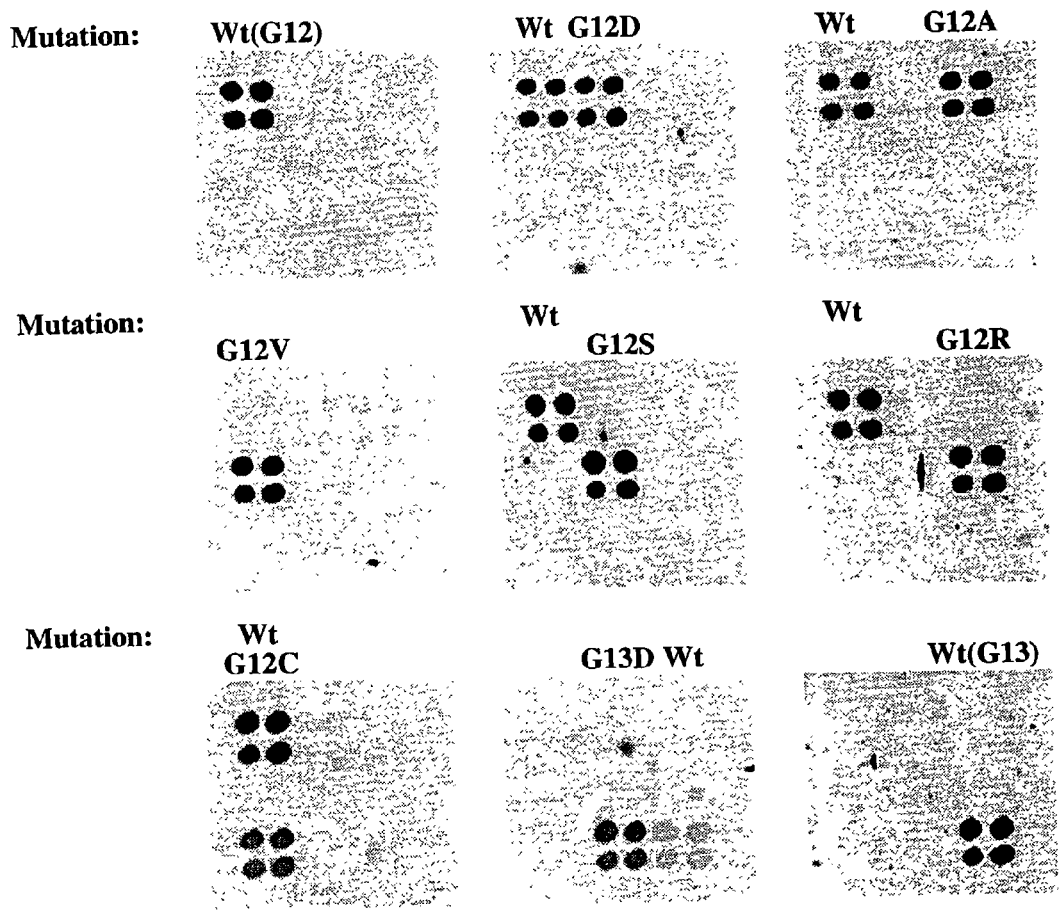

FIG. 53 shows the array hybridization of K-ras LDR products. Arrays were hybridized for 1 hour at 65° C. in a hybridization oven with nine individual LDR reactions (17 μL) diluted to 55 μL with 1.4X hybridization buffer. Following hybridization, arrays were washed for 10 minutes at room temperature in 300 mM bicine pH 8.0, 10 mM $MgCl_2$, 0.1% SDS. The arrays were analyzed on an Olympus AX70 epifluorescence microscope equipped with a Princeton Instruments TE/CCD-512 TKBM1 camera. The images were collected using a 2 second exposure time. All nine arrays displayed signals corresponding to the correct mutant and/or wild-type for each tumor or cell line sample. The small spots seen in some of the panels, i.e. near the center of the panel containing the G13D mutant, are not incorrect hybridizations, but noise due to small bubbles in the polymer.

Figure 54:
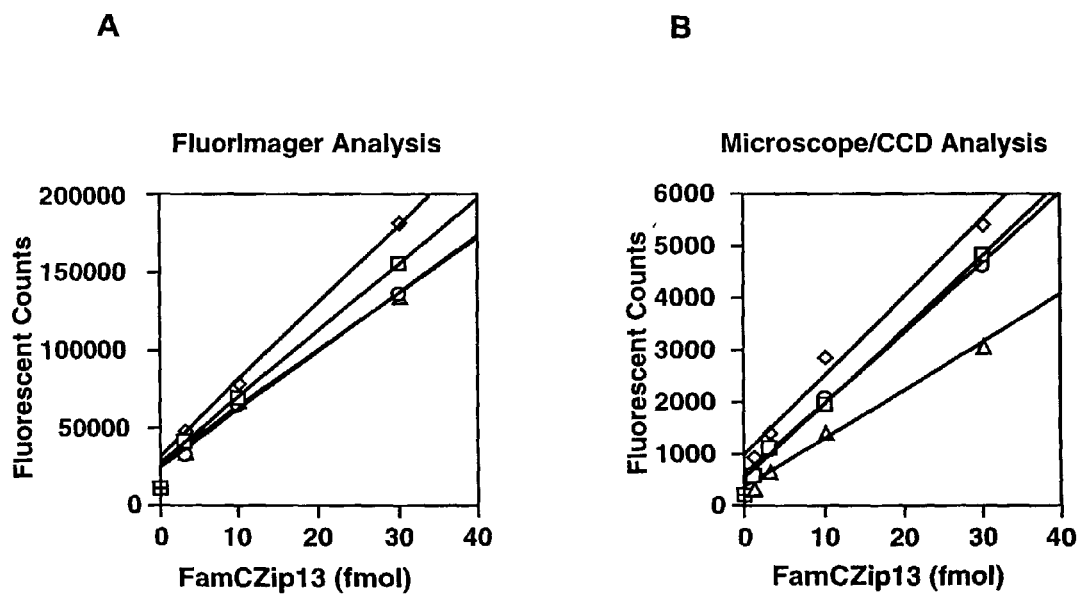

FIGS. 54A-B show the quantification of minority fluorescently-labeled oligonucleotide probe captured by a universal addressable array using two different detection instruments. Hybridizations were carried out using 55 μl hybridization buffer containing 4,500 fmole fluorescently-labeled common probes, 9×500 fmole of each unlabeled, addressable array-specific portion-containing discriminating probe, and 1 to 30 fmol CZip13 oligonucleotide. FIG. 54A shows the quantification of the amount of captured CZip13 oligonucleotide using a Molecular Dynamics 595 FluorImager. FIG. 54B shows the quantification of the amount of captured CZip13 oligonucleotide using an Olympus AX70 epifluorescence microscope equipped with a Princeton Instruments TE/CCD-512 TKBM1 camera.

FIG. 55 shows how an allelic imbalance can be used to distinguish gene amplification from loss of heterozygosity (i.e. LOH) in tumor samples which contain stromal contamination.

Figure 56:
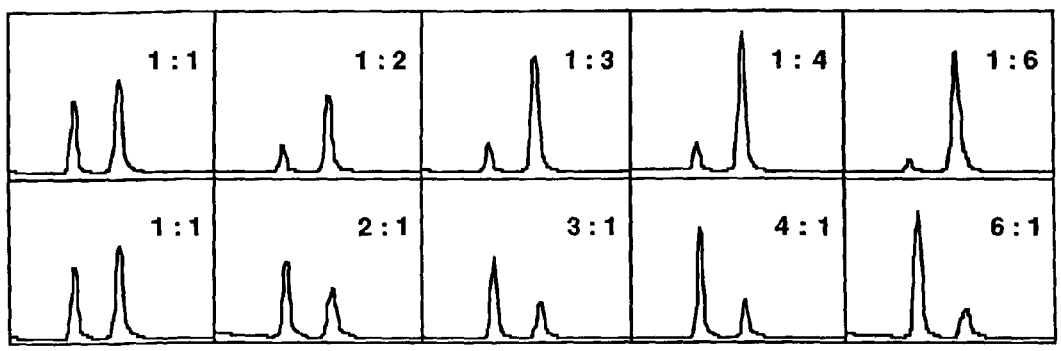

FIG. 56 shows the PCR/LDR quantification of different ratios of K-ras G12V mutant to wild-type DNA. LDR reactions were carried out in a 20 μl reaction containing 2 pmol each of the discriminating and wild type ("wt") probe, 4 pmol of the common probe and 1 pmol total of various ratios of PCR product (pure wt and pure G12V mutant) from cell lines (HT29 and SW620). LDR reactions were thermally cycled for 5 cycles of 30 sec at 94° C. and 4 min. at 65° C., and quenched on ice. 3 μl of the LDR reaction product was mixed with 1 μl of loading buffer (83% formamide, 83 mM EDTA, and 0.17% Blue Dextran) and 0.5 ml TAMRA 350 molecular weight marker, denatured at 94° C. for 2 minutes, chilled rapidly on ice prior to loading on a 8 M urea-10% polyacrylamide gel, and electrophoresed on an ABI 373 DNA sequencer at 1400 volts. Fluorescent ligation products were analyzed and quantified using the ABI GeneScan 672 software (Perkin-Elmer Biosystems, Foster City, Calif.). The amount of product obtained was calculated using the peak area and from the calibration curve (1 fmol=600 peak area units). The normalized ratio was obtained by multiplying or dividing the absolute ratio by the 1:1 absolute ratio.

FIGS. 57A-B are schematic drawings showing PCR/LDR procedures using addressable DNA arrays where there are 2 alternative labeling schemes for capture on the array.

Figure 58:
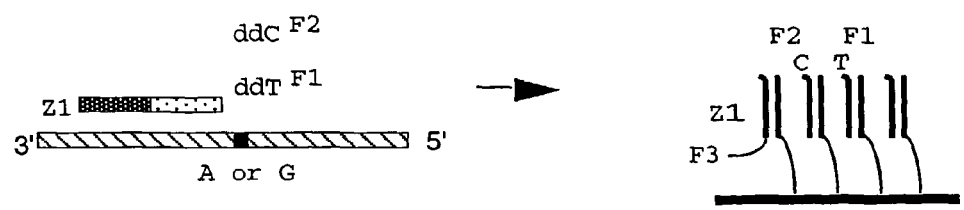

FIG. 58 is a schematic diagram showing a labeling scheme for PCR/SNUPE with addressable array capture.

FIGS. 59A-B are schematic drawings showing a labeling scheme for PCR/LDR with gene array capture.

FIG. 60 is a schematic diagram showing a labeling scheme for LDR/PCR with addressable array capture.

FIG. 61 is a diagram showing a labeling scheme for LDR/PCR with lambda exonuclease digestion and addressable array capture.

FIGS. 62A-B are schematic drawings showing 2 alternative dual label strategies to quantify LDR signal using addressable DNA arrays.

FIG. 63 shows the detection of gene amplification in tumor samples which contain stromal contamination using addressable array-specific portions on the discriminating oligonucleotide probe.

FIG. 64 shows the detection of gene amplification in tumor samples which contain stromal contamination using addressable array-specific portions on the common oligonucleotide probe.

FIG. 65 shows the detection of heterozygosity (i.e. LOH) in tumor samples which contain stromal contamination using addressable array-specific portions on the discriminating oligonucleotide probes.

FIG. 66 shows the detection of heterozygosity (i.e. LOH) in tumor samples which contain stromal contamination using addressable array-specific portions on the common oligonucleotide probes.

FIG. 67 shows the calculations for the detection procedure shown in FIG. 63.

FIG. 68 shows the calculations for the detection procedure shown in FIG. 64.

FIG. 69 shows the calculations for the detection procedure shown in FIG. 65.

FIG. 70 shows the calculations for the detection procedure shown in FIG. 66.

Figure 71:
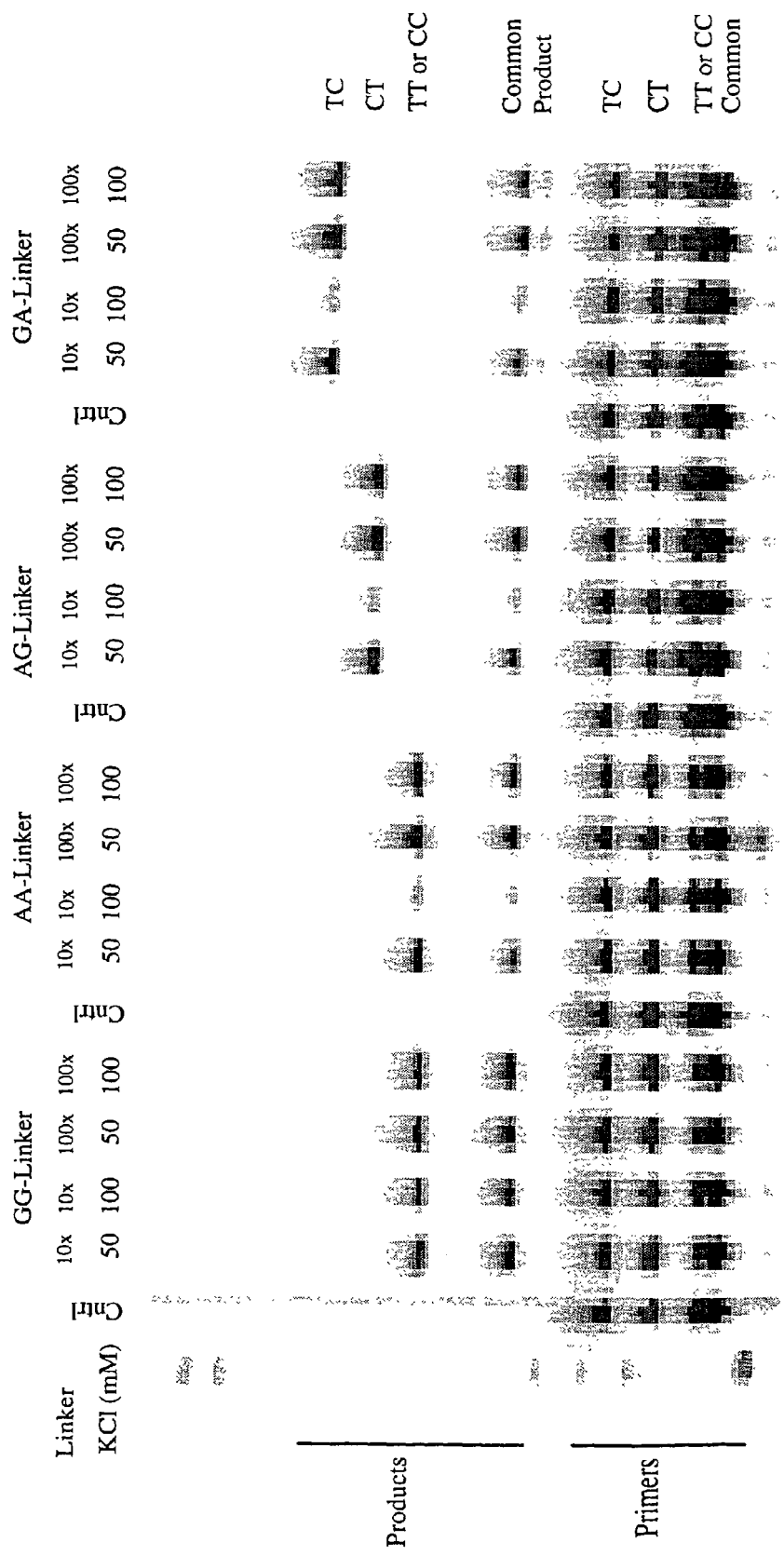

FIG. 71 shows the fidelity of T4 DNA ligase on synthetic target/linker. T4 DNA ligase assays were performed with linkers containing 2 base 3' overhangs (GG, AA, AG, and GA) and synthetic targets containing 2 base 3' complementary or mismatched overhangs (CC, TT, TC, and CT). Products represent both top and bottom strand ligation products. Synthetic targets were designed such that the common strand (top strand) provided a 39 nucleotide product (common product), while the specific strand (bottom strand) provided a 48 (CC, TT), 52 (CT), or 56 (TC) nucleotide product. Only the correct complement product is observed, while there were no misligations. Since TT- and CC-targets result in the same length products, TT-targets are not present in GG-linker assays and CC-targets are not present in AA-linker assays. For AG- and GA-linker assays, all four targets (TC-, CT-, CC-, and TT-) are present. Synthetic complementary target was present at 5 nM, and each linker/adapter was present at either 50 nM (=10× concentration), or 500 nM (=100× concentration).

Figure 72:
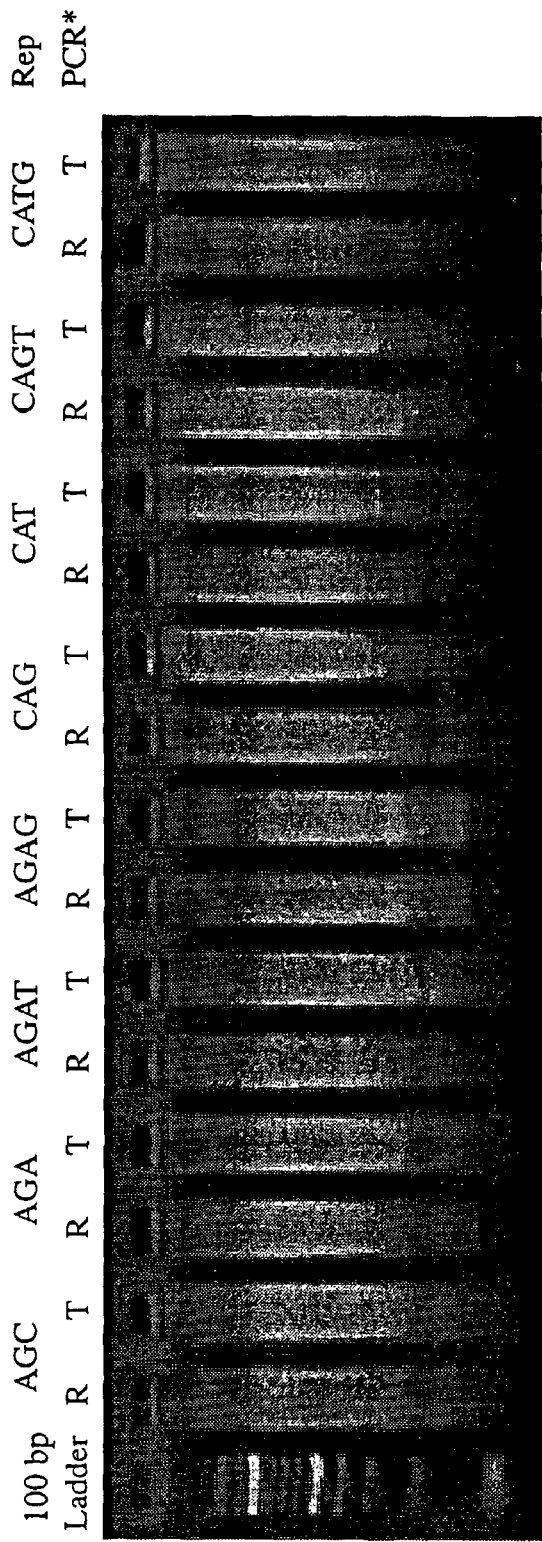

FIG. 72 shows DrdI representations of human genomic DNA. The DrdI representation of human genomic DNA was generated by "regular PCR" and "touchdown PCR" using 3 and 4 base selection PCR primers. The six lanes following the 100 bp ladder lane were the PCR amplification of DrdI AG-overhang fragments of human genome by regular PCR and touchdown PCR using AGC, AGA, AGAT, and AGAG selection primers, respectively. The last six lanes were the PCR amplification of DrdI CA-overhang fragments of human genome by regular PCR and touchdown PCR using CAG, CAT, CAGT, and CATG selection primers, respectively.

Figure 73:
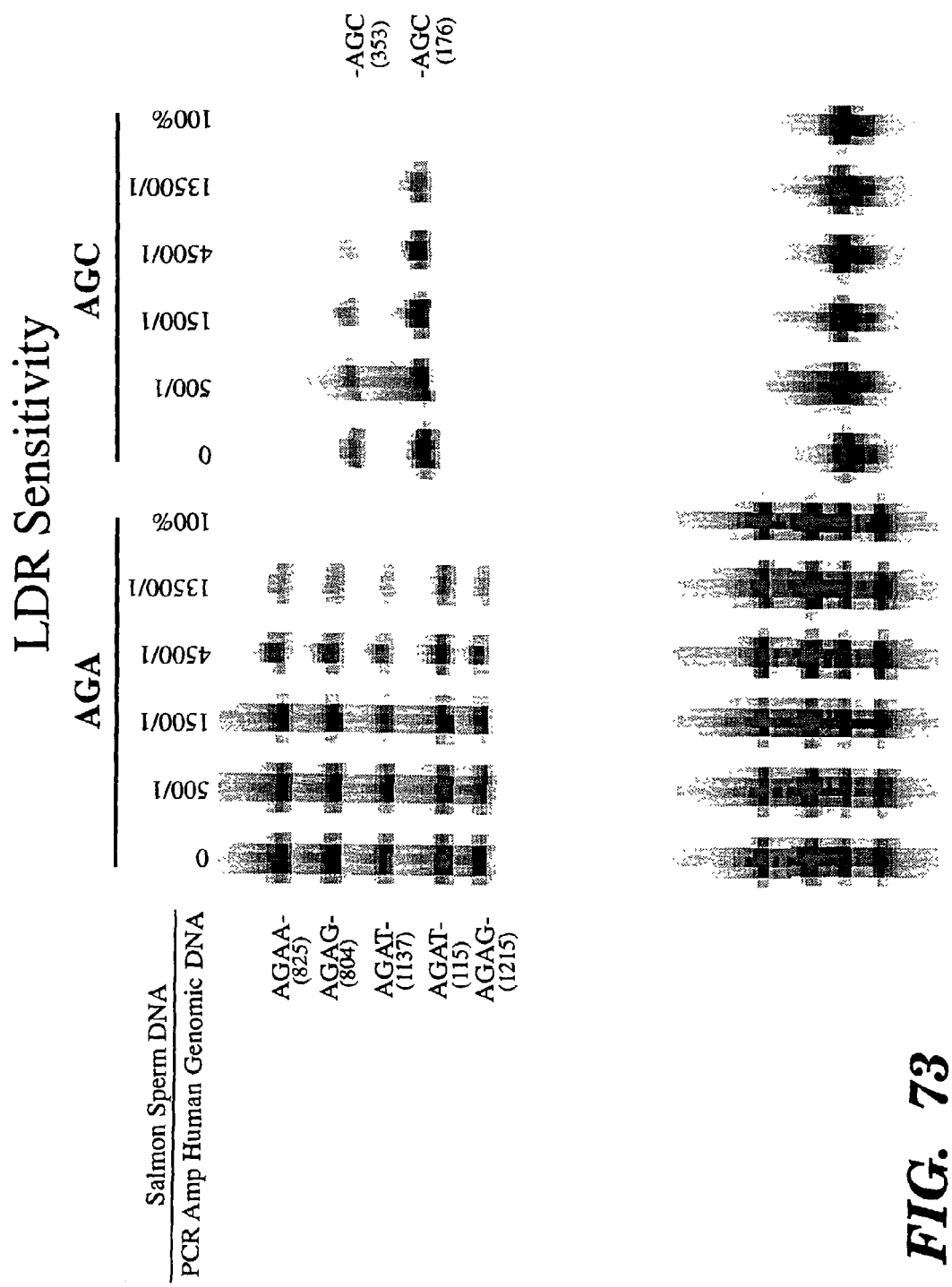

FIG. 73 shows the sensitivity of a PCR/LDR reaction. Human genomic DNA was subjected to PCR amplification using region specific primers, followed by LDR detection using LDR probes specific to the amplified regions. Aliquots of 3 μl of the reaction products were mixed with 3 μl of loading buffer (83% formamide, 8.3 mM EDTA, and 0.17% Blue Dextran) and 0.5 μl Rox-1000, or TAMRA 350 molecular weight marker, denatured at 94° C. for 2 min., chilled rapidly on ice prior to loading on an 8 M urea-10% polyacrylamide gel, and electrophoresed on an ABI 373 DNA sequencer at 1400 volts. Fluorescent ligation products were analyzed and quantified using the ABI Gene Scan software. The first six lanes were the results of an LDR assay of PCR amplified human genomic DNA using probes which amplify fragments which should be present in AGA DrdI representations; without salmon sperm DNA, and 500, 1,500, 4,500, 13,500 fold dilutions in 10 μg salmon sperm DNA, and 10 μg salmon sperm DNA alone, respectively. The last six lanes were the results of an LDR assay of PCR amplified human genomic DNA using probes which amplify fragments which should be present in AGC DrdI representations; without salmon sperm DNA, and 500, 1,500, 4,500, 13,500 fold dilutions in 10 μg salmon sperm DNA, and 10 μg salmon sperm DNA alone, respectively.

Figure 74:
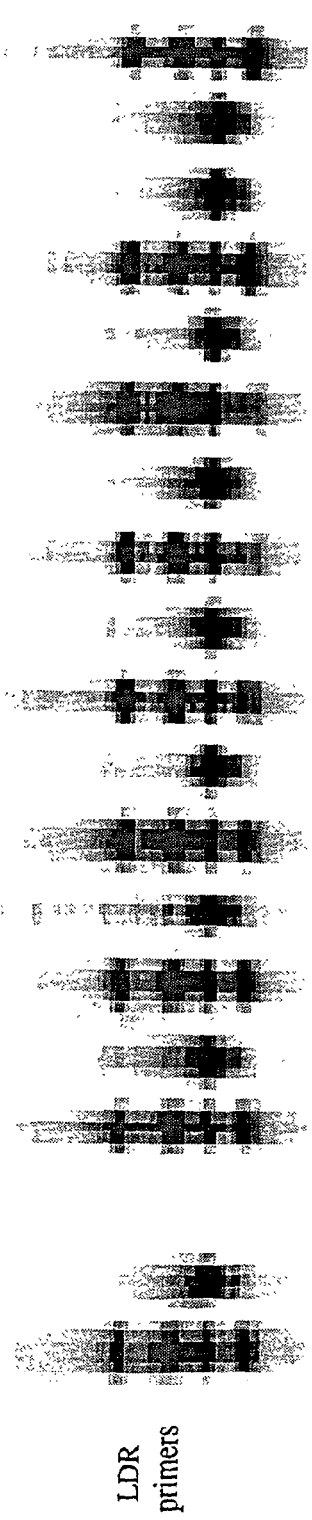

FIG. 74 shows LDR detection of AG-overhang representations of the human genome. DrdI representations were generated by the "regular PCR" and the "touchdown PCR" using common probe MTCG228 and 3 and 4 base selection PCR primers AGAP60, AGCP61, AGATP62, and AGAGP63. The presence of specific fragments in the representation were detected by LDR using probes specific to the amplified regions (Tables 16). In the REF lane, used as the standard, were LDR results of PCR products generated from probes designed for each of the targeted regions in the human genome. The labels on the left refer to the four bases present at the DrdI site and the number in parenthesis represents the predicted length of the DrdI-MspI/TaqI fragment. The four lanes following the REF lane were the LDR results of detecting representation generated by regular PCR and touchdown PCR using AGC reach in primer AGCP61, respectively. The four lanes under AGA representation were the LDR results of detecting representation generated by regular PCR and touchdown PCR with AGA reach in primer AGAP60, respectively. The four lanes under AGAT representation were the LDR results of detecting representation generated by regular PCR and touchdown PCR with AGAT reach in primer AGATP62, respectively. The four lanes under AGAG representation were the LDR results of detecting representation generated by regular PCR and touchdown PCR with AGAG reach in primer AGAGP63, respectively.

Figure 75:
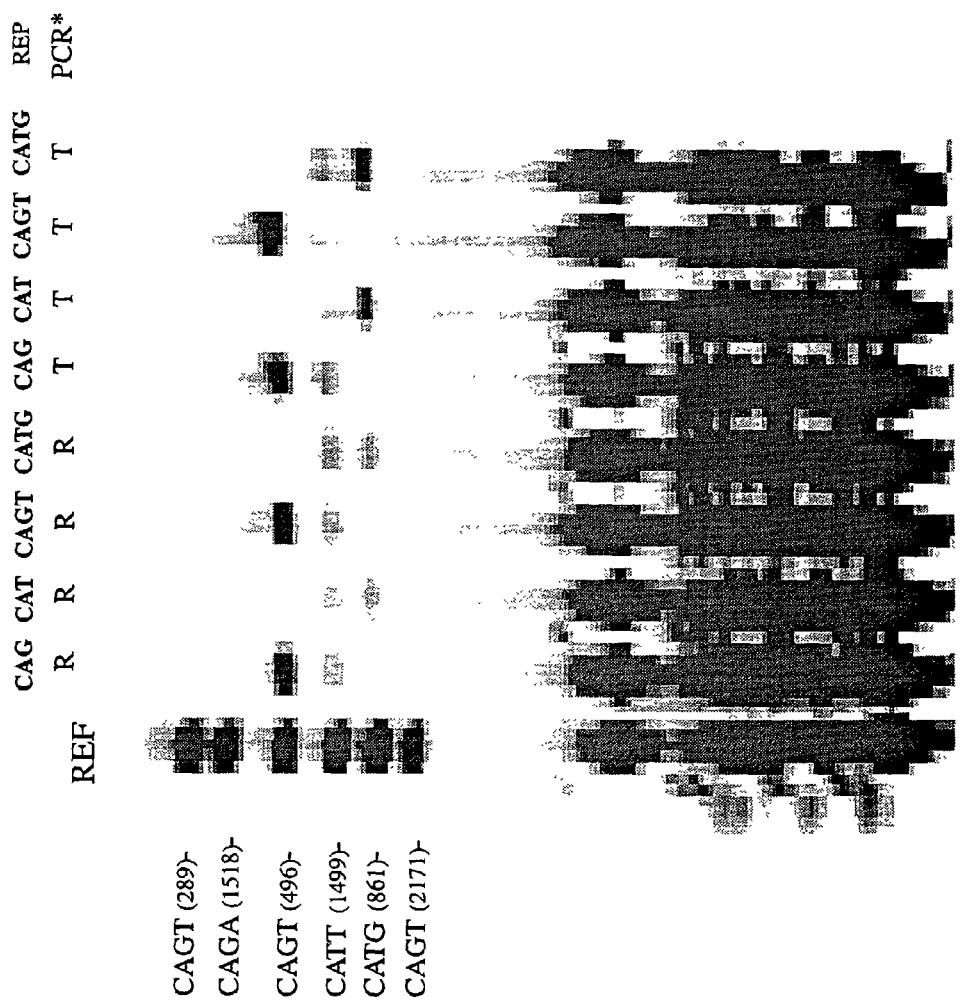

FIG. 75 shows LDR detection of CA-overhang representations of the human genome. DrdI representations were generated by the "regular PCR" and the "touchdown PCR" using common probe MTCG228 and 3 and 4 base selection PCR primers CATP58, CAGP59, CATGP64, and CAGTP65. Presence of specific fragments in the representation were detected by LDR using probes specific to the amplified regions (Table 17). In the REF lane, used as the standard, were LDR results of PCR products generated from probes designed for each of the targeted regions in the human genome. The labels on the left refer to the four bases present at the DrdI site and the number in parenthesis represents the predicted length of the DrdI-MspI/TaqI fragment. The four lanes following REF lane were the LDR results of detecting representations generated by "regular PCR" with CAGP59, CATP58, CAGTP65, and CATGP64 reach in probes, respectively. The last four lanes were the LDR results of detecting representations generated by "touchdown PCR" with CAGP59, CATP58, CAGTP65, and CATGP64 reach in probes, respectively.

DETAILED DESCRIPTION OF THE INVENTION

The present invention is directed to a method of assembling genomic maps of an organism's DNA or portions thereof. A library of an organism's DNA is provided where the individual genomic segments or sequences are found on more than one clone in the library. Representations of the genome are created, and nucleic acid sequence information is generated from the representations. The sequence information is analyzed to determine clone overlap from a representation. The clone overlap and sequence information from different representations is combined to assemble a genomic map of the organism.

Summary of DrdI Island Approach to Accelerate Alignment of Clones.

The DrdI island approach obtains a representation of the sequence in a genome which may be used to complete the map of the genome, to find mapped SNPs, and to evaluate genome differences and their association with diseases.

The first step of the procedure is to form a library of genomic DNA in cosmid, bacteriophage P1, or bacterial artificial chromosome ("BAC") clones. Each clone of the library is cut with a restriction enzyme into a plurality of fragments which have degenerate ends. Unique linkers are ligated to the degenerate ends. Internal sequence information in the clones may be obtained by sequencing off the linkers. This creates 1 kb "islands" of sequence surrounding the restriction sites which are within that clone. In essence, a "representation" of the genome in the form of "islands" is created, but the islands are attached to random clones and hence the clone overlap can be determined.

Depending on the particular restriction site used, an average of 5-8 different sets of sequencing runs are performed on the random clones (and up to 16 if needed), creating the representations of the genome. The sequence information from one set (e.g., a sequencing primer ending with 3' AA) may be used to align clones based on an analysis of overlaps between singlet, doublet, and even triplet reads. In addition, a given clone contains interpretable sequence information from at least two sets, and often from all 5-8 sets. Thus, the information from different sets on the same clone may also be used to align clones.

Once an overlapping map of the human genome is created, it becomes a powerful tool for completing the entire genomic sequence as well as identifying mapped SNPs. This procedure permits 100,000 SNPs to be identified by a shotgun method which immediately gives their map position. Further, these SNPs are amenable for use in a high throughput detection scheme which uses a universal DNA array.

1. Preparation of Genomic DNA

In order to carry out the mapping procedure of the present invention, the genomic DNA to be mapped needs to be divided into a genomic library comprising a plurality of random clones. The genomic library can be formed and inserted into cosmid clones, bacteriophage P1 vectors, or bacterial artificial chromosome clones ("BAC") as described in Chapters 2, 3, and 4 of Birren, et. al., *Genomic Analysis—A Laboratory Manual* Vol. 3 (Cold Spring Harbor Laboratory Press 1997), which is hereby incorporated by reference.

When producing cosmid clones, a genomic DNA library may be constructed by subjecting a sample of genomic DNA to proteinase K digestion followed by partial enzymatic digestion with MboI to form DNA fragments of random and varying size of 30-50 kb. Cosmid vectors with single cos sites can be digested with BamHI to linearize the vector followed by dephosphorylation to prevent religation. Cosmid vectors with dual cos sites can be digested with XbaI to separate the two cosmid sites and then dephosphorylated to prevent religation. The vector and genomic DNA are ligated and packaged into lambda phage heads using in vitro packaging extract prepared from bacteriophage lambda. The resulting phage particles are used to infect an *E. coli* host strain, and circularization of cosmid DNA takes place in the host cell.

In forming bacteriophage P1 vector libraries, genomic DNA is subjected to partial digestion with a restriction enzyme like Sau3AI followed by size fractionation to produce 70 to 100 kb DNA fragments with Sau3AI 5' overhangs at each end. A bacteriophage P1 cloning vector can be treated sequentially with the ScaI and BamHI restriction enzymes to form short and long vector arms and dephosphorylated with BAP or CIP to prevent religation. The pac site can then be cleaved by incubation with an extract prepared by induction of a bacteriophage lysogen that produces appropriate bacteriophage P1 pac site cleavage proteins (i.e. Stage I reaction). After the pac site is cleaved, the DNA is incubated with a second extract prepared by induction of a bacteriophage lysogen that synthesizes bacteriophage P1 heads and tails but not pac site cleavage proteins (i.e. Stage II reaction). The genomic DNA and vector DNA are then ligated together followed by treatment with Stage I and, then, Stage II extract of pac site cleavage proteins. Unidirectional packaging into the phage head is initiated from the cleaved pac end. After the phage head is filled with DNA, the filled head is joined with a phage tail to form mature bacteriophage particles. The P1 DNA is then incorporated into a bacterial host cell constitutively expressing the Cre recombinase. The phage DNA is cyclized at loxP sites, and the resulting closed circular DNA is amplified.

In producing BAC libraries, genomic DNA in agarase is subjected to partial digestion with a restriction enzyme followed by size separation. BAC vectors are digested with a restriction enzyme and then dephosphorylated to prevent religation. Suitable restriction enzymes for digestion of the BAC vectors include HindIII, BamHI, EcoRI, and SphI. After conducting test ligations to verify that clones with low background will be produced, the genomic DNA and BAC DNA are ligated together. The ligated genomic and BAC DNA is then transformed into host cells by electroporation. The resulting clones are plated.

II. DrdI Island Approach
A Single Restriction/Ligation Reaction is Used to Obtain Internal Sequences of Clones at DrdI Sites.

Once the individual clones are produced from genomic DNA and separated from one another, as described above, the individual clones are treated in accordance with the DrdI approach of the present invention.

FIG. 1 is a schematic drawing showing the sequencing of DrdI islands in random plasmid or cosmid clones in accordance with the present invention. The random plasmid or cosmid clones produced as described above are amplified. Nucleic acid amplification may be accomplished using the polymerase chain reaction process. The polymerase chain reaction process is the preferred amplification procedure and is fully described in H. Erlich, et. al., "Recent Advances in the Polymerase Chain Reaction," *Science* 252: 1643-50 (1991); M. Innis, et. al., *PCR Protocols: A Guide to Methods and Applications*, Academic Press: New York (1990); and R. Saiki, et. al., "Primer-directed Enzymatic Amplification of DNA with a Thermostable DNA Polymerase," *Science* 239: 487-91 (1988), which are hereby incorporated by reference. Long range PCR procedures are described in Cheng, et al., "Long PCR," *Nature*, 369(6482):684-5 (1994) and Cheng, et al., "Effective Amplification of Long Targets From Cloned Inserts and Human Genomic DNA," *Proc Natl Acad Sci USA*, 91(12): 5695-9 (1994), which are hereby incorporated by reference.

In carrying out a polymerase chain reaction process, the target nucleic acid, when present in the form of a double stranded DNA molecule, is denatured to separate the strands. This is achieved by heating to a temperature of 85-105° C. Polymerase chain reaction primers are then added and allowed to hybridize to the strands, typically at a temperature of 50-85° C. A thermostable polymerase (e.g., *Thermus aquaticus* polymerase) is also added, and the temperature is then adjusted to 50-85° C. to extend the primer along the length of the nucleic acid to which the primer is hybridized. After the extension phase of the polymerase chain reaction, the resulting double stranded molecule is heated to a temperature of 85-105° C. to denature the molecule and to separate the strands. These hybridization, extension, and denaturation steps may be repeated a number of times to amplify the target to an appropriate level.

The amplified clones are then incubated with a DrdI restriction enzyme, a T4 ligase, and a linker at 15° C. to 42° C., preferably 37° C., for 15 minutes to 4 hours, preferably 1 hour. As shown in FIG. 1, the DrdI restriction enzyme cuts both strands of the clone where indicated by the arrows and the T4 ligase couples a doubled stranded linker to the right hand portion of the cut clone to form a double stranded ligation product, as shown in FIG. 1. In the embodiment depicted, the linker has an AA overhang, but, as discussed infra, DrdI will cut any 6 bases between a GAC triplet and GTC triplet, leaving a 3' double base (i.e. NN) overhang. Therefore, the DrdI island technique of the present invention utilizes a different linker for each of the non-palindromic, 3' double base overhangs to be identified.

After the different linkers are ligated to the fragments of DNA produced by DrdI digestion to form a phosphorylated site containing, in the case of FIG. 1, a 3' AA overhang, the T4 ligase and the restriction enzyme (i.e. DrdI) are inactivated by heating at 65° C. to 98° C., preferably 95° C., for 2 minutes to 20 minutes, preferably 5 minutes. As shown in FIG. 1, a sequencing primer is contacted with the ligation product after it is denatured to separate its two strands. For the linker depicted, the sequencing primer has a 3' AA overhang and nucleotides 5' to the overhang which makes the primer suitable for hybridization to one strand of the ligation product. Sequencing primers adapted to hybridize to the ligation products formed from the other linkers are similarly provided. With such sequencing primers, a dideoxy sequencing reaction can be carried out to identify the different DrdI cleavage sites. Dideoxy sequencing is described in Chadwick, et al., "Heterozygote and Mutation Detection by Direct Automated Fluorescent DNA Sequencing Using a Mutant Taq DNA Polymerase," *Biotechniques*, 20(4):676-83 (1996) and Voss, et al., "Automated Cycle Sequencing with Taquenase: Protocols for Internal Labeling, Dye Primer and 'Doublex' Simultaneous Sequencing," *Biotechniques*, 23(2):312-8 (1997), which are hereby incorporated by reference. In situations where the results of dideoxy sequencing with primers having a 2 base 3' end (i.e. NN) are too difficult to interpret due to priming three or more fragments during the sequencing reaction, additional selectivity can be achieved by performing 4 separate dideoxy sequencing reactions for each linker. For example, with respect to the linker 3' AA overhang, sequencing primers having 3' ends of AAA, AAC, AAG, and AAT can be utilized to obtain sequences for DrdI cleavages filled with the AA-containing linker. This technique is amenable to automation. In cases where there is insufficient DNA template to conduct dideoxy sequencing, this sequencing step can be preceded by a PCR amplification procedure. Suitable PCR amplification conditions are described above.

The results of the above-described sequencing procedure indicates the number of times a particular linker sequence is present in an individual clone. If a particular linker sequence appears only one time in a given clone, it is referred to as a unique or singlet sequence, while the presence of a particular linker sequence two times is referred to a doublet, three times is referred to a triplet, etc. The fragments with the different 2 base overhangs (e.g., AA, AC, AG, CA, GA, and GG) constitute representations, and the representations for different clones are then examined to determine if there is any commonality (i.e. the clones overlap). Based on this analysis, the different clones are assembled into a genomic map.

The enzyme DrdI (GACNNNN^NNGTC) (SEQ. ID. No. 182) leaves a 3' NN overhang in the middle of 6 bases of degenerate sequence. The 16 NN sites which may be created fall into three groups—self-complementary (Group I), 6 non-complementary (Group II), and the other 6 non-complementary dinucleotides (Group III) as follows.

| Group I | Group II | Group III |
|---------|----------|-----------|
| CG      | AG       | CT        |
| GC      | AC       | GT        |
| AT      | CA       | TG        |
| TA      | GA       | TC        |
|         | AA       | TT        |
|         | GG       | CC        |

Group I has complementary overhangs. Thus, a given linker would ligate to both sides of the cut site, so sequencing reactions would provide double reads on the same lane and would not be worth pursuing. Further, the complementary linkers can ligate to each other, forming primer dimers. Therefore, sites which generate CG, GC, AT, or TA ends will be ignored.

Groups II and III are ideal. Linkers with unique sequences (for a subsequent sequencing run) ending in AG, AC, CA, GA, AA, and GG can be used in a first ligation reaction. Linkers ending in the other six dinucleotides (i.e. CT, GT, TG, TC, TT, and CC) can be used in a second ligation reaction.

To reduce the number of sequencing runs needed, sequences should be obtained from the overhang which requires linker adapters whose 3' two bases end in AA, AC, AG, CA, GA, and GG. This avoids use of both linkers and sequencing primers which contain or end in a "T" base. Such linkers or primers are more susceptible to misligations or mispriming since T-G mismatches give higher rates of misligation or polymerase extension than any of the other mismatches.

The advantage of using DrdI is that it leaves a 2 base 3' overhang on a split palindrome. Thus, the product of a PCR reaction may be immediately used in a DrdI restriction/ligation reaction, without requiring time consuming purification of the PCR fragment. Polymerase won't extend the 3' overhang ends generated by DrdI.

DrdI sites are eliminated by ligation of the linkers, but are recreated and cut again if two PCR fragments are ligated together. The DrdI linker is phosphorylated so both strands ligate. Since the end is non-complementary, it cannot ligate to itself. Thus, all free DrdI ends will contain linkers.

Figure 3:
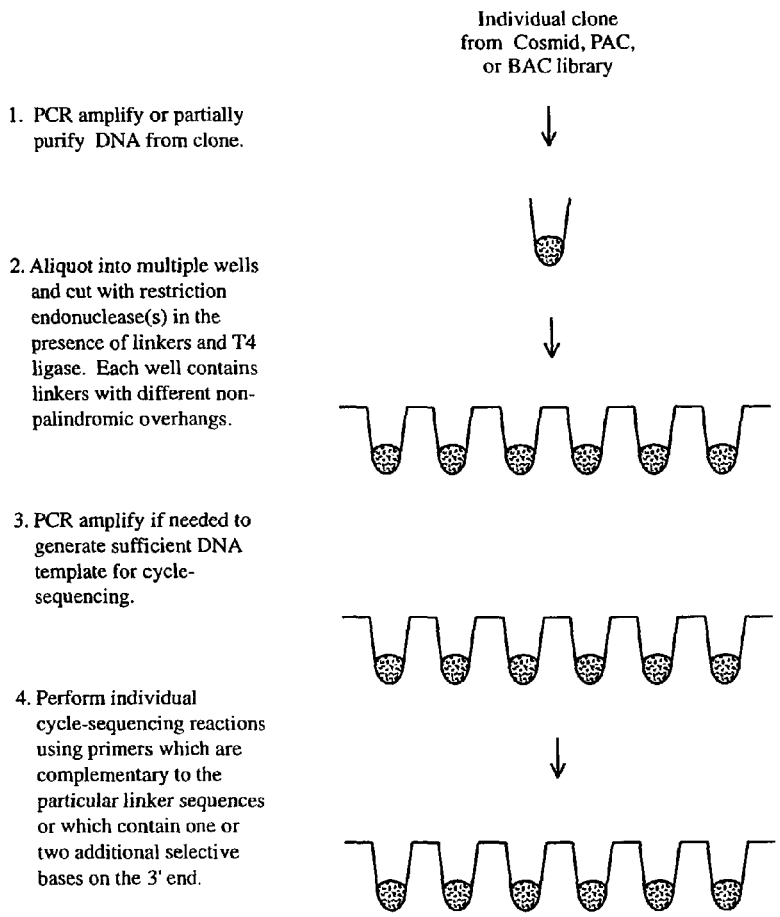
FIG. 3 is a schematic drawing of a second embodiment for sequencing restriction enzyme generated representations.

As noted above, the linkers of Group II or Group III can used together. As shown in FIGS. 2 and 3, there are 2 schemes for separately carrying out each of the DrdI island sequencing procedures for each group.

As shown in FIG. 2, one scheme involves using a single tube or well: (1) to PCR amplify or partially purify DNA from individual clones from the cosmid, PAC, or BAC libraries; (2) to incubate with DrdI, T4 ligase, and the 6 divergent linkers with nonpalindromic 3' double base overhangs; and, optionally, (3) to PCR amplify to generate sufficient DNA template for dideoxy sequencing. At this point, the material to be sequenced is aliquoted into multiple (e.g., 6) tubes or wells with each tube or well being used to carry out one of the 6 separate sequencing reactions for each of the DrdI cleavage sites filled by the 6 linkers of Group II or Group III. If sequencing primers with an additional base are needed to overcome sequencing reads which are difficult to interpret (as discussed above), these primers can be added to the tube or well used to carry out the sequencing of the cleavage site for their respective linker.

FIG. 2 provides a scheme for sequencing representations of BAC clones. Two approaches may be considered for preparing DNA. One rapid approach is to pick individual colonies into lysis buffer and lyse cells under conditions which fragment chromosomal DNA but leave BAC DNA intact. Chromosomal DNA is digested by the ATP dependent DNase from Epicentre which leaves CCC and OC BAC DNA intact. After heat treatment to inactivate the DNase, restriction digestion, ligation of linker adapters, and PCR amplification are all performed in a single tube. The products are then aliquoted and sequencing is performed using specific primers to the adapters. This first approach has the advantage of obviating the need to grow and store 300,000 BAC clones.

An alternative approach is to pick the colonies into 1.2 ml growth media and make a replica into fresh media for storage before pelleting and preparing crude BAC DNA from a given liquid culture similar as described above. This second approach has the advantage of producing more BAC DNA, such that loss of an island from PCR dropout is less likely. Further, this approach keeps a biological record of all the BACs, which may become useful in the future for techniques such as exon trapping, transfection into cells, or methods as yet undeveloped.

As shown in FIG. 3, the second scheme involves using a single tube or well to PCR amplify or partially purify DNA from individual clones from the cosmid, PAC, or BAC libraries. The PCR product can then be aliquoted into multiple (e.g., 6) tubes or wells: (1) to incubate with DrdI, T4 ligase, and the 6 divergent linkers with nonpalindromic 3' double base overhangs; (3), optionally, to PCR amplify to generate sufficient DNA template for dideoxy sequencing; and (3) to carry out one of the 6 separate sequencing reactions for each of the DrdI cleavage sites filled by the 6 linkers of Group II or Group III. As to step (3), if sequencing primers with an additional base are needed to overcome sequencing reads which are difficult to interpret (as discussed above), these primers can be added to the tube or well used to carry out the sequencing of the cleavage site for their respective linker.

As shown in FIG. 4, DNA sequencing can be carried out directly from PCR-amplified DNA without primer interference, the PCR primers from the original PCR reaction may be removed by using riboU containing primers and destroying them with either base or (using dU) with UNG. This is achieved by incorporating ribonucleotides directly into PCR primers. Colonies are then picked into microwell PCR plates. The primers containing ribose, on average every fourth nucleotide, are added. The preferred version would use r(U) in place of dT, which simplifies synthesis of primers. After PCR amplification, in the presence of dNTPs and Taq polymerase, 0.1N NaOH is added and the PCR product is heated at 95° C. for 5 minutes to destroy unused primers. The PCR product is then diluted to 1/10th of the volume in 2 wells and forward and reverse sequencing primers are added to run fluorescent dideoxy sequencing reactions.

Another approach to sequence DNA directly from PCR-amplified DNA uses one phosphorylated primer, lambda exonuclease to render that strand and the primer single stranded, and shrimp alkaline phosphatase to remove dNTPs. This is commercially available in kit form from Amersham Pharmacia Biotech, Piscataway, N.J. A more recent approach to sequence DNA directly from PCR-amplified DNA uses ultrafiltration in a 96 well format to simply remove primers and dNTPs physically, and is commercially available from Millipore, Danvers, Mass.

FIG. 5 shows an alternative embodiment of the DrdI island sequencing procedure of the present invention. In this embodiment, individual BAC clones are cut with the restriction enzymes DrdI and MspI in the presence of linkers and T4 ligase. This is largely the same procedure as that described with reference to FIG. 1 except that the MspI restriction enzyme is utilized to reduce the length of the fragment to a size suitable for PCR amplification. In FIG. 5, the subtleties of the linker-adapter ligations and bubble PCR amplification to select only the DrdI-MspI fragments are detailed. As in FIG. 1, the linker for the DrdI site is phosphorylated and contains a 3' two base overhang (e.g., a 3' AA overhang as in FIG. 5). A separate linker is used for the MspI site which replaces the portion of the BAC DNA to the right of the MspI site in FIG. 5. The MspI linker is not phosphorylated and contains a bubble (i.e. a region where the nucleotides of this double stranded DNA molecule are not complementary) to prevent amplification of unwanted MspI-MspI fragments. The T4 ligase binds the DrdI and MspI linkers to their respective sites on the BAC DNA fragments with biochemical selection assuring that most sites contain linkers.

After the different linkers are ligated to the fragments of DNA produced by DrdI digestion to form a phosphorylated site containing, in the case of FIG. 5, a 3' AA overhang, the T4 ligase and the restriction enzymes (i.e. DrdI and MspI) are inactivated by heating at 65° C. to 98° C., preferably 95° C., for 2 minutes to 20 minutes, preferably 5 minutes. As shown in FIG. 5, the ligation product is amplified using a PCR procedure under the conditions described above. For the linker depicted, one amplification primer has a 3' AA overhang and nucleotides 5' to the overhang which makes the primer suitable for hybridization to the bottom strand of the ligation product for polymerization in the 3' to 5' direction. The other sequencing primer, for the linker depicted in FIG. 5, has a 5' CG overhang which makes this primer suitable for hybridization to the top strand of the ligation product for polymerization in the 5' to 3' direction. Amplification primers adapted to hybridize to the ligation products formed from the other linkers are similarly provided. As described with reference to FIG. 4, PCR amplification is carried out using primers with ribose U instead of dT, adding dNTPs and Taq polymerase, adding NaOH, and heating at 85° C. to 98° C., preferably 95° C., for 2 minutes to 20 minutes, preferably 5 minutes to inactivate any unused primer.

After amplification is completed and the amplification product is neutralized and diluted, dideoxy sequencing can be conducted in substantially the same manner as discussed above with reference to FIG. 1. If necessary, a separate dideoxy sequencing procedure can be conducted using a sequencing primer which anneals to the MspI site linker. This is useful to generate additional sequence information associated with the DrdI island.

FIG. 6 shows a variation of the scheme for amplifying DrdI islands for sequencing directly from small quantities of BAC DNA. Individual BAC clones are cut with the restriction enzymes DrdI, MspI, and TaqI in the presence of linkers and T4 ligase. This is largely the same procedure as described in FIG. 5 except that the MspI and TaqI restriction enzymes are used to reduce the length of the fragment to a size suitable for PCR amplification. As in FIG. 5, the linker for the DrdI site is phosphorylated and contains a 3' two base overhang (e.g., a 3' AA overhang as in FIG. 6). A separate linker is used for the MspI or TaqI site which replaces the portion of the BAC DNA to the right of the MspI or TaqI site in FIG. 6. This MspI/TaqI linker is phosphorylated, contains a 3' blocking group on the 3' end of the top strand, and contains a bubble to prevent amplification of unwanted MspI-MspI, TaqI-MspI, or TaqI-TaqI fragments. While the linker can ligate to itself in the phosphorylated state, these linker dimers will not amplify. Phosphorylation of the linker and use of a blocking group eliminates the potential artifactual amplification of unwanted MspI-MspI, TaqI-MspI, or TaqI-TaqI fragments. T4 ligase attaches the DrdI and MspI/TaqI linkers to their respective sites on the BAC DNA fragments with biochemical selection assuring that most sites contain linkers. The ligation product is PCR amplified using primers complementary to the linkers. After amplification is completed, dideoxy sequencing can be performed as described above.

FIG. 7 describes the three levels of specificity in using the DrdI island approach.

Specificity of the DrdI Linker Ligations and Subsequent Sequencing Reactions.

The specificity of T4 thermostable DNA ligases is compared below in Table 3.

TABLE 3

Fidelity of T4 and different thermostable DNA ligases.

| | | C-G match at 3'-end | T-G mismatch at 3'-end | T-G mismatch at penultimate 3'-end | | |
|---|---|---|---|---|---|---|
| | | -----GTC P-----F | | -----GTT P-----F | | |
| | | -----CAG------- | | -----CAG------- | | |
| | | | -----GTC P-----F | | | |
| | | | -----CGG------- | | | |
| Ligase | Concentration (nM) | Initial Rate of C-G match (fmol/) | Initial Rate of T-G mismatch at 3'-end (fmol/) | Initial Rate of T-G mismatch at penultimate 3'-end (fmol/) | Ligation fidelity 1[a] | Ligation fidelity 2[b] |
| T4 | 0.5 | $1.4 \times 10^2$ | 2.8 | 7.1 | $5.0 \times 10^1$ | $1.9 \times 10^1$ |
| T. th-wt | 1.25 | $5.5 \times 10^1$ | $6.5 \times 10^{-2}$ | $2.9 \times 10^{-1}$ | $8.4 \times 10^2$ | $1.9 \times 10^2$ |
| T th-K294R | 12.5 | $1.5 \times 10^2$ | $2.9 \times 10^{-2}$ | $3.8 \times 10^{-1}$ | $5.3 \times 10^3$ | $4.0 \times 10^2$ |

TABLE 3-continued

Fidelity of T4 and different thermostable DNA ligases.

| Ligase | Concentration (nM) | C-G match at 3'-end -----GTC P-----F -----CAG------- Initial Rate of C-G match (fmol/) | T-G mismatch at 3'-end -----GTC P-----F -----CGG------- Initial Rate of T-G mismatch at 3'-end (fmol/) | T-G mismatch at penultimate 3'-end -----GTT P-----F -----CAG------- Initial Rate of T-G mismatch at penultimate 3'-end (fmol/) | Ligation fidelity 1[a] | Ligation fidelity 2[b] |
|---|---|---|---|---|---|---|
| T. Sp AK16D | 12.5 | $1.3 \times 10^2$ | $2.5 \times 10^{-2}$ | $1.2 \times 10^{-1}$ | $5.2 \times 10^3$ | $1.1 \times 10^3$ |
| Aquifex sp. | 12.5 | $9.9 \times 10^1$ | $2.9 \times 10^{-2}$ | $2.6 \times 10^{-1}$ | $3.5 \times 10^3$ | $3.8 \times 10^2$ |

The reaction mixture consisted of 20 mM Tris-HCl, pH 7.6, 10 mM MgCl$_2$, 100 mM KCl, 10 mM DTT, 1 mM NAD$^+$, 20 µg/ml BSA, and 12.5 nM nicked DNA duplex substrates. T4 DNA ligase fidelity was assayed at 37° C., Thermostable ligase fidelity was assayed at 65° C.. Fluorescently labeled products were separated on an ABI 373 DNA sequencer and quantified using the ABI GeneScan 672 software
[a]Ligation fidelity 1 = Initial Rate of C-G match/Initial Rate of T-G mismatch at 3'-end
[b]Ligation fidelity 2 = Initial Rate of C-G match/Initial Rate of T-G mismatch at penultimate 3'-end.

Both the thermostable and the T4 ligase show the highest degree of mismatch ligation for G:T or T:G mismatches. Consequently, by studying the fidelity of these reactions, the limits of mismatch discrimination may be determined.

While the thermostable ligases exhibit 10 to 100-fold greater fidelity than T4 ligase, the later enzyme is far more efficient in ligating 2 base overhangs. Therefore, ligation, in accordance with the present invention, should be performed using T4 ligase. There are three degrees of specificity: (i) ligation of the top strand requires perfect complementarity at the 3' side of the junction; (ii) ligation of the bottom strand requires perfect complementarity at the 3' side of the junction; and (iii) extension of polymerase off the sequencing primer is most efficient if the 3' base is perfectly matched. All three of these reactions demonstrate 50-fold or greater discrimination if the match or mismatch is at the 3' end and 20-fold or greater discrimination if the match or mismatch is at the penultimate position to the 3' end.

How to Interpret the Results:

A computer simulation was performed on 4 known sequenced BAC clones from chromosome 7q31. The distribution of DrdI sites in these clones and their overhangs is shown in FIGS. 8-11. There are 38 non-palindromic DrdI sites in about 550 kb of DNA, or an average of 1 non-palindromic DrdI site per 15 kb.

The average 30-40 kb clone should be cut about three times with DrdI to generate non-palindromic ends. Again, palindromic ends are discounted, so the average clone needs to be a little bigger to accommodate the extra silent cuts and still get an average of 3 non-palindromic cuts. It should be noted, however, that as long as there are 2 or more DrdI sites which are singlets (i.e. present once in the clone) or doublets (present twice in the clone) in all of the clones to be aligned, such alignment can be successfully achieved. In the best case scenario, each of the overhangs is unique (i.e. a singlet), so 6 unique sequencing runs are generated, and these are connected in matched pairs (i.e. the sequence generated from the primers ending in AA is connected to the sequence generated from primers ending in TT), so about 3×1 kb "DrdI islands" of sequence are somewhere within the 30-40 kb flanked by the two 500-800 base-pair anchors.

Now if two random 30-40 kb clones overlap, the chances are excellent that they will either run into each other on the ends, or, alternatively, 1 to 3 of the internal sequences will be identical. There will be a few case where two clones overlap and different internal 1 kb sequences are obtained, because there is a small probability of having a DrdI polymorphism. However, these will simply add to the density of sequence which may run into or overlap with existing markers.

Figure 8:
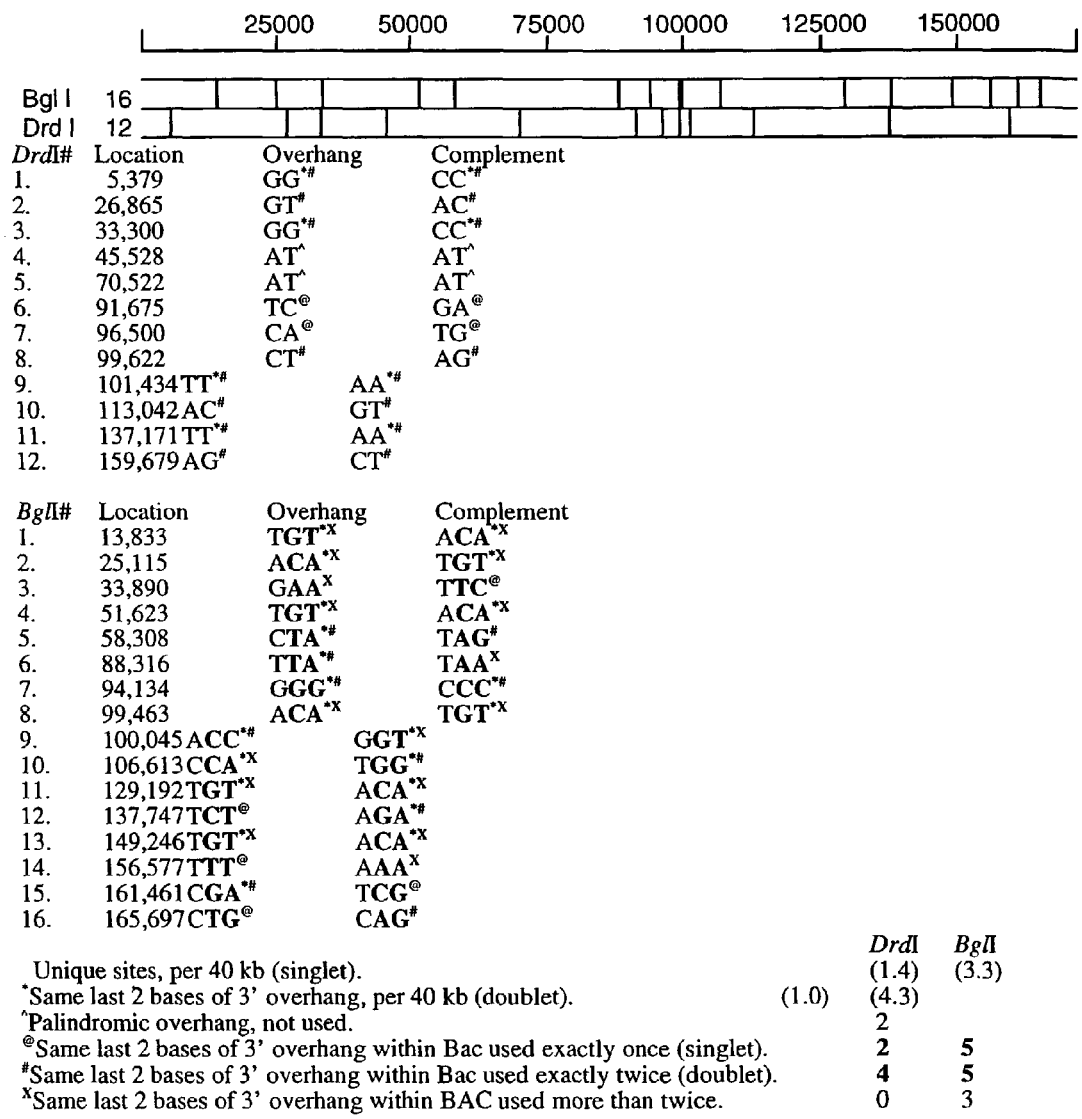
FIG. 8 shows the DrdI and BglI site frequencies per 40 kb in the Met Oncogene BAC from the 7q31 chromosome. The locations of the 12 DrdI and 16 BglI sites in a 171,905 bp clone are shown pictorially and in tabular form, indicating the type of overhang and the complement to that overhang. For this clone, per 40 kb, the unique sites (i.e. singlets) are as follows: 1.4 of such unique DrdI sites and 3.3 of such unique BglI sites. In this clone, per 40 kb, the sites with the 3' overhang having the same last 2 bases—doublets (i.e. *) are as follows: 1.0 of such DrdI sites and 4.3 of such BglI sites. The number of palindromic overhangs not used (i.e. ^) is as follows: 2 overhangs for DrdI and 0 overhangs for BglI. The number of sites with the 3' overhang having the same last 2 bases within the BAC clone used exactly once—singlets (i.e. @) is as follows: 2 of such DrdI sites and 5 of such BglI sites. The number of sites with the 3' overhang having the same last 2 bases within the BAC clone used exactly twice—doublets (i.e. #) is as follows: 4 of such DrdI sites and 5 of such BglI sites. The number of sites with the 3' overhang having the same last 2 bases within the BAC clone used more than twice (i.e. X) is as follows: 0 of such DrdI sites and 3 of such BglI sites.

As shown in FIG. 8, use of the DrdI approach in mapping the Met Oncogene in a BAC clone from the 7q31 chromosome identifies 12 DrdI sites within the 171,905 bp shown. The overhangs and complements shown in the positions set forth in FIG. 8 are based on the known sequence in GenBank. More particularly, there are TC and CA singlets and GG, GT, CT, and TT doublets (either in the overhang or its complement) for the DrdI islands. Since the sum of singlets and doublets is greater than or equal to 2, this fingerprint for the Met Oncogene in a BAC clone can be used to determine the positional relationship of this clone with respect to other clones in the library as described infra.

FIG. 10 shows how the DrdI approach is used in mapping the HMG gene in a BAC clone from the 7q31 chromosome. Within the 165,608 bp shown, there are 11 DrdI sites with the known sequences used to identify the overhangs and complements in the positions set forth in FIG. 10. More particularly, there are TT, GT, and GA singlets and CT and GG doublets (either in the overhang or its complement) for the DrdI islands. Since the sum of singlets and doublets is greater than or equal to 2, this fingerprint for the Met Oncogene in a BAC clone can be used to determine the positional relationship of this clone with respect to other clones in the library, as describe infra.

FIG. 12 shows the use of the DrdI approach in mapping the Pendrin gene in a BAC clone from the 7q31 chromosome to identify 10 DrdI sites within the 97,943 bp shown. The overhangs and complements shown in the positions set forth in FIG. 12 are based on the known sequence in GenBank. Specifically, there are 3 singlets (i.e. CC, TT, and GA), 1 doublet (i.e. AA), and 1 multiplet (i.e. CT) (either in the overhang or its complement) for the DrdI islands. Since the sum of singlets and doublets is greater than or equal to 2, this fingerprint for the Pendrin gene in a BAC clone can be used to determine the positional relationship of this clone with respect to other clones in the library, as described infra.

FIG. 14 shows how the DrdI approach is used in mapping the alpha2(I) gene in a BAC clone from the 7q31 chromosome. There are 11 DrdI sites within the 116,466 bp with the known sequences used to identify the overhangs and complements shown in the positions set forth in FIG. 14. There are 2 singlets (i.e. AG and GG) and 4 doublets (i.e. AA, TG, GT, and TC) (either in the overhang or its complement) for the DrdI islands. Since the sum of singlets and doublets is 2 or greater, this fingerprint for the alpha2(I) gene can be used to determine the positional relationship of this clone with respect to other clones in the library, as described infra.

Two Special Cases Need to be Considered:

In the first case, the clone has no internal DrdI sites with non-palindromic ends. This will occur on occasion. Again, computer analysis on the four fully sequenced BAC clones (about 550 kb of DNA) showed two areas which would leave gaps in the cosmid contigs. This does not preclude overlapping such clones to larger superstructures (i.e. BACs and YACs).

The solution to this problem is to use a second enzyme with a comparable frequency in the human genome. By slightly modifying the procedure, 16 linker/primer sets may be used on split palindrome enzymes which generate a 3 base 3' overhang. Since the overhang is an odd number of bases, it is not necessary to exclude the palindromic two base sequences AT, TA, GC, and CG. To reduce the number of ligations from 64 (all the different possible 3 base overhangs) to 16, the linkers and primers are degenerate at the third position, i.e. end with NTC or NGC. As noted above, since there are 3 levels of specificity in the ligation and sequencing step, the third base degeneracy will not interfere with the fidelity of the reaction. With 3 base overhangs, multiplet sequences which are difficult to interpret may be teased apart by either: (i) using linkers and primers which lack the $3^{rd}$ base degeneracy, or (ii) using sequencing primers which extend an extra base on the 3' end of the primer.

Of the 4 commercially available split palindrome enzymes which generate a 3 base 3' overhang, BglI (GC-CNNNNANGGC) (SEQ. ID. No. 187) and DraIII (CACNNN^GTG) (SEQ. ID. No. 212) are present at low enough frequencies to be compatible with DrdI. There are 60 BglI sites in about 550 kb of the four sequenced BAC clones, or an average of 1 BglI site per 9 kb. The frequency of the other split palindrome enzymes in human DNA are: DraIII (1 per 8 kb), AlwnI (1 per 4 kb), and PflMI (1 per 3 kb).

Although there are some type IIs enzymes which will allow the same 2 base overhang 3' ligation, they are not split palindromes and hence simultaneous cutting and ligation will only provide the sequence from one side. This can be an advantage for some enzymes, as described for SapI below.

FIGS. 8, 10, 12, and 14 show how the enzyme BglI can generate a 3 base 3' overhang which can be used in accordance with the present invention.

FIG. 8 shows the use of the BglI approach in mapping the Met Oncogene in a BAC clone from the 7q31 chromosome. There are 16 BglI sites within the 171,905 bp shown with known sequences used to identify the overhangs and complements. More particularly, there are 5 singlets (i.e. the CT, TT, TG, TC, and CG overhangs) and 5 doublets (i.e. the TA, GG, CC, GA, and AG overhangs) (either in the overhang or its complement) for the BglI islands. Since the sum of the singlets and doublets is greater than or equal to 2, this fingerprint for the Met Oncogene in a BAC clone can be used to determine the positional relationship of this clone with respect to other clones in the library, as described infra.

FIG. 10 shows the use of the BglI approach in mapping the HMG gene in a BAC clone from the 7q31 chromosome. Within the 165,608 bp shown, there are 12 BglI sites with known sequences used to identify the overhangs and complements in the positions set forth in FIG. 9. Specifically, there are 5 singlets (i.e. the GT, AA, AC, GC, and CC overhangs) and 4 doublets (i.e. the AG, TC, TT, and CA overhangs) (either in the overhang or its complement) for the BglI islands. Since the sum of the singlets and doublets is greater than or equal to 2, this fingerprint for the Met Oncogene in a BAC clone can be used to determine the positional relationship of this clone with respect to other clones in the library, as described infra.

FIG. 12 shows the use of the BglI approach in mapping the Pendrin gene in a BAC clone from the 7q31 chromosome to identify the 17 BglI sites within the 97,943 bp shown. The overhangs and complements shown in the positions set forth in FIG. 10 are based on known sequences. Specifically, there is 1 singlet (i.e. the TC overhang) and 5 doublets (i.e. TA, GT, CC, TT, and AA overhangs) (either in the overhang or its complement) for the BglI islands. Since the sum of the singlets and doublets is greater than or equal to 2, this fingerprint for the Pendrin gene in a BAC clone can be used to determine the positional relationship of this clone with respect to other clones in the library, as described infra.

FIG. 14 shows how the use of the BglI approach is used in mapping the alpha2(I) gene in a BAC clone from the 7q31 chromosome. There are 15 BglI sites within the 116,466 bp with known sequences used to identify the overhangs and complements shown in the positions set forth in FIG. 11. There are 4 singlets (i.e. the AA, TT, GC, and GG overhangs) and 7 doublets (i.e. the TA, GA, CG, TC, AA, CC, and AC overhangs) (either in the overhang or its complement) for the BglI islands. Since the sum of the singlets and doublets is greater than or equal to 2, this fingerprint for the alpha2(I) gene can be used to determine the positional relationship of this clone with respect to other clones in the library, as described infra.

Similarly, FIGS. 9, 11, 13, and 15 show how the enzyme SapI can also generate 3 base 3' overhangs in accordance with the present invention. FIG. 16 is a schematic drawing showing the sequencing of BglI islands in random BAC clones in accordance with the present invention. This is largely the same as the embodiment of FIG. 7, except that a different enzyme is used. In this embodiment, individual BAC clones are cut with the restriction enzymes BglI and MspI in the presence of linkers and T4 ligase. As in FIG. 7, the linker for the BglI site is phosphorylated and contains a 3' three base overhang (e.g., a 3' NAC overhang). A separate linker is used for the MspI site which replaces the portion of the BAC clone DNA to the right of the MspI site in FIG. 7. The MspI linker is not phosphorylated and contains a bubble (i.e. a region where the nucleotides of this double stranded DNA molecule are not complementary) to prevent amplification of unwanted MspI-MspI fragments. The T4 ligase binds the BglI and MspI linkers to their respective sites on the BAC clone DNA with biochemical selection assuring that most sites contain linkers.

After the different linkers are ligated to the fragments of DNA produced by BglI digestion to form a phosphorylated site containing, in the case of FIG. 16, a 3' NAC overhang, the T4 ligase and the restriction enzymes (i.e. BglI and MspI) are inactivated at 65° C. to 98° C., preferably 95° C., for 2 minutes to 20 minutes, preferably 5 minutes. As shown in FIG. 16, the ligation product is amplified using a PCR procedure under the conditions described above. For the linker depicted, one amplification primer has a 3' AC overhang and nucleotides 5' to the overhang which makes the primer suitable for hybridization to bottom strand of the ligation product for polymerization in the 3' to 5' direction. Amplification primers adapted to hybridize to the ligation products formed from the other linkers are similarly provided. As described with reference to FIG. 6, PCR amplification is carried out using primers with ribose U instead of dT, adding dNTPs and Taq polymerase, adding NaOH, and heating at 85° C. to 98° C., preferably 95° C., for 2 minutes to 20 minutes, preferably 5 minutes to inactivate any unused primer.

After amplification is completed and the amplification product is neutralized and diluted, dideoxy sequencing can be conducted in substantially the same manner as discussed above with reference to FIG. 1. If necessary, a separate dideoxy sequencing procedure can be conducted using a sequencing primer which anneals to the MspI site linker. This is useful to generate additional sequence information associated with the BglI island.

Another departure from the schematic of FIG. 5 is that, in the scheme of FIG. 16, a separate linker ligation procedure is carried out with the portion of the BAC clone on the left side of FIG. 16. The primer utilized in this procedure is phosphorylated and ends with a 3' NTA overlap sequence.

FIG. 17 is a schematic drawing showing the sequencing of SapI islands in random BAC clones in accordance with the present invention. This is largely the same as the embodiment of FIG. 5, except that a different enzyme is used. In this embodiment, individual BAC clones are cut with the restriction enzymes SapI and MspI in the presence of linkers and T4 ligase. As in FIG. 5, the linker for the SapI site is phosphorylated and contains a 3' three base overhang (e.g., a 3' NUG overhang). A separate linker is used for the MspI site which replaces the portion of the BAC DNA to the right of the MspI site as in FIG. 5. The MspI linker is not phosphorylated and contains a bubble (i.e. a region where the nucleotides of this double stranded DNA molecule are not complementary) to prevent amplification of unwanted MspI-MspI fragments. The T4 ligase binds the SapI and MspI linkers to their respective sites on the BAC DNA with biochemical selection assuring that most sites contain linkers.

After the different linkers are ligated to the fragments of DNA produced by SapI digestion to form a phosphorylated site containing, in the case of FIG. 5, a 3' NUG overhang, the T4 ligase and the restriction enzymes (i.e. SapI and MspI) are inactivated at 65° C. to 98° C., preferably 95° C., for 2 minutes to 20 minutes, preferably 5 minutes. As shown in FIG. 15, the ligation product is amplified using a PCR procedure under the conditions described above. For the linker depicted, one amplification primer has a 3' NTG overhang and nucleotides 5' to the overhang which makes the primer suitable for hybridization to the bottom strand of the ligation product for polymerization in the 3' to 5' direction. The other sequencing primer, for the linker depicted in FIG. 17, has a 5' CA overhang which makes this primer suitable for hybridization to the top strand of the ligation product for polymerization in the 5' to 3' direction. Amplification primers adapted to hybridize to the ligation products formed from the other linkers are similarly provided. As described with reference to FIG. 4, PCR amplification is carried out using primers with ribose U instead of dT, adding dNTPs and Taq polymerase, adding NaOH, and heating at 85° C. to 98° C., preferably 95° C., for 2 minutes to 20 minutes, preferably 5 minutes to inactivate any unused primer.

After amplification is completed and the amplification product is neutralized and diluted, dideoxy sequencing can be conducted in substantially the same manner as discussed above with reference to FIG. 1. If necessary, a separate dideoxy sequencing procedure can be conducted using a sequencing primer which anneals to the MspI site linker. This is useful to generate additional sequence information associated with the SapI island.

In a second case, the clone has two DrdI sites with the same 3' overhangs. Thus, the sequencing reads have two bases at each position. The probability of NOT having an overlap is 6/6×5/6×4/6=20/36=0.55. So the probability of having an overlap is 1−0.55=0.45, or about every other clone. At first glance, this is may appear to cause a problem, but, in fact, it is very useful. Rather than discarding these reads, on average every 4th base will be the same in both reads and, thus, clearly distinguishable. Thus, a read of this form will be entered into the database as such: G---A-----C--C----T---AA-----T, etc. The current computer programs which look for overlap examine 32 bases at a time, which is essentially unique in the genome, so the first 128 bases of a double-primed sequencing run creates a unique "signature". This can be checked against the existing sequences in the database as well as against the DrdI sequences generated from other clones. It will line up either with a single read (i.e. when only one of the sites overlaps) or as an identical double read (i.e. when both sites overlap). It is reasonably straightforward to do a "subtraction" of one sequence from the double sequence to obtain the "hidden" sequence.

Evaluation of the BAC clones reveals a few instances where the same overhang would appear in two DrdI sites from neighboring random 30-40 kb clones. This requires that additional neighboring clones are found in a larger contig. If a region remains intractable to analysis, because there are too many DrdI sites with the identical overhangs, alternative enzymes BglI and DraIII may be used. A second solution to sequencing reads which are difficult to interpret is to use four separate sequencing reactions with primers containing an additional base on the 3' end, as depicted at the bottom of FIG. 1.

One advantage about generating DrdI islands is the format of the data. The sequence information always starts at the same position. Thus, the computer programs can be vastly simpler than previous lineup algorithms. A computer program sets up bins to score identity. For example:

```
                                            SEQ. ID. No. 1
        GATTCGATCGTAGCGTGTAGCAAGTAGCTAATTCGATCCA.
                               |            SEQ. ID. No. 2
        GATTCGATCGTAGCGTGTAACAAGTAGCTAATTCGATCCA.
``` i.e. 39/40 match, score as an overlap (with an SNP at position 20).

Further simplifying the computer analysis, sequence information in the DrdI analysis is generated in 12 separate sets, corresponding to each overhang, and these sets are virtually exclusive. The probability of having a polymorphism right at the 2 base 3' overhang is very small (about 2 in 1,000), and, even if the polymorphism does occur, it will make two sequences jump to new bins, making it very easy to double-check existence of such polymorphisms.

The above scheme has a built in redundancy, because each forward sequence on a DrdI site is matched to a reverse sequence. It may be more cost effective to ligate primers which give only one sequence read off a DrdI site. The above example just doubles the probability of obtaining a sequence which overlaps with either known STS's or with the two 500 base-pair sequences from the end of the clone.

III. Singlet and Doublet DrdI Island Approach

Extending the DrdI Island Approach to Allow for Alignment of BACs.

On average, a given BAC will contain 2-3 unique sequences (called "singlets"), 2-4 sequences which are the consequence of two overlapping runs (called "doublets") and 0-1 sequences which are the consequence of three or more overlapping runs, which may be un-interpretable multisequences. In order to construct BAC clone overlaps, it is necessary to have at least two readable (doublets or singlets) sequencing runs for a given BAC.

The probabilities of obtaining two readable sequencing runs from a BAC clone containing from 2 to 20 DrdI sites are as follows.

A given restriction site may appear multiple times in a given BAC clone. Therefore, it is necessary to determine the frequency of unique and doubly represented restriction sites in a BAC clone. Sites which appear only once in a BAC clone will generate a clean sequence and will be called singlets in the calculations. Sites which appear exactly twice should still reveal useful sequencing data once every four bases on average and will be known as doublets in the calculations.

The DrdI enzyme generates a degenerate 2 base 3' overhang. After eliminating palindromic sequences for the degenerate positions, there are 6 different overhangs which can be ligated after digestion of a BAC with DrdI.

The SapI and BglI enzymes generate degenerate 3 base 5' and 3' overhangs, respectively. 16 possible tails can be picked to ensure specific ligation and to simplify the complexity of the sequencing reactions.

Below is an analysis of the possible ways that these restriction enzyme sites can be distributed in BAC clones containing between 1 and 36 restriction sites. From the representative BAC clones, the (non-palindromic overhang) DrdI site appears from 8-10 times, the BglI site appears from 12-17 times, and the SapI site appears from 12 to 25 times in human DNA. Note that the BglI site is used on both sides of the cut, so for the calculations below, one doubles the number of BglI sites in the BAC when calculating "N".

The probability of each site is p=1/n where n=6 for DrdI and n=16 for SapI or BglI.

For a given restriction sequence R, the probability of a given site not being R is q. q=1−p=1−1/n.

The probability of all N sites in a given BAC not being the sequence R is $P(absent)=q^N$.

The probability of R appearing once and only once in N sites in a given BAC is:

$$P(singlet)=p \times q^{(N-1)} \times N$$

The probability of R appearing twice and only twice in N sites in a given BAC is:

$$P(doublet)=p^2 \times q^{(N-2)} \times Comb(N,2)=p^2 \times q^{(N-2)} \times (N)(N-1)/2$$

Where Comb(N,n) is the number of ways that n items can be picked from a set of N available items.

The probability that at least one of the 6 possible DrdI sites is a singlet:

$$P(\text{at least one singlet})=1-(1-P(singlet))^6$$

The probability that at least one of the 16 possible SapI or BglI sites is a singlet:

$$P(\text{at least one singlet})=1-(1-P(singlet))^{16}$$

The probability that at least one of the 6 possible DrdI sites is either a singlet or a doublet is:

$$Psd=P(singlet)+P(doublet)$$

$$P(\text{at least one singlet or doublet})=1-(1-Psd)^6$$

The probability that at least one of the 16 possible SapI or BglI sites is either a singlet or a doublet is:

$$Psd=P(singlet)+P(doublet)$$

$$P(\text{at least one singlet or doublet})=1-(1-Psd)^{16}$$

The probability of one and only one singlet or doublet for DrdI is:

$$P(\text{exactly one singlet or doublet})=6 \times Psd \times (1-Psd)^5$$

$$P(\text{exactly one singlet})=6 \times P(singlet) \times (1-P(singlet))^5$$

The probability of one and only one singlet or doublet for SapI or BglI is:

$$P(\text{exactly one singlet or doublet})=16 \times Psd \times (1-Psd)^{15}$$

$$P(\text{exactly one singlet})=16 \times P(singlet) \times (1-P(singlet))^{15}$$

For the BAC clones to be informative for constructing overlapping contigs, one needs at least two readable sequences per clone. Calculations are provided for at least two singlets or doublets, or the more stringent requirement of at least two singlets.

The probability of at least two singlets or doublets for DrdI is:

$$P(\text{at least two singlets or doublets})=P(\text{at least one singlet or doublet})-P(\text{exactly one singlet or doublet})=1-(1-Psd)^6-6 \times Psd \times (1-Psd)^5$$

The probability of at least two singlets for DrdI is:

$$P(\text{at least two singlets})=P(\text{at least one singlet})-P(\text{exactly one singlet})=1-(1-P(singlet))^6-6 \times P(singlet) \times (1-P(singlet))^5$$

The probability of at least two singlets or doublets for SapI or BglI is:

$$P(\text{at least two singlets or doublets})=P(\text{at least one singlet or doublet})-P(\text{exactly one singlet or doublet})=1-(1-Psd)^{16}-16 \times Psd \times (1-Psd)^{15}$$

The probability of at least two singlets for SapI or BglI is:

$$P(\text{at least two singlets})=P(\text{at least one singlet})-P(\text{exactly one singlet})=1-(1-P(singlet))^{16}-16 \times P(singlet) \times (1-P(singlet))^{15}$$

(Note: For small values, the charts below are not completely accurate.)

| N | P(absent) | P(singlet) | P(doublet) | P(sd) | P(at least two singlets or doublets) | P(at least two singlets) |
|---|---|---|---|---|---|---|
| 1 | 0.83333 | 0.16667 | 0.00000 | 0.16667 | 0.26322 | 0.26322 |
| 2 | 0.69444 | 0.27778 | 0.02778 | 0.30556 | 0.59175 | 0.53059 |
| 3 | 0.57870 | 0.34722 | 0.06944 | 0.41667 | 0.79174 | 0.67569 |
| 4 | 0.48225 | 0.38580 | 0.11574 | 0.50154 | 0.89207 | 0.74399 |
| 5 | 0.40188 | 0.40188 | 0.16075 | 0.56263 | 0.93897 | 0.76963 |
| 6 | 0.33490 | 0.40188 | 0.20094 | 0.60282 | 0.96032 | 0.76963 |
| 7 | 0.27908 | 0.39071 | 0.23443 | 0.62514 | 0.96946 | 0.75200 |
| 8 | 0.23257 | 0.37211 | 0.26048 | 0.63259 | 0.97213 | 0.72083 |
| 9 | 0.19381 | 0.34885 | 0.27908 | 0.62793 | 0.97048 | 0.67876 |
| 10 | 0.16151 | 0.32301 | 0.29071 | 0.61372 | 0.96501 | 0.62813 |
| 11 | 0.13459 | 0.29609 | 0.29609 | 0.59219 | 0.95532 | 0.57134 |
| 12 | 0.11216 | 0.26918 | 0.29609 | 0.56527 | 0.94059 | 0.51093 |
| 13 | 0.09346 | 0.24301 | 0.29161 | 0.53461 | 0.91981 | 0.44939 |
| 14 | 0.07789 | 0.21808 | 0.28351 | 0.50159 | 0.89211 | 0.38901 |
| 15 | 0.06491 | 0.19472 | 0.27260 | 0.46732 | 0.85690 | 0.33166 |
| 16 | 0.05409 | 0.17308 | 0.25962 | 0.43270 | 0.81412 | 0.27875 |
| 17 | 0.04507 | 0.15325 | 0.24520 | 0.39845 | 0.76430 | 0.23117 |
| 18 | 0.03756 | 0.13522 | 0.22987 | 0.36509 | 0.70850 | 0.18936 |
| 19 | 0.03130 | 0.11894 | 0.21410 | 0.33304 | 0.64826 | 0.15335 |
| 20 | 0.02608 | 0.10434 | 0.19824 | 0.30258 | 0.58537 | 0.12290 |
| 21 | 0.02174 | 0.09129 | 0.18259 | 0.27388 | 0.52173 | 0.09756 |
| 22 | 0.01811 | 0.07970 | 0.16737 | 0.24707 | 0.45911 | 0.07677 |
| 23 | 0.01509 | 0.06944 | 0.15276 | 0.22220 | 0.39906 | 0.05994 |
| 24 | 0.01258 | 0.06038 | 0.13887 | 0.19925 | 0.34280 | 0.04646 |
| 25 | 0.01048 | 0.05241 | 0.12579 | 0.17820 | 0.29121 | 0.03578 |
| 26 | 0.00874 | 0.04542 | 0.11356 | 0.15899 | 0.24480 | 0.02739 |
| 27 | 0.00728 | 0.03931 | 0.10221 | 0.14152 | 0.20376 | 0.02085 |
| 28 | 0.00607 | 0.03397 | 0.09172 | 0.12569 | 0.16805 | 0.01580 |

-continued

| N | P(absent) | P(singlet) | P(doublet) | P(sd) | P(at least two singlets or doublets) | P(at least two singlets) |
|---|---|---|---|---|---|---|
| 29 | 0.00506 | 0.02932 | 0.08210 | 0.11142 | 0.13742 | 0.01192 |
| 30 | 0.00421 | 0.02528 | 0.07330 | 0.09858 | 0.11148 | 0.00896 |
| 31 | 0.00351 | 0.02177 | 0.06530 | 0.08706 | 0.08977 | 0.00670 |
| 32 | 0.00293 | 0.01872 | 0.05804 | 0.07677 | 0.07180 | 0.00500 |
| 33 | 0.00244 | 0.01609 | 0.05149 | 0.06758 | 0.05706 | 0.00372 |
| 34 | 0.00203 | 0.01381 | 0.04559 | 0.05940 | 0.04509 | 0.00276 |
| 35 | 0.00169 | 0.01185 | 0.04029 | 0.05214 | 0.03544 | 0.00204 |
| 36 | 0.00141 | 0.01016 | 0:03555 | 0.04571 | 0.02771 | 0.00151 |

Using these equations, for SapI or BglI the probabilities are:

| N | P(absent) | P(singlet) | P(doublet) | P(sd) | P(at least two singlets or doublets) | P(at least two singlets) |
|---|---|---|---|---|---|---|
| 1 | 0.93750 | 0.06250 | 0.00000 | 0.06250 | 0.26411 | 0.26411 |
| 2 | 0.87891 | 0.11719 | 0.00391 | 0.12109 | 0.59371 | 0.57480 |
| 3 | 0.82397 | 0.16479 | 0.01099 | 0.17578 | 0.79985 | 0.76694 |
| 4 | 0.77248 | 0.20599 | 0.02060 | 0.22659 | 0.90679 | 0.87145 |
| 5 | 0.72420 | 0.24140 | 0.03219 | 0.27359 | 0.95777 | 0.92673 |
| 6 | 0.67893 | 0.27157 | 0.04526 | 0.31684 | 0.98104 | 0.95624 |
| 7 | 0.63650 | 0.29703 | 0.05941 | 0.35644 | 0.99146 | 0.97240 |
| 8 | 0.59672 | 0.31825 | 0.07426 | 0.39251 | 0.99610 | 0.98156 |
| 9 | 0.55942 | 0.33565 | 0.08951 | 0.42516 | 0.99818 | 0.98692 |
| 10 | 0.52446 | 0.34964 | 0.10489 | 0.45453 | 0.99912 | 0.99016 |
| 11 | 0.49168 | 0.36057 | 0.12019 | 0.48076 | 0.99956 | 0.99217 |
| 12 | 0.46095 | 0.36876 | 0.13521 | 0.50397 | 0.99977 | 0.99342 |
| 13 | 0.43214 | 0.37452 | 0.14981 | 0.52433 | 0.99987 | 0.99419 |
| 14 | 0.40513 | 0.37812 | 0.16385 | 0.54198 | 0.99993 | 0.99463 |
| 15 | 0.37981 | 0.37981 | 0.17725 | 0.55706 | 0.99995 | 0.99483 |
| 16 | 0.35607 | 0.37981 | 0.18991 | 0.56972 | 0.99997 | 0.99483 |
| 17 | 0.33382 | 0.37833 | 0.20178 | 0.58010 | 0.99998 | 0.99466 |
| 18 | 0.31296 | 0.37555 | 0.21281 | 0.58836 | 0.99998 | 0.99432 |
| 19 | 0.29340 | 0.37163 | 0.22298 | 0.59462 | 0.99999 | 0.99382 |
| 20 | 0.27506 | 0.36675 | 0.23227 | 0.59902 | 0.99999 | 0.99313 |
| 21 | 0.25787 | 0.36101 | 0.24068 | 0.60169 | 0.99999 | 0.99225 |
| 22 | 0.24175 | 0.35457 | 0.24820 | 0.60277 | 0.99999 | 0.99112 |
| 23 | 0.22664 | 0.34752 | 0.25485 | 0.60236 | 0.99999 | 0.98972 |
| 24 | 0.21248 | 0.33996 | 0.26064 | 0.60060 | 0.99999 | 0.98801 |
| 25 | 0.19920 | 0.33199 | 0.26560 | 0.59759 | 0.99999 | 0.98593 |
| 26 | 0.18675 | 0.32369 | 0.26975 | 0.59344 | 0.99999 | 0.98342 |
| 27 | 0.17508 | 0.31514 | 0.27312 | 0.58825 | 0.99998 | 0.98041 |
| 28 | 0.16413 | 0.30638 | 0.27574 | 0.58212 | 0.99998 | 0.97684 |
| 29 | 0.15387 | 0.29749 | 0.27766 | 0.57515 | 0.99997 | 0.97264 |
| 30 | 0.14426 | 0.28851 | 0.27890 | 0.56741 | 0.99997 | 0.96771 |
| 31 | 0.13524 | 0.27950 | 0.27950 | 0.55900 | 0.99996 | 0.96199 |
| 32 | 0.12679 | 0.27048 | 0.27950 | 0.54998 | 0.99994 | 0.95539 |
| 33 | 0.11886 | 0.26150 | 0.27894 | 0.54044 | 0.99992 | 0.94783 |
| 34 | 0.11144 | 0.25259 | 0.27785 | 0.53043 | 0.99989 | 0.93924 |
| 35 | 0.10447 | 0.24377 | 0.27627 | 0.52003 | 0.99985 | 0.92955 |
| 36 | 0.09794 | 0.23506 | 0.27424 | 0.50929 | 0.99980 | 0.91869 |

Graphs showing the probabilities of two or more singlets or doublets of DrdI, SapI, or BglI sites in BACs containing from 2 to 36 sites are shown in FIG. 17A.

For the average of 8-12 non-palindromic DrdI sites per BAC clone, the probability is from 94%-97% of containing at least two readable (singlet or doublet) sequences. For the same clones, from 51%-72% will contain at least two singlet sequences, making alignment even easier for those clones.

Thus, the overwhelming majority of BAC clones will contain at least two readable (doublets or singlets) sequencing runs. Contigs may be constructed off DrdI doublet sequencing runs since two doublet runs may be used to determine BAC overlap, even if individual singlet sequences are unknown. Further, since the BAC library will represent a 5-fold coverage of the genome, sequences which were buried within three overlapping runs in one BAC clone will be represented as either singlets of doublets in neighboring BAC clones. Surprisingly, the doublet data will even allow for mapping virtually all DrdI islands onto the BAC clones.

How to Collect the Data:

In the past "Gemini proteins" (i.e. proteins with duplicated domains) were constructed. When using a sequencing primer which hybridizes to the duplicated region, one obtains a sequencing run with a single read which turns into a double read as the sequencing reaction extends past the duplicated region. Bands were clearly visible for both sequences and the precise sequence could be determined by subtracting the "known" sequence from the doublet sequence. New automated DNA sequencing machines give excellent peak to peak resolution and would be able to read doublet and even triplet sequences for hundreds of bases.

How to Interpret the Results:

A computer simulation was performed on 4 known sequenced BAC clones from chromosome 7, and each clone generated at least 5 readable sequences. A computer simulation of DrdI site sequences was performed on the first 5 such sites in BAC RG253B13. The first 80 bp of sequence from each of these positions was compared for either "concordant" or "discordant" alignment tests for a doublet sequence.

To understand the power of aligning DrdI sites, it is important to realize there are only about 200,000 to 300,000 DrdI sites in the human genome. Further, since these are being sequenced in 6 different sets, there are about 35,000 to 50,000 DrdI sites in a given set. Thus, to distinguish a given sequence from others, it must be unique at only one in 50,000 (not one in 3 billion) sites.

A key advantage for generating DrdI islands is the format of the data. The sequence information always starts at the same position. The GTC half of the DrdI site is retained in the sequencing read, thus assuring that the sequences are always aligned correctly (see e.g. FIG. 18 where sequences 1, 2, 3, 4, and 5 (i.e. SEQ. ID. Nos. 3, 4, 5, 6, and 7, respectively) are aligned at the GTC motif). All the sequences have the same orientation. There is no need to compare multiple alignments or try the reverse sequence for alignment. Thus, computer programs can be vastly simpler than previous lineup algorithms.

When comparing two singlet sequences, the uniqueness is determined for any stretch of 8 bases (i.e. $4^8$=65,536). When comparing a doublet sequence with a singlet sequence, the uniqueness may be determined either (1) by scoring identity at 8 bases in the doublet sequence with the singlet sequence (represented by vertical bars (i.e. |) in FIG. 18), or (2) by scoring 16 bases (i.e. $2^{16}$=65,536) where the singlet sequence is consistent with either of the bases in the doublet at that position (represented by a comma in FIG. 18 (i.e. ,).

For example, in FIG. 18, when analyzing the doublet to singlet concordant sequences, the vertical line (i.e. |) indicates identity where the corresponding base for the doublet and for the singlet are all the same. On the other hand, the comma (i.e. ,) indicates consistency in that one of the bases in the doublet is the same as the corresponding base in the singlet. In this example, there is concordance (i.e. the sequences must match), because the number of bases, aside from the GTC motif, which are identical (i.e. 12) is greater than 8 and which are consistent (i.e. 63) exceeds 16. On the other hand, with regard to the doublet to singlet discordant sequences, there are no vertical lines (i.e. |) or commas (i.e. ,) and, as indicated by the Xs, there are numerous bases where neither base from the doublet can match the corresponding base in the singlet. As a result, the doublet and the singlet cannot be from the same clone (i.e. they are discordant).

When comparing a doublet read to another doublet read, the sequences will contain a shared concordant read if there are at least 16 bases where either doublet sequence has an identical base which is consistent with one or the other of the two bases represented in the other doublet sequence. For example, in the concordance comparison of a doublet in a first clone to a doublet in a second clone of FIG. 18, the vertical line (i.e. |) indicates identity where both bases of one doublet are the same as one corresponding base in the other doublet. On the other hand, the comma (i.e. ,) indicates consistency in that there are 2 different corresponding bases in one doublet which are the same as the corresponding bases in the other doublet. For example, in FIG. 18, there is concordance, because, aside from the GTC motif, the number of bases with identity (i.e. 26) (as indicated by |) added to the number of bases with consistency (i.e. 17) (as indicated by a comma) (i.e. 26+17=43) exceeds 16. Turning to doublet to doublet analysis for discordance in FIG. 18, there are no vertical lines or commas, but, at several bases, there are Xs, indicating that neither base from one doublet matches a corresponding base from the other doublet. This is, perhaps, the most striking example of the power of this approach in that it easily shows if two multiple bases do not overlap. In a random comparison of a doublet and a singlet sequence, there are only 3 positions which are identical (|), and 38 which are discordant (X). When comparing different doublets with one another, there are 12 discordant sites where one doublet has a single base (X), and 5 discordant sites where all four bases were present (two from one doublet, two from the other doublet; x). For simplicity, positions where more than two bases are read will not be considered, even though those positions are still informative.

FIG. 18 also shows doublet to triplet analyses for concordant and discordant sequences. These procedures are carried out in substantially the same fashion as the doublet to doublet analysis described above. However, the vertical line (i.e. |) now indicates identity where both bases of one doublet are the same as one corresponding base in the triplet or all bases of the triplet are the same as one corresponding base in the doublet. On the other hand, the comma (i.e. ,) indicates consistency in that there are 2 different corresponding bases in the doublet which are the same two of the corresponding bases in the triplet.

Again, the sequences will contain a shared concordant read if there are at least 16 cases where either doublet or triplet sequence has an identical base which is consistent with one or the other of the two bases represented in the other sequence. For example, in the alignment of cordant sequences for the doublet to triplet in FIG. 18, there are 12 such positions in the first 80 bp. However, there are also 14 positions where the two reads have the same two bases at that positions, bringing the total concordant positions to 26, well in excess of the 16 positions required. Comparing a doublet with a triplet yielded 11 discordant sites. The prediction is that one SNP will be observed every 1,000 bases, so single base discordance representing SNPs will be rare but also easily distinguished from the average of 10 to 40 discordant sites when comparing doublets with triplet, doublet, and singlet sequences.

Thus, in as few as 80 bases of sequence, one can easily discern if there is a common or discordant DrdI sequence within the two reads which are being compared, when the two reads contain a singlet, doublet, or even a triplet.

Using Smaller Representational Fragments as an Alternative Approach to Alignment of BACs The previous section described an approach to interpret singlet, doublet, and triplet sequences generated from representations of individual BAC clones using as few as 80 bases of sequence information. The assumption was made that when more than one fragment is generated from a given representation (i.e. DrdI site AA overhang), then those fragments would be present in about equal amounts. Further, the above approach requires specialized software to interpret a sequencing read where more than one base is called at a given position. As an alternative to deconvoluting doublet and triplet sequencing runs, other enzymes may be used to create short representational fragments. Such fragments may be differentially enriched via ultrafiltration to provide dominant signal, or, alternatively, their differing length provides unique sequence signatures on a full length sequencing run, such that unique sequences for more than one fragment can be interpreted on a single sequencing lane.

For human DNA within BACs, MseI can be substituted for MspI/TaqI, resulting in generation of much shorter representational fragments (FIGS. 19A-19D and FIGS. 20A-20D). Bubble linkers for MspI/TaqI on one hand and for MseI on the other hand are disclosed in Table 4.

TABLE 4

New MspI/TaqI and MseI bubble linkers.

New MspI/TaqI linkers

| | | |
|---|---|---|
| MTCG225 | 5' GAC ACG TCA CGT <u>CTC GAG</u> TCC TA 3' | (SEQ. ID. No. 8) |
| MTCGO326R | 3' Bk-TGC AGT GCA <u>ACA</u> CTC AGG ATGC 5' | (SEQ. ID. No. 9) |
| MTCG225 | 5' GAC ACG TCA CGT <u>CTC GAG</u> TCC TA 3' | (SEQ. ID. No. 10) |
| MTCGp326R | 5' pCGT AGG ACT C<u>AC AA</u>C GTG ACG T - Bk | (SEQ. ID. No. 11) |
| MTCGO326R | 5' CGT AGG ACT C<u>AC AA</u>C GTG ACG T - Bk | (SEQ. ID. No. 12) |
| MTCG227 | 5' GAC ACG TCA CGT <u>CTC GAG</u> TCC TsAsC 3' | (SEQ. ID. No. 13) |
| MTCG228 | 5' GAC ACG TCA CGT <u>CTC GAG</u> TCC TAC 3' | (SEQ. ID. No. 14) |

New MseI linkers (MseI site = TTAA)

| | | |
|---|---|---|
| MSTA275 | 5' GAC ACG TCA CGT <u>CTC GAG</u> TCC TC 3' | (SEQ. ID. No. 15) |
| MSTAO276R | 3' Bk-TGC AGT GCA <u>ACA</u> CTC AGG <u>AGAT</u> 5' | (SEQ. ID. No. 16) |
| MSTA275 | 5' GAC ACG TCA CGT <u>CTC GAG</u> TCC TC 3' | (SEQ. ID. No. 17) |

TABLE 4-continued

New *MspI/TaqI* and *MseI* bubble linkers.

```
MSTAp276R  5' pTAG AGG ACT CAC AAC GTG ACG T - Bk    (SEQ. ID. No. 18)

MSTAo276R  5'  TAG AGG ACT CAC AAC GTG ACG T - Bk    (SEQ. ID. No. 19)

MSTA278    5' GAC ACG TCA CGT CTC GAG TCC TCT AA 3'  (SEQ. ID. No. 20)
```

MseI cleaves human genomic DNA approximately every 125 bp. In contrast, when using MspI/TaqI as the second enzyme, the average size fragment is greater than 1,000 bp. Many of the larger fragments (i.e. greater than 2,000 bp) will not amplify as well as smaller fragments in a representation, i.e. they will be lost to the sequencing gel. Therefore, in a DrdI-MseI representation, the number of unique fragments lost during PCR amplification may be greatly reduced. This can increase the number of amplified fragments per BAC and can facilitate alignment of BACs.

DrdI representations of individual BACs can be used to link BACs together to form contigs. For BACs that generate a doublet sequence, "singlet" sequence information can still be obtained as long as the fragments are of different lengths. For example, an AG DrdI/MseI representation of BAC RG253B13 results in two fragments of length 115 and 353 bases. Sequencing of these two fragments simultaneously will result in two distinct regions of sequence. The first region (approx. 1-141 bases) will consist of an overlap sequence in which sequence information from both fragments will be observed. The last 25 bases of this sequence will be the linker adapter sequence on the MseI adapter. Thus, one can easily distinguish when the shorter fragment "ends" on the sequencing run. In all likelihood, it will also be more abundant and, hence, provide a stronger signal for those bases which were derived from that shorter fragment. If this stronger signal is not sufficient to recognize the unique sequence, then ultrafiltration (i.e. use of Amicon filters YM30 and YM125 (made by Millipore, Danvers, Mass.)) may be used to enrich for "smaller" vs. "larger" fragments. The second region (approx. 141-353 bases) will consist only of sequence information from the longer fragment. Therefore, for any doublet in which the fragments are of different length, a "singlet" sequence will be generated for the non-overlapping region of the longer fragment. This non-overlapping region of the doublet can be utilized as a "singlet" in order to overlap BACs. A minimum of 8 unique bases for a given distance from the DrdI site is sufficient to uniquely identify the sequence in the human genome, because the DrdI site provides an additional 6+2=8 bases of unique sequence, bringing the total to 16 bases.

How to Align the BAC Clones to Create a Complete Contig of the Entire Human Genome.

As mentioned earlier, there are only about 200,000 to 300,000 DrdI sites in the human genome. Since these are being sequenced in 6 different sets, there are about 35,000 to 50,000 DrdI sites in a given set. Alignment of the BAC clones is a simple process of constructing contigs in each of the 6 sets.

Consider creating contigs in the sequencing set whose linker primer ends in "GG". Suppose a given BAC=B1 clone contains a doublet sequence of #1 & #2. By searching the database one finds a second BAC=B2 clone containing a doublet sequence of #2 & #3. This implies that BAC clones B1 and B2 overlap, and further the order of the DrdI islands are #1, #2, and #3. (The approach for determining individual sequence runs #1, #2, and #3 are explained below.) Consider then additional BACs: B3 with islands #3, #4, and #5, B4 with #4 & #6, B5 with #6, and B7 with #6 & #7. Then the BAC clone overlap is B1-B7 and the sequences are in the order: #1, #2, #3, #5, #4, #6, #7. In other words, the DrdI islands not only line up the BAC clone overlaps, they also provide the order they appear in the linear sequence.

How frequent are the individual members of a set? With one non-palindromic DrdI site every 10-15 kb, the average distance between two DrdI sites with the same dinucleotide overhang sequence is 60 to 75 kb, or on average one to two such sites per BAC clone. Computer simulation on four BAC clones demonstrated 2 duplex sites separated by less than 25 kb, 5 duplex sites separated by between 25 kb and 50 kb, 2 duplex sites separated by between 50 kb and 75 kb, and 2 duplex sites greater than 75 kb apart. Thus, a 5-fold coverage of a region of DNA will create BAC clones with an average of two same overhang sites per BAC clone, but many such sites will be represented as either singlet or doublet reads in neighboring overlapping BAC clones.

On a rare occasion, a long stretch of human DNA will lack a DrdI site with a given dinucleotide overhang (i.e. GG), such that even larger BAC clones of 175-200 kb would not include two such sites. However, the BAC clone contigs are being pieced together using six sets of DrdI sequence information. This is akin to using six different restriction enzymes to create a restriction map of pBR322. Thus, a "gap" in the contig is easily filled using sequence information from one of the other 5 sets. The average BAC of 8-12 DrdI sites contains sequence information ranging from 4 to all 6 of the different contig sets. Thus, by combining the contig building among the 6 different sets, the entire genome contig can be built.

Using the DrdI Island Database to Obtain Unique Singlet Sequences from Overlapping Doublet and Triplet BAC Clones.

When BAC overlaps are found, the data may be immediately used to deduce unique singlet sequences at essentially all of the DrdI sites. As the simplest case, when comparing a doublet with a singlet sequence, subtraction of the singlet sequence will reveal the other singlet in the doublet sequence. In most cases, a doublet will be represented again as a singlet in a neighboring BAC. In some cases, two or three doublets will be connected in a series. Even one singlet at the end of a string of doublets may be used to deduce the unique sequences of the individual DrdI islands.

Remarkably, just three overlapping doublets may be used to determine all four individual singlet sequences. For example, as shown in FIG. 17, 4 unique singlet DrdI sequences from 2 overlapping doublet BAC clone sequences are obtained by aligning them as shown and comparing the corresponding bases. The common sequence between two doublets will either be identical, i.e. AA compared with AA (S), the same in one doublet allowing assignment, i.e. AA compared with AC indicates the common base is "A" (s), different among the doublets, also allowing assignment, i.e. AG compared with AC indicates the common base is "A" (d), or indeterminate, i.e. AC compared with AC does not reveal the base (i). On average, 3 out of every 4 positions will allow assignment of the common sequence base. Based upon this analysis, the sequence common in each doublet can be determined with a nucleotide at each location receiving an S, s, or d designation. In this manner, a sequence is identified with locations having the i designation being assigned alternative bases. FIG. 21 shows how the sequences for #2 and #3 are determined in this fashion. This information can then be used to compare the consensus sequences of #2 and #3 from which one can determine the overlap. With only 2 indeterminant bases, the sequences for #2 and #3 can be found. Sequence information for #1 and #4 can then be obtained.

The same analysis may be applied to alignment of one of the doublets with another neighboring doublet (or even triplet). See FIG. 22. Although the sequence which is common between these sets is different from the original doublet comparison, the two consensus sequences may now be compared with the original doublet sequencing run. The probability that the indeterminate sequence in one sequence is at the same position as the other sequence is $\frac{1}{4} \times \frac{1}{4} = \frac{1}{16}$ for the doublet-doublet-doublet comparison and $\frac{1}{4} \times \frac{7}{16} = \frac{7}{64}$ for the doublet-doublet-triplet comparison. The remaining portions of the sequence, i.e. $\frac{15}{16}$ and $\frac{57}{64}$ of the sequence is determined, and this allows one to deduce the remaining singlet sequences.

In the simulation of a doublet-doublet-doublet comparison, 78 out of 80 bases could be uniquely assigned for all four singlet sequences. In the doublet-doublet-triplet comparison 73 out of 80 bases could be uniquely assigned for all three singlet sequences. This is far in excess of the 8 bases required to uniquely identify a given singlet sequence.

Sequencing of DrdI Island PCR Fragments from BACs, or Directly Off BACs.

As discussed supra, a method was provided for sequencing DNA directly from the plasmid or cosmid clone by PCR amplification of the insert. While PCR amplification has not been demonstrated for DNA of BAC clone length, the DrdI island may be PCR amplified by using a second frequent cutter enzyme to create small fragments for amplification. The second enzyme would contain a two base 5' overhang such that ligation/cutting could proceed in a single reaction tube. The ligation primers/PCR primers can be designed such that only DrdI-second enzyme fragments amplify. PCR primers may be removed by using ribose containing primers and destroying them with either base (i.e. 0.1N NaOH) or using dU and UNG. An alternative approach to amplification directly from PCR-amplified DNA uses ultrafiltration in a 96 well format to simply remove primers and dNTPs physically, and is commercially available from Millipore.

Examples of frequent enzymes with TA overhangs (and frequency in the human genome) are: BfaI (CTAG, 1 every 350 bp), Csp6I (GTAC, 1 every 500 bp) and MseI (TTAA, 1 every 133 bp). For fragments with larger average sizes, four base recognition enzymes with CG overhangs may be used: MspI (CCGG, 1 every 2.1 kb), HinP1I (GCGC, 1 every 2.5 kb), and TaqI (TCGA, 1 every 2.6 kb).

There is a chance that the second site enzyme cleaves either too close to a DrdI site to generate sufficient sequence or, alternatively, too distantly to amplify efficiently. This site will simply not be scored in the database, just at DrdI sites with palindromic overhangs (i.e. AT) are not scored. If it is critical to obtain that precise sequence information, the problem may be addressed by using a different second enzyme. One advantage of using the "CG" site enzymes is that average fragment sizes will be larger and, consequently, will be amenable to generating neighboring sequence information from the second site if needed. This may be helpful for increasing the density of internal sequence information linked to a BAC clone or plasmid/cosmid clone.

Plasmids containing colE1 replication origins (i.e. pBR322, pUC derivatives) are present at high copy number which may be increased to 100's by growing clones for two days or to 1,000's by amplification with chloramphenicol. This should provide sufficient copy number such that it is not necessary to separate plasmid/cosmid DNA from host bacterial chromosomal DNA. On the other hand, BAC clone vectors are based on the F factor origin of replication may be present at copy numbers equal or only slightly higher than the bacterial chromosome. Thus, it will probably be necessary to partially purify BAC clone DNA from bacterial chromosome DNA. The relative advantages and disadvantages of PCR amplification followed by direct sequencing vs. rapid purification of plasmid, cosmid, or BAC clone followed by sequencing need to be determined experimentally.

Alternative Enzymes; SapI and BglI.

There may be regions of the genome which contain less than two readable DrdI sequences. One solution to this problem is to use a second enzyme with a comparable frequency in the human genome. By slightly modifying the procedure, 16 linker/primer sets may be used on split palindrome enzymes which generate a 3 base 3' overhang. Since the overhang is an odd number of bases, it is not necessary to exclude the palindromic two base sequences AT, TA, GC, and CG. To reduce the number of ligations from 64 (all the different possible 3 base overhangs) to 16, the linkers and primers are degenerate at the third position, i.e. end with NTC or NGC. Since there are 3 levels of specificity in the ligation and sequencing step, the third base degeneracy will not interfere with the fidelity of the reaction.

Of the 4 commercially available split palindrome enzymes which generate a 3 base 3' overhang, BglI (GC-CNNNN^NGGC (SEQ. ID. No. 21)) and DraIII (CACNNN^GTG) are present at low enough frequencies to be compatible with DrdI. There are 60 BglI sites in about 550 kb of the four sequenced BAC clones, or an average of 1 BglI site per 9 kb. Since the linkers can ligate to both sides of a BglI site, there are twice as many ends, (i.e. sequences) generated as with the DrdI sites. See FIG. 16. Using BglI, there are two levels of specificity for creating a unique representation: (i) ligation of the top strand, and (ii) extension of the sequencing primer with polymerase. Unlike DrdI, the use of a last base degeneracy in the BglI linker does not allow one to determine sequence information from only one side. If there are too many BglI sites in a given BAC, or there is a need to obtain singlet sequence information, one may obtain additional specificity by designing primers which reach in one additional base on the 3' side of the ligation junction (i.e. GCCNNNN^NGGC (SEQ. ID. No. 22)). As with DrdI, the conserved G$\overline{G}$C on the 3' side of the cut site allows all sequences in a set to be easily compared in the correct alignment. As with the DrdI site, use of a second enzyme or enzyme pair (MspI and/or TaqI) and corresponding linkers allows for specific amplification of the BglI site fragments (See FIG. 16A).

One type IIs enzyme, SapI (GCTCTTCN1/4), generates a 3 base 5' overhang 3' which allows for unidirectional ligation, i.e. simultaneous cutting and ligation will only provide the sequence from one side. See FIG. 17. There are 69 SapI sites in about 550 kb of the four sequenced BAC clones, or an average of 1 SapI site per 8 kb. One advantage of SapI is that most vectors lack this site. Two disadvantages of SapI are the 5' 3 base overhang will be filled in if using the enzyme after a PCR amplification, and the need to test a few (5-10) different starting positions to align doublet or triplet sequences precisely with each other. If there is a need to obtain a singlet sequence, one may obtain additional specificity by designing primers which reach in one or two additional base on the 3' side of the ligation junction (i.e. GCTCTTCN^NNNNN (SEQ. ID. No. 23)). One big advantage of using this enzyme is the majority of SapI sequences yield singlet reads.

The probabilities of obtaining two readable sequencing runs from a BAC clone containing from 2 to 36 BglI or SapI sites have been calculated. For the average of 12-17 BglI sites per BAC clone (=24-34 ends), the probability is 99.9% for containing at least two readable (singlet or doublet) sequences. For the same clones, from 93%-98% will contain at least two singlet sequences, making alignment even easier for those clones. For the average of 12-25 SapI sites per BAC clone, the probability is 99.9% for containing at least two readable (singlet or doublet) sequences. For the same clones, from 98.8%-99.3% will contain at least two singlet sequences, making alignment even easier for those clones (see FIG. 17A).

Although there are a total of 16 different ligation primers which may be used with the BglI or SapI sites (indeed, up to 64 may be used), it is not necessary to use all of them. Given the frequency of BglI sites in the human genome, and the fact that a single site provides two non-symmetric overhangs, 8 different ligation primers would be sufficient. Should a BglI site be present in low abundance repetitive DNA, that overhang would also not be used. Simulation on a dozen BAC clones would provide a more complete assessment of which 8 primers should be chosen for a BglI representation. With SapI, each site provides one non-symmetric overhang, so the majority of SapI sites per BAC clone provide singlet or doublet reads. Thus, anywhere from 6 to 10 different ligation primers may be chosen to provide a robust set of SapI islands to assure overlap of all the BAC clones. The advantage of using BglI or SapI with 6 to 10 different ligation primers is that additional primers may be used as needed on only those BAC clones which represent the ends of contigs. The underlying concept is that each unique linker creates a set of sequences which may be linked through singlet and doublet reads, or BAC clone overlap, or both.

Presence of DrdI or Other Sites in BAC or Plasmid Vectors.

One important technical note is that the most common BAC vector, pBeloBAC11 (Genbank Accession #U51113 for complete DNA sequence) and the common plasmid vectors contain 4 and 2 DrdI sites respectively.

Thus, one needs to fine tune the experimental approach to circumvent restriction sites in the vector sequences. The three basic approaches are to (i) remove the restriction sites from the vector before constructing the library, (ii) destroy the vector restriction sites in clones from a given library, or (iii) suppress amplification of vector fragments using sequence specific clamping primers.

Restriction sites can be removed from the BAC vector pBeloBAC11 which contains 4 DrdI sites, 4 BglI sites, and 2 SapI sites. See FIG. 21. The procedure for removing DrdI sites in a single cloning step will be described, and it is generally applicable to all the sites. One of the tricks of split palindrome enzymes which generate a 3 base 3' overhang such as BglI (GCCNNNN^NGGC (SEQ. ID. No. 21)), DraIII (CACNNN^GTG), AlwnI (CAGNNN^CTG), and PflMI (CCANNNN^NTGG (SEQ. ID. No. 24)) is that there is a high chance of creating fragments where all the sticky ends are unique. In such a case, a plasmid may be cleaved with the enzyme, one or more pieces replaced, and, then, in the presence of T4 ligase, the plasmid reassembles correctly and can be recovered by transforming into E. coli. The replacement fragments lack the DrdI site(s) such that silent mutation(s) are introduced into any open reading frames. The replacement fragments are generated by overlap PCR, and the ends of such PCR fragments converted to unique overhangs using the split palindrome enzyme (i.e. BglI). To illustrate with pBeloBAC11, two overlap PCR primers are designed to eliminate the DrdI site at 1,704, and the fragment is generated using two primers just outside BglI sites at 634 and 2,533. This fragment is cleaved with BglI after PCR amplification. Likewise, six overlap PCR primers are designed to eliminate the DrdI sites at 2,616, 3,511, and 4,807 and the whole fragment is generated using two primers just outside BglI sites at 2,533 and 6,982. This fragment is also cleaved with BglI after PCR amplification. The fragments are mixed with BglI cut pBeloBAC11, and ligase is added, in the presence of DrdI. Thus, circular ligation products containing the newly PCR amplified fragments lacking DrdI sites are selected for, and recovered after transformation into E. coli. The pBeloBAC11 vector has been modified (in collaboration with New England Biolabs) essentially as described above to create vector pBeloBAC11 No DrdI, which as its name implies, lacks DrdI sites. The same principle may be used to remove the SapI sites and even the BglI sites or all 10 sites if desired. In the latter case, the split palindrome enzyme PflMI (4 sites in pBeloBAC11) would be used. The same procedure may be applied to plasmid vectors such as pUC19, which contain only 2 each of DrdI and BglI sites and no SapI sites. See FIG. 24.

The vector restriction site or its sequence can be destroyed by treating the vector-insert DNA with various restriction enzymes. The vector sites can be eliminated so that the (DrdI) enzyme does not cut at that position or, alternatively, generates such a small sequence (i.e. 10-20 bases) that overlap from vector sequence only minimally interferes with interpretation of the data. This may appear as extra work; however, when using simultaneous restriction/ligation conditions, it is simply a matter of including (an) additional restriction endonuclease(s) in the same mixture. The linker primers will not ligate onto the other restriction site overhangs as they are not compatible.

Representational amplification from BACs may be modified to suppress amplification of vector fragments using sequence specific clamping primers. The pBeloBAC11 and pBACe3.6 vectors both contain DrdI sites complementary to AA-, CA-, and GA-overhangs. Clamping oligonucleotides which bind specific DrdI fragments (i.e. vector derived) and block annealing of PCR primers or PCR amplification, were designed as PNA or propynyl derivatives and are listed in Tables 5 and 6.

TABLE 5

PNA designed for suppression of DrdI sites associated with the pBeloBAC11 vector.

| Primer | Sequence ($NH_2 \rightarrow CONH_2$) | |
|---|---|---|
| CA-PNA27-3 | $NH_2$ GCC AGT CGG AGC ATC AGG $CONH_2$ | (SEQ. ID. No. 25) |
| GA-PNA23-4 | $NH_2$ CCC CGT GGA TAA GTG GAT $CONH_2$ | (SEQ. ID. No. 26) |

TABLE 5-continued

PNA designed for suppression of DrdI sites associated with the pBeloBAC11 vector.

| Primer | Sequence (NH$_2$ → CONH$_2$) | |
|---|---|---|
| GA-PNA25-2 | NH$_2$ ACA CGG CTG CGG CGA GCG CONH$_2$ | (SEQ. ID. No. 27) |
| AA-PNA21 | NH$_2$ GCC GCC GCT GCT GCT GAC CONH$_2$ | (SEQ. ID. No. 28) |

TABLE 6

Propynyl Primers designed for suppression of *DrdI* sites associated with the pBeloBAC11 vector.

| Primer | Sequence (5' → 3') | |
|---|---|---|
| AA Dcl PY3 | 5' GsCs(pC) sGsCs(pC) sGCT G(pC)T G(pC)T GA(pC) GG(pT) GTG A(pC)G TT -Bk 3' | (SEQ. ID. No. 29) |
| GA Cl PY6 | 5' GsAs(pC) sTsGsT s(pC)AT T(pT)G AGG G(pT)G AT(pT) TGT (pC)AC A(pC) T GAA AGG G-Bk 3' | (SEQ. ID. No. 30) |
| GA Cl PY10 | 5'GsAs(pT) sAsGsT s(pC)TG AGG G(pT)T AT(pC) TGT (pC)AC AGA T(pT)T GAG GG(pT) GG-Bk 3' | (SEQ. ID. No. 31) |
| CA Cl PY14 | 5' CsAs(pT) sAsGsT s(pC)AT GAG (pC)AA (pC)AG TTT (pC)AA TGG (pC)CA GT(pC) GG - Bk 3' 3' | (SEQ. ID. No. 32) |

The designations (pC) and (pT) represent propynyl-dC and propynyl-dT, respectively.

The PNA oligonucleotides were designed to maximize Tm values in an 18 mer sequence, while attempting to also maximize pyrimidine content and avoiding three purines in a row. The propynyl derivative oligonucleotides were designed to overlap the DrdI site by two bases, and to contain a total of about 5 to 9 and preferably 7 propynyl dC and propynyl dU groups to increase the Tm, as well as about 4 to 8 and, preferably, 6 thiophosphate groups at the 5' side to avoid 5'-3' exonuclease digestion by Taq polymerase during amplification. (Propynyl derivatives are known to increase oligonucleotide Tm values by approximately 1.5-1.7° C. per modification, while thiophosphate modifications slightly reduce Tm values by about 0.5° C. per modification). These propynyl derivative clamping oligonucleotides were from approximately 25 to 40 bases in length. Alternative propynyl designs which do not overlap the DrdI site would also be predicted to suppress vector amplification. Alternative nucleotide modifications which both increase Tm values and prevent 5'-3' exonuclease digestion by Taq polymerase, such as 2'o-methyl derivatives, may also be used. Tm values for both PNA and propynyl derivative clamps were generally above 85° C. and, preferably, above 90° C. to achieve effective clamping. When the propynyl derivative clamping oligonucleotides were synthesized without either the propynyl or thiophosphate modifications, they were insufficient to effectively block amplification of vector sequences. In general, reactions using 10 ng of digested/linker ligated BAC DNA were subjected to 30-35 cycles (94° C., 15 sec., 65° C., 2 minutes) of PCR amplifications using 25 picomoles each of primers and 50 picomoles of the corresponding clamp. These conditions were sufficient to allow for amplification of insert DrdI representational fragments while inhibiting amplification of the vector sequences. The principles of using PNA clamps to suppress amplification of undesired fragments have been described in the literature (Cochet O. et. al. "Selective PCR Amplification of Functional Immunoglobulin Light Chain from Hybridoma Containing the Aberrant MOPC 21-Derived V kappa by PNA-mediated PCR Clamping," *Biotechniques* 26:818-822 (1999) and Kyger E. et. al. "Detection of the Hereditary Hemochromatosis Gene Mutation by Real-time Fluorescence Polymerase Chain Reaction and Peptide Nucleic Acid Clamping," *Anal Biochem* 260:142-148 (1998), which are hereby incorporated by reference).

IV. Comparison of DrdI Island Approach with Other Endonucleases

Different Approaches to Generate Representations of the Genome.

The DrdI is a unique restriction endonuclease. It has an infrequent 6 base recognition sequence and generates a degenerate 2 base 3' overhang (GACNNNN^NNGTC). Sequences adjacent to a DrdI site may be PCR amplified using the 2 degenerate bases in the overhang to define a representation, and an adjacent more common site (such as MspI). The degenerate 2 base 3' overhang allows for both biochemical selection and bubble PCR to assure that only the DrdI island amplifies (and not the more abundant MspI-MspI fragments). Using DrdI, there are three levels of specificity for creating a unique representation: (i) ligation of the top strand, (ii) ligation of the bottom strand linker, and (iii) extension of the sequencing primer with polymerase. In addition, if there are too many DrdI sites in a given BAC clone, or there is a need to obtain singlet sequence information, one may obtain additional specificity by designing primers which reach in one or two additional bases on the 3' side of the ligation junction (i.e. GACNNNNNNGTC (SEQ. ID. No. 33)), since the central degenerate bases are determined by the specificity of the ligation reaction (i.e. GACNNNN^NNGTC (SEQ. ID. No. 33)). Further, the conserved GTC on the 3' side of the cut site allows all sequences in a set to be easily compared in the correct alignment. Finally, the degenerate 2 base overhang allows one to obtain sequence information from either one, or the other, or both sides of the DrdI site.

However, there may be a need to consider other restriction endonuclease sites, for example, when starting with a library made from a BAC vector with too many DrdI sites.

The use of split palindromic enzymes which generate a 3 base 3' overhang, such as BglI (GCCNNNN^NGGC (SEQ. ID. No. 21)) and type IIs enzyme, like SapI (GCTCTTCN1/4), which generates a 3 base 5' overhang are described above.

A seemingly simple solution to obtaining sequence information is to use a symmetric palindromic enzyme, such as BamHI, which cuts the BAC at several places. FIG. 25 is a schematic drawing showing the sequencing of BamHI islands in random BAC clones in accordance with the present invention. This procedure is largely the same as was described previously for DrdI, BglI, and SapI islands with respect to FIGS. 1, 5, 16, and 17. After linker ligation, some of the fragments will be under 4 kb and, thus, will amplify in a PCR reaction. The idea here is to amplify all the fragments in a single tube and, then, obtain a representation through use of carefully designed sequencing primers. The selectivity in this type of representation is achieved by using a sequencing primer, whose last two bases extend beyond the BamHI site (i.e. G^GATTCNN). It would be difficult to achieve a specificity of 3 bases beyond the site. In the example of the 170 kb BAC containing the Met Oncogene, there was considerable clustering of the sites which were close enough to amplify effectively. The results of using BamHI as the restriction enzyme are shown in FIGS. 26A-26B.

It is also difficult to find an enzyme which cleaves the DNA frequently enough that some fragments are under 4 kb, but not so frequent that too many fragments amplify, as when using EcoRI or HindIII. Use of enzymes which are less frequent due to a TAG stop codon in one of the potential reading frames (AvrII, C^CTAGG; NheI, G^CTAGC, and SpeI A^CTAGT) also have problems with clustering. The results of using these enzymes as the restriction enzyme in accordance with the present invention are shown in FIGS. 27A-27C.

Other symmetric palindromic enzymes which may be used are: KpnI, SphI, AatII, AgeI, XmaI, NgoMI, BspEI, MluI, SacII, BsiWI, PstI, and ApaLI.

To overcome the above clustering problem, one could use an enzyme which cuts more frequently due to a degeneracy, but then use linkers with only one of the 2 or 4 possible degeneracies such that only a few fragments amplify. For example, AccI has 4 different recognition sequences (GT^MKAC=GT^ATAC, GT^AGAC, GT^CTAC, and GT^C-GAC), and BsiHKAI also has 4 different recognition sequences (GWGCW^C=GAGCA^C, GAGCT^C, GTG-CA^C, and GTGCT^C). Again, the selectivity in this type of representation is achieved by using a sequencing primer, whose last two bases extend beyond the BsiHKAI site (i.e. GAGCA^CNN). The advantage of these types of restriction sites is that a non-palindromic overhang may be used for the linker. In simulations of these sites on the 171 kb BAC, only a few fragments amplify, including some which would provide too few bases of sequence information to be meaningful (i.e. 19-44 bp). FIG. 28 is a schematic drawing showing the sequencing of BsiHKAI islands in random BAC clones in accordance with the present invention. This procedure is largely the same as was described previously for DrdI, BglI, and SapI islands with respect to FIGS. 1, 5, 16, and 17. The results of using BsiHKAI and AccI as the restriction enzymes are shown in FIGS. 29A-29B.

An alternative is to use an infrequent restriction endonuclease site with a middle base degeneracy in combination with a more frequent cutter, analogous to use of DrdI as described earlier. By using a primer for only one of the degenerate sequences, one can obtain sequence information from either one or the other side of the site, such as by using SanDI (GG^GWCCC). Here, however, all the fragments are amplified simultaneously in the initial PCR, and selectivity is achieved by using a sequencing primer, whose last two bases extend beyond the recognition site (GG^GWCCCNN). Another site, SexAI (A^CCWGGT), may also work, however, the 5 base overhang may be large enough to allow substantial misligations of primer to overhangs containing a mismatch. In simulations on the 171 kb BAC, all SanDI and SexAI sites were singlet or doublet reads. FIG. 30 is a schematic drawing showing the sequencing of SanDI islands in random BAC clones in accordance with the present invention. This procedure is largely the same as was described previously for DrdI, BglI, and SapI islands with respect to FIGS. 1, 5, 16, and 17. The results of using SanDI and SexAI as restriction enzymes are shown in FIGS. 31A-31B.

RsrII (CG^GWCCG) is an enzyme which provides the same overhang, but is found less frequently than SanDI. For cases where a higher frequency site is required, the enzymes PpuI (RG^GWCCY), AvaII (G^GWCC), EcoO109 (RG-^GNCCY), or Bsu36I (CC^TNAGG) may be used.

Presence of DrdI or Other Sites in BAC or Plasmid Vectors.

One important technical note is that the most common BAC vector, pBeloBAC11 contains 4 DrdI sites, 4 BglI sites, 2 SapI sites, 6 AccI sites, 8 BsiHKAI sites, 1 SpeI site, 1 BamHI site, and 1 SexAI site. See FIGS. 23 and 32-34.

As discussed above, there are three basic approaches to circumvent the problem of the cloning vector having its own restriction sites: (i) remove the restriction sites from the vector before constructing the library, (ii) destroy the vector restriction sites in clones from a given library, or (iii) ignore the vector restriction sites and use more selective sequencing primers. For the sites described above, the AccI, BsiHKAI, SpeI, and BamHI sites do not require additional modification of the pBeloBAC11 vector, because the amplification strategy with these sites need two neighboring sites of the correct sequence to create a PCR fragment. In addition, pBeloBAC11 does not contain any AvrII, NheI, or SanDI sites.

Distribution of Representative DrdI and SanDI Sites in the Genome.

A number of advanced BLAST searches of the current dbest and dbsts databases were performed to determine if there are any unanticipated biases in the distribution of DrdI and in a smaller survey of SanDI sites.

Distribution of Representative DrdI Sites in the Genome.

1. Query: GACAAAANNGTC (SEQ. ID. No. 34)
Expect 100
Filter: None
Other Advanced Options: M=1 N=–4 S=12 S2=12
Non-redundant DBEST Division 1,814,938 sequences; 685,416,569 total letters.
DBSTS Division 59,288 sequences; 21,143,395 total letters.

```
Query:   1 GACAAAAAGTC 12    dbest    51  dbsts   3
Query:   1 GACAAAACGTC 12    dbest    20  dbsts  (0)
Query:   1 GACAAAAGGTC 12    dbest    28  dbsts   1
Query:   1 GACAAAATGTC 12    dbest    77  dbsts   4
Query:   1 GACAAAACAGTC 12   dbest    86  dbsts  (0)
Query:   1 GACAAAACCGTC 12   dbest     5  dbsts  (0)
```

-continued

```
Query:   1 GACAAAACGCTC 12   dbest    4 dbsts (0)
Query:   1 GACAAAACTGTC 12   dbest   96 dbsts  3
Query:   1 GACAAAAGAGTC 12   dbest   62 dbsts  1
Query:   1 GACAAAAGCGTC 12   dbest    6 dbsts (0)
Query:   1 GACAAAAGGGTC 12   dbest   20 dbsts  4
Query:   1 GACAAAAGTGTC 12   dbest   89 dbsts  1
Query:   1 GACAAAATAGTC 12   dbest    9 dbsts  4
Query:   1 GACAAAATCGTC 12   dbest    4 dbsts  1
Query:   1 GACAAAATGGTC 12   dbest   29 dbsts (0)
Query:   1 GACAAAATTGTC 12   dbest   45 dbsts  2
Total =                              633       24
```

2. Query: GACAAACNNGTC (SEQ. ID. No. 35)
Expect 100
Filter: None
Other Advanced Options: M=1 N=−4 S=12 S2=12
Non-redundant DBEST Division 1,814,938 sequences; 685,416,569 total letters.
DBSTS Division 59,288 sequences; 21,143,395 total letters.

```
Query:   1 GACAAACAAGTC 12   dbest   49 dbsts  2
Query:   1 GACAAACACGTC 12   dbest   47 dbsts  2
Query:   1 GACAAACAGGTC 12   dbest   20 dbsts  5
Query:   1 GACAAACAGGTC 12   dbest   22 dbsts  5
Query:   1 GACAAACCAGTC 12   dbest   29 dbsts  1
Query:   1 GACAAACCCGTC 12   dbest   14 dbsts  1
Query:   1 GACAAACCGGTC 12   dbest    3 dbsts (0)
Query:   1 GACAAACCTGTC 12   dbest   17 dbsts  3
Query:   1 GACAAACGAGTC 12   dbest   21 dbsts (0)
Query:   1 GACAAACGCGTC 12   dbest   15 dbsts  1
Query:   1 GACAAACGGGTC 12   dbest    8 dbsts (0)
Query:   1 GACAAACGTGTC 12   dbest   33 dbsts  7
Query:   1 GACAAACTAGTC 12   dbest   15 dbsts  1
Query:   1 GACAAACTCGTC 12   dbest    8 dbsts (0)
Query:   1 GACAAACTGGTC 12   dbest   40 dbsts  2
Query:   1 GACAAACTTGTC 12   dbest   59 dbsts  2
Total =                              400       32
```

3. Query: GACAAAGNNGTC (SEQ. ID. No. 36)
Expect 100
Filter: None
Other Advanced Options: M=1 N=−4 S=12 S2=12
Non-redundant DBEST Division 1,814,938 sequences; 685,416,569 total letters.
DBSTS Division 59,288 sequences; 21,143,395 total letters.

```
Query:   1 GACAAAGAAGTC 12   dbest   43 dbsts  0
Query:   1 GACAAAGACGTC 12   dbest    6 dbsts  1
Query:   1 GACAAAGAGGTC 12   dbest   62 dbsts  2
Query:   1 GACAAAGATGTC 12   dbest   29 dbsts  5
Query:   1 GACAAAGCAGTC 12   dbest   31 dbsts  3
Query:   1 GACAAAGCCGTC 12   dbest   49 dbsts (0)
Query:   1 GACAAAGCGGTC 12   dbest    5 dbsts (0)
Query:   1 GACAAAGCTGTC 12   dbest    5 dbsts  1
Query:   1 GACAAAGGAGTC 12   dbest   15 dbsts  1
Query:   1 GACAAAGGCGTC 12   dbest    8 dbsts  1
Query:   1 GACAAAGGGGTC 12   dbest   36 dbsts (0)
Query:   1 GACAAAGGTGTC 12   dbest   14 dbsts (0)
Query:   1 GACAAAGTAGTC 12   dbest    7 dbsts (0)
Query:   1 GACAAAGTCGTC 12   dbest   21 dbsts (0)
Query:   1 GACAAAGTGGTC 12   dbest   94 dbsts  4
Query:   1 GACAAAGTTGTC 12   dbest   21 dbsts (0)
Total =                              446       18
```

4. Query: TCTGGGACCCNN (SEQ. ID. No. 37)
Expect 100
Filter: None
Other Advanced Options: M=1 N=−4 S=12 S2=12
Database: Non-redundant Database of GenBank STS Division 59,293 sequences; 21,148,385 total letters.

|  |  | Dbsts |
|---|---|---|
| Query: | 1 TCTGGGACCCAA 12 | 3 |
| Query: | 1 TCTGGGACCCAC 12 | 1 |
| Query: | 1 TCTGGGACCCAG 12 | 7 |
| Query: | 1 TCTGGGACCCAT 12 | 2 |
| Query: | 1 TCTGGGACCCCA 12 | 6 |
| Query: | 1 TCTGGGACCCCC 12 | 6 |
| Query: | 1 TCTGGGACCCCG 12 | 1 |
| Query: | 1 TCTGGGACCCCT 12 | 5 |
| Query: | 1 TCTGGGACCCGA 12 | (0) |
| Query: | 1 TCTGGGACCCGC 12 | 1 |
| Query: | 1 TCTGGGACCCGG 12 | 3 |
| Query: | 1 TCTGGGACCCGT 12 | (0) |

-continued

| | Dbsts |
|---|---|
| Query: 1 TCTGGGACCCTA 12 | 2 |
| Query: 1 TCTGGGACCCTC 12 | 8 |
| Query: 1 TCTGGGACCCTG 12 | 3 |
| Query: 1 TCTGGGACCCTT 12 | 5 |
| Total | 53 |

The advanced BLAST search requires a minimum of 12 bases to look for an exact match. In the initial stages of doing this search, the database computer went down (probably unrelated); however, as a precaution, responses for a particular sequence search were limited to 100. Since the dbest database contains about ¼ nonhuman sequence, such sequences were removed in tallying the total for that search. Thus, any number between 75 and 100 most probably reflects a lower value for that particular DrdI site. Nevertheless, since many dbest searches returned less than 100 hits, it is unlikely that a particular total is grossly under-represented. Nevertheless, to be accurate, the following values should be viewed as lower estimates.

For the DrdI site, there are 6 non-palindromic two base 3' overhangs to consider: AA, AC, AG, CA, GA, and GG. Searches were performed on a representation of AA, AC, and AG sequences. The first two bases in the middle N6 degenerate sequence were arbitrarily chosen as "AA", the next two bases were AA, AC, or AG, and the last two bases were entered 16 times for each of the NN possibilities.

For all three searches (i.e., GACAAAAANNGTC (SEQ. ID. No. 34), GACAAACNNGTC (SEQ. ID. No. 35), and GACAAAGNNGTC (SEQ. ID. No. 36)), sequences containing a CG dinucleotide in either database or a "TAG" trinucleotide in the dbest database were, as expected, underrepresented. The STS database is too small to draw major conclusions; however, the totals on all three searches were within 2-fold of each other.

For the STS database of less than 21,000,000, 18-32 hits of human sequence were obtained which correlates to 1 site in 700,000-1,100,000 bases.

For the dbest database of less than 685,000,000, 400-633 hits of human sequence were obtained which correlates to 1 site in 1,100,000 to 1,700,000 bases.

Again, the middle N6 has 4096 different sequences. Because of the palindromic nature of GACAAAAAAGTC (SEQ. ID. No. 38), whenever it was searched, the program automatically also searched GACTTTTTGTC (SEQ. ID. No. 39), and each middle AA sequence was searched with 16 different flanking dinucleotides. All the sequences with a middle AA or TT is 4096/8=512, then divide by 16=32.

For the best results, 400, 446, and 633 sequences in 685,000,000 is equivalent to 1,752, 1,953, and 2,772 sequences, respectively, in 3,000,000,000. It should be a little more, because the 685,000,000 contains approximately ¼ sequence which is non-human DNA.

So the total number of DrdI sites with AC, AG, and AA overhangs are 32×1,752; 1,953; and 2,772;=56,064; 62,496; and 88,704 sites, respectively. Since A-T bases are somewhat more frequent in the genome than G-C bases, the above numbers are a slight over-representation. This occurs, because they are based on numbers obtained using "AA" as the arbitrarily chosen invariant first two bases in the DrdI internal sequence. For the other 3 middle 2 base overhangs, "CA" is predicted to be as frequent as "AG", i.e. about 60,000 sites; "GA" (whose complement is "TC") is predicted to be as frequent as "AC", i.e. about 55,000 sites; and "GG" (whose complement is "CC") is predicted to be less frequent than "AC", i.e. about 45,000 sites.

The above calculations are consistent with the earlier prediction of 200,000 to 300,000 non-palindromic DrdI sites per genome; i.e. on average of 33,000 to 50,000 sites for each overhang.

Less detailed searches with SanDI were performed by arbitrarily choosing the first 3 bases of a 12 base sequence as "TCT" and using the GGGACCC site with the last two bases being entered 16 times for each of the NN possibilities.

For the STS database of less than 21,000,000, 53 hits of human sequence were obtained which equals 1 site in 400,000 bases. 53 in 21,000,000 is equivalent to 7,571 in 3,000,000,000. Since there are 64 different combinations for the first 3 bases, that gives a prediction of 484,571 SanDI sites in the genome. These may be divided into 16 sets, on average of 30,000 sites per set.

The database searches demonstrate the distribution of DrdI sites (as well as SanDI and other selected sites) allow for the creation of from 5 to 16 sets based on specific 2 base overhangs or neighboring 2 bases, where each set has from about 30,000 to about 90,000 members, and may be used to create entire genome overlapping contig maps.

Option 1: 1,800,000 Short Sequencing Reactions Generate Approximately 100,000-150,000 DrdI Islands to Create an Entire BAC Contig.

FIG. 2 provides a scheme for sequencing representations of BAC clones. Two approaches may be considered for preparing DNA. One rapid approach is to pick individual colonies into lysis buffer and lyse cells under conditions which fragment chromosomal DNA but leave BAC DNA intact. Chromosomal DNA is digested by the ATP dependent DNase from Epicentre which leaves CCC and OC BAC DNA intact. After heat treatment to inactivate the DNase, restriction digestion, ligation of linker adapters, and PCR amplification are all performed in a single tube. The products are then aliquoted and sequencing is performed using specific primers to the adapters. This first approach has the advantage of obviating the need to grow and store 300,000 BAC clones.

An alternative approach is to pick the colonies into 1.2 ml growth media and make a replica into fresh media for storage before pelleting and preparing crude BAC DNA from a given liquid culture similar as described above. This second approach has the advantage of producing more BAC DNA, such that loss of an island from PCR dropout is less likely. Further, this approach keeps a biological record of all the BACs, which may become useful in the future for techniques such as exon trapping, transfection into cells, or methods as yet undeveloped.

FIG. 5 is an expanded versions of FIG. 2 detailing the subtleties of the linker-adapter ligations and bubble PCR amplification to select only the DrdI-MspI fragments. FIG. 7 describes the three levels of specificity in using the DrdI island approach.

With an average BAC size of 100-150 kb, total of 20,000 to 30,000 BAC clones would cover the human genome, or 300,000 clones would provide at least 10-fold coverage. For each clone, one requires 6 sequencing runs for a total of 1,800,000 sequencing reactions. However, only 80 bp of sequence is required to deconvolute singlet/doublet information. At a conservative estimate of 1 run per hour of 96 reaction, with 24 loadings/day, this equals 2,304 sequencing reads/PE 3700 machine/day. Assume access to 200 machines.

1,800,000/2,304 sequencing reads/machine/day=885 machines days/200 machines=4.4 days The above would provide about 80 bp anchored sequence information for about 100,000 to 150,000 DrdI sites, spaced on average every 20-30 kb.

If the machine is run to read 200-300 bp, this equals 1,240 reads/day, then:

1,800,000/1,240 sequencing reads/machine/day=1,452 machines days/200 machines=7.3 days The above would provide about 200-300 bp anchored sequence information for about 100,000 to 150,000 DrdI sites, spaced on average every 20-30 kb.

If the machine is run to read 500-600 bp, this equals 760 reads/day, then:

1,800,000/760 sequencing reads/machine/day=2,368 machines days/200 machines=11.8 days The above would provide about 500-600 bp anchored sequence information for about 100,000 to 150,000 DrdI sites, spaced on average every 20-30 kb.

Experiments will be needed to access the quality of reads and ability to deconvolute the sequence when reading out 80, 200, or 500 bp. In simulations, it was noted that doublets often contained one smaller and one larger fragment. Thus, useful information may be obtained from a long read, where the first 200 bases are predominantly from the shorter fragment (reading as a strong singlet sequence with a weak doublet behind it), and when that fragment ends, the weaker sequence from the larger fragment will be easy to read and interpret (See FIGS. 35A-35G). This may require the algorithm to include alignment of fragments starting at a later position; however, this should not be too difficult.

Option 2: 3,600,000 Short Sequencing Reactions Generate Approximately 150,000-200,000 DrdI Islands to Create an Entire BAC Contig.

Should pilot studies suggest that some sequence reads are difficult to interpret, two sets of DrdI islands can be generated for each BAC clone, one set consisting of AA, AC, AG, CA, GA, or GG overhangs, while the other set consists of TT, GT, CT, TG, TC, or CC overhangs. Although most sequences would be represented in both sets, each would rescue DrdI islands lost from the other set due to either the neighboring TaqI or MspI site being too close (resulting in amplification of a very short fragment which lacks the number of bases required to determine uniqueness) or too far (resulting in weak or no amplification of the longer fragment). In such a circumstance, the number of sequencing runs would double, but the number of useable sequences for alignments would also increase. For the example of the Met oncogene containing BAC on 7q31, the first six linker set provides 3 singlet and 3 doublet sequences. The second six linker set provides an additional 2 singlet and 3 doublet sequences (See FIGS. 35A-35G). Using this very conservative approach, 3,600,000 sequencing runs would be required:

3,600,000/2,304 sequencing reads/machine/day=1,770 machines days/200 machines=8.8 days The above would provide about 80 bp of nchored sequence information for about 150,000 to 200,000 DrdI sites, spaced on average every 15-20 kb.

If the machine is run to read 200-300 bp, this equals 1,240 reads/day, then:

3,600,000/1,240 sequencing reads/machine/day=2,904 machines days/200 machines=14.6 days The above would provide about 200-300 bp anchored sequence information for about 150,000 to 200,000 DrdI sites, spaced on average every 15-20 kb.

If the machine is run to read 500-600 bp, this equals 760 reads/day, then:

3,600,000/760 sequencing reads/machine/day=4,736 machines days/200 machines=23.6 days Add to this sequencing, both ends of the 300,000 BAC clones (using unique primers to the two ends and bubble PCR)=600,000/760 sequencing reads/machine/day=790 machines days/200 machines=3.9 days The above would provide about 500-600 bp anchored sequence information for about 150,000 to 200,000 DrdI sites, spaced on average every 15-20 kb. This is approximately 75 million to 120 million anchored bases and is from a 2.5% to 4% representation of the genome. With a 10-fold coverage, and reasonably clean reads, one should be able to identify about 100,000 to 170,000 anchored SNPs in 23.6 days. Further, the ends of the BAC clones will, providing sequencing reads of average length 325 bases for about 75% of the end, for an additional 145 million bases. The BAC end sequences are not completely anchored since one cannot determine orientation of the ends with respect to other BAC clones unless the end sequence fortuitously overlaps with another end sequence in the opposite orientation (predicted to occur 325/150,000 bp=0.2% of the clones.) Nevertheless, the BAC end sequences are relatively anchored and will provide confirming sequence information once the random sequence from 10 kb insert clones are collected. The total of 28 days sequencing will provide 7.5 to 9% of anchored and relatively anchored genomic sequence.

Alternatively, one can create DrdI libraries of 5-pooled individuals DNA in pUC vectors to find the SNPs. As described previously, a size-selection of fragments between 200 and 1,000 bp will provide a 0.26% representation of the genome (average size of 580 bp; number of fragments is 19,700) for a single overhang. If the latter number is multiplied by 12 different overhangs, a 10-fold coverage is provided, and both strands are sequenced, 20,000×12×10=2,400,000 sequencing runs are obtained.

2,400,000/760 sequencing reads/machine/day=3,158 machines days/200 machines=15.8 days Thus, if the initial reads from the BAC libraries are exceptionally clean, then long reads of 500-600 bp may be used to create an anchored representation with 100,000 to 170,000 SNPs, and can be completed in 23.6+3.9=27.5 days. Alternatively, much shorter runs may be used for the initial BAC sequencing, and, then, higher quality runs may be used to extend the anchors and create a 200,000 SNP library in 8.8+15.6+3.9=28.3 days.

Option 3: 2,400,000 Short Sequencing Reactions Generate Approximately 150,000-200,000 BglI Islands to Create an Entire BAC Contig.

One concept is to increase the number of anchored sites in a given BAC. The BglI restriction endonuclease generates a 3 base 3' overhang, but may also be used to create a representation (See FIG. 14). Since the overhang is an odd number of bases, it is not necessary to exclude the palindromic two base sequences AT, TA, GC, and CG. To reduce the number of ligations from 64 (all the different possible 3 base overhangs) to 16, the linkers and primers are degenerate at the last position, i.e. end with a 3' ACN or AAN. (Please note: Greater specificity may be achieved by using the degeneracy at the 3' end of the linker adapter.) Since there are 3 levels of specificity in the ligation and sequencing step (see FIG. 36), the third base degeneracy will not interfere with the fidelity of the reaction.

Again, with an average BAC size of 100-150 kb, a total of 20,000 to 30,000 BAC clones would cover the human genome, or 300,000 clones would provide at least 10-fold coverage. For each clone, one requires 8 sequencing runs for a total of 2,400,000 sequencing reactions. Using the same assumptions as above:

2,400,000/2,304 sequencing reads/machine/day=1042 machines days/200 machines=5.2 days The above would provide about 80 bp anchored sequence information for about 150,000 to 200,000 BglI sites, spaced on average every 15-20 kb.

If the machine is run to read 200-300 bp, this equals 1,240 reads/day, then:

2,400,000/1,240 sequencing reads/machine/day=1,935 machines days/200 machines=9.7 days The above would provide about 200-300 bp anchored sequence information for about 150,000 to 200,000 BglI sites, spaced on average every 15-20 kb.

If the machine is run to read 500-600 bp, this equals 760 reads/day, then:

2,400,000/760 sequencing reads/machine/day=3,158 machines days/200 machines=15.8 days The above would provide about 500-600 bp anchored sequence information for about 150,000 to 200,000 BglI sites, spaced on average every 15-20 kb.

Option 4: 4,800,000 Short Sequencing Reactions Generate Approximately 200,000-250,000 BglI Islands to Create an Entire BAC Contig.

Should pilot studies suggest that some sequence reads are difficult to interpret, two sets of BglI islands can be generated for each BAC clone, one set consisting of AAN, CAN, GAN, TAN, AGN, CGN, GGN, or TGN overhangs, while the other set consists of ACN, CCN, GCN, TCN, ATN, CTN, GTN, or TTN overhangs. While most sequences would be represented in both sets, each would rescue BglI islands lost from the other set due to either the neighboring TaqI or MspI site being too close (resulting in amplification of a very short fragment which lacks the number of bases required to determine uniqueness) or too far (resulting in weak or no amplification of the longer fragment). In such a circumstance, the number of sequencing runs would double, but the number of useable sequences for alignments would also increase. For the example of the Met oncogene containing BAC on 7q31, the first eight linker set provides 5 singlet and 3 doublet sequences. The second eight linker set provides an additional 3 doublet sequences (See FIGS. 35A-35G). The set of non-palindromic linker adapters may be mixed, as long as the complement is not also included in the mixer. For example, to choose sites which will allow the PCR primers to end in only a C or A, the set of AAN, CAN, GAN, TAN, ACN, CCN, GCN, and TCN overhangs may be used (See FIGS. 35D-35E). This set allows design of PCR primers with 3' bases of either "A" or "C", which tend to give less mis-priming than primers with 3' "G" or "T", which may give false PCR amplification products resulting from polymerase extension of a T:G mismatched base. In this BAC, the TGT or ACA overhang appeared too frequently, suggesting it may be associated with a repetitive element. For the purposes of these calculations, the complete set of 16 linkers would require 4,800,000 sequencing runs, although less linkers would most probably suffice:

4,800,000/2,304 sequencing reads/machine/day=2083 machines days/200 machines=10.4 days The above would provide about 80 bp anchored sequence information for about 200,000 to 250,000 BglI sites, spaced on average every 12-15 kb.

If the machine is run to read 200-300 bp, this equals 1,240 reads/day, then:

4,800,000/1,240 sequencing reads/machine/day=3,871 machines days/200 machines=19.4 days The above would provide about 200-300 bp anchored sequence information for about 200,000 to 250,000 BglI sites, spaced on average every 12-15 kb.

If the machine is run to read 500-600 bp, this equals 760 reads/day, then:

4,800,000/760 sequencing reads/machine/day=6,316 machines days/200 machines=31.6 days The above would provide about 500-600 bp anchored sequence information for about 200,000 to 250,000 BglI sites, spaced on average every 12-15 kb.

Add to this sequencing both ends of the 300,000 BAC clones (using unique primers to the two ends and bubble PCR)=600,000/760 sequencing reads/machine/day=790 machines days/200 machines=3.9 days The above would provide about 500-600 bp anchored sequence information for about 200,000 to 250,000 BglI sites, spaced on average every 12-15 kb. This is approximately 100 million to 150 million anchored bases and is from a 3% to 5% representation of the genome. With a 10-fold coverage, and reasonably clean reads, one should be able to identify about 130,000 to 200,000 anchored SNPs in 31.6 days. Further, the ends of the BAC clones will provide an additional 145 million bases of relatively anchored sequences. The total of 36 days sequencing will provide 8 to 10% of anchored and relatively anchored genomic sequence.

As described above, one can create BglI libraries of 5-pooled individuals DNA in pUC vectors to find the SNPs. A size-selection of fragments between 200 and 1,000 bp will provide a 0.26% representation of the genome for a single overhang (about 20,000 fragments). If the latter number is multiplied by 16 different overhangs, a 10-fold coverage is provided, and both strands are sequenced, there are 20,000×16×10=3,200,000 sequencing runs.

3,200,000/760 sequencing reads/machine/day=4,210 machines days/200 machines=21.0 days Thus, if the initial reads from the BAC libraries are exceptionally clean, then long reads of 500-600 bp may be used to create an anchored representation with 130,000 to 200,000 SNPs, and can be completed in 31.6+3.9=35.5 days. Alternatively, much shorter runs may be used for the initial BAC sequencing, and then higher quality runs may be used to extend the anchors and create a 250,000 SNP library in 10.4+21.0+3.9=35.3 days.

Option 5: 4,200,000 Short Sequencing Reactions Generate Approximately 250,000-300,000 DrdI and BglI Islands to Create an Entire BAC Contig.

An alternative strategy is to combine the best of both representations, using 6 non-palindromic linker-adapters for the DrdI overhangs, and 8 non-palindromic linker-adapters for the BglI overhangs (see FIG. 37.) If the multiplex PCR of 14 different linker-adapter sets does not amplify all fragments in sufficient yield, then the BAC DNA may be aliquoted initially into two or more tubes. Further, unique primer sets may be used to increase yield of a PCR fragment prior to the sequencing reaction. The advantages of such a hybrid representation is that it maximizes the distribution of independent sequence elements. As noted above, should any DrdI or BglI site be frequently found in repetitive elements, that overhang can be removed from the representation. For the full representation, the hybrid approach uses 6+8=14 sequencing runs for each BAC:

4,200,000/2,304 sequencing reads/machine/day=1,823 machines days/200 machines=9.1 days The above would provide about 80 bp anchored sequence information for about 250,000 to 350,000 DrdI and BglI sites, spaced on average every 8-12 kb.

If the machine is run to read 200-300 bp, this equals 1,240 reads/day, then:

4,200,000/1,240 sequencing reads/machine/day=3,387 machines days/200 machines=16.9 days The above would provide about 200-300 bp anchored sequence information for about 250,000 to 350,000 DrdI and BglI sites, spaced on average every 8-12 kb.

If the machine is run to read 500-600 bp, this equals 760 reads/day, then:

4,200,000/760 sequencing reads/machine/day=5,526 machines days/200 machines=27.6 days The above would provide about 500-600 bp anchored sequence information for about 250,000 to 350,000 DrdI and BglI sites, spaced on average every 8-12 kb. This is approximately 125 million to 210 million anchored bases and is from a 4.2% to 7% representation of the genome. With a 10-fold coverage, and reasonably clean reads, one should be able to identify about 180,000 to 300,000 anchored SNPs in 31.6 days. Further, the ends of the BAC clones will provide an additional 145 million bases of relatively anchored sequences. The total of 32 days sequencing will provide 9.2 to 12% of anchored and relatively anchored genomic sequence.

As described above, one can create BglI libraries of 5-pooled individuals' DNA in pUC vectors to find the SNPs. A size-selection of fragments between 200 and 1,000 bp will provide a 0.26% representation of the genome for a single overhang (about 20,000 fragments). If the latter number is multiplied by 16 different overhangs, a 10-fold coverage is provided, and both strands are sequenced, 20,000×14×10=2, 800,000 sequencing runs are obtained.

2,800,000/760 sequencing reads/machine/day=3,684 machines days/200 machines=18.4 days Thus, if the initial reads from the BAC libraries are exceptionally clean, then long reads of 500-600 bp may be used to create an anchored representation with 180,000 to 300,000 SNPs, and can be completed in 27.6+3.9=31.5 days. Alternatively, much shorter runs may be used for the initial BAC sequencing, and then higher quality runs may be used to extend the anchors and create a 240,000 SNP library in 9.1+ 18.4+3.9=31.4 days. In summary, a month and a day of sequencing on 200 machines will provide a valuable database containing anchored and mapped sequence islands of 500- 600 bases on average every 8-12 kb with approximately 240, 000 mapped SNP's.

IV. Creating a DrdI Island Database of Mapped SNPs and Using a Universal DNA Array for High Throughput Detection of SNPs.

Use of the DrdI Island Approach for Alignment of Plural Clones

FIGS. 38 to 45 show how the DrdI island approach of the present invention can be utilized to align 4 hypothetical BAC clones containing 8 to 12 non-palindromic DrdI sites. In this example, the 6 linkers with the Group II dinucleotide overhangs (i.e. AG, AC, CA, GA, AA, and GG) are used. The DrdI sites are labeled 1a, 1b, 1c . . . 2a, 2b, . . . up to 6a, 6b, . . . The numeral represents the type of non-palindromic 2 base overhang for that DrdI site: 1=AA, 2=AC, 3=AG, 4=CA, 5=GA, and 6=GG. The lower-case letter represents the first=a, second=b, third=c, and so on, for each unique sequence with that particular non-palindromic 2 base overhang. As described more fully below, each of the 6 linkers generates a separate representation of overlapping islands on the 4 different BAC clones. When the different representations obtained with each linker in the DrdI island analysis are combined, the alignment of the BAC clones can be determined.

In each of FIGS. 38-44, the top panel illustrates the actual position of each DrdI site within each BAC, the DrdI island data generated from each of these BAC clones is provided in the table below. After obtaining sequence information in each clone, one compares the sequences in each column and determines if the two entries are concordant or discordant as described supra. The BAC clones overlap if the entries in that column are concordant. The BAC clones do not overlap if all the entries in all the columns are discordant. Since a large scale sequencing project will produce from about 30,000 to 90,000 entries in each column, virtually all the clones will be discordant with each other, only a few will overlap with each other at a given point in the contig. The number of different ways to establish overlap between two BAC clones is considerable.

In FIG. 38, the DrdI island approach is used to determine sites with AA overhangs. When the procedure described supra with respect to FIG. 1 is carried out, for AA overhangs, BAC clone I is found to have a triplet, BAC clone II has a doublet, BAC clone III has a doublet, and BAC clone IV has a singlet. Based on these results and dideoxy sequencing, the DrdI islands in these clones are found to have 5 different sequences with AA overhangs (i.e. sequences 1a to 1e) at defined positions in 1 or more of the 4 BAC clones, as shown in FIG. 38. Based on this data alone, concordances (i.e. an indication that 2 or more clones are contiguous) are found between clones I and III (i.e. sequence 1b in the triplet in clone I and the doublet of clone III), clones II and III (i.e. sequence 1e in the doublet in clone II and the doublet of clone III), clones III and IV (i.e. sequence 1e in the doublet in clone III and the singlet of clone IV), and clones II and IV (i.e. sequence 1e in the doublet in clone II and the singlet of clone IV). On the other hand, discordances (i.e. an indication that 2 or more clones are not contiguous) are found between clones I and II (i.e. there is no overlap between the 1a, 1b, and 1c sequences of clone I and the 1b and 1e sequences of clone II) and clones I and IV (i.e. there is no overlap between the 1a, 1b, and 1c sequences of clone I and the 1e sequences of clone IV). Based on the identification of these concordances and discordances, a tentative alignment for some of clones I to IV can be determined, as shown at the bottom of FIG. 38.

FIG. 39 shows how the DrdI island approach is used to determine the sequences of sites with AC overhangs and, based upon this information, to tentatively align the 4 hypothetical BAC clones. Using the analysis described above with respect to FIG. 38, but for the AC overhangs, 3 concordances and 2 discordances are identified and the tentative alignment of the 4 hypothetical BAC clones is determined, as shown in FIG. 39. As noted above, the results of FIG. 38 identified concordance among BACS I through IV based on overlapping sequences. However, as shown with respect to FIG. 39, a concordance cannot be deduced between BAC I and III, since there are no overlaps in the identified sequences.

FIG. 40 shows how the DrdI island approach is used to determine the sequences of sites with AG overhangs and, based upon this information, to tentatively align the 4 hypothetical BAC clones. Using the analysis described above with respect to FIG. 38, but for the AG overhangs, 2 concordances and 2 discordances are identified and the tentative alignment of the 4 hypothetical BAC clones is determined, as shown in FIG. 40. Overlap between BAC II & III, or BAC III & IV could not be deduced using the AG overhang site alone.

FIG. 41 shows how the DrdI island approach is used to determine the sequences of sites with CA overhangs and, based upon this information, to tentatively align the 4 hypothetical BAC clones. Using the analysis described above with respect to FIG. 38, but for the CA overhangs, 4 concordances and 2 discordances are identified and the tentative alignment of the 4 hypothetical BAC clones is determined, as shown in FIG. 41.

FIG. 42 shows how the DrdI island approach is used to determine the sequences of sites with GA overhangs and, based upon this information, to tentatively align the 4 hypothetical BAC clones. Using the analysis described above with respect to FIG. 38, but for the GA overhangs, 1 concordance and 2 discordances are identified and the tentative alignment of only 2 of the 4 hypothetical BAC clones is determined, as shown in FIG. 42.

FIG. 43 shows how the DrdI island approach is used to determine the sequences of sites with GG overhangs and, based upon this information, to tentatively align the 4 hypothetical BAC clones. Using the analysis described above with respect to FIG. 38, but for the GG overhangs, no concordances and 1 discordance are identified and the tentative alignment of the 4 hypothetical BAC clones cannot be determined, as shown in FIG. 43. In FIG. 43, there is a doublet in clone I based on the presence of sequences 6a and 6b, a singlet based on the presence of sequence 6c, and a multiplet in clone III based on the presence of sequences 6a, 6b, 6c, and 6d. In view of multiplet in clone III, the sequence of the DrdI island GG overhangs cannot be determined. However, a set of 4 sequencing primers can be used to extend one base beyond the GG overhang (i.e. the 3' end of the primers contains GGA, GGC, GGG, and GGT) to obtain additional information. However, it is not necessary to do so in this case, because the data for the other overhangs shows that concordance exists between clones I and III and between clones III and IV.

The analyses conducted in conjunction with FIGS. 38 to 43 can be combined to obtain a listing of the sequences obtained for each of the dinucleotide overhangs, a listing of the concordances, and a listing of the discordances, as shown in FIG. 44. Based on this information, the unique and overlapping DrdI islands in the 4 hypothetical BAC clones can be identified and the clones themselves aligned, in accordance with FIG. 45. In this hypothetical, as illustrated, the order of the clones is as follows: I, III, IV, and II. This result was determined on a very conservative basis. For example, although sequence 6c is unique to clone IV, the multiplet of GG sequences in clone III precludes an unambiguous assignment for the position of this sequence. Also, the listing does not order the DrdI sites which are unique to a given clone. Finally, one can arrange the information to achieve a contig of the map position of the DrdI sites which correspond to the individual BAC clones. The DrdI sites are grouped into 6 sets allowing a rough determination of the BAC clone alignment. Certain sites remain unmapped, such as 6c—although one may surmise that it probably overlaps with clone III, since clone II lacks a DrdI site with a GG overhang. The precise order of DrdI sites within a grouping cannot be determined from this data alone, but will be easily obtained from sequence information on smaller cosmid clones, once the BAC contig is completed.

Examples of Alignment of Human DNA BAC Contigs Using DrdI Islands

The simulations in the previous section demonstrate how the DrdI alignment is achieved. BAC overlaps in the genome databases were rare. The following are examples from 3 contigs on chromosome 7. FIGS. 46A-46E show representational fragments which would be obtained with DrdI/MspI/TaqI digests. FIGS. 47A-47E show representational fragments which would be obtained with DrdI/MseI digests. The fragments which allow one to establish overlap have appropriate symbols next to them to show that they are in more than one BAC.

For an example using DrdI/MspI/TaqI digests, contig 1941 contains 3 BACs. BAC RG253B13 overlaps with RG013N12 based on the DrdI/MspI/TaqI fragments generated from DrdI AG (115 and 353 bp), AC (381 bp), CA (559 bp), GA (3,419 bp; may not amplify) and AA (192 and 597 bp) overhangs. BAC RG013N12 overlaps with RG300CO3 based on the DrdI/MspI/TaqI fragments generated from DrdI AG (1,137 bp), CA (16 bp, may be too small), and AA (2,328 bp).

For example, using DrdI/MseI digests, contig T002144 contains 5 BACs. BAC RG022J17 overlaps with RG067E13 based on the DrdI/MseI fragments generated from DrdI AG (338 bp), GA (17, 77, and 586 bp), AA (273 bp), and GG (55 bp) overhangs. BAC RG067E13 overlaps with RG011J21 based on the DrdI/MseI fragments generated from DrdI AC (71 bp). BAC RG011J21 overlaps with RG022C01 based on the DrdI/MseI fragments generated from DrdI AG (92 bp), AA (48 bp), and GG (42 bp) overhangs. Note that establishing overlap between RG022C01 and RGO43K06 would require either using the other DrdI overhangs (in this case TT) or, alternatively, having more BACs in the library.

900,000 Short Sequencing Reactions will be Needed to Create an Entire BAC Contig Using the DrdI Islands Approach: Completed in 39 Days Using 10 of the Perkin Elmer 3700 Machines.

As described above, the DrdI island procedure is amenable to automation and requires just a single extra reaction (simultaneous cleavage/ligation) compared to dideoxy sequencing. Use of 6 additional primers is compatible with microtiter plate format for delivery of reagents (6 at a time). Further, only very short sequences of 80 to 100 bases are more than sufficient to determine concordance or discordance with other entries into the database.

With an average BAC size of 100-150 kb, a total of 20,000 to 30,000 BAC clones would cover the human genome, or 150,000 clones would provide 5-fold coverage. For each clone, one requires 6 sequencing runs for a total of 900,000 sequencing reactions. At a conservative estimate of 1 run per hour of 96 reactions, with 24 loadings/day, this equals 2,304 sequencing reads/PE 3700 machine/day.

Thus, the DrdI approach for overlapping all BAC clones providing a 5-fold coverage of the human genome would require only 39 days using 10 of the new PE 3700 DNA sequencing machines.

The complete set of DrdI islands provided six sets to determine overlap. The number of islands within a BAC can be increased by using a second representation, such as BglI. Further, this example used only 4 hypothetical clones with minimal coverage, in the actual human genome sequencing, there will be a 10-fold coverage of the genome. The precise order of DrdI sites within a grouping cannot be determined from this data alone, but will be easily obtained from sequence information on smaller 10 kb plasmid clones, once the BAC contig is completed.

Completing the Entire Genome Sequence Based on the BAC DrdI and BglI Islands.

The total unique sequence in the hybrid DrdI-BglI island database will be approximately 125 million to 210 million anchored bases with an additional 145 million bases of relatively anchored sequences from the BAC ends. This will provide 9.2 to 12% of anchored and relatively anchored genomic sequence, or approximately $1/10^{th}$ of the entire genome will be ordered on the human genome. This is sufficient density to allow for a shotgun sequencing of total genomic DNA from the ends of 10 kb clones. The shotgun cloning will require only a 5-fold coverage of the genome since the islands are relatively dense. At an average of 1 kb reads (i.e. 2 sequencing reactions of 500 bp/clone), 3,000,000 clones would provide 1-fold coverage and 15,000,000 clones would provide a 5-fold coverage. Since sequence information will be obtained from both ends, the process will require almost 200 days.

30,000,000/760 sequencing reads/machine/day=39,
473 machines days/200 machines=197 days On average, each $10^{th}$ clone will immediately overlap with one of the ordered island sequences in the above database (9.2 to 12% of genome). Overlap is determined using unique sequences near the ends of a given island. An algorithm is designed to choose 32 unique bases on each side of the island which is not part of a repetitive sequence. This 32 base sequence will be designated a "Velcro island". Thus, for the 250,000 to 350,000 DrdI and BglI ordered islands in the database, there will be between 500,000 and 700,000 "Velcro islands". As sequence information is generated, it is queried in 32 bit portions to see if it has either perfect 32/32 or almost perfect 31/32 alignment with one of the Velcro sequences. If yes, then the neighboring 20 bases on each side (if available) are also queried to determine if this is a true overlap. When this overlap is achieved, it generates 3 new "Velcro islands" and removes one of them from the database. One of the new Velcro islands is the distal sequence on the 500 bases which overlap with the original DrdI island. The other two new Velcro islands are the end portions of the 500 base sequence attached to this particular clone, either approximately 10 kb upstream, or downstream of the DrdI island, depending on orientation. If any of the new Velcro regions is in a repeat sequence, it is removed from the Velcro database. This reduces formation of false contigs. These two new Velcro islands are immediately queried against all other DrdI and BglI islands in the BAC contig region. In the example in FIGS. 42-43, islands 1e, 2c, and 4c all map to the same contig region. This type of analysis is repeated with each new random plasmid sequence, thus initially creating more Velcro islands, and subsequently creating less Velcro islands as the genomic sequence fills in. Each genome equivalent will hit from 80% to 90% of the Velcro islands, expanding each island by an average of 500 bases, +a bridge of another 500 bases or about 400 to 600 million bases. Thus, on a first pass, ordered information should increase from about 9%-12% to about 21%-32% the genome. The remaining clones are rescanned into the new Velcro database, which now has from 2 to 2.5-fold more islands, allowing more connectivity points which now increase to about 800 to 1,200 million bases, or about 47%-72% the genome and with a third and fourth pass, this approach leads to a complete sequence of the entire genome. The genome is substantially filled in by the 5-fold coverage.

Construction of a finished genomic sequence over a 1 megabase region was simulated using a random number generator which provided sequence read start points for 5,000 "random" clones, with the assumption that each start point provided 500 bases of sequence. To each of these, another 500 bases of sequence was included at a random distance of 8 to 12 kb downstream. The randomly generated sites were sorted by position and queried for presence of sequencing gaps. This was based on the conservative requirement for 40 bp overlap between two sequence runs. Thus, sequence start points more than 460 bases apart were scored as gapped. Two types of gaps need to be considered: (i) Gaps in sequence information between the two 500 bases generated from a random clone, which will be filled in as needed, and (ii) Gaps between two unrelated clones which are not bridged. In the 1 megabase region, there were 74 small gaps which were in-between a given clone. Of these, 50 gaps were between 460 and 560 bases, i.e. less than 100 bases from the nearest anchored sequence. Thus, extending the sequencing read from 500 to 600 bases would close these 50 regions. The remaining 24 sites are less than 500 bp away from an anchored site and can be filled in when the region in question is being closely scrutinized for important genes.

The 1 megabase region also contained 26 gaps in between two unrelated clones which were not bridged. Of these, 21 were between 460 and 560 bases, i.e. less than 100 bases from the nearest anchored sequence. Thus, extending the sequencing read from 500 to 600 bases would close these 21 regions. The remaining 6 sites need to be filled in using primer walking. Five of these sites were within 500 bp, and the remaining site was within 1,000 bp—thus, each of these regions can be closed using sequencing primers from both sides of the anchored sequence. The same primers are used to PCR amplify the region from the genome and then sequence it. On average, 12 sequencing/PCR primers will be required to close 6 gaps per megabase. For the entire human genome at 3,000 megabases: 3,000×12=36,000 primers and sequencing runs. There are a number of commercial vendors synthesizing primers, many of whom claim capacity of "1,000's of oligo's per day", so at a conservative estimate of 2,000 primers/day@$20/primer, the synthesis run would require 18 days.

36,000/760 sequencing reads/machine/day=47
machines days/200 machines=0.23 days

The grand total is:
Mapped DrdI and BglI islands with over 200,000 SNPs; 10-fold coverage of BACs w/ends=31.5 days
Random 10 kb plasmid clones; 5-fold coverage of entire genome=197 days
Closure of gaps using primer walking=18.5 days Total:=247 days BAC Clone Derived Singlets are Used to Align Plasmid DrdI Islands to Generate a Comprehensive DrdI SNP Database.

The singlet sequences deduced from deconvoluting the BAC clone contig database (see above) will be used to align more complete DrdI islands generated by sequencing in both directions from cosmid or plasmid clones. About 200,000 to 300,000 DrdI islands are predicted in the human genome. The DrdI islands are a representation of $1/15^{th}$ to $1/10^{th}$ of the genome.

As described above, 500,000 plasmid or cosmid clones of average size 30-40 kb will provide 5 to 6-fold coverage of the human genome. These plasmids and cosmids will be generated from a mixture of 10 individual's DNA to provide a rich source of SNPs. Initially, only 6 primers will be used per plasmid/cosmid to identify those DrdI sites present in the clone. A subsequent run will be performed with the correct overhang linkers for generating the sequence of the opposite strand for those DrdI sites present in that clone, as well as using more selective primers for obtaining unique sequence information from doublet or triplet reads. An average of 3 sites per clone will rapidly generate 1,500,000,000 bases of sequence information from the DrdI sites, plus the 500,000,000 bases of unique sequence information from the ends of the clones. The 1,500,000,000 bases of sequence information from the DrdI sites will contain the same regions resequenced an average of 5-6 times providing 250,000,000 to 300,000,000 bases of unique sequence and ample amounts of SNP information. This comprehensive DrdI island approach will require on average 12 sequencing runs per clone to determine the unique singlet DrdI sequences, for a total of 6,000,000 sequencing runs.

This comprehensive DrdI island approach will provide from 250,000 to 430,000 SNPs. It has been estimated that 30,000 to 300,000 SNPs will be needed to map the positions of genes which influence the major multivariate diseases in defined populations using association methods. Further, the above SNP database will be connected to a closed BAC clone map of the entire genome. A more rapid approach to finding SNPs is provided below.

A Novel Shotgun Approach to Generate a Mapped DrdI SNP Database, which is Amenable to High-Throughput Detection on a DNA Array.

In the above-described procedure for PCR-amplifying the DrdI island directly from a BAC clone by using a second frequent cutter enzyme to create small fragments for amplification was described. The second enzyme (e.g. MspI) can contain a two base 5' overhang such that ligation/cutting could proceed in a single reaction tube. The ligation primers/PCR primers can be designed such that only DrdI-second enzyme fragments amplify.

A detailed evaluation of 4 sequenced BAC clones from 7q31 shows that ideally, the second enzyme should be a mixture of both TaqI and MspI.

TaqI is known to retain some activity at 37° C., and, thus, the entire reaction containing DNA, adapter linkers, DrdI, TaqI, MspI, and T4 ligase may be carried out in a homogeneous reaction at 37° C. Further, TaqI becomes irreversibly denatured at 75° C. Therefore, a heat step prior to the PCR reaction is sufficient to inactivate all the enzymes.

A close analysis of the length of fragments generated in a DrdI, TaqI, and MspI cleavage/ligation/amplification reveals that not every DrdI site is amplified (on the assumption that fragments above 4 kb will not amplify well in a mixture containing much smaller amplicons.) Further, in a competition, where one fragment is small (i.e. 200 bp) compared to a much larger fragment (i.e. 2,000 bp), the smaller one will generate more PCR product, which may be sufficient to swamp out the sequencing ladder in the first 200 bases. Ironically, this only aids in the analysis of the sequence information, because comparisons of singlet with singlet reads is the easiest to interpret.

In one BAC clone, RG364P16, the DrdI sites are positioned such that the AA, AC, AG, CA, GA, and GG overhangs used in the linker would generate only 3 fragments below about 4,000 bp. Actually, the first site would generate an additional product to a TaqI or MspI site within the BAC vector. See FIG. 48. Even three sites are sufficient to determine clone overlap. Nevertheless, if needed, linkers containing the complement TT, GT, CT, TG, TC, and CC overhangs would provide additional sequences at some of the other DrdI sites.

For creating the representation required for shotgun cloning, 1 µg of pooled genomic DNA (200 ng each from 5 individuals=10 chromosome equivalents)=150,000 copies of the genome=0.25 attomoles of genomes or 0.5 attomoles of each gene is used. This procedure is shown in FIG. 49 and is largely the same as that described with reference to FIG. 5, except after PCR amplification, the PCR product is cut with XmaI and XhoI enzymes. The resulting digested product is separated on a gel. The fragments of 200 to 1000 bp are cloned into the corresponding sites of a vector. The inserts can be sequenced to build a mapped SNP database. This procedure is described in more detail below.

The pooled DNA is cut with DrdI, TaqI, and MspI, in the presence of phosphorylated DrdI adapters containing a unique 2 base 3' overhang (i.e. AA) as well as a methylated XmaIII site ($C^{m5}CCGGG$) in the adapter sequence, in the presence of unphosphorylated TaqI and MspI adapters containing 2 base 5' CG overhangs as well as a methylated XhoI site ($CTCG^{m6}AG$) in the adapter sequence, and in the presence of T4 ligase, such that the linkers are added to their respective overhangs in a homogeneous reaction at 37° C. The adapters are methylated so they are not cut by TaqI and MspI during this reaction. Enzymes are inactivated by heating at 85° C. to 98° C., preferably 95° C., for 2 to 20 minutes, preferably for 5 minutes.

Alternatively, the MspI/TaqI adapter is phosphorylated, contains a 3' blocking group on the 3' end of the top strand, and contains a bubble to prevent amplification of unwanted MspI-MspI, TaqI-MspI, or TaqI-TaqI fragments. While the linker can ligate to itself in the phosphorylated state, these linker dimers will not amplify. Phosphorylation of the linker and use of a blocking group eliminates the potential artifactual amplification of unwanted MspI-MspI, TaqI-MspI, or TaqI-TaqI fragments. T4 ligase attaches the DrdI and MspI/TaqI linkers to their respective sites on the human genome fragments with biochemical selection assuring that most sites contain linkers (See FIG. 49A). The adapters are methylated so they are not cut by TaqI and MspI during this reaction.

Unmethylated PCR primers are now added in excess of the adapters and used for PCR amplification of the appropriate fragments. Of the approximately 50,000 DrdI sites, approximately 70% will give fragments under 4 kb (based on the computer simulation of DrdI sites on 4 BAC clones, where 27/38 non-palindromic DrdI sites had TaqI or MspI sites within 4 kb). Thus, about 35,500 fragments will be amplified. Again, from the simulations, where fragments totaling 24.8 kb are amplified from 550 kb of BAC clone DNA which is 4.5% of the genome, given that only $\frac{1}{6}^{th}$ of those fragments are amplified in a unique overhang representation which is 0.75% representation of the genome. However, for size-selected fragments of between 200 and 1,000 bp, only 15/38 fragments, representing a total of 8.7 kb are amplified from 550 kb of BAC DNA, and $\frac{1}{6}^{th}$ of this which is 0.26% representation of the genome (average size of 580 bp; number of fragments is 19,700).

A limited PCR amplification of 11-12 cycles (assuming 90% efficiency per cycle) will give a good representation and produce about 2 µg of final mixed fragments product in the 200-1,000 bp range, without a major distortion or bias of the representation. The mixed fragments are separated on an agarose gel (i.e. low melting agarose from Seakem) the correct size fragment region excised, purified by standard means, and then cleaved with XmaIII (heteroschizomer of SmaI) and XhoI and inserted into the corresponding sites in a standard vector, such as pUC18. The library will contain multiple copies of the approximately 19,700 fragments in the representation. The above procedure can be modified such that the library will contain more or less fragments in the representation. For example, a size-selection between 200 and 2,000 bp will slightly increase the library to approximately 25,000 fragments in the representation. For making larger libraries, more than one linker for the DrdI site overhang may be used, e.g. both AA and AC overhangs would double the library to approximately 40,000 fragments in the representation. All the non-palindromic overhangs which are non-complementary (i.e. AA, AC, AG, CA, GA, GG) may be used to make an even larger library of approximately 120,000 fragments in the representation. For making smaller libraries, a PCR primer with one or two additional selective bases on the 3' end is used during the PCR amplification step. For example, use of a DrdI site linker with an AA overhang and a PCR primer with an AAC 3' end overhang would reduce the library to approximately 5,000 fragments in the representation. The ideal size of the library will depend on the sequencing capacity of the facility (See Table 7). Other restriction endonucleases with degenerate overhangs as the primary enzyme may be used to create the representational library, such as BglI, DraIII, AlwNI, PflMI, AccI, BsiHKAI, SanDI, SexAI, PpuI, AvaII, EcoO109, Bsu36I, BsrDI, BsgI, BpmI, SapI, or an isoschizomer of one of the aforementioned enzymes. Palindromic restriction endonucleases may also be used to create the representational library, such as BamHI, AvrII, NheI, SpeI, XbaI, KpnI, SphI, AatII, AgeI, XmaI, NgoMI, BspEI, MluI, SacII, BsiWI, PstI, ApaLI, or an isoschizomer of one of the aforementioned enzymes.

TABLE 7

Shotgun cloning of DrdI representation.

| DrdI Type | Frequency in Genome | Fragment size (kbp) | # Amplified Sequences | # SNPs in Sequences | Fraction of Genome. |
|---|---|---|---|---|---|
| AAC | 12,500 | 0.2-1 | 5,000 | 4,100 | 0.07% |
| AAC, AAA | 25,000 | 0.2-1 | 9,850 | 8,200 | 0.13% |
| AA | 50,000 | 0.2-1 | 19,700 | 16,400 | 0.26% |
| AA, AC | 100,000 | 0.2-1 | 39,400 | 32,800 | 0.52% |
| 6 overhangs | 300,000 | 0.2-1 | 118,200 | 98,400 | 1.56% |

When using shotgun cloning to amplify genomic DrdI representations for SNP discovery, it is critical that the amplification procedure does not introduce false SNPs from polymerase errors during amplification. The use of proofreading polymerases such as Pfu polymerase should minimize such errors. When creating representational libraries with primer selectivity using a proofreading polymerase, use of probes with 3' thiophosphate linkages is preferred to avoid removal of selective bases from the primer.

An alternative approach to minimize false SNPs is to preselect the representational fragments, and/or avoid amplification altogether. This may be achieved by using biotinylated linker/adapters to a specific DrdI overhang, followed by purification of only those fragments using streptavidin beads. Such primer sequences are listed in Table 8.

TABLE 8

DrdI and Msp/Taq Bubble linkers and PCR primers for representational shotgun cloning.

| Primer | Sequence (5' → 23') |
|---|---|
| DAA1 | 5' Biotin-C18 spacer- GAA TAC CCG GGA TGA CTA CGT GTA A 3' (with m above second GGA) (SEQ. ID. No. 40) |
| DAA2R | 5' pA CAC GTA GTC ATC CCG GGT ATT C 3' (with m above CCG) (SEQ. ID. No. 41) |
| DAAP3 | 5' GAA TAC CCG GGA TGA CTA CGT GTsA sA 3' (SEQ. ID. No. 42) |
| DAC5 | 5' Biotin-C18 spacer- GAT ACC CGG GAT GAG TAC- GAC A 3' (with m above CGG) (SEQ. ID. No. 43) |
| DAC6R | 5' pT GTC GTA CTC ATC CCG GGT ATC 3' (with m above CCG) (SEQ. ID. No. 44) |
| DACP7 | 5' GAT ACC CGG GAT GAG TAC GAC AsAsC 3' (with m above CGG) (SEQ. ID. No. 45) |
| DAG9 | 5' Biotin-C18 spacer- GAT ACC CGG GAT GAG TAC GTC AAG 3' (with m above CGG) (SEQ. ID. No. 46) |
| DAG10R | 5' pT GAC GTA CTC ATC CCG GGT ATC 3' (with m above CCG) (SEQ. ID. No. 47) |
| DAGP11 | 5' GAT ACC CGG GAT GAG TAC GTC AsAsG 3' (SEQ. ID. No. 48) |
| DCA13 | 5' Biotin-C18 spacer- GAT TAC CCG GCA TGA CTA CGT ATC A 3' (with m above CCG) (SEQ. ID. No. 49) |
| DCAGAGG141822R | 5' pA TAC GTA GTC ATC CCG GGT AAT C 3' (with m above CCG) (SEQ. ID. No. 50) |
| DCAP15 | 5' GAT TAC CCG GGA TGA CTA CGT ATsCs A 3' (SEQ. ID. No. 51) |
| DGA17 | 5' Biotin-C18 spacer- GAT TAC CCG GGA TGA CTA CGT ATG A 3' (with m above CCG) (SEQ. ID. No. 52) |
| DCA19 | 5' GAT TAC CCG GGA TGA CTA CGT ATsG sA 3' (SEQ. ID. No. 53) |

TABLE 8-continued

*DrdI* and *Msp/Taq* Bubble linkers and PCR primers for representational shotgun cloning.

| Primer | Sequence (5' → 23') | |
|---|---|---|
| DGG21 | 5' Biotin-C18 spacer- GAT TAC CCG GGA TGA CTA CGT ATG G 3' (m above second G of ATG) | (SEQ. ID. No. 54) |
| DGGP23 | 5' GAT TAC CCG GGT AGA CTA CGT ATsG sG 3' | (SEQ. ID. No. 55) |
| MTCG225 | 5' GAC ACG TCA CGT CTC GAG TCC TA 3' | (SEQ. ID. No. 56) |
| MTCGp32GR | 5' pCGT AGG ACT CAC AAC GTG ACG T - Bk | (SEQ. ID. No. 57) |
| MTCGO326R | 5' CGT AGG ACT CAC AAC GTG ACG T - Bk | (SEQ. ID. No. 58) |
| MTCG227 | 5' GAC ACG TCA CGT CTC GAG TCC TsAsC 3' | (SEQ. ID. No. 59) |
| MTCG228 | 5' GAC ACG TCA CGT CTC GAG TCC TAC 3' | (SEQ. ID. No. 60) |

Using sufficient starting DNA, the representations may be generated by ligating on biotinylated linkers, removing unreacted linkers, for example, by ultrafiltration on an Amicon YM30 or YM50 filter, and, then, binding only those representational fragments containing the ligated biotinylated linker to streptavidin magnetic beads. After a 30 min. incubation with constant agitation, the captured fragments are purified by magnetic separation, and, then, the complementary strand is melted off the biotinylated strand at 95° C. for 30 seconds and rapidly recovered. The single-stranded DNA is converted to double stranded DNA (without methyl groups) using a few (2-5) rounds of PCR with a proofreading polymerase such as Pfu polymerase. Alternatively, non-methylated linkers (listed in Table 9) containing a small mismatch on the biotinylated strand may be used, followed by the above steps of ligation, capture, and purification.

TABLE 9

New *DrdI* linkers/primers for representational shotgun cloning (no amplification).

| Primer | | Sequence (5'→3') | |
|---|---|---|---|
| DAA101 | (New) | 5' Biotin-C18 spacer- GAA TAC AAG GGA TGA CTA CGT GTA A 3' | (SEQ. ID. No: 61) |
| DAA102R | (New) | 5' pA CAC GTA GTC ATC CCG GGT ATT C 3' | (SEQ. ID. No. 62) |
| DAAP3 | | 5' GAA TAC CCG GGA TGA CTA CGT GTsA sA 3' | (SEQ. ID. No. 63) |
| DAC105 | (New) | 5' Biotin-C18 spacer- GAT ACA _A_ GG GAT GAG TAC-GAC 3' | (SEQ ID No. 64) |
| DAC106R | (New) | 5' pT GTC GTA CTC ATC CCG GGT ATC 3' | (SEQ. ID. No. 65) |
| DACP7 | | 5' GAT ACC CGG GAT GAG TAC GAC AsAsC 3' | (SEQ. ID. No. 66) |
| DAG109 | (New) | 5' Biotin-C18 spacer- GAT ACA _A_ GG GAT GAG-TAC GTC AAG 3' | (SEQ. ID. No. 67) |
| DAG110R | (New) | 5' pT GAC GTA CTC ATC CCG GGT ATC 3' | (SEQ. ID. No. 68) |
| DAGP11 | | 5' GAT ACC CGG GAT GAG TAC GTC AsAsG 3' | (SEQ. ID. No. 69) |
| DCA113 | (New) | 5' Biotin-C18 spacer- GAT TAC AAG GGA TGA CTA CGT ATC A 3' | (SEQ. ID. No. 70) |
| DCAGAGG141822R2 | (New) | 5' pA TAC GTA GTC ATC CCG GGT AAT C 3' | (SEQ. ID. No. 71) |
| DCAP15 | | 5' GAT TAC CCG GGA TGA CTA CGT ATsCs A 3' | (SEQ. ID. No. 72) |
| DGA117 | (New) | 5' Biotin-C18 spacer- GAT TAC AAG GGA TGA CTA CGT ATG A 3' | (SEQ. ID. No. 73) |
| DGA19 | | 5' GAT TAC CCG GGA TGA CTA CGT ATsG sA 3' | (SEQ. ID. No. 74) |

TABLE 9-continued

New DrdI linkers/primers for representational shotgun cloning (no amplification).

| Primer | | Sequence (5'→3') | |
|---|---|---|---|
| DGG121 | (New) | 5' Biotin-C18 spacer- GAT TAC AAG GGA TGA CTA CGT ATG G 3' | (SEQ. ID. No. 75) |
| DGGP23 | | 5' GAT TAC CCG GGT AGA CTA CGT ATsG sG 3' | (SEQ. ID. No. 76) |

The resultant single strands are subsequently converted to double strands by extension of a perfectly matched, non-methylated primer using a proofreading polymerase such as Pfu polymerase. This procedure avoids PCR amplification altogether, but requires a large amount of starting genomic DNA.

With an average of one SNP every 700 bp, the 19,700 fragments will contain about 16,400 SNPs. To find the most abundant SNPs, a 6-fold coverage of these fragments should suffice. This would amount to 118,400 sequencing runs from one direction and, for clones above 500 bp in length, an additional 50% (59,200 runs) from the other side of the fragment, for a total of 177,600 sequencing runs.

For 500 bp reads, estimating 1 run per 2 hours of 96 reaction, with 12 loadings/day, this equals 1,152 sequencing reads/machine/day. Thus, the shotgun cloning/sequencing of unique DrdI islands for finding mapped SNPs in a 6-fold coverage of the human genome would require only 15.4 days using 10 of the new PE 3700 DNA sequencing machines.

For obtaining SNPs using the other 5 representations (AC, AG, CA, GA, and GG), would take an additional 77 days yielding a total of 98,500 SNPs. To double this amount, one would evaluate SNPs using the complement overhangs (TT, GT, CT, TG, TC, and CC), which would require a simultaneous mapping from the original BAC library.

In summary, the entire human genome may be mapped using the DrdI island approach, and, using the shotgun representation cloning approach, 197,000 mapped SNPs would be generated in just 88 days using 30 of the PE 3700 DNA sequencing machines.

High-Throughput Detection of SNPs in a DrdI Island Representation on a DNA Array.

A good PCR amplification, starting with 100 pmoles of each primer in 20 µl generates about 3 µg of DNA total about 40 cycles. For a 500 bp fragment, that is about 9 picomoles total=about 0.5 picomoles/µl. However, when PCR amplifying a mixture of fragments, one can generate a larger quantity of product, since product reannealing is the limiting factor in a typical PCR reaction. A good representation can generate 1-2 µg product per µl, or a conservative 20 µg product in a 20 µl reaction. For a 500 bp fragment, that is about 60 picomoles total=about 3 picomoles/µl. To make a representation for the DNA array, the concept is to selectively amplify a subset of the representation such that sufficient product is formed allowing for LDR discrimination of each SNP allele and addressable array capture/detection.

A procedure for making a representation of genomic DNA which will amplify about 8,750 fragments, of which about 4,100 will contain mapped SNPs for evaluation on a 4,096 address universal addressable array is shown in FIG. 49. Start with 100 ng of human DNA=15,000 copies=0.025 attomoles of each allele. The DNA is cut with DrdI, TaqI, and MspI, in the presence of phosphorylated DrdI adapters containing a unique two base 3' overhang (i.e. AA) and unphosphorylated TaqI and MspI adapters containing two base 5', and in the presence of T4 ligase, such that the linkers are added to their respective overhangs in a homogeneous reaction at 37° C. (See FIG. 50). Alternatively, the MspI/TaqI adapter is phosphorylated, contains a 3' blocking group on the 3' end of the top strand, and contains a bubble. Phosphorylation of the linker and use of a blocking group eliminates the potential artifactual amplification of unwanted MspI-MspI, TaqI-MspI, or TaqI-TaqI fragments. T4 ligase attaches the DrdI and MspI/TaqI adapters to their respective sites on the human genome fragments with biochemical selection assuring that most sites contain linkers (See FIG. 50A). In carrying out this procedure, the initial steps are similar to those shown in FIG. 5, up to and including the PCR amplification phase which occurs immediately prior to sequencing, are followed. However, in this procedure, the representation is derived from the total genomic DNA of a biological sample, be it from germ-line or tumor cells, not from a BAC clone. Further, the PCR primer may have one or two additional base(s) on the 3' end to obtain a representation of the correct # of fragments (about 8,750 in the example provided). In addition, after PCR amplification, the amplification product is subjected to a ligase detection reaction ("LDR") procedure to detect single base changes, insertions, deletions, or translocations in a target nucleotide sequence. The ligation product of the LDR procedure is then captured on an addressable array by hybridization to capture probes fixed to a solid support. This use of LDR in conjunction with the capture of a ligation product on a solid support is more fully described in WO 97/31256 to Cornell Research Foundation, Inc. and Gerry, N. et al., "Universal DNA Array with Polymerase Chain Reaction/Ligase Detection Reaction (PCR/LDR) for Multiplex Detection of low Abundance Mutations," *J. Mol. Biol.* 292:251-262 (1999), which are hereby incorporated by reference.

In brief, however, this procedure involves providing a plurality of oligonucleotide probe sets. Each set is characterized by (a) a first oligonucleotide probe, having a target-specific portion and an addressable array-specific portion and (b) a second oligonucleotide probe, having a target-specific portion and a detectable reporter label. The oligonucleotide probes in a particular set are suitable for ligation together when hybridized adjacent to one another on a corresponding target nucleotide sequence, but have a mismatch which interferes with such ligation when hybridized to any other nucleotide sequence present in the sample. The PCR amplification product, described in FIG. 50, the plurality of oligonucleotide probe sets, and the ligase are blended to form a mixture which is subjected to one or more ligase detection reaction cycles. The ligase detection reaction cycles include a denaturation treatment, where any hybridized oligonucleotides are separated from the target nucleotide sequences, and a hybridization treatment, where the oligonucleotide probe sets hybridize at adjacent positions in a base-specific manner to their respective target nucleotide sequences, if present in the sample, and ligate to one another to form a ligated product sequence containing (a) the addressable array-specific portion, (b) the target-specific portions connected together, and (c) the detectable reporter label. The oligonucleotide probe sets may hybridize to nucleotide sequences in the PCR amplification product other than their respective target nucleotide sequences but do not ligate together due to a presence of one or more mismatches. As a result, the nucleotide sequences and oligonucleotide probe sets individually separate during the denaturation treatment.

A support with different capture oligonucleotides immobilized at particular sites is used in conjunction with this process. The capture oligonucleotides have nucleotide sequences complementary to the addressable array-specific portions. The mixture, after being subjected to the ligase detection reaction cycles, is contacted with the support under conditions effective to hybridize the addressable array-specific portions to the capture oligonucleotides in a base-specific manner. As a result, the addressable array-specific portions are captured on the support at the site with the complementary capture oligonucleotide. Reporter labels of the ligated product sequences captured to the support at particular sites are detected. This permits the presence of one or more target nucleotide sequences in the sample to be identified.

The ligase detection reaction process phase of the present invention is preceded by the representational polymerase chain reaction process of the present invention. The preferred thermostable ligase is that derived from *Thermus aquaticus*. This enzyme can be isolated from that organism. M. Takahashi, et al., "Thermophillic DNA Ligase," *J. Biol. Chem.* 259:10041-47 (1984), which is hereby incorporated by reference. Alternatively, it can be prepared recombinantly. Procedures for such isolation as well as the recombinant production of *Thermus aquaticus* ligase as well as *Thermus themophilus* ligase) are disclosed in WO 90/17239 to Barany, et. al., and F. Barany, et al., "Cloning, Overexpression and Nucleotide Sequence of a Thermostable DNA-Ligase Encoding Gene," *Gene* 109:1-11 (1991), which are hereby incorporated by reference. These references contain complete sequence information for this ligase as well as the encoding DNA. Other suitable ligases include *E. coli* ligase, T4 ligase, Pyrococcus ligase, as well as those listed in Table 3.

The hybridization step, which is preferably a thermal hybridization treatment, discriminates between nucleotide sequences based on a distinguishing nucleotide at the ligation junctions. The difference between the target nucleotide sequences can be, for example, a single nucleic acid base difference, a nucleic acid deletion, a nucleic acid insertion, or rearrangement. Such sequence differences involving more than one base can also be detected. Preferably, the oligonucleotide probe sets have substantially the same length so that they hybridize to target nucleotide sequences at substantially similar hybridization conditions.

Figure 51:
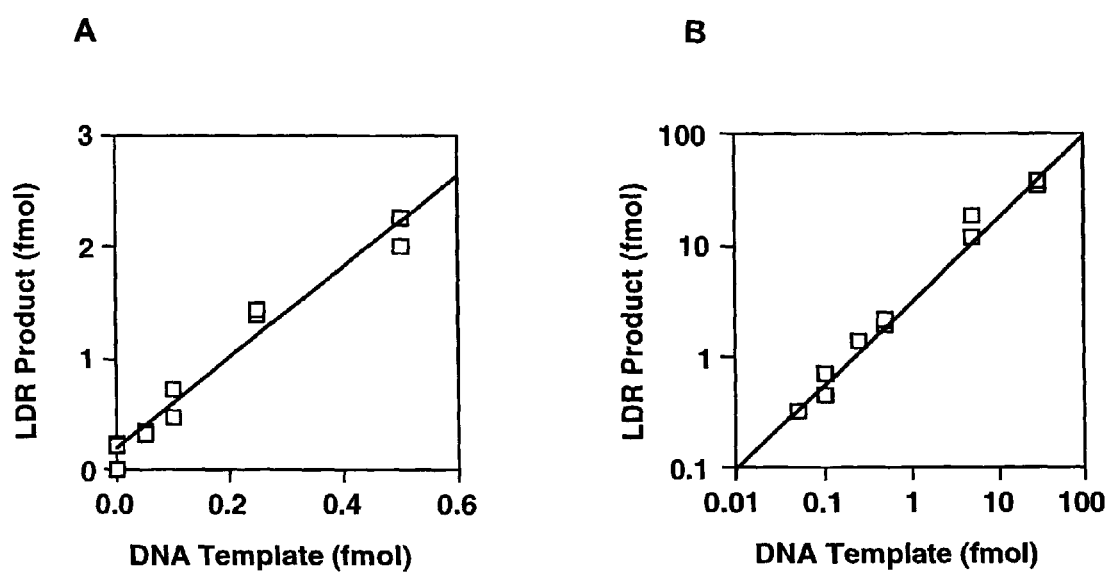

The process of the present invention is able to detect nucleotide sequences in the sample in an amount of 100 attomoles to 250 femtomoles. Quantitative detection of G12V mutation of the K-ras gene, from 100 attomoles to 30 femtomoles using two LDR probes in the presence of 10 microgram salmon sperm DNA is shown in FIG. 51. By coupling the LDR step with a primary polymerase-directed amplification step, the entire process of the present invention is able to detect target nucleotide sequences in a sample containing as few as a single molecule. Furthermore, PCR amplified products, which often are in the picomole amounts, may easily be diluted within the above range. The ligase detection reaction achieves a rate of formation of mismatched ligated product sequences which is less than 0.005 of the rate of formation of matched ligated product sequences.

Once the ligation phase of the process is completed, the capture phase is initiated. During the capture phase of the process, the mixture is contacted with the support at a temperature of 45-90° C. and for a time period of up to 60 minutes. Hybridizations may be accelerated by adding volume exclusion, chaotropic agents, or $Mg^{2+}$. When an array consists of dozens to hundreds of addresses, it is important that the correct ligation products have an opportunity to hybridize to the appropriate address. This may be achieved by the thermal motion of oligonucleotides at the high temperatures used, by mechanical movement of the fluid in contact with the array surface, or by moving the oligonucleotides across the array by electric fields. After hybridization, the array may be washed sequentially with a low stringency wash buffer and then a high stringency wash buffer.

It is important to select capture oligonucleotides and addressable nucleotide sequences which will hybridize in a stable fashion. This requires that the oligonucleotide sets and the capture oligonucleotides be configured so that the oligonucleotide sets hybridize to the target nucleotide sequences at a temperature less than that which the capture oligonucleotides hybridize to the addressable array-specific portions. Unless the oligonucleotides are designed in this fashion, false positive signals may result due to capture of adjacent unreacted oligonucleotides from the same oligonucleotide set which are hybridized to the target.

Several approaches have been tested to produce universal addressable arrays. One hundred different 2- and 3-dimensional matrices were tested; the current formulation uses an acrylamide/acrylic acid copolymer containing low levels of bis-acrylamide crosslinker. The polymer surfaces were prepared by polymerizing the monomer solution on glass microscope slides pretreated with a silane containing an acryl moiety. Amino-modified address oligonucleotides containing a hexaethylene oxide spacer were hand-spotted onto NHS preactivated slides and coupled for 1 hour at 65° C. in a humidified chamber. Following coupling, the polymer was soaked in a high salt buffer for 30 minutes at 65° C. to remove all uncoupled oligonucleotides. Both activated and arrayed surfaces can be stored under dry conditions for several months with no decrease in activity.

Hybridization conditions were varied with respect to temperature, time, buffer, pH, organic solvents, metal cofactors, volume exclusion agents, and mixing conditions, using test fluorescently-labeled zip-code complementary probes. Under a variety of conditions, no cross-hybridization was observed between even closely related addresses, with signal-to-noise of at least 50:1. Different addresses hybridize at approximately the same rate yielding approximately the same quantity of fluorescent signal when normalized for oligonucleotide coupled per address. The probes diagrammed in FIG. 52 were synthesized and tested in a multiplex PCR/LDR reaction on cell line DNA containing known K-ras mutations. Each array identified the mutation correctly with signal-to-noise of at least 20:1 (FIG. 53). Further, this demonstrates the ability of the universal array to detect two single-nucleotide polymorphisms simultaneously: the wild-type and mutant sequence are present in all panels except from normal cells or from the cell line containing only the G12V mutant DNA.

The detection phase of the process involves scanning and identifying if ligation of particular oligonucleotide sets occurred and correlating ligation to a presence or absence of the target nucleotide sequence in the test sample. Scanning can be carried out by scanning electron microscopy, confocal microscopy, charge-coupled device, scanning tunneling electron microscopy, infrared microscopy, atomic force microscopy, electrical conductance, and fluorescent or phosphor imaging. Correlating is carried out with a computer.

To determine DNA array capture sensitivity, mixtures of an excess of unlabeled to labeled probe were tested. This simulates an LDR reaction where an excess of unligated probes compete with the labeled LDR products for hybridization to the array. DNA arrays were hybridized in quadruplicate with from 100 amoles to 30 fmol FamCZip13 (synthetic 70-mer LDR product) mixed with a full set of K-ras LDR probes (combined total of 9 pmol of discriminating and common probes) under standard conditions. The arrays were analyzed on a Molecular Dynamics FluorImager 595 and an Olympus AX70 epifluorescence microscope equipped with a Princeton Instruments TE/CCD-512 TKBM1 camera. A signal-to-noise ratio of greater than 3:1 was observed even when starting with a minimum of 3 fmol FamCZip13 labeled-probe within 4,500 fmol Fam label and 4,500 fmol addressable array-specific portion in the hybridization solution (see FIG. 54). Using the microscope/CCD instrumentation, a 3:1 signal-to-noise ratio was observed even when starting with 1 fmol labeled product (see FIG. 54). Thus, either instruments can readily quantify LDR product formed by either K-ras allele at the extremes of allele imbalance (from 6-80 fmol, see Table 11.)

For both instruments, a linear relationship is observed between labeled FamCZip13 added and fluorescent counts captured. Each array was plotted individually, and variation in fluorescent signal between arrays may reflect variation in amount of oligonucleotide coupled due to manual spotting and/or variation in polymer uniformity. Rehybridization of the same probe concentration to the same array is reproducible to +/−5%, with capture efficiency from 20 to 50%. Since the total of both labeled and unlabeled addressable array-specific portions which complement a given address remains unchanged (at 500 fmol) from LDR reaction to LDR reaction, this result demonstrates the ability to quantify the relative amount of LDR product using addressable array detection. Since the relationship between starting template and LDR product retains linearity over 2 orders of magnitude with a similar limit of sensitivity at about 100 amols (see FIG. 51), combining PCR/LDR allele discrimination with array-based detection will provide quantifiable results.

As shown in FIG. 50, in embodiment A, the LDR oligonucleotide probe sets have a probe with the discriminating base labeled at its opposite end (i.e. fluorescent groups F1 and F2), while the other probe has the addressable array-specific portion (i.e. Z1). Alternatively, in embodiment B, the LDR oligonucleotide probe sets have a probe with the discriminating base and the addressable array-specific portion at its opposite end (i.e. Z1 and Z2), while the other probe has the label (i.e. fluorescent label F). When contacted with the support, the ligation products of embodiment A are captured at different sites but the same array address and ligation products are distinguished by the different labels F1 and F2. When the support is contacted with the ligation products of embodiment B, the different ligation products all have the same label but are distinguished by being captured at different addresses on the support. In embodiment A, the ratio of the different labels identifies an allele imbalance. Likewise, such an imbalance in embodiment B is indicated by the fluorescence ratio of label F at the addresses on the support.

In carrying out this procedure, one may start with 100 ng of human DNA=15,000 copies=0.025 attomoles of each allele. The DNA is cut with DrdI, TaqI, and MspI, in the presence of phosphorylated DrdI adapters containing a unique two base 3' overhang (i.e. AA) and unphosphorylated TaqI and MspI adapters containing two base 5', and in the presence of T4 ligase, such that the linkers are added to their respective overhangs in a homogeneous reaction at 37° C. Enzymes are inactivated by heating at 85° C. to 98° C., preferably 95° C., for 2 to 20 minutes, preferably for 5 minutes. PCR amplification using a primer complementary to the DrdI adapter with an additional 3' base, i.e. (3' AAC) and a primer complementary to the other adapter will give a representation of 0.19% of the total genomic DNA.

A PCR amplification of 30 to 35 cycles will give a good representation and produce about 10-20 µg of final mixed fragments. Some variation of thermocycling conditions may be required to obtain a broad representation of the majority of fragments at high yield. The PCR amplification will contain an average of $1.5 \times 10^9$ copies for each allele of the approximately 8,750 fragments in the representation. This is equivalent to an average yield of 2.5 fmoles of each product. The larger fragments will yield less PCR product (about 1 fmole each), while the smaller fragments will yield a greater amount of product (from 5-10 fmole each).

The same approach may be used for amplifying SNP containing fragments using either a different base on the 3' end, or alternatively, a different DrdI overhang. A total of 24 representation PCR reactions generate the amplicon sets for testing all 98,000 SNPs. Further, fragments amplified in the smaller representation may also be cloned and sequenced to find SNPs.

The above procedure can be modified such that the representation will contain more or less fragments, and/or improve the yield of all fragments. For example, a size-selection between 200 and 2,000 bp prior to PCR amplification may improve the yield of fragments in the representation. For making larger representations, more than one linker for the DrdI site overhang may be used, e.g., both AA and AC overhangs, and PCR primers complementary to the DrdI adapter with an additional 3' base (i.e. 3' AAC and 3' ACC) would double the representation to approximately 17,500 fragments. Alternatively, more than one PCR primer complementary to the DrdI adapter with an additional 3' base (i.e. 3' AAC and 3' AAT) would also double the representation to approximately 17,500 fragments. Larger representations may be used if PCR amplification generates sufficient product for detection on the above described universal array, and/or as detection sensitivity improves. For making smaller representations, one or two PCR primers with two additional selective bases on the 3' end is used during the PCR amplification step, i.e. (3'AAAC+3'AAAG) would reduce the representation to approximately 4,400 fragments, while use of just one primer (3'AAAC) would reduce the representation to approximately 2,200 fragments. The ideal size of the representation will depend on the number of SNPs which will be detected (See Table 10). Other restriction endonucleases with degenerate overhangs as the primary enzyme may be used to create the representation, such as BglI, DraIII, AlwNI, PflMI, AccI, BsiHKAI, SanDI, SexAI, PpuI, AvaII, EcoO109, Bsu36I, BsrDI, BsgI, BpmI, SapI, or an isoschizomer of one of the aforementioned enzymes. Palindromic restriction endonucleases may also be used to create the representation, such as BamHI, AvrII, NheI, SpeI, XbaI, KpnI, SphI, AatII, AgeI, XmaI, NgoMI, BspEI, MluI, SacII, BsiWI, PstI, ApaLI, or an isoschizomer of one of the aforementioned enzymes.

TABLE 10

High-throughput detection of SNPs on a DNA array

| DrdI Type | Frequency in Genome | # Amplified Sequences | # SNPs in Sequences | Fraction of Genome | Yield of each allele (fmol). |
|---|---|---|---|---|---|
| AAAC, | 3,125 | 2,187 | 1,025 | 0.05% | 4-40 |
| AAAC, AAAG | 6,250 | 4,375 | 2,050 | 0.09% | 2-20 |
| AAC | 12,500 | 8,750 | 4,100 | 0.19% | 1-10 |
| AAA, AAC | 25,000 | 17,500 | 8,200 | 0.38% | 0.5-5 |

Large Scale Detection of SNPs Using DrdI Island Representations and DNA Array Capture.

New technologies to identify and detect SNPs specifically provide tools to further understanding of the development and progression of colon cancer. One can determine chromosome abnormalities by quantifying allelic imbalance on universal DNA arrays using specific SNPs at multiple loci. This approach has the potential to rapidly identify multiple gene deletions and amplifications associated with tumor progression, as well as lead to the discovery of new oncogenes and tumor suppressor genes.

Competitive and real time PCR approaches require careful optimization to detect 2-fold differences. Unfortunately, stromal contamination may reduce the ratio between tumor and normal chromosome copy number to less than 2-fold. Consider two samples: one with 4-fold amplification of the tumor gene (thick black line) and 50% stromal contamination, the other with loss of heterozygosity (LOH, one chromosome containing the gene is missing, thin black line) and 40% stromal contamination (See FIG. 55). Using either microsatellite or SNP analysis, both samples would show an allele imbalance of 2.5:1 for the tumor gene (black), and allele balance for the control gene (gray, FIG. 55, first line). Comparing the ratio of the tumor gene in the tumor sample to the control gene over the ratio of the tumor gene in the normal sample (normalized to the same number of cells) to the control gene, the stromal contamination reduces the ratio from the amplified sample to 1.75 and increases the ratio from the LOH sample to 0.7 (FIG. 55, second line). These ratios are exceedingly difficult to distinguish from 1.0 by competitive PCR. However, by using SNP analysis to compare the ratio of tumor to control allele (i.e. thick line) over the ratio of normal to control allele, then it may be possible to distinguish gene amplification (thick black line) with a ratio of 2.5 from LOH (thin black line) with a ratio of 0.4 (FIG. 55, bottom line). It is important that relative allele signal can be accurately quantified.

To determine if PCR/LDR allows accurate quantification of mutant and wild-type K-ras alleles, PCR-amplified fragments derived from pure cell lines were mixed in varying ratios and analyzed in a competitive three LDR probe system in which upstream discriminating probes specific for either the wild-type or the G12V mutant allele competed for a downstream probe common to both alleles (FIG. 56). Optimal quantification was achieved by using LDR probes in slight excess of K-ras template and limiting LDR cycles so products were in the linear range for fluorescent quantification on an ABI 373 sequencer. Under these conditions, mutant/wt ratios from 1:6 to 6:1 could be accurately quantified, and when normalized to the 1:1 products were within 10% of the predicted value (Table in FIG. 56). Similar results were obtained using probe sets for G12D, G12C, and G13D. Quantitative LDR was performed on PCR-amplified DNA isolated from 10 colorectal carcinoma cell lines. Four cell lines contained either pure mutant or wild-type ("wt") alleles, three contained approximately equal amounts of mutant and wt alleles (0.7-1.1), and three contained an increased ratio of mutant:wt alleles (1.8-4.0). Allelic imbalance was highly correlated to the proportion of cellular p21 ras protein present in the activated, GTP-bound form. These data support the conclusion that allelic imbalance with amplification of the mutant K-ras gene is a second genetic mechanism of K-ras activation.

Genomic DNA was extracted from 44 archival primary colon cancers known to contain a point mutation in the K-ras gene, amplified using PCR primers specific for exon 1 of K-ras, and quantified with competitive LDR. The percentage of stromal cell contamination in primary colon cancers was estimated by an independent pathologist for each sample and this value was used to correct the mutant:wt ratio (Table 11). K-ras allelic imbalance was calculated to be 2-fold or greater whenever the corrected mutant/wt ratio measured by LDR exceeded 2 (Table 11). To evaluate the impact of K-ras allelic imbalance in this group of patients, disease-specific survival curves were obtained by the Kaplan-Meier method using the log-rank test. While tumors with wild-type or non-amplified K-ras mutations (mutant:wt ratio<2) showed similar survival trends, tumors with amplification of K-ras (ratio>2) had a significantly worse survival compare to mutant tumors without allelic imbalance (p=0.03) and to wt tumors (p=0.0001). Thus, gene amplification is an important second mechanism of K-ras activation and negatively impacts on disease-specific survival in colon cancer.

TABLE 11

Corrected ratios of mutant K-ras to wild-type alleles in primary colon cancers.

| | Representative samples with K-ras mutation And low-level allele imbalance (<2) | | | | Representative samples with K-ras mutation and high-level allele imbalance (>2) | | | |
|---|---|---|---|---|---|---|---|---|
| Tumor # | Genotype | Observed mutant: wt ratio | % Tumor | Corrected mutant: wt ratio | Tumor # | Genotype | Observed mutant, wt ratio | % Tumor | Corrected mutant: wt ratio |
| 11 | G12D | 0.3 | 50 | 0.9 | 17 | G12C | 0.6 | 30 | 3.4 |
| 9 | G12C | 0.3 | 40 | 1.2 | 27 | G12A | 0.7 | 30 | 4.0 |
| 23 | G12C | 0.4 | 50 | 1.2 | 6 | G12V | 0.7 | 30 | 4.0 |
| 12 | G12C | 0.5 | 60 | 1.2 | 14 | G12D | 0.9 | 50 | 2.7 |
| 3 | G12V | 0.5 | 50 | 1.5 | 29 | G12A | 1.2 | 40 | 4.8 |
| 10 | G12V | 0.5 | 50 | 1.5 | 30 | G12D | 1.2 | 50 | 3.6 |
| 37 | G12A | 0.6 | 60 | 1.4 | 38 | G12V | 1.3 | 60 | 3.0 |
| 21 | G12D | 0.6 | 50 | 1.8 | 13 | G12C | 1.4 | 70 | 2.6 |

TABLE 11-continued

Corrected ratios of mutant K-ras to wild-type alleles in primary colon cancers.

| Representative samples with K-ras mutation And low-level allele imbalance (<2) | | | | Representative samples with K-ras mutation and high-level allele imbalance (>2) | | | |
|---|---|---|---|---|---|---|---|
| Tumor # | Genotype | Observed mutant: wt ratio | % Tumor | Corrected mutant: wt ratio | Tumor # | Genotype | Observed mutant, wt ratio | % Tumor | Corrected mutant: wt ratio |

| Tumor # | Genotype | Observed mutant: wt ratio | % Tumor | Corrected mutant: wt ratio | Tumor # | Genotype | Observed mutant, wt ratio | % Tumor | Corrected mutant: wt ratio |
|---|---|---|---|---|---|---|---|---|---|
| 19 | G12S | 0.6 | 50 | 1.8 | 25 | G12V | 1.7 | 30 | 9.6 |
| 31 | G12D | 0.7 | 60 | 1.6 | 35 | G12D | 2.0 | 40 | 8.0 |

Colon cancer tumors with known K-ras genotype were analyzed to determine the degree of allelic imbalance using a modified PCR/LDR technique. The mutant/wt ratio was determined experimentally and corrected based on the estimated percentage of stromal contamination in the microdissected tumor specimen, using the formula: X mutant/wt (Observed) × (% T + 2(1 − % T))/% T, where X = Corrected mutant/wt ratio of Chromosomes, and % T = Percentage of tumor cells in section. Allelic imbalance was considered significant when the ratio was more than 2.0 (e.g., at least two copies of the mutant allele compared to one copy of the wt allele in the tumor). For low mutant:wt ratios, allele imbalance may also be due to loss of the normal K-ras allele in the tumor cell, e.g., an observed mutant:wt ratio of 0.5 with 50% of the cells from the tumor (samples #3 & #10) may reflect one mutant allele in the tumor cell to two wild-type alleles in the normal cell. Under these calculations X = mutant/wt (Observed) × 2(1 − % T)/% T = 0.5 × 2(1 − 0.5)/0.5 = 1 mutant K-ras allele in the tumor cell, with LOH of the other allele. The left side of the table shows representative samples in which allelic imbalance was minimal while the right side of the table shows representative samples in which the K-ras mutant allele is amplified. The table demonstrates that the corrected mutant:wt ratio is dependent on both the observed ratio and the percentage of stromal contamination in the sample.

The above data demonstrates that PCR/LDR may be used to accurately quantify mutant and wild-type K-ras alleles using an automated DNA sequencer to detect the fluorescent signal. Further, the work above demonstrated that femtomole amounts of CZip fluorescently-labeled product in picomole quantities of total probe and label can be captured at its cognate address and quantified using either FluorImager or CCD detection.

The use of fluorescently-labeled oligonucleotides on DNA arrays have the advantages of multiple labels, long lifetimes, ease of use, and disposal over traditional radiolabels. However, the efficiency of fluorescent emissions from a given fluorophore is dependent on multiple variables (i.e. solvation, pH, quenching, and packing within the support matrix) which makes it difficult to produce accurate calibration curves. This problem may be effectively circumvented by using two fluorescent labels and determining their ratio for each address (Hacia, et al., "Detection of Heterozygous Mutations in BRCA1 Using High Density Oligonucleotide Arrays and Two-Colour Fluorescence Analysis," *Nature Genetics*, 14(4): 441-7 (1996); DeRisi, et al., "Use of a cDNA Microarray to Analyse Gene Expression Patterns in Human Cancer," *Nature Genetics*, 14(4):457-60 (1996); Schena, et al., "Parallel Human Genome Analysis: Microarray-Based Expression Monitoring of 1000 Genes", *Proc. Nat'l. Acad. Sci. USA*, 93(20):10614-9 (1996); Shalon, et al., "A DNA Microarray System for Analyzing Complex DNA Samples Using Two-Color Fluorescent Probe Hybridization," *Genome Research*, 6(7):639-45 (1996); and Heller, et al., "Discovery and Analysis of Inflammatory Disease-Related Genes Using cDNA Microarrays," *Proc. Nat'l. Acad. Sci. USA*, 94(6):2150-5 (1997), which are hereby incorporated by reference).

Below two sets of alternative dual labeling strategies are addressed. In the first set, shown in FIG. 57, signal is quantified by using a fluorescent label on the array surface at the address. In the second and preferred set, shown in FIG. 62, signal is quantified by using a small percentage of fluorescent label on the probe which contains the capture oligonucleotide complement.

The first set of dual label strategies to quantify LDR signal using addressable DNA arrays is shown in FIGS. 57A-B. In FIG. 57A, the common LDR probe for both alleles contains a fluorescent label (F1) and the discriminating probe for each allele contains a unique address-specific portion. Following hybridization of the LDR reaction mixture to an array composed of fluorescently-labeled (F2) ligation product, the ratio of F1/F2 for each address can be used to determine relative percent mutation or allelic imbalance. In FIG. 57B, the common probe for both alleles contains an address-specific portion and the discriminating probe for each allele contains a unique fluorescent label, F1 or F2. Following LDR, the reaction mixture is hybridized to an array and the ratios of F1/F2 for each address can again be used to determine relative percent mutation or allelic imbalance. In addition, by adding a third label, F3, to the oligonucleotide coupled to the surface it will be possible to quantify each allele separately. One method of determining allele imbalance compares $(F1_{captured\ signal}/F2_{address\ signal})$ where the matched tumor and normal samples are hybridized to two different arrays (where variability in addresses is less than 10%, achieved by printing two arrays on the same slide). The allele imbalance is calculated for each sample by the formula $\{(F1_{Allele\ 1:\ tumor}/F2_{Address\ 1})/(F1_{Allele\ 2:\ tumor}/F2_{Address\ 2})\}/\{(F1_{Allele\ 1:\ normal}/F2_{Address\ 1})/(F1_{Allele\ 2:\ normal}/F2_{Address\ 2})\}$. Even if considerable variance between addresses remains, the overall calculation for the ratio of allele imbalance will remain accurate, provided the identical reusable array is used for both tumor and normal samples, in which case the above equation simplifies to $(F1_{Allele\ 1:\ tumor}/F1_{Allele\ 1:\ normal})/(F1_{Allele\ 2:\ tumor}/F1_{Allele\ 2:\ normal})$.

The advantages of using the present invention compared to other detection schemes are as follows: this approach to polymorphism detection has three orthogonal components: (i) primary representational PCR amplification; (ii) solution-phase LDR detection; and (iii) solid-phase hybridization capture. Therefore, background signal from each step can be minimized, and consequently, the overall sensitivity and accuracy of the method of the present invention are significantly enhanced over those provided by other strategies. For example, "sequencing by hybridization" methods require: (i) multiple rounds of PCR or PCR/T7 transcription; (ii) processing of PCR amplified products to fragment them or render them single-stranded; and (iii) lengthy hybridization periods (10 h or more) which limit their throughput. Additionally, since the immobilized probes on these arrays have a wide range of $T_m$s, it is necessary to perform the hybridizations at temperatures from 0° C. to 44° C. The result is increased background noise and false signals due to mismatch hybridization and non-specific binding, for example, on small insertions and deletions in repeat sequences. In contrast, the present approach allows multiplexed PCR in a single reaction, does not require an additional step to convert product into single-stranded form, and can readily distinguish all point mutations including polymorphisms in mononucleotide and short dinucleotide repeat sequences. This last property expands the number of polymorphisms which may be considered for SNP analysis to include short length polymorphisms, which tend to have higher heterozygosities. Alternative DNA arrays suffer from differential hybridization efficiencies due to either sequence variation or to the amount of target present in the sample. By using divergent sequences for the addressable array-specific portion (i.e. zip-code) with similar thermodynamic properties, hybridizations can be carried out at 65° C., resulting in a more stringent and rapid hybridization. The decoupling of the hybridization step from the mutation detection stage offers the prospect of quantification of LDR products, as we have already achieved using gel-based LDR detection.

Arrays spotted on polymer surfaces provide substantial improvements in signal capture compared with arrays spotted directly on glass surfaces. The polymers described above are limited to the immobilization of 8- to 10-mer addresses; however, the architecture of the presently described polymeric surface readily allows 24-mer addresses to penetrate and couple covalently. Moreover, LDR products of length 60 to 75 nucleotide bases are also found to penetrate and subsequently hybridize to the correct address. As additional advantages, the polymer gives little or no background fluorescence and does not exhibit non-specific binding of fluorescently-labeled oligonucleotides. Finally, addresses spotted and covalently coupled at a discrete address do not "bleed over" to neighboring spots, hence obviating the need to physically segregate sites, e.g., by cutting gel pads.

Nevertheless, alternative schemes for detecting SNPs using a primary representational PCR amplification have been considered and are briefly included herein. Since the representations are the consequence of amplification of fragments containing two different adapters, the procedure may be easily modified to render single stranded product which is preferred for "sequencing by hybridization" and single nucleotide polymerase extension ("SNUPE") detection. Thus, one linker adapter may contain a T7 or other RNA polymerase binding site to generate single-stranded fluorescently labeled RNA copies for direct hybridization. Or, one strand may be biotinylated and removed with streptavidin coated magnetic beads. Another alternative option is to put a 5' fluorescent group on one probe, and a phosphate group on the 5' end of the other probe and treat the mixture with Lambda Exonuclease. This enzyme will destroy the strand containing the 5' phosphate, while leaving the fluorescently labeled strand intact.

For detection using single nucleotide polymerase extension ("SNUPE"), a probe containing an addressable array-specific portion on the 5' end, and a target-specific portion on the 3' end just prior to the selective base is hybridized to the target. Fluorescently labeled dye-dioxynucleotides are added with a high fidelity polymerase which inserts the labeled base only if the complementary base is present on the target (FIG. 58). The ratios of F1/F2 for each address can be used to determine relative percent mutation or allelic imbalance.

Alternatively, LDR products may be distinguished by hybridizing to gene specific arrays (FIGS. 59A-B). This may be achieved by hybridizing to the common probe (FIG. 59A) or across the ligation junction (FIG. 59B). A "universal" nucleotide analog may be incorporated into the address so that neither allele product hybridizes better to the array. Again, the ratios of F1/F2 for each address can be used to determine relative percent mutation or allelic imbalance.

For large representations, or direct detection of any SNPs in the absence of a representation, LDR/PCR may be used (FIG. 60). In this scheme, the discriminating probes contain universal probes with unique addressable portions on the 5' side, while the common probes have universal primers on the 3' side. The upstream probe has the addressable array-specific portion in-between the target-specific portion and the universal probe portion, i.e. the probe will need to be about 70 bp long. After an LDR reaction, the LDR products are PCR amplified using the universal PCR primer pair, with one primer fluorescently labeled. To avoid ligation independent PCR amplification, it may be necessary to incorporate a series of blocking groups on the 3' end of the downstream common probe (excellent successes have been achieved by applicants with thiophosphate linkages of the last four O-methyl riboU bases), and treat the ligation products with Exo III. See WO 97/45559, which is hereby incorporated by reference.

The addressable array-specific portion is now in the middle of a double-stranded product. For maximum capture efficiency, it may be desirable to render the product single-stranded, either with T7 RNA polymerase or with biotinylated probe. One alternative option is to put a 5' fluorescent group on one probe, and a phosphate group on the 5' end of the other probe and treat the mix with Lambda Exonuclease (See FIG. 61). This enzyme will destroy the strand containing the 5' phosphate, while leaving the fluorescently labeled strand intact.

The final products are then captured on the addressable array at the specific addresses. The ratio of signal at Z1/Z2 can be used to determine relative percent mutation or allelic imbalance. It may be difficult to quantify subtle differences of allele imbalance since the different addressable array-specific portions may alter the ratio of alleles in the final PCR product. Nevertheless, LDR/PCR may aid in quantification of LOH and gene amplifications at multiple loci simultaneously.

FIG. 62 presents the second set of dual label strategies to quantify LDR signal using addressable DNA arrays. In FIG. 62A, the common LDR probe for both alleles contains a fluorescent label (F1) and the discriminating probe for each allele contains a unique addressable sequence. A small percentage of each discriminating probe contains a fluorescent label F2. Following hybridization of the LDR reaction mixture to an array, the ratio of F1/F2 for each address can be used to determine relative percent mutation or allelic imbalance. By placing the second fluorescent label on both discriminating probes, one controls for differences in either address spotting or hybridization kinetics of each individual address. For example, consider that 10% of the discriminating probes contain F2. Consider a sample containing 3-fold more of the C allele than the T allele. After an LDR reaction, 20% of the common probe has been ligated to form the T-specific product containing address-specific portion Z1, and 60% has formed the C-specific product containing address-specific portion Z2. Due to differences in spotting, the array captures 50% of the Z1 signal, but only 30% of the Z2 signal. F1/F2 for Z1=(50% of 20%)/(50% of 10%)=10%/5%=2. F1/F2 for Z2= (30% of 60%)/(30% of 10%)=18%/3%=6. By taking the ratio of F1/F2 for Z1 to F1/F2 for Z2, 6/2=3 is obtained which accurately reflects the allele imbalance in the sample.

In FIG. 62B, the common probe for both alleles contains an addressable sequence and the discriminating probe for each allele contains a unique fluorescent label, F1 or F2. Following LDR, the reaction mixture is hybridized to an array and the ratios of F1/F2 for each address can again be used to determine relative percent mutation or allelic imbalance. In addition, by adding a small percentage of common probe containing label F3, it is possible to quantify each allele separately.

Dual label hybridization to the same address using dye combinations of fluorescein/phycoerythrin, fluorescein/Cy5 Cy3/rhodamine, and Cy3/Cy5 have been used successfully (Hacia, et al., "Detection of Heterozygous Mutations in BRCA1 Using High Density Oligonucleotide Arrays and Two-Colour Fluorescence Analysis," *Nature Genetics,* 14(4): 441-7 (1996); DeRisi, et al., "Use of a cDNA Microarray to Analyse Gene Expression Patterns in Human Cancer," *Nature Genetics,* 14(4):457-60 (1996); Schena, et al., "Parallel Human Genome Analysis: Microarray-Based Expression Monitoring of 1000 Genes," *Proc. Nat'l. Acad. Sci. USA,* 93(20):10614-9 (1996); Shalon, et al., "A DNA Microarray System for Analyzing Complex DNA Samples Using Two-Color Fluorescent Probe Hybridization," *Genome Research,* 6(7):639-45 (1996); and Heller, et al., "Discovery and Analysis of Inflammatory Disease-Related Genes Using cDNA Microarrays," *Proc. Nat'l. Acad. Sci. USA,* 94(6):2150-5 (1997), which are hereby incorporated by reference). A list of potential dyes which may be used in the labeling schemes described above is provided in Table 12. For the above schemes to be successful, the dye sets used should not interfere with each other.

TABLE 12

List of Dyes which may be used for fluorescent detection of SNPs.

| Dye | Abs. Max (nm) | Em. Max (nm) |
|---|---|---|
| Marina Blue | 365 | 460 |
| Flourescein | 495 | 520 |
| TET | 521 | 536 |
| TAMRA | 565 | 580 |
| Rhodamine | 575 | 590 |
| ROX | 585 | 610 |
| Texas Red | 600 | 615 |
| Cy2 | 489 | 506 |
| Cy3 | 550 | 570 |
| Cy3.5 | 581 | 596 |
| Cy5 | 649 | 670 |
| Cy5.5 | 675 | 694 |
| Cy7 | 743 | 767 |
| Spectrum Aqua | 433 | 480 |
| Spectrum Green | 509 | 538 |
| Spectrum Orange | 559 | 588 |
| BODIPY FL | 505 | 515 |
| BODIPY R6G | 530 | 550 |
| BODIPY TMR | 545 | 575 |
| BODIPY 564/6570 | 565 | 575 |
| BODIPY 581/591 | 580 | 600 |
| BODIPY TR | 595 | 625 |
| BODIPY 630/650 | 640 | 650 |

A representational PCR amplification will contain an average of $1.5 \times 10^9$ copies of each allele of approximately 8,750 fragments in the representation. This is equivalent to an average yield of 2.5 fmoles of each product. The larger fragments will yield less PCR product (about 1 fmole each), while the smaller fragments will yield a greater amount of product (from 5-10 fmole each). Of these 8,750 fragments, about 4,100 will contain SNPs. As demonstrated above, the representational PCR/LDR/universal array capture scheme should have the requisite sensitivity to detect gene amplification or loss of heterozygosity at the vast majority of these SNPs simultaneously.

This scheme has immediate utility for detecting allele imbalance in tumors. An initial array of 4,096 addresses may be used to find general regions of gene amplifications or LOH. Subsequently, arrays may be used to pinpoint the regions using more closely-spaced SNPs.

A major advantage of the representational PCR amplification is the ability to amplify approximately 8,750 fragments proportionally to their original copy number in the original sample. While some fragments may amplify more than others, repeated amplification of normal samples will reveal fragments whose PCR and LDR products are consistently amplified to similar yields. Thus, for a given fragment which is either amplified or lost in the tumor (designated "g") there will be at least one fragment which retains normal yields (designated "c") For each allele pair (g1, g2) which is imbalanced, there is a control locus (c1, c2) which exhibits heterozygosity in both the normal and tumor sample. To determine if a given allele has been amplified or deleted, the ratio of ratios between matched tumor and normal samples is calculated, e.g., $r=(g1_{tumor}/c1_{tumor})/(g1_{normal}/c1_{normal})$. If $r>2$ then g1 is amplified, if $r<0.5$, then g1 is deleted. The identical calculation is also applied to the matched alleles, g2 and c2 which should yield a value of approximately 1.0, except for cases such as K-ras, where one allele may be lost while the other (mutated) allele is amplified. These calculations may be performed with additional informative SNPs in a given region matched with different control regions. Certain SNP/control pairs will amplify at similar rates and, hence, more accurately reflect relative gene copy number.

Examples of the different schemes for distinguishing gene amplification from loss of heterozygosity are illustrated in FIGS. 63-66. These four figures demonstrate how representational PCR/LDR with addressable array capture may be used to distinguish amplification of genes at the DNA level (FIGS. 63-64) or, alternatively, loss of one chromosomal region at that gene (LOH, FIGS. 65-66). Detection of differences using the address complements on the discriminating probes are illustrated in FIGS. 63 and 65, while placing the address complements on the common probes are illustrated in FIGS. 64 and 66.

FIGS. 63-64 illustrate schematically (using pictures of 4 cells) a cancer where the tumor cells (jagged edges) have 4 copies each of one tumor gene allele (C), one copy each of the other tumor gene allele (T), and one copy each of the normal gene alleles (G, A). The normal cells (ovals) have one copy each of the tumor gene alleles (C, T), and one copy each of the normal gene alleles (G, A). By using representational PCR/LDR with addressable array capture (as described above), one can demonstrate that the one tumor gene allele (C) is present at a higher ratio (i.e. 2.5) than the other tumor gene allele as well as the other normal alleles, even in the presence of 50% stromal contamination. Thus, that allele is amplified.

In particular, after the sample of cells is treated to recover its constituent DNA, which is PCR amplified, the amplified DNA is subjected to an LDR procedure. In FIG. 63, the discriminating base is on the oligonucleotide probe with a different addressable array-specific portion for each different discriminating base, while the other oligonucleotide probe is always the same and has the same label. FIG. 64 has the discriminating base on the oligonucleotide probe with the label with different labels being used for each different discriminating base, while the other oligonucleotide probe is always the same and has the same addressable array-specific portion. In either case, whether distinguished by hybridization at different array locations using the same label or by hybridization at any location with each ligation product being distinguished and identified by its label, it is apparent that there is a ratio of C to T alleles of 2.5 and a ratio of G to A alleles of 1.0.

FIGS. 65-66 illustrate schematically (using pictures of 5 cells) a cancer where the tumor cells (jagged edges) have no copies each of one tumor gene allele (T), one copy each of the other tumor gene allele (C), and one copy each of the normal gene alleles (G, A). The normal cells (ovals) have one copy each of the tumor gene alleles (C, T), and one copy each of the normal gene alleles (G, A). By using representational PCR/LDR with addressable array capture (as described above), one can demonstrate that the one tumor gene allele (T) is present at a lower ratio (i.e. 0.4) than the other tumor gene allele as well as the other normal alleles, even in the presence of 40% stromal contamination. Thus, that allele has been lost, i.e. the cell has undergone loss of heterozygosity.

In particular, after the sample of cells is treated to recover its constituent DNA, which is PCR amplified, the amplified DNA is subjected to an LDR procedure. In FIG. 65, the discriminating base is on the oligonucleotide probe with a different addressable array-specific portion for each different discriminating base, while the other oligonucleotide probe is always the same and has the same label. FIG. 66 has the discriminating base on the oligonucleotide probe with the label with different labels being used for each different discriminating base, while the other oligonucleotide probe is always the same and has the same addressable array-specific portion. In either case, whether distinguished by hybridization at different array locations using the same label or by hybridization at any location with each ligation product being distinguished and identified by its label, it is apparent that there is a ratio of C to T alleles of 2.5 and a ratio of G to A alleles of 1.0.

For each example, 10% of the probes containing an addressable array-specific portion are labeled with a fluorescent group (F2 in FIGS. 63 and 65, F3 in FIGS. 64 and 66). To illustrate that LDR ligation efficiencies are not always identical among two alleles of a given gene, in each example, the ratio of C:T tumor gene allele ligations in the normal cells will be set at 60%:40%; while the ratio of G:A control gene allele ligations in the normal cells will be set at 45%:55%. To simplify the calculations, the chromosomes observed in the illustration will be multiplied by 1,000 to obtain a representative value for the amount of ligation product formed in arbitrary fluorescent units. In addition, the total number of probes containing an addressable array-specific portion in a reaction will be arbitrarily set at 100,000, such that 10% of 100,000=10,000 labeled addressable array-specific portion (although not all addresses) will be equally captured. The calculations for the analyses of FIGS. 63-66 are set forth in FIGS. 67-70, respectively.

Further, to illustrate that the technique is independent of either array address spotting or hybridization kinetics, the percent of probes captured will be randomly varied between 30% and 60%. This concept will work even in the absence of a "control" fluorescent label on either the addressable array-specific portion (described herein, FIG. 62) or fluorescent label on the array addresses. This may be achieved by printing two sets of identical arrays on the same polymer surface side-by-side, where both polymer and amount spotted at each address is relatively consistent, using the first array for the tumor sample, and the second array for the normal control. Alternatively, the same array may be used twice, where results are quantified first with the tumor sample, then the array is stripped, and re-hybridized with the normal sample. Large Scale Detection of SNPs Using DrdI Island Representations and DNA Array Capture: Use in Association Studies.

The above sections emphasized the use of SNPs to detect allelic imbalance and potentially LOH and gene amplification associated with the development of colorectal cancer. The PCR/LDR addressable array scheme may also aid in finding low risk genes for common diseases using "identity by descent" (Lander, E. S., "The New Genomics: Global Views of Biology," Science, 274(5287):536-9 (1996) and Risch, et al., "The Future of Genetic Studies of Complex Human Diseases," Science, 273(5281):1516-7 (1996), which are hereby incorporated by reference). In ethnic populations, chromosomal regions in common among individuals with the same disease may be localized to approximately 2 MB regions using a combination of genome mismatch scanning and chromosomal segment specific arrays (Cheung, et al., "Genomic Mismatch Scanning Identifies Human Genomic DNA Shared Identical by Descent," Genomics, 47(1):1-6 (1998); Cheung, et al., "Linkage-Disequilibrium Mapping Without Genotyping," Nat Genet, 18(3):225-230 (1998); McAllister, et al., "Enrichment for Loci Identical-by-Descent Between Pairs of Mouse or Human Genomes by Genomic Mismatch Scanning," Genomics, 47(1):7-11 (1998); and Nelson, et al., "Genomic Mismatch Scanning: A New Approach to Genetic Linkage Mapping," Nat Genet, 4(1):11-8 (1993), which are hereby incorporated by reference). SNPs near the disease gene (i.e. in linkage disequilibrium) will demonstrate allele imbalance compared with the unaffected population. If the SNP is directly responsible for increased risk, then the allele imbalance will be much higher, e.g., the APCI1307K polymorphism is found in 6% in the general Ashkenazi Jewish population, but at approximately 30% among Ashkenazi Jews diagnosed with colon cancer, who have a family history of colon cancer (Laken, et al., "Familial Colorectal Cancer in Ashkenazim Due to a Hypermutable Tract in APC," Nature Genetics, 17(1):79-83 (1997), which is hereby incorporated by reference). If the actual T->A transversion responsible for the condition has been identified, then a SNP analysis to demonstrate allele imbalance will be observed by comparing allele frequency in up to 20 unaffected individuals (94% T, 6% A alleles) to those affected individuals with a family history (70% T, 30% A allele).

Alternatively, suppose the SNP is an ancestral G,A polymorphism found on a DrdI island near the APC gene (with allele frequencies of 0.5) which predates the founder T→A transversion. Suppose this event occured in the A allele, termed A*, and is in linkage disequilibrium, i.e. recombination has not altered the ancestral haplotype (Lander, E. S., "The New Genomics: Global Views of Biology," Science, 274(5287):536-9 (1996) and Risch et al., "The Future of Genetic Studies of Complex Human Disease," Science, 273 (5281):1516-7 (1996), which are hereby incorporated by reference). Then, the allele frequencies are: G=0.5, A=0.44, and A*=0.06. Expanding the formula $(p+q+r)^2=1$ gives expected genotype frequencies of GA=0.44, GG=0.25, AA=0.19, GA*=0.06, AA*=0.05, and A*A*=0.004.

To illustrate the predicted allele imbalance at this ancestral G,A polymorphism, compare predicted allele frequencies in 1,000 normal individuals and 1,000 disease individual with a family history of colon cancer. Then for the normals, 1,000 chromosomes will be scored as the G allele and 1,000 chromosomes will be scored as the A allele (containing 880 "A" and 120 "A*"). Among the affected individuals with a family history, approximately 30% (Laken, et al., "Familial Colorectal Cancer in Ashkenazim Due to a Hypermutable Tract in APC," Nature Genetics, 17(1):79-83 (1997), which is hereby incorporated by reference) or 300 individuals contain the A* allele (comprised of GA*, AA*, or A*A*) and the remaining 70% or 700 individuals do not (comprised of GG, AA, or GA). The number of individuals for each genotype is determined by the number of individuals in category×expected genotype frequency/total of genotype frequency in category. For example, the number of individuals with GA=700×0.44/0.88=350. Other values are: GG=196; AA=156; GA*=159, AA*=132, and A*A*=9 (This calculation assumes that A*A* has the same risk as AA*; the number is small enough to be inconsequential). Summation of the number of each allele yields 350+(196×2)+159=901 G alleles and 350+(156×2)+159+(132×2)+(9×2)=1,099 A alleles, or approximately a 45% G: 55% A allele imbalance. Observation of this imbalance in 400 affected individuals (=800 alleles) would have a p value of 0.005.

Thus, for isolated populations (e.g., Ashkenazi Jews), evaluation of allele imbalance at ancestral polymorphisms by comparing unaffected with affected individuals has the potential for identifying nearby genes with common polymorphisms of low risk. Evaluation of multiple SNPs using PCR/LDR with DNA array detection should aid this analysis. Since the SNP arrays are quantitative, it may be possible to determine allele frequency from pooled DNA samples. Allele number from 4 combined individuals may be calculated by quantifying allele ratios, i.e. ratio of 1:1=4:4 for the two alleles; ratio of 1:1.67=alleles of 3:5; ratio of 1:3=alleles of 2:6; ratio of 1:7=alleles of 1:7; and if one allele is absent then the other is present on all 8 chromosomes represented in the pooled sample. Such ratios may be distinguished using array detection, which would reduce the above experimental analysis to evaluation of 100 pooled normal and 100 pooled affected samples.

A complete set of about 100,000 SNPs will place a SNP every 30 kb. This would require 25 arrays of 4,096 addresses. When comparing association for 400 disease individuals with 400 normal controls, this would require 20,000 array scans and provide the data on 80,000,000 SNPs in the population. PCR and LDR reactions take 2 hours each, but may be done in parallel. The current scheme would only require 20,000 PCR reactions, followed by 20,000 LDR reactions, and finally 20,000 DNA array hybridizations (1 hr), and scannings (a few minutes per array). This is far more efficient than the current technology which evaluates one SNP at a time.

The SNP DNA array analysis simultaneously provides predicted association for all the affected genes of any prevalent disease (e.g., Alzheimers, heart disease, cancer, diabetis). It will find both positive and negative modifier genes, it will find genes with low penetrance increase for risk, and will map to within 30 kb of all genes which influence the disease. This approach will allow for pinpointing additional polymorphisms within the disease associated genes, opening the prospect for customized treatments and therapies based on pharmacogenomics.

EXAMPLES

Example 1

Demonstration of T4 DNA Ligase Fidelity in Ligating Linker/Adapters to Only Their Complementary 2 Base 3' Overhangs Using Synthetic Targets Ligation reactions with T4 DNA ligase and a variety of linker/adapters (GG-, AA-, AG-, and GA-) and synthetic targets (Tables 13 and 14) were performed to determine the fidelity of T4 DNA ligase under various experimental conditions.

TABLE 13

*DrdI* and *Msp/Taq* Bubble linkers and PCR primers for BAC clones

| Primer | Sequence (5'→3') | |
|---|---|---|
| BAA29 | 5' TAG ACT GCG TAC TCT AA 3' | (SEQ. ID. No. 77) |
| BAA3034R | 5' pA GAG TAC GCA GTC TAC GAC TCA GG 3' | (SEQ. ID. No. 78) |
| BAAP31 | 5' CCT GAG TCG TAG ACT GCG TAC TCT AA 3' | (SEQ. ID. No. 79) |
| BAAP32-FAM | 5' FAM-CCT GAG TCG TAG ACT GCG TAC TCT AA 3' | (SEQ. ID. No. 80) |
| BAC33 | 5' TAG ACT GCG TAC TCT AC 3' | (SEQ. ID. No. 81) |
| BACP35 | 5' CCT GAG TCG TAG ACT GCG TAC TCT AC 3' | (SEQ. ID. No. 82) |
| BACP36-FAM | 5' FAM-CCT GAG TCG TAG ACT GCG TAC TCT AC 3' | (SEQ. ID. No. 83) |
| BAG37 | 5' TAG ACT GCG TAC TCA AG 3' | (SEQ. ID. No. 84) |
| BAG37b | 5' Biotin-C18-ACT GAG TCG TAG ACT GCG TAC TCA AG 3' | (SEQ. ID. No. 85) |
| BAG38R | 5' pT GAG TAC GCA GTC TAC GAC TCA GT 3' | (SEQ. ID. No. 86) |
| BAGP39 | 5' ACT GAG TCG TAG ACT GCG TAC TCA AG 3' | (SEQ. ID. No. 87) |
| BAGP40-FAM | 5' FAM-ACT GAG TCG TAG ACT GCG TAC TCA AG 3' | (SEQ. ID. No. 88) |
| BCA41 | 5' TAG ACT GCG TAC TCT CA 3' | (SEQ. ID. No. 89) |
| BAC41b | 5' Biotin-C18-ACT GAG TCG TAG ACT GCG TAC TCT CA 3' | (SEQ. ID. No. 90) |
| BCA4246R | 5' pA GAG TAC GCA GTC TAC GAC TCA GT 3' | (SEQ. ID. No. 91) |
| BCAP43 | 5' ACT GAG TCG TAG ACT GCG TAC TCT CA 3' | (SEQ. ID. No. 92) |
| BCAP44-FAM | 5' FAM-ACT GAG TCG TAG ACT GCG TAC TCT CA 3' | (SEQ. ID. No. 93) |
| BGA45 | 5' TAG ACT GCG TAC TCT CA 3' | (SEQ. ID. No. 94) |
| BGAP47 | 5' ACT GAG TCG TAG ACT GCG TAC TCT CA 3' | (SEQ. ID. No. 95) |
| BGAP48-FAM | 5' FAM-ACT GAG TCG TAG ACT GCG TAC TCT GA 3' | (SEQ. ID. No. 96) |
| BGG49 | 5' TAG ACT GCG TAC TAT GG 3' | (SEQ. ID. No. 97) |
| BGG50R | 5' pA TAG TAC GCA GTC TAC GAC TCA GT 3' | (SEQ. ID. No. 98) |
| BGGP51 | 5' ACT GAG TCG TAG ACT GCG TAC TAT GG 3' | (SEQ. ID. No. 99) |
| BGGP52-FAM | 5' FAM-ACT GAG TCG TAG ACT GCG TAC TAT GG 3' | (SEQ. ID. No. 100) |

TABLE 14

Targets for ligation experiments in synthetic system.

| Primer | Sequence (5'→3') | |
|---|---|---|
| L53FL | 5' pCAT TCA GGA CCT GGA TTG GCG A- Fluoroscein 3' | (SEQ. ID. No. 101) |
| TT54R-FAM | 5' Fam-TCG CCA ATC CAG GTC CTG AAT GTT 3' | (SEQ. ID. No. 102) |
| CC55R-FAM | 5' Fam-TCG CCA ATC CAG GTC CTG AAT GCC 3' | (SEQ. ID. No. 103) |
| CT56-FAM | 5' Fam-attaTCG CCA ATC CAG GTC CTG AAT GCT 3' | (SEQ. ID. No. 104) |
| TC57-FAM | 5' Fam-attaattaTCG CCA ATC CAG GTC CTG AAT GTC 3' | (SEQ. ID. No. 105) |

Synthetic targets were fluorescently labeled with Fam and of different lengths such that correct perfect match from unwanted mismatch ligations could be distinguished when separating products on a sequencing gel. Reactions were performed in a 20 µL volume in a modified T4 DNA ligase buffer (20 mM Tris-HCl (pH 7.5), 10 mM $MgCl_2$, 10 mM dithiothreitol, 1 mM dATP, and 2.5 µg/ml BSA) and contained 5 nM ligation target. Products were separated on a denaturing polyacrylamide sequencing gel and quantified using an ABI 373 automated sequencer and GENESCAN software. The effect of T4 DNA ligase enzyme concentration (100 U or 400 U, New England Biolabs units), KCl concentration (50 mM or 100 mM), linker/adapter concentration (50 or 500 nM linker/adapter), temperature (15° C. or 37° C.), and time (1 hr or 16 hr) on T4 ligase fidelity and activity was examined.

All of the reactions generated the correct ligation product with no detectable misligation product (FIG. 71). The total concentration of linker/adapter and KCl concentration sometimes had an effect on overall activity. From these assays, the optimal conditions for ligation reactions associated with the DrdI representational approach was determined to be 100 U T4 DNA ligase (New England Biolabs units), 500 nM linker/adapter, 50 mM KCl, 20 mM Tris-HCl (pH 7.5), 10 mM $MgCl_2$, 10 mM dithiothreitol, 1 mM dATP, and 2.5 µg/ml BSA in a 20 µL reaction incubated at 37° C. for 1 h. This condition is the preferred condition, because it is compatible with the restriction enzymes used to generate DrdI representations. Although this condition is optimal for T4 DNA ligase, detectable activity was observed under all of the tested combinations of parameters listed above. For other linker adapter sequences of restriction enzyme overhangs, conditions may be optimized using this assay.

Example 2

Demonstration of Restriction Digestion and Specific Ligation of Linker/Adapters to Their Complementary Overhangs Followed by PCR Amplification of the Correct Fragment Specificity and reproducibility of DrdI Restriction/Ligation/PCR were tested in two vectors (pBeloBAC11 and pBACe3.6) and a BAC clone. BAC DNA (5-10 ng) was digested with DrdI, MspI, and TaqI and, simultaneously, ligated with 500 nM of the appropriate linker/adapters in the presence of T4 DNA ligase. Linker/adapters containing 2 base 3' overhangs complementary to the DrdI site (BAA29+ BAA3034R for AA overhangs, BAC33+BAA3034R for AC overhangs, BAG37+BAG38R for AG overhangs, BCA41+ BCA4246R for CA overhangs, BGA45+BCA4246R for GA overhangs, and BGG49+BGG50R for GG overhangs) are listed in Table 13. Linker/adapters containing 2 base 5' overhangs complementary to the CG overhang of MspI or TaqI sites (MTCG225+MTCG0326R or MTCGp326R) are listed in Table 8. The MTCG225/MTCG0326R and MTCG225/MTCGp326R linker adapters contain a bubble to avoid unwanted MspI-MspI, TaqI-MspI, or TaqI-TaqI fragment amplifications. This digestion/ligation reaction was performed in a buffer containing 20 mM Tris-HCl (pH 7.5), 10 mM $MgCl_2$, 50 mM KCl, 10 mM dithiothreitol, 1 mM dATP, and 2.5 µg/ml BSA. Reactions were incubated at 37° C. for one hour followed by an 80° C. incubation for 20 min in order to heat inactivate the enzymes. Since TaqI is a thermophilic enzyme, 10-fold more units were used to counterbalance the 10-fold lower activity at 37° C. This enzyme is fully inactivated by the above heating step.

To remove fragments and linkers with sizes smaller than 100 bps, the digestion/ligation reaction was microcentrifuged with an Amicon YM-50. First, the sample was centrifuged at 8000 rpm for 8 min, then the filter was inverted and the desired products were recovered by centrifuging at 6000 rpm for 3 min. After recovery, the sample volume was brought up to 20 µL with $ddH_2O$ for PCR amplification.

PCR reactions contained the YM-50 purified digestion/ligation reaction (20 µl), 1×PCR buffer (10 mM Tris-HCl (pH 8.3), 50 mM KCl), 4 mM $MgCl_2$, 0.4 mM dNTPs, 1.25 U AmpliTaq Gold, and 0.5 µM PCR primers in a 50 µl reaction. The PCR reactions were initially incubated at 95° C. for 10 min (to activate AmpliTaq Gold polymerase) followed by 35 cycles of 94° C., 15 sec; 65° C., 2 min.

Assays performed with pBeloBAC11 or pBACe3.6 resulted in even amplification of 2 fragments for GA-overhangs and 1 fragment each for AA- or CA-overhangs as predicted based on the presence of these overhangs in the plasmids. Similar assays were performed with BAC RG253B13 and also generated the expected results (2 fragments for GA-overhangs and 3 fragments for AA-overhangs respectively, see FIGS. 46A-B and D). The larger 3,419 bp GA fragment was not observed, because it was not expected to be amplified. These results demonstrate that the restriction digestion was sufficiently complete and the ligation and PCR reactions were specific for the desired products.

Example 3

Suppression of Amplification of Vector Derived Sequence While Amplifying the Correct Fragment The PCR amplification of DrdI fragments derived from the vector sequence were suppressed using PNA or propynyl clamping oligos. A slightly modified protocol was used when PCR amplifying DrdI fragments containing AA, CA, or GA overhangs from BACs derived from the pBeloBAC11 or pBACe3.6 vector. The pBeloBAC11 and pBACe3.6 vectors both contain DrdI sites complementary to AA-, CA-, and GA-overhangs, and amplification of these vector fragments needed to be suppressed. Clamping oligos which bind specific DrdI fragments (i.e. vector derived) and block annealing of PCR primers, were designed as PNA or propynyl derivatives (Tables 5 and 6).

BAC DNA (5-10 ng) was digested with DrdI, MspI, and TaqI and simultaneously ligated with 500 nM of the appropriate linker/adapters in the presence of T4 DNA ligase in a buffer containing 20 mM Tris-HCl (pH 7.5), 10 mM $MgCl_2$, 50 mM KCl, 10 mM dithiothreitol, 1 mM dATP, and 2.5 µg/ml BSA. Reactions were incubated at 37° C. for one hour followed by an 80° C. incubation for 20 min in order to heat inactivate the enzymes. Fragments and excess linker/adapter less than 100 bp were removed by ultrafiltration on Amicon YM50 filters as described above. PCR reactions contained the YM-50 purified digestion/ligation reaction (20 µl), 1× PCR buffer (10 mM Tris-HCl (pH 8.3), 50 mM KCl), 4 mM $MgCl_2$, 0.4 mM dNTPs, 1.25 U AmpliTaqGold, 1 µM of clamping oligos, and 0.5 µM PCR primers in a 50 µl reaction. The PCR reactions were initially incubated at 95° C. for 10 min (to activate AmpliTaq Gold polymerase) followed by 35 cycles of 94° C., 15 sec; 65° C., 2 min. DrdI Restriction/ Ligation/PCR assays were performed with pBACe3.6 and 1 µM clamping oligos. In one reaction, AA-linker/adapters were ligated to digested vector. This sample was PCR amplified in the presence of a AA-clamping oligo specific for suppressing amplification of AA-DrdI fragment associated with only the vector sequence. No vector derived PCR product was observed with both the PNA and propynyl clamping oligos. In a subsequent experiment, CA- and AA-linker/ adapters were present simultaneously in the digestion/ligation reaction of pBACe3.6. This reaction was then PCR amplified in the presence of 1 µM AA-clamping oligo (either PNA or propynyl derivative). No AA-product was observed with both the PNA and propynyl clamping oligo, but the amplification of the CA-fragment was unaffected by the presence of the AA-clamp. Similar assays were performed with BAC RG253B13 and also generated the expected number of amplified fragments, depending on which clamps were being used. These results demonstrate the ability of PNA or propynyl clamping oligos to specifically suppress amplification of an undesired fragment, while having no measurable effect on the amplification of desired fragments.

Example 4

Enrichment of DrdI Representational Fragments Using Biotinylated Linker/Adapters and Streptavidin Purification Creation of a library of representational fragments is required to rapidly sequence those fragments and discover SNPs. While a PCR amplification reaction may enrich for a particular representation, there also is the possibility of generating false SNPs through polymerase error. An approach to minimizing false SNPs is to pre-select the representational fragments, and/or avoid amplification altogether. This may be achieved by using biotinylated linker/adapters to a specific DrdI overhang, followed by purification of only those fragments using streptavidin beads.

While genomic DNA will ultimately be used for this task, BAC DNA was used in this example since proof of the correct selection is easily achieved by demonstrating that the correct fragments amplified. BAC DNA (5-10 ng) was digested with DrdI, MspI, and TaqI and simultaneously ligated with 500 nM of the appropriate linker/adapters in the presence of T4 DNA ligase. Linker/adapters containing 2 base 3' overhangs complementary to the DrdI site (BAG37b+BAG38R for AG overhangs and BCA41b+BCA4246R for CA overhangs) are listed in Table 13. Linker/adapters containing 2 base 5' overhangs complementary to the CG overhang of MspI or TaqI sites (MTCG225+MTCG0326R or MTCGp326R) are listed in Table 8. The MTCG225/MTCG0326R and MTCG225/ MTCGp326R linker adapters contain a bubble to avoid unwanted MspI-MspI, TaqI-MspI, or TaqI-TaqI fragment amplifications. This digestion/ligation reaction was performed in a buffer containing 20 mM Tris-HCl (pH 7.5), 10 mM $MgCl_2$, 50 mM KCl, 10 mM dithiothreitol, 1 mM dATP, and 2.5 µg/ml BSA. Reactions were incubated at 37° C. for one hour followed by an 80° C. incubation for 20 min in order to heat inactivate the enzymes. Fragments and excess linker/ adapter less than 100 bp were removed by ultrafiltration on Amicon YM50 filters as described above.

The purification procedure was as follows: (streptavidin magnetic beads and the purification protocol were obtained from Boehringer Mannheim, Indianapolis, Ind.) 10 µl of (10 µg/µl) magnetic beads were washed three times with binding buffer $TEN_{100}$ (10 mM Tris-HCl (pH7.5), 1 mM EDTA, 100 mM NaCl). The sample (YM-50 purified digestion/ligation reaction) volume was brought up to 100 µl in binding buffer and incubated with washed beads for 30 min (constantly shaking using a neutator or rotating platform). The pellet was washed 2 times with $TEN_{1000}$ (10 mM Tris-HCl (pH7.5), 1 mM EDTA, 1000mM NaCl) and then washed once in 1× PCR buffer (10 mM Tris-HCl (pH 8.3), 50 mM KCl), 4 mM $MgCl_2$). The sample was eluted in 30 µl 1× PCR buffer by incubating at 95° C. for 5 min, capturing the beads in the magnetic stand for 30 sec at 95° C., followed by immediate removal of the supernatant at the bench. After the streptavidin purification, dNTPs (0.4 mM final concentration), PCR primers (0.5 µM final) and dd$H_2O$ is added to the purified sample to increase the volume to 50 µl. AmpliTaqGold (1.25 U) is added, with PCR reactions initially incubated at 95° C. for 10 min (to activate AmpliTaq Gold polymerase), followed by 35 cycles of 94° C., 15 sec; 65° C., 2 min.

In assays with pBACe3.6, biotinylated CA-linker/adapters, and non-biotinylated AA linker/adapters, streptavidin purification resulted in only the CA-linker fragment being PCR amplified. Conversely, both CA- and AA-linker fragments were amplified in the control assay without the streptavidin purification step. This result demonstrates that streptavidin purification can be utilized to enrich for specific linker/ adapter products prior to the PCR amplification.

Example 5

Amplification of DrdI Representations from the S. cerevisiae Genome

The more complex S. cerevisiae genome (16 Mb) was chosen as a more complex model system than individual BACs, but still at $\frac{1}{200}^{th}$ the complexity of the human genome. 100 ng of S. cerevisiae genomic DNA was subjected to the same protocol as the BAC DNA as described above. Digestion/ligation reactions were PCR amplified using 7 separate primers with either 2 or 3 base selectivity (AC, CA, GA, AG, GG, CAG, and CAT). A fragment appeared as a band above background in the CA-representation, suggesting the presence of a repetitive element. This band was 2- to 4-fold stronger in the CAG representation, yet absent in the CAT representation. This indicates that PCR primers can also be utilized to alter the size and complexity of a representation. Inclusion of a size filtration step (Amicon YM-50) before PCR amplification resulted in amplification of a broader representation (based on size) as assayed on an agarose gel.

Example 6

Amplification of DrdI Representations from the Human Genome

Human DNA has a complexity of 3,500 Mb, and is predicted to contain about 300,000 DrdI sites. A DrdI representation using three bases of selectivity should amplify about 8,750 fragments, yielding about 0.2% of the genome. A DrdI representation using four bases of selectivity should amplify about 2,200 fragments, yielding about 0.05% of the genome. 100 ng of human genomic DNA obtained from Boehringer-Mannheim was digested with 10 U DrdI, 20 U MspI, and 100 U TaqI and simultaneously ligated with 500 nM of the appropriate DrdI linker/adapter and 1,000 nM of the MspI/TaqI linker/adapter in the presence of T4 DNA ligase. Linker/adapters containing 2 base 3' overhangs complementary to the DrdI site (BAG37+BAG38R for AG overhangs, and BCA41+BCA4246R for CA overhangs) are listed in Table 13. Linker/adapters containing 2 base 5' overhangs complementary to the CG overhang of MspI or TaqI sites (MTCG225+MTCG0326R) are listed in Table 8. This digestion/ligation reaction was performed in a buffer containing 20 mM Tris-HCl (pH 7.5), 10 mM MgCl$_2$, 50 mM KCl, 10 mM dithiothreitol, 1 mM dATP, and 2.5 µg/ml BSA. Reactions were incubated at 37° C. for one hour followed by an 80° C. incubation for 20 min in order to heat inactivate the enzymes. Fragments and excess linker/adapter less than 100 bp were removed by ultrafiltration on Amicon YM50 filters as described above.

PCR reactions contained the YM-50 purified digestion/ligation reaction (20 µl), 1× PCR buffer (10 mM Tris-HCl (pH 8.3), 50 mM KCl), 4 mM MgCl$_2$, 0.4 mM dNTPs, 1.25 U AmpliTaqGold, and 0.5 µM PCR primers in a 100 µl reaction. The PCR primer on the MspI/TaqI side was MTCG228 and is listed in Table 8. The PCR primers on the DrdI side were complementary to the linker/adapter, and had either 3 or 4 bases of specificity (e.g. primer CATP58=3 base CAT specificity, primer CAGP59=3 base CAG specificity, primer AGAP60=3 base AGA specificity, primer AGAP61=3 base AGC specificity, primer AGATP62=4 base AGAT specificity, primer AGAGP63=4 base AGAG specificity, primer CATGP64=4 base CATG specificity, and primer CAGTP65=4 base CAGT specificity) and are listed in Table 15.

TABLE 15

PCR primers for representational PCR/LDR/Arrays.

| Primer | Sequence (5'→3') | |
|---|---|---|
| CATP58 | 5' CT GAG TCG TAG ACT GCG TAC TCT CAT 3' | (SEQ. ID. No. 106) |
| CAGP59 | 5' CT GAG TCG TAG ACT GCG TAC TCT CAG 3' | (SEQ. ID. No. 107) |
| AGAP60 | 5' CT GAG TCG TAG ACT GCG TAC TCA AGA 3' | (SEQ. ID. No. 108) |
| AGCP61 | 5' CT GAG TCG TAG ACT GCG TAC TCA AGC 3' | (SEQ. ID. No. 109) |
| AGATP62 | 5' CT GAG TCG TAG ACT GCG TAC TCA AGA T 3' | (SEQ. ID. No. 110) |
| AGAGP63 | 5' CT GAG TCG TAG ACT GCG TAC TCA AGA G 3' | (SEQ. ID. No. 111) |
| CATGP64 | 5' CT GAG TCG TAG ACT GCG TAC TCT CAT G 3' | (SEQ. ID. No. 112) |
| CAGTP65 | 5' CT GAG TCG TAG ACT GCG TAC TCT CAG T 3' | (SEQ. ID. No. 113) |

The "regular PCR" reactions were initially incubated at 95° C. for 10 min (to activate AmpliTaq Gold polymerase) followed by 35 cycles of 94° C., 15 sec; 65° C., 2 min. Another set of PCR condition called "touchdown PCR" was tested in addition to the "regular PCR" as described previously. The "touchdown PCR" protocol consisted of heating for 10 min at 95° C. followed by 8 cycles of denaturing for 15 sec at 94° C., annealing/extension for 2 min at 72° C. The annealing/extension temperature was reduced 1° C. for each cycle until a final temperature of 64° C. Another 30 cycles of PCR were performed with denaturing 15 sec at 94° C. and annealing/extension for 2 min at 64° C. Each sample was performed in quadruplicate, and the 400 µl PCR products were pooled and concentrated by ultrafiltration on Amicon YM50 filters as described above. Final samples were brought up in 20 µl TE.

PCR amplification of human genome representations (CA- or AG-linker/adapters) were performed with a variety of 3 and 4 base selection primers (e.g., CAG, CAT, CAGT, CATG, AGC, AGA, AGAT, and AGAG). The agarose gel analysis demonstrated apparently equal and broad representation for each of the above PCR primers (FIG. 72).

To verify that these human genomic DrdI representations were selecting the appropriate fragments, LDR assays were performed to probe for specific fragments within a given representation. LDR conditions used 4 µl of the concentrated representational fragments from the above mentioned PCR reactions, 1× Tth DNA ligase buffer (20 mM Tris-HCl pH 8.5, 5 mM MgCl$_2$, 100 mM KCl, 1 mM DTT, 1.25 mM NAD$^+$), 2.5 nM LDR probes. Tth DNA ligase (in buffer containing 10 mM Tris-HCl pH 8.0, 1 mM EDTA, 1 mg/ml BSA) was added to the reaction to a final concentration of 5 nM. The LDR reaction was carried out with 20 cycles of heating at 95° C. for 15 sec and ligation at 64° C. for 2 min. Three microliters of the LDR reaction product was loaded on the gel and the gel image was read by GeneScan Analysis 2.02. Control assays containing PCR products generated from primers (Tables 16 and 17) designed for each of the targeted regions demonstrated the integrity of LDR assays (FIG. 73).

TABLE 16

Primers Designed for Detection of Polymorphisms Near *DrdI* Sites by PCR/LDR.

| Primer | Sequence (5'→3') | |
|---|---|---|
| Uni A primer | GGAGCACGCTATCCCGTTAGAC | (SEQ. ID. No. 114) |
| Uni B2 primer | CGCTGCCAACTACCGCACATC | (SEQ. ID. No. 115) |
| B13 AGA fp1 | GGAGCACGCTATCCCGTTAGACCCCTGCAATGACTCCCCATTTC | (SEQ. ID. No. 116) |
| B13 AGA rp1 | CGCTGCCAACTACCGCACATCAGTAGGGCTGGGGCATCAGAAC | (SEQ. ID. No. 117) |
| B13 AGA Fam1 (F-1) | Fam aGCTTCAGACACACCAGGCAC = 47 | (SEQ. ID. No. 118) |
| B13 AGA -Com1 (C-1) | pATTTAGTTCTTCCTTCTTGCCTCTGC-Bk | (SEQ. ID. No. 119) |
| B13 AGC fp2 | GGAGCACGCTATCCCGTTAGACATTGTGGAAGACAGTGTGGTGATTC | (SEQ. ID. No. 120) |
| B13 AGC rp2 | CGCTGCCAACTACCGCACATCCATGGCATATATGTGCCACATTTTC | (SEQ. ID. No. 121) |
| B13 AGC Fam2 (F-2) | FamAAGCATGCTGCTGTAAAGACACA = 52C | (SEQ. ID. No. 122) |
| B13 AGC -Com2 (C-2) | PTGCACATGTATGTTTATTGCAGCACTATT-Bk | (SEQ. ID. No. 123) |
| E19 AGC fp3 | GGAGCACGCTATCCCGTTAGACGTGTTAGCCAGGATGGTCTCCATCC | (SEQ. ID. No. 124) |
| E19 AGC rp3 | CGCTGCCAACTACCGCACATCCATGGGTGGGGTAACAGAAAGAAAC | (SEQ. ID. No. 125) |
| E19 AGC Fam3 (F-3) | FamGACAATTATCCTGATTTGGGACC = 48C | (SEQ. ID. No. 126) |
| E19 AGC -Com3 (C-3) | pTTACCTTCAGATGGTTTTCCCTCCT-Bk | (SEQ. ID. No. 127) |
| C03 AGA fp4 | GGAGCACGCTATCCCGTTAGACTAGTGTCTAGGGATAGAGGAGAAC | (SEQ. ID. No. 128) |
| C03 AGA rp4 | CGCTGCCAACTACCGCACATCCTCCTGACATTATGGAGAGCCTTAC | (SEQ. ID. No. 129) |
| C03 AGA Fam4 (F-4) | FamAATGCCACACTTCAGATTTTGATAC = 50 | (SEQ. ID. No. 130) |
| C03 AGA -Com4 (C-4) | pTTGCAGGATCCTATTTCTGGCACTA-Bk | (SEQ. ID. No. 131) |
| UniAprimer | GGAGCACGCTATCCCGTTAGAC | (SEQ. ID. No. 132) |
| UniB2primer | CGCTGCCAACTACCGCACATC | (SEQ. ID. No. 133) |
| P20 AGA fp5 | GGAGCACGCTATCCCGTTAGACGGACTTCTCCCCACTACAACATAGATTC | (SEQ. ID. No. 134) |
| P20 AGA rp5 | CGCTGCCAACTACCGCACATCTTTATCAGCAACATGAAAACAGACTAAC | (SEQ. ID. No. 135) |
| P20 AGA Fam5 (F-5) | FamTGTGGAATTTATCATTTAATTTAGCTTC = 56 | (SEQ. ID. No. 136) |
| P20 AGA -Com5 (C-5) | pAGTGAACCGTTCTTTCCAGATTATTTTG-Bk | (SEQ. ID. No. 137) |
| K23 AGA fp6 | GGAGCACGCTATCCCGTTAGACAGAATAGAATGCTTGCAATTGATCAC | (SEQ. ID. No. 138) |
| K23 AGA rp6 | CGCTGCCAACTACCGCACATCATGTCAATTTGTTGGGGTTATACAAC | (SEQ. ID. No. 139) |
| K23 AGA Fam6 (F-6) | Fam aaaaAGGAGGGTGACAGTGAACCTG = 53 | (SEQ. ID. No. 140) |
| K23 AGA -Com6 (C-6) | pGAGGTAAAATTCAACAATTCATTTGCTT-Bk | (SEQ. ID. No. 141) |
| J17 AGA fp7 | GGAGCACGCTATCCCGTTAGACGTGCAGACAAGAGAATGTCAAGTTTC | (SEQ. ID. No. 142) |
| J17 AGA rp7 | CGCTGCCAACTACCGCACATCAGAGGCTGGAAAAATAAATCCAATACA | (SEQ. ID. No. 143) |
| J17 AGA Fam7 (F-7) | FamGATCAGAAACCACAGGAAATTTG = 44 | (SEQ. ID. No. 144) |
| J17 AGA -Com7 (C-7) | pATTTATGCCAGCCCTGCATCCC-Bk | (SEQ. ID. No. 145) |
| AGATP62 | CTGAGTCGTAGACTGCGTACTCTAGAT | (SEQ. ID. No. 146) |
| AGAGP63 | CTGAGTCGTAGACTGCGTACTCTAGAG | (SEQ. ID. No. 147) |

TABLE 16-continued

Primers Designed for Detection of Polymorphisms Near DrdI Sites by PCR/LDR.

| Primer | Sequence (5'→3') | |
|---|---|---|
| CATGP64 | CTGAGTCGTAGACTGCGTACTCTCATG | (SEQ. ID. No. 148) |
| CAGTP65 | CTGAGTCGTAGACTGCGTACTCTCAGT | (SEQ. ID. No. 149) |

TABLE 17

Primers designed for detection of polymorphisms near DrdI sites by PCR/LDR/Array Hybridization.

| Primer | Sequence (5'→3') | |
|---|---|---|
| Uni A primer | GGAGCACGCTATCCCGTTAGAC | (SEQ. ID. No. 150) |
| Uni B2 primer | CGCTGCCAACTACCGCACATC | (SEQ. ID. No. 151) |
| GS056H18.2 forward | GGAGCACGCTATCCCGTTAGACGATGAGCTTACACAGGCACTGATTAC | (SEQ. ID. No. 152) |
| GS056H18.2 reverse | CGCTGCCAACTACCGCACATCTATTGGTGACTGATGAAAATGTCAAAC | (SEQ. ID. No. 153) |
| GS056H18.2 | Fam-tGTCAAGAAAGTGTATTTAGCTTACAAAC = 58 | (SEQ. ID. No. 154) |
| GS056H18.2 -Com2 | PTATTAACAGCCTGTTTTACCCTACTTTTG-Bk | (SEQ. ID. No. 155) |
| RG083J23 forward | GGAGCACGCTATCCCGTTAGACGCACCTTATCTTGGCTTTTCTATTC | (SEQ. ID. No. 156) |
| RG083J23 reverse | CGCTGCCAACTACCGCACATCAAGCATATTACATCATGTCATCACTTC | (SEQ. ID. No. 157) |
| RG083J23 | Fam-TTCGTTTCTCTTTATCCACACC = 52 | (SEQ. ID. No. 158) |
| RG083J23 -Com3 | pATGGGAAATGTCTTTTACAATGTACATAAC-Bk | (SEQ. ID. No. 159) |
| RG103H13 forward | GGAGCACGCTATCCCGTTAGACCAGCCATGTGATTCCCTGTGTAC | (SEQ. ID. No. 160) |
| RG103H13 reverse | CGCTGCCAACTACCGCACATCCTGCATTGTACAATGCATGCATAC | (SEQ. ID. No. 161) |
| RG103H13 | Fam-aaatataaACTAAATGAATCAAAGATAGAGTGAATG = 60 | (SEQ. ID. No. 162) |
| RG103H13 -Com4 | pTATGCATGCATTGTACAATGCAGG-Bk | (SEQ. ID. No. 163) |
| RG103H13.2 forward | GGAGCACGCTATCCCGTTAGACTTCTGATAGAGTCGTTTTGTGCTTC | (SEQ. ID. No. 164) |
| RG103H13.2 reverse | CGCTGCCAACTACCGCACATCCATTTTAGGATCTGGGAAGCATTAC | (SEQ. ID. No. 165) |
| RG103H13.2 | Fam-TTTTTCCTCCCATCCAAATTC = 46 | (SEQ. ID. No. 166) |
| RG103H13.2 -Com5 | pAGAGACCCTAGAATTCTAGCGATGG-Bk | (SEQ. ID. No. 167) |
| UniAprimer | GGAGCACGCTATCCCGTTAGAC | (SEQ. ID. No. 168) |
| UniB2primer | CGCTGCCAACTACCGCACATC | (SEQ. ID. No. 169) |
| RG118D07 forward | GGAGCACGCTATCCCGTTAGACCCTTGGAAAGCAGGTGCAAATC | (SEQ. ID. No. 170) |
| RG118D07 reverse | CGCTGCCAACTACCGCACATCAAATAACAACTGCATTACTCCATCATC | (SEQ. ID. No. 171) |
| RG118D07 | Fam-aaTGAAAAAATCCAATATTGGTCTG = 55 | (SEQ. ID. No. 172) |
| RG118D07 Com6 | pTGTGTGAAAGTGTAAATGTATACGTGTATG-Bk | (SEQ. ID. No. 173) |
| RG343P13 forward | GGAGCACGCTATCCCGTTAGACCTGTCAAGCAGGGAATTGGATAC | (SEQ. ID. No. 174) |
| RG343P13 reverse | CGCTGCCAACTACCGCACATCCCTTTCTGATTTCAGTTGCTAGTTTC | (SEQ. ID. No. 175) |
| RG343P13 | Fam-GAGACCAAACCAGGGAGAAAG = 50 | (SEQ. ID. No. 176) |
| RG343P13 -Com-7 | pTACAGAGAGAGCAAAGAGAGTTCAGAC-Bk | (SEQ. ID. No. 177) |
| RG363E19.2 forward | GGAGCACGCTATCCCGTTAGACTGGAGGTCCTAGCCAGAGCAAC | (SEQ. ID. No. 178) |
| RG363E19.2 reverse | CGCTGCCAACTACCGCACATCGGTATTGCCTTTCTGATTTAGCTTTC | (SEQ. ID. No. 179) |

TABLE 17-continued

Primers designed for detection of polymorphisms near DrdI sites by PCR/LDR/Array Hybridization.

| Primer | Sequence (5'→3') | |
|---|---|---|
| RG363E19.2 | Fam-aGCCCAAAAGCTCCTTCAGC = 48 | (SEQ. ID. No. 180) |
| RG363E19.2-Com-9 | pTGATAAACAACTTCAGCAAAGTTTCAGG-Bk | (SEQ. ID. No. 181) |

In addition, these control PCR products were diluted up to 10,000-fold into 10 µg salmon sperm DNA. Even in this vast excess of noncomplementary DNA, LDR assays still identified the desired products.

The targeted DrdI-MspI/TaqI fragments ranged in size from 130 to 1,500 bp and were derived from AG- or CA-linker/adapters. LDR assays of the human representational libraries demonstrated that the representations were even and that increasing base reach-in generated a more specific library (FIGS. 74 and 75). This result demonstrates that LDR is sensitive enough to identify a specific DrdI-MspI/TaqI fragment within a given representation.

Altering the PCR conditions to "touchdown" amplification resulted in more LDR product with no apparent change in the relative distribution of fragments. These results demonstrated that the DrdI representational approach was able to generate an even and specific representation of the human genome.

Although the invention has been described in detail for the purpose of illustration, it is understood that such detail is solely for that purpose, and variations can be made therein by those skilled in the art without departing from the spirit and scope of the invention which is defined by the following claims.

---

What is claimed:

1. A method of assembling a map of an organism's genome or portions thereof comprising:

providing a library of an organism's DNA, wherein individual genomic segments are found in more than one clone in the library with at least some of the said individual genomic segments have overlapping DNA sequences;

creating representations of the genomic segments in individual clones by selecting a subpopulation of genomic segments out of a larger set of the genomic segments in each of the individual clones, wherein said selecting a subpopulation of genomic segments comprises: subjecting more than one individual clone to a restriction endonuclease, wherein the restriction endonuclease is effective in recognizing a restriction site recognition sequence and cleaving the DNA in said more than one individual clone at a restriction site of the restriction site recognition sequence thereby creating a plurality of clone fragments having 2 base overhangs and adding 1 to 12 linker-adapters, each of which is non-palindromic, to the overhangs in the presence of ligase and the restriction endonuclease and producing a plurality of clone fragments comprising said 1 to 12 linker-adapters, wherein said plurality of clones fragments comprising said 1 to 12 linker-adapters are selected as the representations, wherein the linker-adapters contain single stranded overhangs of a formula NN/N'N' where said NN/N'N' is selected from the group consisting of AA/TT, AC/GT, AG/CT, CA/TG, GA/TC, and GG/CC;

generating DNA sequence information from the representations;

analyzing the DNA sequence information thereby determining clone overlap from the representations; and combining said clone overlap and DNA sequence information from the representations thereby assembling a map of the organism's genome or portions thereof.

2. The method according to claim 1, wherein said adding 1 to 12 linker-adapters is carried out by adding 4 to 6 of said linker-adapters.

3. The method according to claim 1, wherein the restriction endonuclease is selected from the group consisting of DrdI, BglI, DraIII, AlwNI, PflMI, AccI, BsiHKAI, SanDI, SexAI, PpuI, AvaII, EcoO109, Bsu36I, BsrDI, BsgI, BpmI, SapI, and isoschizomers thereof.

4. The method according to claim 1, wherein said generating DNA sequence information is carried out by DNA sequencing reactions using one or more sequencing primers.

5. The method according to claim 4, wherein the sequencing primers have a 5' sequence that is complementary to the linker-adapters and have a 3' sequence that is complementary to the 2 base overhangs and/or adjacent to the restriction site recognition sequence in the DNA sequencing reactions to obtain sequence information adjacent to the restriction site.

6. The method according to claim 5, wherein said one or more sequencing primers are 1 to 12 sequencing primers, wherein the sequencing primers have 3' ends of NN or N'N', with said N being any nucleotide and said N' being the complement of said N.

7. The method according to claim 4, wherein said one or more sequencing primers are 1 to 16 sequencing primers wherein the sequencing primers have 3' ends of NAA, NAC, NAG, NAT, NCA, NCC, NCG, NCT, NGA, NGC, NGG, NGT, NTA, NTC, NTG, or NTT, with said N being any nucleotide.

8. The method according to claim 4, wherein the quantity of the sequencing primers is 1 to 16 sequencing primers to obtain DNA sequence information adjacent to the restriction site wherein the sequencing primers having 3' ends of NAA, NAC, NAG, NAT, NCA, NCC, NCG, NCT, NGA, NGC, NGG, NGT, NTA, NTC, NTG, or NTT, with said N being any nucleotide.

9. The method according to claim 4, wherein the DNA sequence information generated from the representations comprises unique sequencing data.

10. The method according to claim 4, wherein the DNA sequence information generated from the representations comprises two overlapping sequences.

11. The method according to claim 4, wherein the DNA sequence information generated from the representations comprises three overlapping sequences.

12. The method according to claim 4, wherein the sequencing primers have one or two additional bases on their 3' end used for obtaining unique singlet sequence information.

13. A method of assembling a map of an organism's genome or portions thereof comprising:

providing a library of an organism's DNA, wherein individual genomic segments are found in more than one clone in the library;

creating representations of the genomic segments in individual clones by selecting a subpopulation of genomic segments out of a larger set of the genomic segments in each of the individual clones, wherein said selecting a subpopulation of genomic segments comprises: subjecting more than one individual clone to a restriction endonuclease, wherein the restriction endonuclease is effective in recognizing a restriction site recognition sequence and cleaving the DNA in said more than one individual clone at a restriction site of the restriction site recognition sequence thereby creating a plurality of clone fragments having 2 base overhangs and adding linker-adapters, each of which is non-palindromic, to the overhangs in the presence of ligase and the first restriction endonuclease and producing a plurality of clone fragments comprising said linker-adapters, wherein said plurality of clone fragments comprising said linker-adapters are selected as the representations, wherein the linker-adapters contain single stranded overhangs of a formula NN/N'N' where said NN/N'N' is selected from the group consisting of AA/TT, AC/GT, AG/CT, CA/TG, GA/TC, and GG/CC;

generating DNA sequence information from the representations;

analyzing the DNA sequence information thereby determining clone overlap from the representations, wherein said analyzing the DNA sequence information comprises: analyzing sequencing data generated by deconvoluting one or more singlet, doublet and/or triplet sequences contained in the representations; and combining said clone overlap and DNA sequence information from the representations thereby assembling a map of the organism's genome or portions thereof.

14. The method according to claim 13, wherein said analyzing sequencing data comprises:
comparing data from two singlet sequences in the same representation of said representations and
evaluating data for the two singlet sequences of separate clone fragments in the same representation of said representations for overlap by aligning the sequencing data and scoring identity in at least 8 bases which are beyond the restriction recognition sequence with less than 3 discordant positions.

15. The method according to claim 13, wherein said analyzing sequencing data comprises:
comparing data from a singlet sequence and a doublet sequence in the same representation of said representations and
evaluating data for the singlet and doublet sequences contained in the representations for said clone overlap by aligning the sequencing data and either scoring for at least 8 bases which are identical in a doublet sequencing run and a singlet sequencing run and said bases are beyond the restriction recognition sequence or, alternatively, by scoring at least 16 bases which are beyond the restriction recognition sequence where the bases of the singlet sequence corresponds to the bases in the doublet sequence with less than 3 discordant positions.

16. The method according to claim 13, wherein said analyzing sequencing data comprises:
comparing data from a singlet and a triplet sequence in the same representation of said representations and
evaluating data for said clone overlap by aligning the sequencing data, and either scoring identity in at least 8 bases which are identical in a triplet sequencing run and a singlet sequencing run and said bases are beyond the restriction recognition sequence or, alternatively, by scoring at least 16 bases which are beyond the restriction recognition sequence where the bases of the singlet corresponds to the bases in the triplet sequence, with less than 3 discordant positions.

17. The method according to claim 13, wherein said analyzing sequencing data comprises:
comparing two doublet sequences in the same representation of the representations and
evaluating data for said clone overlap by aligning the sequencing data and scoring identity in at least 16 bases which are beyond the restriction recognition sequence where the two doublet sequences has an identical base, or where both said doublet sequences have two identical bases, with less than 3 discordant positions.

18. The method according to claim 13, wherein said analyzing sequencing data comprises:
comparing a doublet sequence and a triplet sequence in the same representation of the representations and
evaluating data for said clone overlap by aligning the sequencing data, and scoring identity in at least 16 bases which are beyond the restriction recognition sequence where either the doublet sequence and the triplet sequence has an identical base, or where the doublet sequence and triplet sequence have two identical bases, with less than 3 discordant positions.

19. The method according to claim 13, wherein said analyzing sequencing data comprises:
comparing two sequences from the same representation of the representations with a singlet, doublet, or triplet sequence; and
evaluating data to determine whether the clones are likely not to overlap.

20. A method of assembling a map of an organism's genome or portions thereof comprising:
providing a library of an organism's DNA, wherein individual genomic segments are found in more than one clone in the library with at least some of the said individual genomic segments have overlapping DNA sequences;
creating representations of the genomic segments in individual clones by selecting a subpopulation of genomic segments out of a larger set of the genomic segments in each of the individual clones, wherein said selecting a subpopulation of genomic segments comprises: subjecting more than one individual clone to a restriction endonuclease, wherein the restriction endonuclease is effective in recognizing a restriction site recognition sequence and cleaving the DNA in said more than one individual clone at a restriction site of the restriction site recognition sequence thereby creating a plurality of clone fragments having an overhang; and adding a linker-adapter which is non-palindromic to the overhang in the presence of ligase and the restriction endonuclease and producing a plurality clone fragments comprising said linker-adapters, wherein said plurality of clone fragments comprising said linker-adapters are selected as the representations, wherein the linker-adapters contain single stranded overhangs of a formula NN/N'N' where NN/N'N' is selected from the group consisting of AA/TT, AC/GT, AG/CT, CA/TG, GA/TC, and GG/CC;
generating DNA sequence information from the representations;
analyzing the DNA sequence information thereby determining clone overlap from the representations; and
combining said clone overlap and DNA sequence information from the representations thereby assembling a map of the organism's genome or portions thereof, wherein said combining said clone overlap and DNA sequence information comprises: comparing the DNA sequence information in a pair of said plurality of clone fragments comprising said linker-adaptors in the representations which have identical contiguous portions.

* * * * *

UNITED STATES PATENT AND TRADEMARK OFFICE
CERTIFICATE OF CORRECTION

| | | |
|---|---|---|
| PATENT NO. | : 8,367,322 B2 | Page 1 of 1 |
| APPLICATION NO. | : 10/198235 | |
| DATED | : February 5, 2013 | |
| INVENTOR(S) | : Barany et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 843 days.

Signed and Sealed this
Eleventh Day of August, 2015

Michelle K. Lee
*Director of the United States Patent and Trademark Office*